US006572864B1

(12) United States Patent
Bukh et al.

(10) Patent No.: US 6,572,864 B1
(45) Date of Patent: Jun. 3, 2003

(54) NUCLEOTIDE AND DEDUCED AMINO ACID SEQUENCES OF THE ENVELOPE 1 GENE OF 51 ISOLATES OF HEPATITIS C VIRUS AND THE USE OF REAGENTS DERIVED FROM THESE SEQUENCES IN DIAGNOSTIC METHODS AND VACCINES

(75) Inventors: Jens Bukh, Bethesda, MD (US); Roger H. Miller, Rockville, MD (US); Robert H. Purcell, Boyds, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/466,601

(22) Filed: Jun. 6, 1995

Related U.S. Application Data

(62) Division of application No. 08/086,428, filed on Jun. 29, 1993.
(51) Int. Cl.[7] ................................................ A61K 39/29
(52) U.S. Cl. ............................... 424/228.1; 424/189.1; 424/93.6; 530/300; 530/328; 530/350; 530/826; 435/69.1; 536/23.1
(58) Field of Search .......................... 424/189.1, 228.1, 424/93.6; 435/69.1; 536/23.1; 530/300, 328, 350, 826

(56) References Cited

U.S. PATENT DOCUMENTS

| | | | | |
|---|---|---|---|---|
| 5,574,132 A | * | 11/1996 | Lacroix | ....................... 530/323 |
| 5,670,153 A | * | 9/1997 | Weiner et al. | ............ 424/189.1 |
| 5,756,312 A | * | 5/1998 | Wiener et al. | .............. 435/69.3 |
| 5,766,845 A | * | 6/1998 | Wiener et al. | .................. 435/5 |
| 6,027,729 A | * | 2/2000 | Houghton et al. | ....... 424/228.1 |

FOREIGN PATENT DOCUMENTS

| | | |
|---|---|---|
| EP | 485 209 | 5/1992 |
| EP | 532 167 | 5/1992 |
| EP | 468 527 | 1/1993 |
| EP | 510 952 | 3/1993 |
| EP | 585 549 | 3/1994 |
| GB | 221 251 1 B | 1/1992 |
| WO | WO 9208734 | 5/1992 |
| WO | WO 9211370 | 7/1992 |
| WO | WO 9219743 | 11/1992 |
| WO | 93/00365 | * 1/1993 |
| WO | WO 9302103 | 2/1993 |
| WO | WO 9306126 | 4/1993 |
| WO | WO 9315193 | 8/1993 |
| WO | WO 9425601 | 11/1994 |
| WO | WO 9221759 | 12/1994 |

OTHER PUBLICATIONS

Bukh et al 1995 Seminars in Liver Disease vol. 15 No. 1: 41–63.*
Farei et al 1992 Science vol. 258: 135–140.*
Seaver 1994 Genetic Engineering News vol. 14 No. 4: 10+14.*
Sevier et al 1981 Clin Chem. vol. 27 No. 11: 1797–1806.*
Okamoto et al. (A) J. Gen. Virol. 72: 2697–2704, 1991.*
Weiner et al. Virol. 180: 842–848, 1991.*
Takeuchi et al. J. Gen. Virol. 71: 3027–3033, 1990.*
Ogata et al. PNAS (USA) 88: 3392–3396, 1991.*
Okamoto et al. (B) Virol. 188: 331–341, 1992.*
Inchaupse et al. PNAS (USA) 88: 10292–10296, 1991.*
Sallberg et al. Clin. Exp. Immunol. 91: 489–494, 1993.*
Ishida et al. J. Clin. Microbiol. 31(4): 936–940, 1993.*
Matsuura et al. J. Virol. 66(3): 1425–1431, 1992.*
Choo, A.L. et al. (1989) Science 244:359–362.
Weiner, A.J. et al. (1990) Lancet 335:1–3.
Kuo, G. et al. (1992) Science 244:362–364.
Okamoto, H. et al. (1992) J. Gen. Virol; 73:673–679.
Bukh, J. et al. (1992) Proc. Natl. Acad. Sci. 89:187–191.
Bukh, J. et al. (1992) Proc. Natl. Acad. Sci. U.S.A. 89:4942–4946.
Cha, T. et al. (1992) Proc. Natl. Acad. Sci. U.S.A. 89:7144–148.
Chan, S–W. et al. (1992) J. Gen. Virol., 73:1131–1141.
Lee, C–H. et al. (1992) J. Clin. Microbio. 30:1602–1604.
Choo, et al. (1991) Proc. Natl. Acad. Sci. U.S.A. 88:2451–2455.
Okamoto, et al. (1992) Virology 188:331–341.
Inchauspe, et al. (1991) Proc. Natl. Acad. Sci. USA 88:10292–10296.
Takamizawa, et al. (1991) J. Virol. 65:1105–1113.
Kato, et al. (1990) Proc. Natl. Acad. Sci. U.S.A. 87:9524–9528.
Okamoto, et al. (1992) Virology 190:894–899.
Ogata, et al. (1991) Proc. Natl. Acad. Sci. USA 88:3392–3396.
Mori, et al. (1992) Biochem. Biophys. Res. Comm. 183:334–342.
Weiner, et al. (1991) Virology 180:842–848.
Hijikata, et al. (1991) Biochem. Biophys. Res. Comm. 175:220–228.
Okamoto, et al. (1990) Japan. J. Exp. Med. 60:167–177.
Takeuchi, et al. (1990) J. Gen. Virol. 71:3027–3033.

(List continued on next page.)

Primary Examiner—Mary K. Zeman
(74) Attorney, Agent, or Firm—Knobbe, Martens, Olson & Bear LLP

(57) ABSTRACT

The nucleotide and deduced amino acid sequences of 51 cDNAs are disclosed where each cDNA encodes the envelope 1 gene of an isolate of hepatitis C virus (HCV). The invention relates to the oligonucleotides, peptides and recombinant envelope 1 proteins derived from these sequences and their use in diagnostic methods and vaccines.

11 Claims, 71 Drawing Sheets

OTHER PUBLICATIONS

Chen et al. (1992) Virology 188:102–113.
Liu, et al. (1992) Gene 114:245–250.
Tanaka, et al. (1992) Virus Research 23:39–53.
Abe, et al. (1992) J. Gen. Virol. 73, 2725–2729.
Honda, et al. (1993) Arch. Virol. 128, 163–169.
Stuyver, L. et al. (1993) Biochem. Biophys. Res. Comm. 192:635–641.
M. Kohara et al., 'Expression and characterisation of glycoprotein gp35 of hepatitis if C virus using recombinant vaccinia virus' J. Gen. Virol., vol. 73, 1992, pp. 2313–2318.
Y. Matsura et al. 'Expression of processed envelope protein of hepatitis C virus in mammalian and insect cells' J. Virol., vol. 66, 1992, pp. 1425–1431.
H. Hsu et al., 'Characterisation of HCV structural proteins with a recombinant baculovirus expression system', Hepatology, vol. 17, No. 5, 1993, pp. 763–771.
C. Ishida et al., 'Detection of antibodies to hepatitis C virus structural proteins', J. Clin. Micro., vol. 31, No. 4, 1993 pp. 936–940.
H. Hada et al. 'Sequence variation in the envelope protein of hepatitis C virus', Acta Med Okayama, vol. 45, No. 5, 1991, pp. 347–355.
H. Okamoto et al., 'Nucleotide sequence of the genomic RNA of hepatitis C virus isolated from a human carrier', J. Gen. Virol., vol. 72, 1991, pp. 2697–2704.
M. Houghton et al. & Abstracts of 3rd Intl. Conf. Current trends in chronically evolving viral hepatitis Oct. 4–7,1992, Pisa, Italy Abstract, J. Hepatol., vol. 17, suppl. 1 1992, p. S10.
M. Sallberg et al., Antigenic regions within the hepatitis C virus envelope and nonstructural proteins, vol. 91, No. 3, 1993, pp. 489–494.

* cited by examiner

FIG. 1A-1

| SEQ ID NO: | Isolate | | |
|---|---|---|---|
| 5 | S14 | 1 | TACCAAGTGCGCAACTCCACGGGGCTTTACCATGTtACCAATGATTGCCCTAACTCGAGTA |
| 1 | DK7 | 1 | TACCAAGTGCGCAACTCCACGGGGCTTTACCATGTCACCAATGATTGCCCTAACTCGAGTA |
| 8 | US11 | 1 | TACCAAGTaCGCAACTCCACGGGGCTTTACCATGTCACCAATGATTGCCCTAACTCGAGTA |
| 4 | DR4 | 1 | CACCAAGTGCGCAACTCTACAGGGGCTTTACCATGTCACCAATGATTGCCCTAATTCGAGTA |
| 3 | DR1 | 1 | CACCAAGTGCGCAACTCTACAGGGGCTTTACCATGTCACCAATGATTGCCCTAATTCGAGTA |
| 2 | DK9 | 1 | TACCAAGTACGCAACTCCtCGGGCCTcTACCATGTCACCAATGATTGCCCTAACTCGAGTA |
| 6 | S18 | 1 | TACCAAGTACGCAACTCCaCGGGCCTTTACCATGTCACCAATGAcTGCCCTAACTCGAGcA |
| 7 | SW1 | 1 | TACCAAGTACGCAACTCCtCGGGCCTTTACCATGTCACCAATGAtTGCCCTAACTCGAGTA |
| 1-8 | consensus | | tACCAAGT-CGCAACTCcaCgGGgCTtTACCATGTcACCAATGATTGCCCTAACTCGAGTA |

FIG. 1A-2

| SEQ ID NO: | Isolate | | |
|---|---|---|---|
| 5 | S14 | 62 | TtGTGTACGAGaCaGCtGATGCtATCCTaCACgCTCCGGGaTGTGTCCCTTGCGTTCGtGA |
| 1 | DK7 | 62 | TcGTGTACGAGGCGGCCGATGCCCATCCTGCACACTCCGGGGTGTGTCCCTTGCGTTCGCGA |
| 8 | US11 | 62 | TTGTGTACGAGGCGGCCGATGCCCATCCTGCACACTCCGGGGTGTGTtCCTTGCGTTCGCGA |
| 4 | DR4 | 62 | TTGTGTACGAGGCGGCCGATGCCCATCCTGCACACTCCGGGGTGTGTCCCTTGCGTTCGCGA |
| 3 | DR1 | 62 | TTGTGTACGAGGCGGCCGATGCCCATCCTGCACACGCCGGGGTGTGTCCCTTGCGTTCGCGA |
| 2 | DK9 | 62 | TTGTGTACGAGGCGGCCGATGCCCATCCTGCACgCCGCCGGGGTGTGTCCCTTGCGTTCGCGA |
| 6 | S18 | 62 | TTGTGTACGAGAGCGGCCGATGCCCATtTCTCCaGGGTGTGTCCCTTGCGTTCGCGA |
| 7 | SW1 | 62 | TTGTGTACGAGACGGCCGATaCCATCCTACACTCTCCGgGGTGTGTCCCTTGCGTTCGCGA |
| 1-8 | consensus | | TtGTGTACGAGgCgGCcGATgCcATcCTgCAc-CtCCgGGgTGTGtCCCTTGCGTTCGCGA |

FIG. 1A-3

| SEQ ID NO: | Isolate | | | |
|---|---|---|---|---|
| 5 | S14 | 123 | GGGTAAACacCTCGAGGTGTTGGGTGGCGATGACCCCACGGTGGCCACCAGGACGGCAAA |
| 1 | DK7 | 123 | GGGTAACGtCTCGAGGTGTGTTGGGTGGCGATGACCCCACGGTGGCCACCAGGAtGGCAAA |
| 8 | US11 | 123 | GGGTAACGCtTCGAGGTGTGTTGGGTGGCGATGACCCCACGGTGGCCACCAGGACGGCAAA |
| 4 | DR4 | 123 | GGGTAAACaCCTCGAGGTGTGTTGGGTGGCGATGACCCCACGGTGGCCACCAGGACGGCAAA |
| 3 | DR1 | 123 | GGGTAAACGCCTCGAGGTGTGTTGGGTGGCGTGACCCCACGGTGGCCACCAGGACGGCAAA |
| 2 | DK9 | 123 | GGGTAACGCCCTCGAaATGTTGGGTGGCGGTGACCCCACGGTGGCCACCAGGACGGCAAg |
| 6 | S18 | 123 | GGGTAACGCCCTCGAgATGTTGGGTGGCcCGGTGGCCCACAGTtGCCACCAGGACGGCAAA |
| 7 | SW1 | 123 | GGaTggCGCCcCGAaagTGTTGGGTGgCGGTGGCGCCCACAGTCGCCACtAGGACGGCAAA |
| 1-8 | consensus | | GGgTaaCgcctCGAggTGTtGGGTggCGgTGaCCCCaCGgTGgCCACcAGGACgGGCAAa |

FIG. 1A-4

| SEQ ID NO: | Isolate | | |
|---|---|---|---|
| 5 | S14 | 184 | CTCCCCgCAaCGCAGCTTCGACGTtACATCGATCTGTCGGGAGcGCCACCCTCTGTT |
| 1 | DK7 | 184 | CTCCCACAgCGCAGCTTCGACGTCACATCGATCTGCTcGTCGGGAGtGCCACCCTCTGTT |
| 8 | US11 | 184 | CTCCCACAACGCAaCTTCGACGTCACATCGATCTGCTCGTCGGGAGCGCCACCCTCTGTT |
| 4 | DR4 | 184 | CTCCCACAACGCAGCTCCGACGTCACATCGATCTGACCTGCTTGTCGGGAGCGCCACCCTCTGCT |
| 3 | DR1 | 184 | CTCCCACAACGCAGCTTCGACGTCACATCGATCTGACCTGCTTGTCGGGAGCGCCACCCTCTGCT |
| 2 | DK9 | 184 | CTCCCACAACGCAGCTTCGACGTCACATCGATCTGCTTGTCGGGAGCGCCACCCTCTGCT |
| 6 | S18 | 184 | CTCCCGCAACGCAGCTTCGACGTCACATCGATCTGCTTGTCGGGAGCGCCACCCTCTGCT |
| 7 | SW1 | 184 | CTCCCtGCAACGCAGCTTCGACGTCACATCGATCTGCTTGTtGGGAGCGCCACCCTCTGCT |
| 1-8 | consensus | | CTCCCc-CAaCGCAgcTTcGACGTcACATCGAtCTGcTtGTcGGgAGcGCCACCCTCTGcT |

| SEQ ID NO: | Isolate | | |
|---|---|---|---|
| 5 | S14 | 245 | CGGCCCCTCTACGTGGGGACTTGTGCGGGTCTGTCTTCTTGTCGGTCAgCTGTTTACCTT |
| 1 | DK7 | 245 | CGGCCCCTCTACGTGGGGACCTGTGCGGGTCTGTCTTCTTGTCGGTCAgCTGTTTACCTT |
| 8 | S11 | 245 | CGGCCCCTCTACGTGGGGACCTGTGCGGGTCTGTCTTTCTTGTCGGTCAAACTGTTTACCTT |
| 4 | DR4 | 245 | CGGCCCCTCTACGTGGGGACtTGTGCGGGTCTGTCTTCCTTGTCGGTCAAACTGTTCACCTT |
| 3 | DR1 | 245 | CGGCCCCTCTACGTGGGGACCTGTGCGGGTCTGTCTTCCTTGTCGGTCAAACTGTTCACCTT |
| 2 | DK9 | 245 | CGGCCCCTCTATGTGGGGACTTGTGCGGGTCTGTCTTCTTCCTTGTCGGCCAAACTGTTCACCTT |
| 6 | S18 | 245 | CGGCCCCTCTATGTGGGGACCTGTGCGGGTCTGTCTTCTTTCGTCAGCCAgCTGTTCACtaT |
| 7 | SW1 | 245 | CGGCCCCTCTACGTGGGGACTTGTGCGGGTCTGTCTTTCTcGTCAGtCAaCTGTTCAgtT |
| 1-8 | consensus | | CGGCCCCTCTAcGTGGGGAC-TGTGCGGGTCTGTCTTtCTTGTCGtCAaCTGTTcAcctT |

| SEQ ID NO: | Isolate | | |
|---|---|---|---|
| 5 | S14 | 306 | CTCTCCCAGGCGCCtCTGGACGACGCAAGaCTGCAATTGTTCTATCTATCCcGGCCATATA |
| 1 | DK7 | 306 | CTCTCCCAGGCGCCACTGGACGACGCAAGGCTGCAATTGTTCTATCTATCCtGGCCATATA |
| 8 | S11 | 306 | CTCTCCCAGaCGCCACTGGACGACGCAAGACGCAGagCTGCAATTGTTCTATCTATCCCGGCCATATA |
| 4 | DR4 | 306 | CTCTCCCAGGCaCCACTGGACAACGCAAGACTGCAATTGTTCCATCTATCCCGGCCATATA |
| 3 | DR1 | 306 | tTCTCCCAGGCGCCACTGGACAACGCAAGACTGCAATTGTTCTATCTATCCCGGCCATATA |
| 2 | DK9 | 306 | CTCCCCCAGaCGCCACTGGACAACGCAAGACTGCAACTGTTCTATCTACCCCGGCCATATt |
| 6 | S18 | 306 | CTCCCCCAGGCGCCACTGGACAACGCAAGACTGCAACTGTTCTTTCTATCTACCCCGGCCATATA |
| 7 | SW1 | 306 | CTCCCCCAGGCGCCACTGGACAACGCAAGACTGtAACTGTTCTATCTATCCGGCCATATA |
| 1-8 | consensus | | cTctCCCAGgCgCCacTGGACaAcGCAagaCTgCAatTGTTctaTCTatCCcGGCCAtATa |

FIG. 1A-7

| SEQ ID NO: | Isolate | | |
|---|---|---|---|
| 5 | S14 | 367 | ACGGGTCAtCGCATGGCaTGGGATATGATGATGAACTGTCCCCTACgACGGCacTGGTAG |
| 1 | DK7 | 367 | ACGGGTCACCGCATGGCgTGGGATATGATGATGAACTGTCCCCTACCACGGCGTTGGTAG |
| 8 | S11 | 367 | ACGGGTCACCGCATGGCaTGGGATATGATGATGAACTGTCCCCTACgCGGCGTTGGTgG |
| 4 | DR4 | 367 | ACGGGcCACCCGCATGGCgTGGGATATGATGATGAACTGTCCCCTACGACAGCGCTGGTAG |
| 3 | DR1 | 367 | ACGGGaCACCGtATGGCaTGGGATATGATGATGAACTGTCCCCTACGACAGCGCTGGTAA |
| 2 | DK9 | 367 | ACGGGTCAtCGCaTGGCgTGGGATATGATGATGAACTGTCCCCTACAgCAGCGCTGGTAA |
| 6 | S18 | 367 | ACGGGTCACCGCATGGCaTGGGATATGATGATGAACTGTCCCCTACAACgGCGCTGGTAA |
| 7 | SW1 | 367 | ACGGGTCACCGCATGGCaTGGGATATGATGATGAACTGTCCCCCACAACaCaGCGCTGGTAg |
| 1-8 | consensus | | ACGGGtCAcCGcATGGCaTGGGATATGATGATGAACTGTCCCCtACgaC-GCgcTGGTag |

FIG. 1A-8

| SEQ ID NO: | Isolate | | |
|---|---|---|---|
| 5 | S14 | 428 | TAGCTCAGCTGCTCCGGATCCCaCAAGCCATCTTGGAtATGATCGCTGGTGCTCACTGGGG |
| 1 | DK7 | 428 | TAGCTCAGCTGCTCCGGATCCCgCAAGCCATCTTGGACATGATCGCTGGTGCTCACTGGGG |
| 8 | S11 | 428 | TAGCTCAGCTGCTCCGGATCCCACAAGCCATCTTGGACATGATCGCTGGTGCTCACTGGGG |
| 4 | DR4 | 428 | TAGCTCAGCTGCTCCGGATCCCACAAGCCATCTTGGACATGATCGCTGGTGCTCACTGGGG |
| 3 | DR1 | 428 | TAGCTCAGCTGCTCCGGATCCCACAAGCCATCTTGGACATGATCGCTGGTGCCCACTGGGG |
| 2 | DK9 | 428 | TGGCTCAGCTGCTCCGGATCCCACAAGCCATCTTGGACATGATCGCTGGaGCCCACTGGGG |
| 6 | S18 | 428 | TGGCGCAGCTGCTCAGGATCCCGCAgGCCAAGCCTGGACATGATCGCTGGTGCCCACTGGGG |
| 7 | SW1 | 428 | TAGCTCAGCTGCTCAGGgTCCCGCAAGCCGTCGTTGGACATGATCGCTGGTGCCCACTGGGG |
| 1-8 | consensus | | TaGCTcAGCTGCTCcGGaTCCC-CAaGCCaTCTTTGGACATGATCGCTGGtGCcCACTGGGG |

FIG. 1A-9

| SEQ ID NO: | Isolate | | |
|---|---|---|---|
| 5 | S14 | 489 | AGTCCTaGCGGGCATAGCGTATTTCTCCATGGTGGGaAAACTGGGCGAAGGTCCTaGTgGTG |
| 1 | DK7 | 489 | AGTCCTgGCGGGCATAGCGTATTTtTCCATGGTGGGGAACTGGGCGAAGGTCCTGGTAGTG |
| 8 | S11 | 489 | AGTCCTAGCGGGCATAGCGTATTTCTCCATGGTGGGGAACTGGGCGAAGGTCCTGGTAGTG |
| 4 | DR4 | 489 | AGTCCTAGCGGGCATAGCGTATTTCTCCATGGTGGGGAACTGGGCGAAGGTCCTGGTAGTG |
| 3 | DR1 | 489 | AGTCCTAGCGGGCATAGCGTATTTCTCCATGGTGGGGAACTGGGCGAAGGTCGTGGTAGTG |
| 2 | DK9 | 489 | AGTCCTAGCGGGCATAGCGTATTTCTCCATGGTGGGGAACTGGGCGAAGGTCGTGGTgGTa |
| 6 | S18 | 489 | AGTCCTAGCGGGCATAGCGTATTTCTCCATGGCGCGGGGAACTGGGCGAAGGTCCTGcTAGTG |
| 7 | SW1 | 489 | AGTCCTAGCGGGCATAGCGTATTTCTCCATGGtGGGGAACTGGGCGAAGGTCCTGaTAGTG |

| 1-8 | consensus | AGTCCTaGCGGGCATAGCGTATTTCTCCAtGGtGGGgAACTGGGCGAAGGTCcTggTaGTg |

FIG. 1A-10

| SEQ ID NO: | Isolate | | |
|---|---|---|---|
| 5 | S14 | CTGCTGCTATTCGCCGGGCGTTGACGCG | 550 |
| 1 | DK7 | CTGCTGCTATTTGCCGGGCGTCGACGCG | 550 |
| 8 | US11 | CTGCTGCTATTTGCCGGGCGTCGACGCG | 550 |
| 4 | DR4 | CTGTTGCTGTTTGCCGGGCGTTGATGCG | 550 |
| 3 | DR1 | CTGTTGCTGTTTGCCGGGCGTTGATGCG | 550 |
| 2 | DK9 | CTGTTGCTGTTTaCCGGGCGTTGATGCG | 550 |
| 6 | S18 | CTGTTGCTGTTTgCCGGGCGTCGATGCG | 550 |
| 7 | SW1 | CTGTTGCTGTTTtCCGGGCGTCGATGCG | 550 |
| 1-8 | consensus | CTGtTGCTgtTTtgCCGGCGTcGAtGCG | |

FIG. 1B-1

| SEQ ID NO: | Isolate | |
|---|---|---|
| 11 | DK1 | 1 TATGAAGTGCGCAACGTGTCCGGGgTGTACCAcGTCACaAACGACTGCTCCAACTCAAGCA |
| 24 | T10 | 1 TATGAAGTGCGCAACGTGTCCGGGaTGTACCATgTCACgAACGACTGCTCCAACTCAAGCA |
| 10 | D3 | 1 TATGAAGTGCGCAACGTGTCCGGGGTGTACCAaGTCACCAAtGACTGTTCCAACTCGAGCA |
| 9 | D1 | 1 TATGAAGTGCGCAACGTGTCCGGGGTGTACCATGTCACGAACGACTGTTCCAACTCGAGCA |
| 14 | HK5 | 1 TATGAAGTGCGCAACGTGTCCGGGGTGTATACCATGTCACGAACGACTGCTCCAACTtAAGCA |
| 15 | HK8 | 1 TATGAAGTGCGCAACGTGTCCGGGATATACCATGTCACGAACGACTGCTCCAACTCAAGCA |
| 12 | HK3 | 1 TATGAAGTGCGCAACGTGTCCGGGGTGTACtATGTCACGAACGACTGCTCCAACTCAAGCg |
| 23 | T3 | 1 TAcGAAGTGCGCAACGTGTCCGGGGTGTACtATGTCACGAACGACTGCTCCAACTCAAGCA |
| 22 | SW2 | 1 TATGAAGTGCGCAACGTGTCCGGGGTGTAtCATGTCACGAACGACTGTTCCAACTCAAGCA |
| 17 | IND8 | 1 TATGAgGTGCGCAACGTGTCCGGGGTGTACCATGTCACGAACGACTGCTCCAACTCAAGTA |
| 16 | IND5 | 1 TATGAAGTGCGCAACGTGTCCGGGGTGTACCATGTCACGAACGACTGCTCCAACTCAAGTA |
| 21 | SA10 | 1 TATGAAGTGCGCAACGTGTCCGGGaTGTACCATGTCACGAACGACTGCTCCAACTCAAGCA |
| 20 | S45 | 1 TATGAAGTGCGCAACGTGTCCGGGgcGTACCATGTCACGAACGACTGCTCCAACTCAAGCA |
| 25 | US6 | 1 TATGAAGTGCGCAACGTGTCCGGGATGTACCATGTCACGAACGACTGCTCCAACTCAAGCA |
| 13 | HK4 | 1 cATGAAGTGCaCAACGTaTCCGGGATcTACCATGTCACGAACGACTGCTCCAACTCAAGTA |
| 18 | P10 | 1 TATGAAGTGCGCAACGTgTCCGGGGTGTACCATGTCACGAACGACTGCTCCAACTCAAGTA |
| 19 | S9 | 1 TATGAAGTGCCAACGTaTCCGGGGCGTACCATGTCACGAACGACTGCTCCAACTCAAGTA |
| 9-25 | consensus | tAtGAaGTGCgCAACGTgTCCGGGgtgTAccATgTCACgAAcGACTGcTCCAACTcaAGca |

FIG. 1B-2

| SEQ ID NO: | Isolate | | |
|---|---|---|---|
| 11 | DK1 | 62 | TcGTGTatGAGGCAGtGGACgTGATCATGCAtaCCCCaGGGTGCGTGCCCTGCGTTCGGGA |
| 24 | T10 | 62 | TtGTGTtTGAGGCAGCGGACttGATCATGCACACCCCGGGTGCGTGCCCTGCGTTCGGGA |
| 10 | D3 | 62 | TcGTGTATGAGAGCAGCGGACGGATCATGCACACCCCGGGTGCGTGCCCTGCGTTCGGGA |
| 9 | D1 | 62 | TtGTGTATGAGAGCAGCGGACATGATCATGCACACCCCGGGTGCGTGCCCTGCGTTCGGGA |
| 14 | HK5 | 62 | TCGTGTAcGAGACAaCGGACATGATCATGCACACCCCGGGTGCGTGCCCTGCGTTCGGGA |
| 15 | HK8 | 62 | TCGTGTATGAaACAGCGGACATGATtATGCATACCCCTGGATGCaTGCCCTGCGTTCGGGA |
| 12 | HK3 | 62 | TCGTGTATGAGACAGCaGACATGATCATGCACATACCCCTGGATGCGTGCCCTGCGTaCGGGA |
| 23 | T3 | 62 | TCGTGTATGAGACAGCGGACATGATCATGCACACCCCGGGTGCGTGCCCTGCGTTCGGGA |
| 22 | SW2 | 62 | TtGTGTATGAGACAGCGGACATGATCATGCACACCCCGGGTGCGTGCCCTGCGTTCGGGA |
| 17 | IND8 | 62 | TtGTGTATGAGGCAGCGGACATGATCATGCACACtCCCGGGTGCGTGCCCTGCGTTCGGGA |
| 16 | IND5 | 62 | TtGTGTATGAGGCAGCGGACATGATCATGCACACCCCGGGTGCGTGCCCTGCGTTCGGGA |
| 21 | SA10 | 62 | TtGTGTATGAGGCAGCGGACATGATCATGCACACCCCGGGTGCGTGCCCTGCGTTCGGGA |
| 20 | S45 | 62 | TtGTGTATGAGGCAGtGGACtGGACgTGATCCTGCACACCCCTGGGTGCGTGCCCTGCGTTCGGGA |
| 25 | US6 | 62 | TtGTGTATGAGGCAGCGGACATGATCATGCACACtCCCGGGTGCCCTGtGTTCGGGA |
| 13 | HK4 | 62 | TtGTGTATGAGGCAGCGGACATGATCATaCCCCGGGTGCCCTGCCTGCGTCGGGA |
| 18 | P10 | 62 | TtGTGTATGAGGCAGCGGACATGATaATGCAcACACCCCGGGTGCGTGCCCTGtGTTCGGGA |
| 19 | S9 | 62 | TtGTGTAcGAGGCAGCGGACgTGATCATGCAATGCACACCCCGGGTGtGCCTGTaCCCGGGA |
| 9-25 | consensus | | TtGTGTatGAggCAgcgGACaTGATcaTGCAcACCCCcGGgTGCgTgCCCTGCcGTtCgGGA |

FIG. 1B-3

| SEQ ID NO: | Isolate | |
|---|---|---|
| 11 | DK1 | 123 GaaCAACcaCTCCCGtTGCTGGGTAGCGCTCACcCCCACGCTCGGCGGCCAGGAACGCCAGC |
| 24 | T10 | 123 GGgCAACTCCTCCCGCTGCTGGGTAGCGCTCACtCCCACGCTCGGCGGCCAGGAACACCAGC |
| 10 | D3 | 123 GGACAACTCCCTCTCGCTGCTGGGTAGCGCTCACCCCCACGCTCGCGGCCTAGGAATAGCAGC |
| 9 | D1 | 123 GGACAACTCCCTCTCGCTGCTGGGTAGCGCTCACCCCCACGCTCGCGGGCTAGGAATGGCAaC |
| 14 | HK5 | 123 aAACAACTCCTCCCGTTGtTGGGTAGCGCTCGcCCCCCACGCTCGCGGCCAGGAACGcCAGC |
| 15 | HK8 | 123 GAACAACTCCTCCCGTTGcTGGGTgGCGCTCACTCCCACGCTCGCGGCCTAGGAAtGTCAGC |
| 12 | HK3 | 123 GAACAACTCCTCCCGCTGtTGGGTAGCGCTCACTCCCACGCTCGCGGCCAGGAACGTCAGC |
| 23 | T3 | 123 GAgCAAtTCCTCCCGCTGCTGGGTAGCGCTtACTCCCACGCTCGCGGCCAGGAACGCCAGC |
| 22 | SW2 | 123 GGcCAACTCCTCCCGCTGCTGGGTAGCGCTCACTCCCACGCTaGCaGCCAGGAACaCCAGC |
| 17 | IND8 | 123 GGGCAAcTtCTCTaGtTGCTGGGTAGCGCTCACTCTCGCGGCCTAGGAACGCCAGC |
| 16 | IND5 | 123 GGGCAAcTCCTCCCGCTGCTGGGTAGCGCTCACTCTCCCACGCTCGCGGCCAGGAACGCCAGC |
| 21 | SA10 | 123 GAACAACTCCTCCCGCTGCTGGGTAGCGCTCACCGCTCGCGGCCAGGAACTCCAGC |
| 20 | S45 | 123 GAACAACTCCTCCCGtTGCTGGGTgGCGCTCACTCCCACGCTCGCGGCCAGGAACTCCAGC |
| 25 | US6 | 123 GGGCAAtTCCTCCCGCTGCTGGGTAGCGCTCACTCCCACGCTCGCGGCCAGGAACGCtAGC |
| 13 | HK4 | 123 GAACAACTCCTCCCGCTGCTGGGTAGCGCTCACTCCCACGCTCGCGGCCAGGAACGCCAGC |
| 18 | P10 | 123 GAACAACTCCTCCCGCTGCTGGGTAGCGCTCACaCTCCCACaCTCGCGGCCtAGGAAttCCAGC |
| 19 | S9 | 123 GggtAACTCCTCCCaaTGCTGGGTgGCGCTCACcCCACGCTCGCGGCCAGGAAcgtCAgC |

9-25 consensus gaacAActcCTCccgcTGcTGGGTagCGCTcacTcCCACGcTCgCGgCcaGGAAcgccAgC

FIG. 1B-4

| SEQ ID NO: | Isolate | | | |
|---|---|---|---|---|
| 11 | DK1 | 184 | aTCCCCACTACGACaATACGACGCCATGTCGATTTGCTCGTTGGGCGGCTGCTTTCTGCT |
| 24 | T10 | 184 | GTCCCCACTACGACgATACGACGCCATGTCGATTTGCTCGTTGGGCGGCTGCTTTCTGCT |
| 10 | D3 | 184 | GTCCCCACTACGACaATACGACGCCATGTCGATTTGCTCGTTGGGCGGCTGCTTTCTGCT |
| 9 | D1 | 184 | GTCCCCACTACGGCgATACGACGCCATGTCGATTTGCTCGTTGGGCGGCTGCTTTCTGCT |
| 14 | HK5 | 184 | GTCCCCACCACGGCAATACGACGCCACGTCGACTTGCTCGTTGGGCGGCTGCTTTCTGCT |
| 15 | HK8 | 184 | GTCCCCACtACGACACAATACGACGCCACGTCGACTTGCTCGTTGGGCGGCTGCTTTCTGCT |
| 12 | HK3 | 184 | GTCCCCACCACGACAATACGACGCCACGTCGACTTGCTCGTTGGGCGGCTGCcTTCTGCT |
| 23 | T3 | 184 | GTCCCCACTAaGACAATACGACGCCACGTCGATTGCTCGTTGGGCGGCTGCTTTCTGtT |
| 22 | SW2 | 184 | GTCCCCACTACGACAATACGACGCCACGTCGATTTGCTCGTTGGGCGGCTGCTTTCTGtT |
| 17 | IND8 | 184 | GTCCCCACTACGACAATACGACGCCACGTCGATTGCTCGTTGGGCGGCTGCTTTCTGTT |
| 16 | IND5 | 184 | GTCtCCACCACGACACaCCACGTCGATTGCTCGTTGGGCGGCTGCTTTCTGTT |
| 21 | SA10 | 184 | GTCCCCACTACGACAATACGACGCCACGTCGATTTGCTCGTTGGGCGGCTGCTTTCTGCT |
| 20 | S45 | 184 | GTCCCCACTACGACAATACGACGtCACGTCGATTGCTCGTTGGGCGGCTGCTTTCTGCT |
| 25 | US6 | 184 | GTCCCCACTACGACAATACGACGCCACGTCGATTGCTCGTTGGGCGGCTaCTTTCTGCT |
| 13 | HK4 | 184 | aTCCCCACTACGACAATACGACGCCATGTCGACTTGCTCGTTGGGCGGCTGCTTTCTGCT |
| 18 | P10 | 184 | GTCCCaACTACGACACGGCAATACGACGCCACGTCGATTTGCTCGTTGGGCGGCTGCTTTCTGCT |
| 19 | S9 | 184 | GTCCCCACCACGaCAATACGACGCCACGTCGAtCATGTCGATTGCTCGTTGGGCGGCTGtTTTCTGCT |
| 9-25 | consensus | | gTCcccActAcGaCaATACGACgcCAcGTCGATTGCTCGTTGGGCGGCTgctTTCTGCT |

FIG. 1B-5

| SEQ ID NO: | Isolate | | |
|---|---|---|---|
| 11 | DK1 | 245 | CCGCTATGTACgTGGgGACCTCTGCGGATCCgTTTTCCTCGTCTCTCCAGCTGTTCACCTT |
| 24 | T10 | 245 | CCGCTATGTAtGTGGGaGACCCTCTGCGGATCTGTTTTCCTCGTCTCTCCAGCTGTTCACCTT |
| 10 | D3 | 245 | CCGCCATGTACGTGGGGGATCTtTGCGGATCTGTTTTCCTCGTCTCTCCAGCTGTTCACCTT |
| 9 | D1 | 245 | CCGCCATGTACGTGGGGGATCTcTGCGGATCTGTTTTCCTCaTCTCCCAGCTGTTCACCCT |
| 14 | HK5 | 245 | CCGCTATGTACGTGGGGGATCTtTGCGGATCTGTTTTCCTCGTCTCTCCAGCTGTTCACCTT |
| 15 | HK8 | 245 | CCGCTATGTACGTGGGGGATCTCTGCGGATCTGTTTTCCTCGTCTCTCCAGCTGTTCACCTT |
| 12 | HK3 | 245 | CCGCTATGTACGTGGGGGATCTCTGCGGATCTGTTTCCTCtGTCTCTCCAGCTGTTCACCTT |
| 23 | T3 | 245 | CCGCTATGTACGTGGGGGATCTCTGCGGATCTGTTTTCCTCGTCTCTCCAGCTGTTCACCTT |
| 22 | SW2 | 245 | CCGtTATGTACGTGGGGGATCTCTGCGGATCTGTTTTCCTCGTCTCTCCAGCTGTTCACCTT |
| 17 | IND8 | 245 | CCGCTATGTACGTGGGGGATCTCTGCGGATCTGTTTTCCTtGTCTCGTCTCCAGCTGTTCACCTT |
| 16 | IND5 | 245 | CCGCTATGTACGTGGGGGATCTaTGCGGATCTGTTTTCCTCGTCTCGTCTCCAGCTGTTCACCTT |
| 21 | SA10 | 245 | CCGCCATGTACGTGGGGGATCTCTGCGGAcCTCTGTTTTCCTCGTCTGTtTCCCAGCTGTTCACCTT |
| 20 | US6 | 245 | CCGCTATGTACGTGGGGGATCTCTGCGGATCTGTTTTCCTCaTCTCCCAGCTGTTCACCTT |
| 25 | S45 | 245 | CCGCTATGTACGTGGGGGATCTCTGCGGGTCCgTTTTCCTCGTTCTCCCAGCTGTTCACCTT |
| 13 | HK4 | 245 | CCGCCATGTACGTGGaGATGATCTCTGCGGATCTGTTTTCCTCGTCTCTCCAGCTGTTCACCTT |
| 18 | P10 | 245 | CCGCTATGTACGTGGGGGACCTgTGCGGATCTGTTtTCCTCGTTtTCCCAGCtGTTCACCaT |
| 19 | S9 | 245 | CCGCTATGTACGTGGGGGACCTgTGCGGATCTGTTTTCCTCaTCTCCCAGCTGTTCACCaT |
| 9-25 | consensus | | CCGctATGTAcGTGGGgGGATcTcTGCGGaTCtGTtttCCTCgTcTcCCAGcTGTTCAccTT |

FIG. 1B-6

| SEQ ID NO: | Isolate | | |
|---|---|---|---|
| 11 | DK1 | 306 | tTCaCCTCGCCGGCATGAGACagcaCAGGACTGCAACTGCTCAATCTATCCCGGCCAcgTt |
| 24 | T10 | 306 | CTCGCCTCGCCGGCATGAGACatttGCAGGACTGCAACTGCTCAATCTATCCCGGCCAtcTG |
| 10 | D3 | 306 | CTCGCCTCGCCGGCATGAGACaGTACAGGAaTGTAACTGCTCAATCTATCCCGGCCACGTG |
| 9 | D1 | 306 | CTCGCCTCGCCGGCATGAGACaGTACAGGAGTGTAAtTGCTCAATCTATCCCGGCCACGTG |
| 14 | HK5 | 306 | CTCGCCTCGACACGAGACAGTACAGGACTGCAACTGCTCAATCTATCCCGGCCACGTA |
| 15 | HK8 | 306 | CTCGCCTCGCCGGACACGAGACAGTACAGGACTGCAACTGCTCAATCTATCCCGGCCACGTA |
| 12 | HK3 | 306 | tTCACCTCGCCGGCACGAGACAGTACAGGACTGCAACTGCTCAATCTATCCCGGCCACGTA |
| 23 | T3 | 306 | CTCGCCTCGCCGGACACGAGACAGTACAGGACTGCAACTGCTCACTCTATCCCGGCCACGTA |
| 22 | SW2 | 306 | CTCGCCTCGCCGGCATGAGACAGTACAGGACTGCAACTGtTCCAATCTATCCCGGCCACGTA |
| 17 | IND8 | 306 | CTCACCGGCCGGCCGCCACGAGACAGTACAGGACTGCAATTGCTCAATCTATCCCGGCCACGTA |
| 16 | IND5 | 306 | CTCACCGGCCGCCGCGAGACAGTACAGGACTGCAATTGCTCCATCTATCCCGGCCACGTA |
| 21 | SA10 | 306 | CTCGCCTCGCCGGCATGAGACAGTACAGGACTGCAATTGCTCAATCTATCCCGGCCACGTA |
| 20 | S45 | 306 | CTCGCCTCGCCGGCATGAGACAGTACAGGACTGCAACTGtTCAATCTATCCCGGCCgCGTA |
| 25 | US6 | 306 | CTCGCCTCGTCGTCaGCAGCATGAGACAGTACAGGACTGCAATTGtTCAATCTATCCCGGCCACGTA |
| 13 | HK4 | 306 | CTCGCCTCGTCGTCaGCAGCATGAGACgGTACAGGACTGCAATTGCTCAATCTATCCCGGCCACGTA |
| 18 | P10 | 306 | CTCaCCTCGCCGGCATtgGACAGGACTGCAATTGttCAATCTATCCtGGCCACGTA |
| 19 | S9 | 306 | CTCGCCCGTcGGCATgaGACAGTACAGAaCAGTACAGAACTGCAATTGCTCAATCTATCCGGaCACGTg |
| 9-25 | consensus | | cTCgCCtCgCcCggcAtgaGACAgtaCAGgAcTGcAAcTGCTCaaTCTATCCgGcCacgTa |

FIG. 1B-7

| SEQ ID NO: | Isolate | | |
|---|---|---|---|
| 11 | DK1 | 367 | TCAGGTCACCGCATGGCTTGGGAtATGATGATGAACTGGTCaCCTACAACAGCcCTAGTGc |
| 24 | T10 | 367 | TCAGGTCACCGCATGGCTTGGGACATGATGATGAACTGGTCGCCTACAACAGCtCTAGTGG |
| 10 | D3 | 367 | ACAGGTCACCGCATGGCTTGGGATATGATGATGAACTGGTCGCCTACAgCAGCCCTAGTGG |
| 9 | D1 | 367 | ACAGGTCACCGtATGGCTTGGGATATGATGATGAACTGGTCACCTACAACAGCCtTAGTGG |
| 14 | HK5 | 367 | ACAGGTCACCGCATGGCTTGGGATATGATGATGAACTGGTCACCTACAACAGCCCTAGTGG |
| 15 | HK8 | 367 | TCAGGTCACCGCATGGCTTGGGATATGATGATGAACTGGTCGCCCACAACAGCCCTAGTGG |
| 12 | HK3 | 367 | TCAGGTCACCGCATGGCTTGGGATATGATGATGAACTGGTCgCCtACAgCAGCCCTAGTGG |
| 23 | T3 | 367 | aCAGGTCACCGCATGGCTTGGGATATGATGATGAACTGGTCgCCcACAaCgGCaCTAGTGG |
| 22 | SW2 | 367 | TCAGGTCACCGCATGGCTTGGGAcATGATGATGAACTGGTCACCTACAGCAGCCCtgGTGG |
| 17 | IND8 | 367 | TCAGGTCACCGCATGGCTTGGGATATGATGATGAACTGGTCACCTACAGCGgCCGCCTAGTGG |
| 16 | IND5 | 367 | TCAGGTCACCGCATGGCcTGGGATATGATGATGAACTGGTCACCTACAGCAGCCCTAGTGG |
| 21 | SA10 | 367 | ACAGGTCACCGCATGGCTTGGGATATGATGATGAACTGGTCACCTACAaCAGCtCTAGTaG |
| 20 | S45 | 367 | ACAGGTCACCGCATGGCTTGGGATATGATGATGAACTGGTCgCCTACAGCAGCCtTAGTGG |
| 25 | US6 | 367 | TCAGGTCACCGCATGGCTTGGGATATGATGATGAACTGGTCACCTACAGCAGCCCTAGTGG |
| 13 | HK4 | 367 | TCAGGTCACCGCATGGCTTGGGATATGATGATGAACTGGTCACCTACAGCAGCCCTAGTGG |
| 18 | P10 | 367 | TCAGGTCACCGCATGGCTTGGGATATGATGATGAACTGGTCGCCTACAGCAGCCCTAGTGG |
| 19 | S9 | 367 | aCAGGTCAtCGCATGGCcTGGGATATGATGATGAACTGGTCGCCtACAcCAGCCCTAGTGG |
| 9-25 | consensus | | tCAGGTCAcCGcATGGCttGGGAtATGATGATGAACTGGTCacCTAcAgCAgCccTaGTgg |

FIG. 1B-8

| SEQ ID NO: | Isolate | | |
|---|---|---|---|
| 11 | DK1 | 428 | TaTCGCAGTTACTCCGaATCCCACAAGCTGTCgTGGACATGGTGgCgGGGGCCCACTGGGG |
| 24 | T10 | 428 | TgTCGCAGTTACTCCGGATCCCCACAAGCTGTCaTGGACATGGTGaCaGGGGCCCACTGGGG |
| 10 | D3 | 428 | TATCGCAGTTACTCCGGATCCCCACAAGCTGTCgTGGACATGGTGGCGGGGGCCCACTGGGG |
| 9 | D1 | 428 | TATCGCAGTTACTCCGGATCCCCACAAGCTGTCgTGGACATGGTGGCGGGGGCCCACTGGGG |
| 14 | HK5 | 428 | TATCGCAGTTACTCCGGATCCCCACAAGCTGTCaTGGACATGGTGGCGGGGGCCCACTGGGG |
| 15 | HK8 | 428 | TGTCGCAGTTACTCCGGATCCCCGCAAGCTGTCgTGGACATGGTGGCGGGGGCCCACTGGGG |
| 12 | HK3 | 428 | TGTCGCAGTTACTCCGGATCCCGCAAGCTaTCGTGGACATGGTGGCGGGGGCCCACTGGGG |
| 23 | T3 | 428 | TGTCGCAaTTACTCCGGATCCCGCAAGCTGTCGTGGACATGGTGGCGGGGGCCCACTGGGG |
| 22 | SW2 | 428 | TGTCGCAGTTgCTCCGGATCCCCACAAGCTGTCGTGGACATGGTGGCGGGGGCCCACTGGGG |
| 17 | IND8 | 428 | TATCGCAGTTaCTCCGGATCCCCACAAGCTGTCGTGGACATGGTGaGCGGGGGCCCACTGGGG |
| 16 | IND5 | 428 | TATCGCAGTTGCTCCGGATCCCCACAAGCTGTCGTGGATATGGTGGCGGGGGCCCACTGGGG |
| 21 | SA10 | 428 | TATCGCAGTTGCTCCGGATCCCCACAAGCTGTCGTGGATATGGTGGCGGGGGCCCACTGGGG |
| 20 | S45 | 428 | TATCGCAGTTACTCCGGATCCCCACAAGCTaTCGTGGACATGGTGGCGGGGGCCCACTGGGG |
| 25 | US6 | 428 | TATCGCAGTTACTCCGGATCCCCACAAGCTGTCaTGGACATGGTGGCGGGaGCCCACTGGGG |
| 13 | HK4 | 428 | TATCGCAGTTACTCCGacTCCCACAAGCTGTCaTGGACATGGTGGCGGGGGCCCACTGGGG |
| 18 | P10 | 428 | TgTCGCAGCTACTCCGGATCCCCACAAGCTaTCtTGGATgTGGTGGCGGGGGCCCACTGGGG |
| 19 | S9 | 428 | TaTCGCAGCTACTCCGGATCCCCACAAGCTgTCaTGGATaTGGTGGCGGGGGCCCACTGGGG |
| 9-25 | consensus | | TaTCGCAgtTaCTCCGgaTCCCaCAAGCTgTCgTGGAcaTGGTggCgGGgGCCCACTGGGG |

FIG. 1B-9

| SEQ ID NO: | Isolate | | |
|---|---|---|---|
| 11 | DK1 | 489 | AGTCCTGGCGCGGGCCTcGCCTACTAcTCCATGGCGGGGAACTGGGCCAAGGTTTTAATTGTG |
| 24 | T10 | 489 | AGTCCTGCGCGGGCCTtGCCTACTATTCCATGGCGGGGAACTGGGCTAAGGTTTTAATTGTG |
| 10 | D3 | 489 | GGTCCTGGCGGGGCCCTCGCCTACTATTCCATGGTGGGGAACTGGGCTAAGGTTTTGATTGTG |
| 9 | D1 | 489 | GGTCCTGGCGGGGCCCTCGCCTACTATTCCATGGTGGGGAACTGGGCTAAGGTTTTGATTGTG |
| 14 | HK5 | 489 | GGTCCTGGCGGGGCCTTGCCTACTATTCCATGGTGGGGaAACTGGGCTAAGGTTTTGATTGTG |
| 15 | HK8 | 489 | AGTCCTAGCGGGGCCTTGCCTACTATTCCATGGTGGGCAACTGGGCTAAGGTTTTGATTGTG |
| 12 | HK3 | 489 | AGTCCTAGCGGGGCCTTGCCTACTATTCCATGGTGGGaAACTGGGCTAAGGTTTTGATTGTG |
| 23 | T3 | 489 | AGTCCTGGCGGGGCCTTGCCTACTATTCCATGGTGGGGAACTGGGCTAAGGTTTTGATTGTG |
| 22 | SW2 | 489 | AGTCCTGGCGGGGCCTTGCCTGCaTACTATTCCATGGTGGGGAACTGGGCTAAGGTTTTGATTGTG |
| 17 | IND8 | 489 | AATCCTGGCGGGGCCTTGCCTACTATTCCATGGTGGGGTAGGAACTGGGCTAAGGTTTTGATTGTG |
| 16 | IND5 | 489 | AATCCTGGCGGGGCCTTGCCTACTATTCCATGGTGGGGTAGGAACTGGGCTAAGGTTTTGATTGTG |
| 21 | SA10 | 489 | AGTCCTaGCGGGGCCTTGCCTACTATTCCATGGTGGGGAACTGGGCTAAGGTTTTGATTGTt |
| 20 | S45 | 489 | AGTCCTGGCGGGGCCTTGCCTACTATTCCATGGTGGGGAACTGGGCTAAGGTTCTGATTGTG |
| 25 | US6 | 489 | AGTCCTGGCGGGGCCTTGCCTACTATTCCATGGTGGGGAACTGGGCTAAGGTTCTGATTGTG |
| 13 | HK4 | 489 | AGTCCTGGCGGGGCCTTGCtTACTATTCCATGGTGGGGAACTGGGCCAAGGTTTTGATTGTG |
| 18 | P10 | 489 | AGTCCTGGCGGGGCCTTGCCTACTATTCCATGGTGGGGAACTGGGCTAAGGTcTTGATTGTG |
| 19 | S9 | 489 | AGTCCTGGCGGGGCCTTGCCTACTATTCCATGGTGGGGAACTGGGCTAAGGTtTTGATTGTG |
| 9-25 | consensus | | agtCCTgGCGGGGCCTtGCCTACTAtTCCATGGtgGGGAACTGGGCtAAGGTtttGATTGTg |

FIG. 1B-10

| SEQ ID NO: | Isolate | |
|---|---|---|
| 11 | DK1 | 550 tTGCTACTCTTTGCCGGCGTTGATGGG |
| 24 | T10 | 550 ATGCTACTCTTTGCCGGCGTTGATGGG |
| 10 | D3 | 550 ATGCTACTCTTTGCTGGCGTcGACGGC |
| 9 | D1 | 550 ATGCTACTCTCTTTGCTGGCGTTGACGGC |
| 14 | HK5 | 550 ATGCTACTtTTTGCCGGCGTTGATGGG |
| 15 | HK8 | 550 ATGCTACTgTTTGCCGGCGTTGATGGG |
| 12 | HK3 | 550 ATGCTACTtTTTGCCGGCGTTGATGGG |
| 23 | T3 | 550 cTGCTACTCTCTTGCCGGCGTTGATGGG |
| 22 | SW2 | 550 ATGCTACTCTTTGCtGGCGTTGACGGG |
| 17 | IND8 | 550 ATGCTACTCTCTTGCCGGCGTTGACGGG |
| 16 | IND5 | 550 ATGCTACTCTCTTGCCGGCGTTGACGGG |
| 21 | SA10 | 550 ATGCTACTCTTTGCCGGCGTTGACGGG |
| 20 | S45 | 550 ATGCTACTCTTTGCCGGCGTTGACGGG |
| 25 | US6 | 550 tTGCTACTCTTTGCCGGCGTTGACGGG |
| 13 | HK4 | 550 ATGCTACTCTTTGCCGGCGTTGACGGG |
| 18 | P10 | 550 ATGCTACTtTTTGCCGGCGTTGACGGa |
| 19 | S9 | 550 ATGCTACTtTTTGCtGGtGTTGACGGg |
| 9-25 | consensus | aTGCTACTCTTTGCcGGcGTTGAcGGg |

FIG. 1C-1

| SEQ ID NO: | Isolate | | |
|---|---|---|---|
| 26 | T2 | 1 | GCCCAAGTGAgGAACACCAgccgCggtTACATGGTGACtAACGACTGTTCcAATGAGAGCA |
| 27 | T4 | 1 | GCaCAAGTGAAGAACACCACTAaCAGCTACACTGGTGACCAACGACTGTTCtAATGACAGCA |
| 28 | T9 | 1 | GCCgAAGTGAAGAACACCAGTACCAGCTACACATGGTGACaAATGACTGTTCCAACGACGCA |
| 29 | US10 | 1 | GtCcAAGTGAAaAACACCAGTACCAGCTAtATGGTGACCAATGACTGCTCCAACGACAGCA |
| 26-29 | consensus | | GcccAAGTGAagAACACCAGtacCaGcTACATGGTGACCAA-GACTGtTCcAA-GAcAGCA |

| SEQ ID NO: | Isolate | | |
|---|---|---|---|
| 26 | T2 | 62 | TCACCTGGCAGCTCCAaGCCGGCGGTtCTCCACGTCCCCGGGGTGTaTCCCGTGtGAGAggct |
| 27 | T4 | 62 | TCACtTGGCAGCTCCAGGCCGGCGGTCCTCCACGTCCTCCACGTCCCCGGGGTGTCCCGTGCGAGAaaac |
| 28 | T9 | 62 | TCACCTGGCAACTCCAGGCCGGCGGTCCTCCACGTCCCCGGGGTGcGTCCCGTGCGAGAgAGT |
| 29 | US10 | 62 | TCACtTGGCAACTtgAGGCtGCGGTCCTCCACGTtCCCGGGGTGtGTCCCGTGCGAGAaAGT |
| 26-29 | consensus | | TCAC-TGGCA-CTccAgGCcGCGGTcCTCCACGTcCCCGGGGTGtgTCCCGTGCGAGA-agt |

FIG. 1C-2

| SEQ ID NO: | Isolate | | |
|---|---|---|---|
| 26 | T2 | 123 | GGGAAATACATCcCGaTGCTGGATACCGGTcaCACCAAACGTGCCGTGCGGCAGCCCCGGC |
| 27 | T4 | 123 | GGGAAATACATCtCGGTGCTGCTGGATACCGGTtCACCAAACGTGCCGTGCGGCAGCCCCGGC |
| 28 | T9 | 123 | tGGAAAAcgCgTCgCGGTGCTGCTGGATACCGGTCTCgCCAAACGTGtGCaGCtGTGCAGCGGCCTGGC |
| 29 | US10 | 123 | gGGAAAAtaCaTCtCGGTGCTGCTGGATACCGGTCTCaCCAAAtGTgCCGTGCAGCGGCCTGGC |
| 26-29 | consensus | | gGGAAAAtaCaTCtCGgTGCTGCTGGATACCGGTctCaCCAAAcGTgCCgGTGc-GC-GCC-GGC |

| SEQ ID NO: | Isolate | | |
|---|---|---|---|
| 26 | T2 | 184 | GCtCTtACGCAGGGCTTGCGGACGCACATGGACACATGGTTGTGATGTCCGCCACGCTCTGCT |
| 27 | T4 | 184 | GCCCTCACGCAGGGCTTGCGGACGCACATtGACACATGGTTGTGATGTCCGCCACGCTCTGCT |
| 28 | T9 | 184 | GCCCTCACGCAGGGCTTGCGGACGCACATGGACACATGGTTGTGATGTCCGCCACGCTCTGCT |
| 29 | US10 | 184 | GCCCTCACGCAGGGCTTGCGGACtCACATGGACACATGGTcGTGATGTCcGCCACGCTCTGCT |
| 26-29 | consensus | | GCcCTcACGCAGGGCTTGCGGACgCACATGGACACATGGTtGTGATGTCCGCCACGCTCTGCT |

FIG. 1C-3

| SEQ ID NO: | Isolate | | |
|---|---|---|---|
| 26 | T2 | 245 | CTGCCCTCTACGTGGGGGACCTCTGCGGCGGGTGATGCTCGCAGCCCAGATGTTCATtGT |
| 27 | T4 | 245 | CTGCTCTCTtTACGTGGGGGACCTCTGCGGCGGGTGATGCTCGCAGCCCAGATGTTCATcGT |
| 28 | T9 | 245 | CCGCTCTCTcTACGTGGGGGGAtCTCTGCGGCGGGTAaATGCTCGCcGCtCAGATGTTCATTaT |
| 29 | US10 | 245 | CCGGCTCTTtTACGTGGGGGACtTCTGCGGtGGGaTgATGCTCGCaGCcCAaATGTTCATTgT |
| 26-29 | consensus | | C-GCtCT-TACGTGGGGGACcTCTGCGGcGGGgTgATGCTCGCaGCCCAgATGTTCATtgT |

| SEQ ID NO: | Isolate | | |
|---|---|---|---|
| 26 | T2 | 306 | CTCGCCCGCgACgcCACTGGtTTGTGCAAGAaTGCAATTGCTCcATCTACCCCggTACCATC |
| 27 | T4 | 306 | CTCGCCGCAACAtCACTGGTTTGTGCAAGAcTGCAATTGCTCtATCTACCCTGGcACCATC |
| 28 | T9 | 306 | CTCGCCGCAgCACCACTGGTTTGTGCAGGAATGCAAACTGCTCCATtTACCCTGGTACCATC |
| 29 | US10 | 306 | CTTCGCCGCGcCACCACTcGTTTGTGCAGGAATGCAACTGCTCCATCTACCCcGGTACCATC |
| 26-29 | consensus | | CTCGCCCGC-aCacCACTgGTTTGTGCA-GAaTGCAA-TGCTCcATcTACCC-GGtACCATC |

FIG. 1C-4

| SEQ ID NO: | Isolate | | |
|---|---|---|---|
| 26 | T2 | 367 | ACTGGACACCGTATGGCATGGGACATGATGATGAACTGGTCGCCCACAGCCACCATGATCC |
| 27 | T4 | 367 | ACTGGACACCGTATGGCATGGGAtATGATGATGAACTGGTCGCCCACggCCACCATGATCC |
| 28 | T9 | 367 | ACTGGACACCGTATGGCATGGGACATGATGATGAACTGGTCGCCCACaaCCACCATGATCt |
| 29 | US10 | 367 | ACCGGgCACCGTATGGCATGGGACATGATGATGAACTGGTCGCCCACggCCACttTGATCc |
| 26-29 | consensus | | ACtGGaCACCGTATGGCATGGGAcATGATGATGAACTGGTCGCCCAC-gCCACcaTGATCc |

| SEQ ID NO: | Isolate | | |
|---|---|---|---|
| 26 | T2 | 428 | TGGCGTACGCGATGCGCGTTCCCGAGGTCATCaTAGACATCaTcgGCGGGGCtCACTGGGG |
| 27 | T4 | 428 | TGGCGTACGCGATGCGCGTTCCCGAGGTCATCaTAGACATCgTtAGCGGGGCaCACTGGGG |
| 28 | T9 | 428 | TGGCGTACGCGATGCGCGTTCCCGAGGTCATCtTAGACATCATCAGCGGaGCtCACTGGGG |
| 29 | US10 | 428 | TGGCGTACGtGATGCGCGTTCCCGAGGTCATCATAGACATCATtAGCGGGGCgCAtTGGGG |
| 26-29 | consensus | | TGGCGTACGcGATGCGCGTTCCCGAGGTCATCaTAGACATCaT-aGCGGGGCtCAcTGGGG |

FIG. 1C-5

| SEQ ID NO: | Isolate | | |
|---|---|---|---|
| 26 | T2 | 489 | CGTCATGTTtGGCTTGGCCTACTTCTCTATGCAGGAGCGTGGGCGAAgGTCATTGTCATC |
| 27 | T4 | 489 | CGTCATGTTCGGCTTGGCCTACTTCTCTATGCAGGAGCGTGGGCGAAaGTCGTTGTCATC |
| 28 | T9 | 489 | CGTCATGTTCGGCCTAGCCTACTTCTCTATGCAGGAGCGTGGGCGAAgGTCGTTGTCATC |
| 29 | US10 | 489 | CGTCtTGTTCGGCttAGCCTACTTCTCTATGCAGGAGCGTGGGCGAAaGTCGTTGTCATC |
| 26-29 | consensus | | CGTCaTGTTcGGCtT-GCCTACTTCTCTATGCAGGAGCGTGGGCGAA-GTCgTTGTCATC |

| SEQ ID NO: | Isolate | | |
|---|---|---|---|
| 26 | T2 | 550 | CTctTGCTGGCtGCTGGGGTGGACGCG |
| 27 | T4 | 550 | CTtcTGCTGGCCGCGTGGGGTGGACGCG |
| 28 | T9 | 550 | CTgtTGCTcaCCGCTGGCGTGGACGCG |
| 29 | US10 | 550 | CTtcTGCTagCCGCTGGgGTGGACGCG |
| 26-29 | consensus | | CTt-TGCTggCcGCTGGGgTGGACGCG |

FIG. 1D-1

| SEQ ID NO: | Isolate | | |
|---|---|---|---|
| 33 | T8 | 1 | GTGGAAGTtAGaAAACAcCAGTTttAGCTACTACGCCACCAATGATTGCTCgAACAACAGCA |
| 30 | DK8 | 1 | GTGGAAGTCAGGAACATCAGTTCcAGCTACTACGCCACCAATGATTGCTCAAACAACAGCA |
| 32 | SW3 | 1 | GTGGAAGTCAGGAACATCAGTTCTAGCTACTACGCCACCAATGATTGCTCAAACAACAGCA |
| 31 | DK11 | 1 | GTGGAAGTCAGGAACATCAGTTCTAGCTACTAtGCCACCAATGATTGCTCAAACAgCAGCA |
| 30-33 | consensus | | GTGGAAGTcAGgAACA-CAGTTctAGCTACTACGCCACCAATGATTGCTCAAACAaCAGCA |

| SEQ ID NO: | Isolate | | |
|---|---|---|---|
| 33 | T8 | 62 | TCACCTGGCAgCTCACCaACGCAGTTCTCCACCTTCCCGGATGCGTCCCATGTGAGAATGA |
| 30 | DK8 | 62 | TCACCTGGCAACTCACCGACGCAGTTCTCCACCTTCCCGGATGCGTCCCATGTGAGAATGA |
| 32 | SW3 | 62 | TCACCTGGCAACTCACCAACGCAGTcCTCCACCTTCCCGGATGCGTCCCATGTGAGAATGA |
| 31 | DK11 | 62 | TCACCTGGCAACTCACCAACGCAGTtCTCCACCTTCCCGGATGCGTCCCgTGTGAGAATGA |
| 30-33 | consensus | | TCACCTGGCAaCTCACCAACGCAGTtCTCCACCTTCCCGGATGCGTCCCaTGTGAGAATGA |

FIG. 1D-2

| SEQ ID NO: | Isolate | |
|---|---|---|
| 33 | T8 | 123 CAATGGCACCcTTGCGCTGCTGGATACAAGTaACACCTAATGTGGCTGTGAAACACCGtGGC |
| 30 | DK8 | 123 CAATGGCACCCTGCGCTGCTGGATACAAGTGACACCTAATGTGGCTGTGAAACACCGGGC |
| 32 | SW3 | 123 AATGGCACCCTGCACTGCTGGATACAAGTGACACCTAATGTGGCTGTGAAACACCGGGC |
| 31 | DK11 | 123 tAATGGCACCCTGCACTGCTGGATACAAGTGACACCTAATGTGGCTGTGAAACACCGGGC |
| 30-33 | consensus | cAATGGCACCcTGC-CTGCTGGATACAAGTgACACCTAATGTGGCTGTGAAACACCGGGC |

| SEQ ID NO: | Isolate | |
|---|---|---|
| 33 | T8 | 184 GCACTCACTCAcAAACCTGCGAACgCAtGTCGACGTGATCGTAATGGCAGCTACGGTCTGCT |
| 30 | DK8 | 184 GCACTtACTCAtAAACCTGCGAACACAGTCGACGTGATCGTAATGGCAGCTACGGTCTGCT |
| 32 | SW3 | 184 GCgCTCACTCACAAACCTGCGAGCACAGTCGACGTGATATGATCGTAATGATCATCGGTCTGCT |
| 31 | DK11 | 184 GCaCTCACTCACAAACCTGCGAGCACAtaTaGATATGATtGTAATGATCGTAATGGCAGCTACGGTCTGCT |
| 30-33 | consensus | GCaCTCACTCAcAAACCTGCGA-CaCA-gTCGA--TGATCGTAATGGCAGCTACGGTCTGCT |

FIG. 1D-3

| SEQ ID NO: | Isolate | | |
|---|---|---|---|
| 33 | T8 | 245 | CGGCCTTGTATGTGGGgACGTgTgTGCGGGGCCCGTGATGATaGCGTCGCAGGCTtTTCATAAT |
| 30 | DK8 | 245 | CGGCCTTGTATGTGGGAGACGTaTGCGGGGCCCGTGATGATCGTGTCGCAGGCTtCTCATAAT |
| 32 | SW3 | 245 | CGGCCTTGTATGTGGGAGACaTGTGCGGGGCCCGTGATGATCGTGTCGCAGGCTTTCATAAT |
| 31 | DK11 | 245 | CGGCCTTGTATGTGGGAGACgTGTGCGGGGCCCGTGATGATCGTGTCGCAGGCTTTCATAgT |
| 30-33 | consensus | | CGGCCTTGTATGTGGGaGaCGTgTgTGCGGGGCCCGTGATGATcGtGTCGCAGGCTtTCATAaT |

| SEQ ID NO: | Isolate | | |
|---|---|---|---|
| 33 | T8 | 306 | ATCGCCaGaAACGCCACAACTTCACCCAGGAGTGCAACTGTTCCATCTACCAAGGTCATATC |
| 30 | DK8 | 306 | ATCGCCtGAACGCCACAACTTTACCCAGGAGTGCAACTGTTCCATCTACCAAGGTCATATC |
| 32 | SW3 | 306 | ATCGCCAGAACGCCACAACTTTACCCACTGTTCCAAGAGTGCAACTGTTCCATCTACCAAGGTCgTATC |
| 31 | DK11 | 306 | ATCGCCAGAACaCCACCACTTTACCCAAGAGTGCAACTGTTCCATCTACCAAGGTCacATC |
| 30-33 | consensus | | ATCGCCaGAACgCCACaACTTtACCCA-GAGTGCAACTGTTCCATCTACCAAGGTCatATC |

FIG. 1D-4

| SEQ ID NO: | Isolate | | |
|---|---|---|---|
| 33 | T8 | 367 | ACCGGCCACCGGCATGGCATGGGACATGATGCTgAAACTGGTCACCAACTCTcACCATGATCC |
| 30 | DK8 | 367 | ACCGGCCACCGGCATGGCATGGGACATGATGCTAAAACTGGTCACCAACTCTTACCATGATCC |
| 32 | SW3 | 367 | ACCGGCCACCGGCATGGCgTGGGACATGATGCTAAAACTGGTCACCAACTCTTACCATGATCC |
| 31 | DK11 | 367 | ACCGGCCACCGCCATGGCaTGGGACATGATGCTtAACTGGTCACCAACTCTcACCATGATCC |
| 30-33 | consensus | | ACCGGCCACCGGCATGGGACATGATGCTaAAACTGGTCACCAACTCT-ACCATGATCC |

| SEQ ID NO: | Isolate | | |
|---|---|---|---|
| 33 | T8 | 428 | TCGCCTAcGCtGCTCGTGTgCCTGAaCTAGtCCCTgAaGTTGTCTTCGGCGGCCATTGGGG |
| 30 | DK8 | 428 | TGCCCTATGCCGCTCGTGTTCCTGAGCTAGCCCTccAgGTTGTCTTCGGCGGCCATTGGGG |
| 32 | SW3 | 428 | TtGCCTATGCCGCTCGTGTTCCTGAGCTAGTCCTTGAAGTTGTCTTCGGCGGCCATTGGGG |
| 31 | DK11 | 428 | TcGCCTATGCCGCCGTGTTCCTGAGCTAGTCCTTGAAGTCGTCTTCGGtGGtCATTGGGG |
| 30-33 | consensus | | TcGCCTATGCcGCtCGTGTcCCTGAgCTAGtCCTTgAaGTTGTCTTCGGcGGCCATTGGGG |

FIG. 1D-5

| SEQ ID NO: | Isolate | | |
|---|---|---|---|
| 33 | T8 | 489 | CGTGGTGTGTTTGGCTTGGCCTATTTCTCCATGCAaGGAGAGCGTGGGCCAAAGTCATCATCGCCATC |
| 30 | DK8 | 489 | CGTGGTGTGTTTGGCTTGGCCTATTTCTCCATGCAgGGAGAGCGTGGGCCAAAGTCATCATTGCCATC |
| 32 | SW3 | 489 | CGTGGTGTGTTTGGCTTGGCCTATTTCTCCATGCAaGGAGAGCGTGGGCCAAGGTCATTGCCATC |
| 31 | DK11 | 489 | tGTGGTGTGTTTGGCTTGGCCTATTTCTCCATGCAgGGAGAGCGTGGGCCAAGGTCATTGCCATC |
| 30-33 | consensus | | cGTGGTGTGTTTGGCTTGGCCTATTTCTCCATGCA-GGAGAGCGTGGGCCAA-GTCATtGCCATC |

| SEQ ID NO: | Isolate | | |
|---|---|---|---|
| 33 | T8 | 550 | CTCCTcCTTGTCGCAGGAGTGGAcGCA |
| 30 | DK8 | 550 | CTCCTtCTTGTCGCAGGAGTGGATGCA |
| 32 | SW3 | 550 | CTCCTgCTTGTCGCAGGAGTGGATGCA |
| 31 | DK11 | 550 | CTCCTtCTTGTaGCAGGAGTGGATGCA |
| 30-33 | consensus | | CTCCTtCTTGTcGCAGGAGTGGAtGCA |

FIG. 1E-1

| SEQ ID NO: | Isolate | | |
|---|---|---|---|
| 35 | DK12 | 1 | tTAGAGTGGCGGAATGTGTCCGGCCTCTAcGTCCTTACCAACGACTGTtCCAATAGCAGTA |
| 36 | HK10 | 1 | CTAGAGTGGCGGAATGTGTCTGGCCCTCTATGTCCTTACCAACGACTGTcCCAATAGCAGTA |
| 37 | S2 | 1 | CTAGAGTGGCGGAATACGTCTGGCCTCTGGCCCTCTATGTCCTcACCAACGACTGTTCCAATAGCAGTA |
| 39 | S54 | 1 | CTAGAGTGGCGGAATACGTCTGGCCCTCTGGCCCTCTATaTCCTTACCAACGACTGTTCCAATAGCAGTA |
| 38 | S52 | 1 | CTAGAGTGGCGGAATACGTCTGGCCCTCTGGCCCTCTATgTCCTTACCAACGACTGTTCCAATAGCAGTA |
| 35-39 | consensus | | CTAGAGTGGCGGAATacGTCTGGCCCTCTATgTCCTtACCAACGACTGTtCCAATAGCAGTA |

| SEQ ID NO: | Isolate | | |
|---|---|---|---|
| 35 | DK12 | 62 | TcGTGTATGAGGCCGATGACGTCATTCTGCACACACCTGGCTGTGTACCTTGTGTTCAGGA |
| 36 | HK10 | 62 | TTGTGTATGAGGCCGATGACGTCATTCTGCACACACCTGGCTGTGTACCTTGTGTTCAGGA |
| 37 | S2 | 62 | TTGTGTATGAGGCCGATGACGTCATTCTGCACACACCTGGCTGTtATTCTGCACACACCTGGCTGTGTACCTTGTGTTCAGGA |
| 39 | S54 | 62 | TTGTGTATGAGGCCGATGACGTCATTCTGCACACACCCGGCTGTGTACCTTGTGTTCAGGA |
| 38 | S52 | 62 | TTGTGTATGAGGCCGATGACGTCATTCTGCACACACCCGGCTGTGTACCTTGTGTTCAGGA |
| 35-39 | consensus | | TtGTGTATGAGGCCGATGACGTcATTCTGCACACCtGGCTGTGTACCTTGTGTTCAGGA |

FIG. 1E-2

| SEQ ID NO: | Isolate | | |
|---|---|---|---|
| 35 | DK12 | 123 | CGGCAATACATCtACGTGCTGGACCTCaGTGACgCCTACAGTGGCAGTCAGGTACGTCGGA |
| 36 | HK10 | 123 | CGGCAATACATCCACGTGCTGGACCTCgGTGACACCTACAGTGGCAGTCAGGTACGTCGGA |
| 37 | S2 | 123 | CGGtAATACATCCACGTGCTGGACCCCAGTGACACCTACAGTGGCAGTCAGGTAtGTCGGA |
| 39 | S54 | 123 | CGGCAATACATCCACGTGCTGGACCCCAGTGACACCTACGGTGGCAGTCAGGTACGTCGGA |
| 38 | S52 | 123 | CGGCAATACATCCAtGTGCTGGACCCCAGTGACACCTACGGTGGCAGTCAGGTACGTCGGA |
| 35-39 | consensus | | CGGcAATACATCCAcGTGCTGGACCcCaGTGACaCCTACaGTGGCAGTCAGGTACGTCGGA |

| SEQ ID NO: | Isolate | | |
|---|---|---|---|
| 35 | DK12 | 184 | GCAACCACCGCtTCGATACGCAGTCATGTGGACCTGCTAGTGGGCGGCCACGATGTGCT |
| 36 | HK10 | 184 | GCAACCACCGCcTCGATACGCAGTCATGTGGACCTGTTAGTGGGCGGCCACGATGTGCT |
| 37 | S2 | 184 | GCAACCACCGCTTCGATACGCAGTCATGTGGACCTATTGgTGGGCGGCCACTATGTGCT |
| 39 | S54 | 184 | GCAACCACCGCTTCGATACGCAGTCATGTGGACCTATTAGTGGGCGGCCACGCTGTGCT |
| 38 | S52 | 184 | GCAACCACCGCTTCGATACGCAGTCATGTGGACCTATTAGTGGGCGGCCACGCTGTGCT |
| 35-39 | consensus | | GCAACCACCGCtTCGATACGCAGTCATGTGGACCTatTaGTGGGCGGCCACgaTGTGCT |

FIG. 1E-3

| SEQ ID NO: | Isolate | | |
|---|---|---|---|
| 35 | DK12 | 245 | CTGCGCTCTACGTGGGtGATgTGTGTGGGGCCGTCTTCCTtGTGGGACAAGCCTTCACGTT |
| 36 | HK10 | 245 | CTGCGCTCTACGTGGGcGATATGTGTGGGGCCGTCTTCCTCGTGGGACAAGCCTTCACGTT |
| 37 | S2 | 245 | CTGCGCTCTACGTGTGGTGATATGTGTGGGGCCGTCTCTTCTCGTGGGACAAGCCTTCACGTT |
| 39 | S54 | 245 | CTGCGCTCTACGTGGGTGATATGTGTGGGGCCGTCTCTTCTCGTGGGACAAGCCTTCACGTT |
| 38 | S52 | 245 | CTGCGCTCTATGTGGGTGATATGTGTGGGGCCGTCTTTCTCGTGGGACAAGCCTTCACGTT |
| 35-39 | consensus | | CTGCGCTCTACGTGGGtGATaTGTGTGGGGCCGTCTCTTcCTcGTGGGACAAGCCTTCACGTT |

| SEQ ID NO: | Isolate | | |
|---|---|---|---|
| 35 | DK12 | 306 | CAGACCTcGTCGCCATCAAAACaGTCCAGACCCTGTAACTGCTCGCTGTACCCAGGCCAtCTT |
| 36 | HK10 | 306 | CAGACCCgCGTCGCCATCAAACGGTCCAGACCCTGTAACTGCTCGCTGTACCCAGGCCAcCTT |
| 37 | S2 | 306 | CAGACCTCGTCGCCATCAAAACGGTCCAGACCCTGTAACTGCTCGCTGTACCCAGGCCATCTT |
| 39 | S54 | 306 | CAGACCTCGTCGCCATCAAAACGGTCCAGACCCTGTAACTGCTCGCTGTACCCAGGCCATCTT |
| 38 | S52 | 306 | CAGACCTCGTCGCCATCAAAACGGTCCAGACCCTGTAACTGCTCGCTGTACCCAGGCCATgTT |
| 35-39 | consensus | | CAGACCTcGTCGCCATCAAAaCgGTCCAGACCCTGTAACTGCTCGCTGTACCCAGGCCAtcTT |

FIG. 1E-4

| SEQ ID NO: | Isolate | | |
|---|---|---|---|
| 35 | DK12 | 367 | TCAGGACATCGAATGGCTTGGGATATGATGATGAATTGGTCCCCGCtGTGGGTATGGTGG |
| 36 | HK10 | 367 | TCAGGACATCGAATGGCTTGGGATATGATGATGAATTGGTCCCCGCcGTGGGTAtGGTGG |
| 37 | S2 | 367 | TCAGGACATCGcATGGCTTGGGATATGATGATGAATTGGTCCCCGCTGTGGGCTGTGGTGG |
| 39 | S54 | 367 | TCAGGACATCGAATGGCTTGGGATATGATGATGAATTGGTCCCCGCTGTGGGTATGGTGG |
| 38 | S52 | 367 | TCAGGACATCGAATGGCTTGGGATATGATGATGAATTGGTCCCCGCTGTGGGTATGGTGG |
| 35-39 | consensus | | TCAGGACATCGaATGGCTTGGGATATGATGATGAATTGGTCCCCGCtGTGGGTATGGTGG |

| SEQ ID NO: | Isolate | | |
|---|---|---|---|
| 35 | DK12 | 428 | TaGCGCACGTCCTGCGtcTGCCCCAGACCTTGTTCGACATAATAGCtGGGGCCCATTGGGG |
| 36 | HK10 | 428 | TGGCCGCACGTCCTGCGgtTGCCCCAGACCTTGTTCGACATAATAGCCGGGGCCCATTGGGG |
| 37 | S2 | 428 | TGGCCGCACGTCCTGCGtTCTGCGtTTGCCCCAGACCgTGTTCGACATAATAGCCGGGGCCCATTGGGG |
| 39 | S54 | 428 | TGGCGCACATCCTGCGATTGCCCCAGACCTTGTTTGACATACTGGCCGGGGCCCATTGGGG |
| 38 | S52 | 428 | TGGCGCACATCCTGCGATTGCCCCAGACCTTGTTTGACATACTGGCCGGGGCCCATTGGGG |
| 35-39 | consensus | | TgGCCGCACgTcCTGCG-tTGCCCCAGACCtTGTTcGACATAaTaGCcGGGGCCCATTGGGG |

FIG. 1E-5

| SEQ ID NO: | Isolate | | |
|---|---|---|---|
| 35 | DK12 | 489 | CATCatTGGCgGGCCTAGCCTATTACTCCATGCAGGGCAACTGGGCCAAGGTCGCTATCATC |
| 36 | HK10 | 489 | CATCTTGGCagGCCTAGCCTATTACTCCATGCAGGGCAACTGGGCCAAGGTCGCTATCATC |
| 37 | S2 | 489 | CATCTTGGCGGGCCTAGCCTATTACTCCATGCAaGGGCAACTGGGCCAAGGTCGCTATCATC |
| 39 | S54 | 489 | CATCTTGGCGGGCCTAGCCTATTATTCTATGCAGGGCAACTGGGCCAAGGTCGCTATCATC |
| 38 | S52 | 489 | CATCTTGGCGGGCCTAGCCTATTATTCTATGCAGGGCAACTGGGCCAAGGTCGCTATtgTC |
| 35-39 | consensus | | CATCtTGGCgGGCCTAGCCTATTAcTCCATGCAggGCAACTGGGCCAAGGTCGCTATcaTC |

| SEQ ID NO: | Isolate | | |
|---|---|---|---|
| 35 | DK12 | 550 | ATGGTTATGTTTTCAGGaGTCGATGCC |
| 36 | HK10 | 550 | ATGGTTATGTTTTCAGGGGTCGATGCC |
| 37 | S2 | 550 | ATGGTTATGTTTTCAGGGGTCGAcGCC |
| 39 | S54 | 550 | ATGATTATGTTTTCAGGGGTCGATGCC |
| 38 | S52 | 550 | ATGATTATGTTTTCAGGGGTCGATGCC |
| 35-39 | consensus | | ATGgTTATGTTTTCAGGgGTCGAtGCC |

FIG. 1F-1

```
SEQ ID NO:   Isolate
    43          Z7     1  GTcAACTATCaCAATGCCTCGGGGCGTCTATCACATCACCAACGACTGCCCGAACTCGAGCA
                          |||||||||| ||||||||||||||||||||||||||||||||||||||||||||||||||
    42          Z6     1  GTtAACTATCgCAATGCCTCGGGGCGTCTATCACGTCACCAACGACTGCCCGAACTCGAGCA 42-43 consensus (Z6)       GTtAACTATCgCAATGCCTCGGGGCGTCTATCACgTCACCAACGACTGCCCGAACTCGAGCA SEQ ID NO:   Isolate
    43          Z7    62  TAatGTGTATGAGGCCCGAACACCACATCCTACACCTCCCAGGGTGTGCGTACCCTGTGAGGGa
                          || |||||||||||||||||||||| ||||||| |||||||||||||||| || ||||||||
    42          Z6    62  TAGTGTATGAGGCCCGAACACCACCAGATCTTACACCTCCCAGGGTGCTgCCCTGTGAGGGt 42-43 consensus (Z6)       TAgTGTATGAGGCCCGAACACCACCAGATCtTACACCTCCCAGGGTGCTTgCCCTGTGAGGGt SEQ ID NO:   Isolate
    43          Z7   123  gGGGAACCAGTCACGCTGCTGGGTGGCCCCTTACTCCCACCGTGGCGCgCCTTATATCGGT
                          |||| || ||||||||||||||||||||||||||||||||||||||||| |||||||||||
    42          Z6   123  tGGGAAtCAGTCACGCTGCTGGGTGGCCCCTTACTCCCACCGTGGCGGtGtCTTATATCGGT 42-43 consensus (Z6)       tGGGAAtCAGTCACGCTGCTGGGTGGCCCCTTACTCCCACCGTGGCGGtGtCTTATATCGGT SEQ ID NO:   Isolate
    43          Z7   184  GCaCCGCTTGAaTCCATCCGGAGACATGTGGACCTGATGGTAGGCGCtGCTACaGTGTGCT
                          || |||||||| |||| || ||||||||||||||||||||| ||||| ||||| |||||||
    42          Z6   184  GCTCCGCTTGAcTCCcTCCGGAGACATGTGGACCTGATGGTGGGCGCCGCTACTGTaTGCT 42-43 consensus (Z6)       GCtCCGCTTGAcTCCcTCCGGAGACATGTGGACCTGATGGTgGGCGCCGCTACTGTaTGCT
```

FIG. 1F-2

| SEQ ID NO: | Isolate | | |
|---|---|---|---|
| 43 | Z7 | 245 | CcGCtCTCTACaTTGGGACCTGTGCGGTGGcGtATTtTTGGTTGGtCAGATGTtTCTTT |
| 42 | Z6 | 245 | CtGCCCCTCTACgTTGGaGAtCTGTGCGGTGGtGCATTCTTGGTTGGcCAGATGTTCTCCTT |
| 42-43 consensus (Z6) | | | CtGCCCCTCTACgTTGGaGAtCTGTGCGGTGGtGCATTCTTGGTTGGcCAGATGTtCTCCTT |

| SEQ ID NO: | Isolate | | |
|---|---|---|---|
| 43 | Z7 | 306 | CCAGCCGCGACGCCACTGGACTACGCAGGACTGCAATTGTTCCATCTAtGCGGGGCAcgTt |
| 42 | Z6 | 306 | CCAGCCGCGACGCCACTGGACTACGCAGGACTGCAATTGTTCtATCTACGCAGGGCATATC |
| 42-43 consensus (Z6) | | | CCAGCCGCGACGCCACTGGACTACGCAGGACTGCAATTGTTCtATCTACgCAGGGCAtaTc |

| SEQ ID NO: | Isolate | | |
|---|---|---|---|
| 43 | Z7 | 367 | ACaGGCCACAGaATGGCATGGGACATGATGATGAACTGGAGTCCCACAACCACCTtGgTCC |
| 42 | Z6 | 367 | ACgGGCCACAGgATGGCATGGGACATGATGATGAACTGGAGTCCCACAACCACCCCTGcTtC |
| 42-43 consensus (Z6) | | | ACgGGCCACAGgATGGCATGGGACATGATGATGAACTGGAGTCCCACAACCACCCTgCTtC |

| SEQ ID NO: | Isolate | | |
|---|---|---|---|
| 43 | Z7 | 428 | TCGCCCAGGTtATGAGGATCCCTAGCACTCaCTGGAGGGCACTGGGG |
| 42 | Z6 | 428 | TCGCCCAGGTcATGAGGATCCCTAGCACTCTTGGTaGAtCTACTCGCTGGAGGGCACTGGGG |
| 42-43 consensus (Z6) | | | TCGCCCAGGTcATGAGGATCCCTAGCACTCTGGTaGAtCTACTCgCTGGAGGGCACTGGGG |

FIG. 1F-3

| SEQ ID NO: | Isolate | | |
|---|---|---|---|
| 43 | Z7 | 489 | taTCCTTaTcGGGgTGGCaTACTTCtGCATGCAAGCTAATTGGGCCAAGGTCATtCTGGTC |
| 42 | Z6 | 489 | CgTCCTTGTtGGGtTGGCtTGGCGTACTTCAGtATGCAAGCTAATTGGGCCAAaGTCATCCTGGTC |
| 42-43 consensus (Z6) | | | cgTCCTTgTtGGGtTGGCgTACTTCaGtATGCAAGCTAATTGGGCCAAaGTCATcCTGGTC |

| SEQ ID NO: | Isolate | | |
|---|---|---|---|
| 43 | Z7 | 550 | CTTTTCCTCTaCGCTGGAGTTGATGCC |
| 42 | Z6 | 550 | CTTTTCCTCTTCGCTGGAGTTGATGCC |
| 42-43 consensus (Z6) | | | CTTTTCCTCTtCGCTGGAGTTGATGCC |

FIG. 1G-1

| SEQ ID NO: | Isolate | | |
|---|---|---|---|
| 45 | SA1 | 1 | GTtCCCTACCGgAATGCCTCTGGGGTTTAcCATGTCACCAATGACTGCCCAAACTCcTCCA |
| 47 | SA5 | 1 | GTCCCCTACCGgAAATGCCTCTGGGGTTTATCATGTCACCAATGATTGCCCAAACTCTTCCA |
| 49 | SA7 | 1 | GTCCCCTACCGgAAATGCCTCcGGGGTTTATCATGTCACCAATGATTGCCCgAACTCTTCCA |
| 46 | SA4 | 1 | GTtCCCTACCGgAAAcGCCTCTGGGGTTTATCATGTCACCAATGATTGCCCAAACTCTTCCA |
| 50 | SA13 | 1 | GTtCCCTACCGgAAATGCCTCTGGGGTTTATCATGTCACCAATGATTGCCCAAACTCTTCCA |
| 48 | SA6 | 1 | GTtCCCTACCGgAATGCCTCTGGGGTGTATCATGTtACCAATGATTGCCCAAACTCTTCCA |
| 45-50 | consensus | | GTtCCcTACCGaAATGCCTCTGGGGTtTATcATGTcACCAATGAtTGCCaAACTCtTCCA |

| SEQ ID NO: | Isolate | | |
|---|---|---|---|
| 45 | SA1 | 62 | TAGTCTACGAGGCTGATAgCCTGGcTGCACGCACCTGGCTGCCCTGTGTCAGGCA |
| 47 | SA5 | 62 | TAGTCTACGAGGCTGATAACCTGATtCTGCACGCACCTGTTGCGTTGCCCTGTGTCAaGgA |
| 49 | SA7 | 62 | TAGTCTAtGAGGCTGAcAACCTGATCCTGCACGCACCTGGTTGCGTTGCCCTGTGTCAGaCA |
| 46 | SA4 | 62 | TAGTCTACGAGGCTGATAACCTGATCCTGCAtGCACGCACCTGGTTGCGTTGCCCTGTGTCAGGCA |
| 50 | SA13 | 62 | TAGTCTACGAGGCTGATAACCTGACCCTGCACGCACCTGGTTGCGTTGCCtTGTGTCAGGCA |
| 48 | SA6 | 62 | TcGTCTACGAGGCTGATGACCTGATCCTGCACGCACCTGGTTGCGTTGCCTGTGTCAGGCA |
|  | SA13 | 62 | TAGTCTACGAGGCTGATGACCTGATCCTGCACGCACCTGGTTGCGTTGCCCTGTGTtAGGCA |
|  | SA6 | 62 | TaGTCTAtGAGGCTGATAACCTGACCTACACGCACCTGGcTGCGTTGCCCTGTGTccGGaA |
| 45-50 | consensus | | TaGTcTAcGAGGCTGAtaaCCTGATc-TgCAcGCACCTGGtTGCGTTGCCCTGTGTcaggcA |

FIG. 1G-2

| SEQ ID NO: | Isolate | | |
|---|---|---|---|
| 45 | SA1 | 123 | AGaTAAATGTCAGTAGGTGCTGGGTCCAAATCACCCCCACACTGTCAGCCCCGAcctTCGGA |
| 47 | SA5 | 123 | AGgTAAATGTCAGTAGGTGCTGGGTCCAAATCACCCCCACACATTGTCAGCCCCGAACCTCGGA |
| 49 | SA7 | 123 | AaATAAATGTCAGTAGGTGCTGGGTCCAAATCACCCCCACACATTGTCAGCCCCGAACCTCGGA |
| 46 | SA4 | 123 | AGATAAATGTCAGTAaGTGCTGGGTCCAAATCACCCCCACGTTGTCAGCCCCGAAtCTCGGA |
| 50 | SA13 | 123 | GGgTAAATGTCAGTAGGTGCTGGGTCCAgATCACCCCCACACTGTCAGCCCCGAGCCTCGGA |
| 48 | SA6 | 123 | GGaTAAATGTCAGTAGaTGCTGGGTtCAtATCACCCCCACACTaTCAGCCCCGAGCCTCGGA |
| 45-50 | consensus | | agaTAAATGTCAGTAggTGCTGGGTcCAaATcACCCCCACa-TgTCAGCCCCGAaccTCGGA |

| SEQ ID NO: | Isolate | | |
|---|---|---|---|
| 45 | SA1 | 184 | GCGGTCACGGCTCCTCTTCGAGGGCcCGTTGACTACTTAGCGGGaGGaGCTGCtCTCTGCT |
| 47 | SA5 | 184 | GCGGTCACGGCTCCTCTTCGAGGGtCGTTGACTACTTAGCGGGaGGGGCTGCCCTCTGCT |
| 49 | SA7 | 184 | GCGGTCACGGCTCCTCTTCGAGGGCCGTTGACTACCTAGCGGGaGGGGCTGCCCTCTGCT |
| 46 | SA4 | 184 | GCGGTCACGGCTCCTCTTCGAGGGCCGTTGACTACTTAGCGGGaGGGGCTGCCCTCTGCT |
| 50 | SA13 | 184 | GCGGTCACGGCTCCTCTTCGAGGGCCGTTGACTACTTAGCGGGGGGGGCTGCCCTtTGCT |
| 48 | SA6 | 184 | GCGGTCACGGCTCCTCTTCGAGGGCCGTTGAtTACTTGGCGGGaGGGGCcGCCCTGTGCT |
| 45-50 | consensus | | GCGGTCACGGCTCCTCCTTCGAGGGCCGTTGACTACTTAGCGGGaGGGGCTGCcCTCTGCT |

FIG. 1G-3

| SEQ ID NO: | Isolate | | |
|---|---|---|---|
| 45 | SA1 | 245 | CCGCACTATACGTCGGcGACGCGTGCGGGGCAGTGTTtcTGGTAGGCCAAATGTTCACCTA |
| 47 | SA5 | 245 | CCGCACTATACGTCGGGGACGCGTGCGGGGCAGTGTTcTTGGTAGGCCAAATGTTCACCTA |
| 49 | SA7 | 245 | CCGCgCTATACGTCGGGGACGCGTGCGGGGCAGTGTTTTGGTAGGCCAgATGTTCAgCTA |
| 46 | SA4 | 245 | CCGCaCTATACGTCGGGGACGCGTGCGGGGCAGTGTTTTTGGTAGGCCAAATGTTCACCTA |
| 50 | SA13 | 245 | CCGCGTTATACGTCGGGGACGCGTGCGGGGCAGTGTTTTTGGTAGGtCAAATGTTCACCTA |
| 48 | SA6 | 245 | CCGCGTTATACGTCGGAGACGCGTGCGGGGCAtTGTGTGCGAGACGCGTGCAGTGTTTTTGGTAGGCCAAATGTTCACCTA |
| 45-50 | consensus | | CCGC-cTATACGTCGGgGACGCGTGCGGGGCAGTGTTttTGGTAGGCCAaATGTTCAcCTA |

| SEQ ID NO: | Isolate | | |
|---|---|---|---|
| 45 | SA1 | 306 | TAGGCCTCGCCGCCAGCATACCACAGTGCAGGACTGCAACTGTTCCATTTACAGTGGCCATATC |
| 47 | SA5 | 306 | TAGGCCTCGCCGCCAGCATACGTGCAGGACTGCAACTGTTCCATTTACAGcGGCCATATC |
| 49 | SA7 | 306 | TAGGCCTCGCCGCCAGCATACGTGCAGGACTGCAACTGTTCCATTTACAGTGGCCATATC |
| 46 | SA4 | 306 | TAGGCCTCGCCGCCAGCACTACGTGCAGGACTGCAAtTGCTCTaTTTACAGTGGCCATATC |
| 50 | SA13 | 306 | TAGcCCTCGCCgGCATAaTgttGTGCAGGACTGCAAGACTGCAACTGTTCCATTTACAGTGGCCAcATC |
| 48 | SA6 | 306 | TAGgCCTCGCCaGCATgcTacgGTaCAGGACTGCTCCATTTACAGTGGCCATATC |
| 45-50 | consensus | | TAGgCCTCGCCaGCAtactacgGTgCAGGACTGCAAcTGTtCCATTTACAGTGGCCATATC |

FIG. 1G-4

| SEQ ID NO: | Isolate | | |
|---|---|---|---|
| 45 | SA1 | 367 | ACCGGCCACCGgATGGCtTGGGACATGATGATGAATTGGTCACCTACGACAGCCTTGCTGA |
| 47 | SA5 | 367 | ACCGGCCACCGAATGGCATGGGACATGATGATGATGAATTGGTCACCTACGACAGCCTTGGTGA |
| 49 | SA7 | 367 | ACCGGCCACCGGAATGGCATGGGACATGATGATGATGAATTGGTCACCTACGACAGCCTTGGTGA |
| 46 | SA4 | 367 | ACCGGCCACCGGATGGCATGGGACATGATGATGAATTGGTCACCTACGACGGCCTTGCTGA |
| 50 | SA13 | 367 | ACCGGCCACCGGATGGCATGGGACATGATGATGAATTGGTCACCTACAACAGCTTTGGTGA |
| 48 | SA6 | 367 | ACtGGCCACCGGATGGCATGGGACATGATGATGAATTGGTCACCcgCgACAGCcTTGGTGA |
| 45-50 | consensus | | ACCGGCCACCGgATGGCaTGGGACATGATGATGAATTGGTCACCtaCgACaGCCTTGgTGA |

| SEQ ID NO: | Isolate | | |
|---|---|---|---|
| 45 | SA1 | 428 | TGGCCCAGaTGCTACGGATCCCCCAGtGTGGTCATaGACATCATaGCCGGGGCCACTGGGG |
| 47 | SA5 | 428 | TGGCCCAGgTGCTACGGATTCCCCAaGTGGTCATtGACATCATTGCCGGGGCCACTGGGG |
| 49 | SA7 | 428 | TGGCCCAGTTGCTACGGATTCCCCAGTGTGGTCATCGACATCATTGCCGGGGCCACTGGGG |
| 46 | SA4 | 428 | TGGCCCAGTTGCTACGGATTCCCCAGTGTGGTCATCGACATCATTGCCGGGGCCACTGGGG |
| 50 | SA13 | 428 | TGGCCCAGTTGtTACGGATTCCCCAGTGTGGTCATTGACATCATTGCCGGGGCCACTGGGG |
| 48 | SA6 | 428 | TGGCCCAaTGCTACGGATTCCCCAGTGTGGTCATTGACATCATTGCCGGGgCCACTGGGG |
| 45-50 | consensus | | TGGCCCAgtTGCTACGGATtCCCCAgtGTGGTCATtGACATCATtGCCGGGGgCCACTGGGG |

FIG. 1G-5

| SEQ ID NO: | Isolate | | |
|---|---|---|---|
| 45 | SA1 | 489 | GGTCTTGTTGCCGCCGCATACTTTGCGTTGCCGCCCAACTGGGCTAAGGTAGTGCTGGTt |
| 47 | SA5 | 489 | GGTCTTGTTCGCCGCCGCATACTTCGCGTTGCCGTCAGCGGCTAAACTGGGCTAAGGTTGTGCTGGTC |
| 49 | SA7 | 489 | GGTCTTGTTCGCCGCCGCATATTTCGCGTTGCCGTCAGCGGCTAAACTGGGCTAAGGTTGTGCTGGTC |
| 46 | SA4 | 489 | GGTCTTGTTtGCCGCCGCATATTTCGCGTTGCCGTCAGCGGCTAAACTGGGCTAAGGTTGTGCTGGTC |
| 50 | SA13 | 489 | GGTCTTGTTCGCCGCCGCATACTaCGCGTTGCCGTCGGCGGCTAAACTGGGCCAAGGTTGTGCTGGTC |
| 48 | SA6 | 489 | GGTCTTGTTCGCCGCCGCtGCATACTtCGCGTTGCCGTCGGCGGCTAAACTGGGCTAAGGTTGTGCTGGTC |
| 45-50 | consensus | | GGTCTTGTTcGCCGccGcaCATAcTtcGGGTC-GCggCTAACTGGGCtAAGGTTgTgCTGGTc |

| SEQ ID NO: | Isolate | | |
|---|---|---|---|
| 45 | SA1 | 550 | CTGTTcCTGTTTGCGGGGTCGATGGC |
| 47 | SA5 | 550 | CTGTTTCTGTTTGCGGGGGTCGATGGC |
| 49 | SA7 | 550 | TTGTTTCTGTTTGCGGGGGTCGATGCC |
| 46 | SA4 | 550 | TTGTTTCTGTTTGCGGGGGTCGATGCC |
| 50 | SA13 | 550 | cTGTTTCTGTTTGCGGGGGTCGATGCC |
| 48 | SA6 | 550 | tTGTTTCTGTTTGCGGGGGTtGATGCC |
| 45-50 | consensus | | -TGTTtCTGTTTGCGGGGGTcGATGcC |

FIG. 1H-1

| SEQ ID NO: | Genotype | |
|---|---|---|
| 30-33 | (IV/2b) | 1 GTGGAAGTCAGAGAACAtCAGTTctAGcTACTAcGCCACCAATGATTGCTCaAACaCAGCA |
| 34 | (2c) | 1 GTGGAGGTCAAGGAGTCAAGGACACCGGCGACTCCTACATGCCGACCAACGATTGCTCCAACTCTAGTA |
| 26-29 | (III/2a) | 1 GcccAAGTGAAGAACACCAGtacCAGcTACATGGTTCCTtACCAACGACTGtTCCAATGAcAGCA |
| 35-39 | (V/3a) | 1 cTAGAGTGGCGGAATacGTCTGGCCTTAtgTCCTtACCAACGACTGTtCCAATAGCAGTA |
| 9-25 | (II/1b) | 1 tAtGAaGTGCgCAACGTgTCCGGGgtgTAccAtGTCACgAAcGACTGcTCCAACTcaAGca |
| 1-8 | (I/1a) | 1 tACCAAGTgCGCAACTCcaCgGGgCTTtTACCATGTcACCAATGAtTGCCCTAAcTCGAGtA |
| 40 | (4a) | 1 GAGCACTACCGGAATGCTTCGGGCATCTATCACATCACGTCACCAACGACTGTCCGAATTCCAGTA |
| 42-43 | (4c) | 1 GTtAACTATCgCAATGCCTCGGGCGTCTATCAcGTCACCAACGACTGCCCGAACTCGAGCA |
| 44 | (4d) | 1 TACAACTATCGCAACAGTCGGGTGTCTACCATGTCACCAATGATTGCCCGAACTCGAGCA |
| 41 | (4b) | 1 GTGCACTACCGGAATGCTTCGGGCGTCTATCATGTCACCAATGATTGCCCTAACACCAGCA |
| 45-50 | (5a) | 1 GTtCCcTACCGaAAtGCCTCTGGGGTtTAtCATGTCACCAATGAtTGCCaAACTCtTCCA |
| 51 | (6a) | 1 CTTACCTACGCAACTCCAGTGGGCTATACCATCTCACAAATGATTGCCCCAACTCCAGCA |

1-51 consensus             A                TA            AC  AA GA TG   C  AA

| SEQ ID NO: | Genotype | |
|---|---|---|
| 30-33 | (IV/2b) | 62 TCACCTTGGCAAcTTCACCaACGCAGTtCTCCACCTTCCCACCTTCCCGAtGCGTCCAtGTGAGAATGA |
| 34 | (2c) | 62 TCGTTTGGCAGCTTGAAGGAGCAGTGCTTCATACTCCTGATGCGTCCTTGTCCCGTGCGAGCGTAC |
| 26-29 | (III/2a) | 62 TCACcTGGCAAcTccAgCCGGTCTTCCTCCACGTcCCCCGGGTGtgTCCCGTGcGAGAaagt |
| 35-39 | (V/3a) | 62 TtGTGTATGAGGCCGATGACGTtCATTCTGCACACACCTGGCTGTGTACCTTGTGTTCAGGA |
| 9-25 | (II/1b) | 62 TtGTGTATgAGgCAgcGGACAtGATcaTGCCATccTgCAcaCTCCGGGGTGTCCCTTGCGTTCGcGA |
| 1-8 | (I/1a) | 62 TAGTCTATGACGAGGCGGCCGATGcCATCACCCTGCCGGGTGTGCCTACCCTGTGTGATGAC |
| 40 | (4a) | 62 TAGTCTATGAAGCTGACGCGAACACGAGATCTACACCTCCCAGGGTGCTgCCCTGTGTGAGGGT |
| 42-43 | (4c) | 62 TAGTGTATGAAACCGATTACCACATTACCACCTCCCGGGATGCGTTCCTTGCGTGAGGGA |
| 44 | (4d) | 62 TAGTGTACGAGACGGCCACCACACATCATGCACCTGCACTTGCCGTGTCCCCGTGTGCGGAC |
| 41 | (4b) | 62 TAGTGTACGAGGCTGATaaCCTGATcCtTgCAcGCACCTGGTGCTGCCTGTGTGTGAGGT |
| 45-50 | (5a) | 62 TaGTCTACGAGCTGATaaCCTGATcttGCAcGCACCTGGTGCTGCCTGTGTGTCaggcA |
| 51 | (6a) | 62 TCGTGCTGGAGGCCGATGCTATGATCTTGCATTGCCTTGACGTGCTTGCCTTGTGTGAGGGT |

1-51 consensus    T    A    T  T CA    CC  GG TG   T CC  TG   G

FIG. 1H-2

| SEQ ID NO: | Genotype | |
|---|---|---|
| 30-33 | (IV/2b) | 123 cAATGgCACCcTGcTGcTGcTGATACAAGTgACACCTAATgTGGCTGTGAAACACCGcGGC |
| 34 | (2c) | 123 CGCCAAGTCTCTCGATgTTgGGTTgGgTGCTgCCGgTTgCCCCCAATCTCGCCATAAGTCAACCTGGC |
| 26-29 | (III/2a) | 123 gGGAAAtaCaTCtCGgTGCTGGATACCGgTtctCaCCAAAcGTgGCcGTgCaGCaGCCcGGC |
| 35-39 | (V/3a) | 123 CGGcAATACATCcAcGTGCTGgACCcCaGTGACaCCTACaGTGGACGTCAGTTACgTCGGA |
| 9-25 | (II/1b) | 123 gaacAActcCTCccgcTGcTGCTGGGTaGCGCTcaCtCCCACgCTcGGcGCAGGAAcgccAgC |
| 1-8 | (I/1a) | 123 GGgTaaCgcctCGAggTGTTgGGTGgCGgTGaCCCCCACgGTgGCCACcAGGGAcGGCAAa |
| 40 | (4a) | 123 TGGGAACACATGCGCTTgCTGgACGCCGgTGACGCCGTGACAGTGGCTGTCGCACACCCGGC |
| 42-43 | (4c) | 123 tGGGAAtCAGTCACGCTGCTGGGTGGCCCTTACTCCACCGTGGCGGTgtCTTATATCGGT |
| 44 | (4d) | 123 AGGGAACAAGTCTACATGCTGGGTGTCTCTCACCCCACCGTGCGCAACATCTGAAT |
| 41 | (4b) | 123 GGAGAATACTTCTCGCTGCTGGGTGCCCTTGACCCCACCGTGCCCGCCCTATCCCAAC |
| 45-50 | (5a) | 123 agaTAATGTCAGTAgGTGCTGGGTcCAaATCACCCCACatTgTCAGCCCCACACCTCGGA |
| 51 | (6a) | 123 CGATGATCGGTCCACCTGTTGGCATGCTGTGACCCTGCCACCCTGGCCATACCAAATGCTTCC |

1-51 consensus                                         TG TGG       T  C  CC A   T  C

| SEQ ID NO: | Genotype | |
|---|---|---|
| 30-33 | (IV/2b) | 184 GCaCTcACTCACAAACCTGCGAaCaCaTgTcGAcaTGATcGTAAtGCAGTACGGTCTGCT |
| 34 | (2c) | 184 GCTCTCACTAAGGGCCTGCCTGGAGCACACATCGATATCATCGTGATCTGCTACGGTCTGTT |
| 26-29 | (III/2a) | 184 GCcCTcACGCAGGGCTTGCGGACGCACATCGACATGGTtGTGATGTCCGCCACGCTCTGCT |
| 35-39 | (V/3a) | 184 GCAACCACCGCtTCGATACGCAGTCAGTGCACCTatTaGTGGGCGCCACgaTGTGCT |
| 9-25 | (II/1b) | 184 gTCcCACTACGaCaATACGACgccCAcGTCGATCGatTTGCTCGTCGATCTGCTTGctTTCTGcT |
| 1-8 | (I/1a) | 184 CTCCCCgCAaCGaCAGCTtCGACTCACATGATCTGCTTGtTCGGGAGCGCCACCCTCTGcT |
| 40 | (4a) | 184 GCTCCGCTTGAGTCGTTCCGGCACATGGACTTAAtGTGGACTTGATGGTGGCGCCACTTGTGTT |
| 42-43 | (4c) | 184 GCtCCGCTTGACTCCCTCCGGAGACGTCAGGCATGTGATGGTGGGCCGCTACtGTaTGCT |
| 44 | (4d) | 184 GCTCCGCTTGAGTCTTTGAGAGCGCAGGTCTTGGATCTGATGGTGCGGCCACTCTCTGCT |
| 41 | (4b) | 184 GCACCGTTAGAGTCCATGCTCCTTCTTCGGAGGGCATGTAGACCTGATGGTGCGGCTACTATGTT |
| 45-50 | (5a) | 184 GCGGTCACGCTTGACTACTTaGCGGaGGgCTgCcCCTtCTGCT |
| 51 | (6a) | 184 ACGCCCGCAACGGGATTCCGCAGCATGTGGATCTTCTTGCGCGGCCCAGTGGTTGCT |

1-51 consensus                    T    G       T GA         T G              GC       T  TG T

FIG. 1H-3

| SEQ ID NO: | Genotype | | |
|---|---|---|---|
| 30-33 | (IV/2b) | 245 CGGCCCTTGTATGTGGaGACGTgTgTGCGGGGGCCGTGATGATcGtGTCGCAGGCTtTCATAaT |
| 34 | (2c) | 245 CTTGCCCTTTATGTGGGGGGACGTGTGTGGCGCTGTGCCCGCTCAGGTCGTCGTCGT |
| 26-29 | (III/2a) | 245 CcGCtCTtTACGTGGGGGAccTCTGCGCGGCGcGGGgTgATGCTCGCaGCcCAgATGTTCATtgT |
| 35-39 | (V/3a) | 245 CTGCGCTCTAcGTGGGtGATaTGTGGGCCGTCTTtCTgTGGGACAAGCCTTCACGTT |
| 9-25 | (II/1b) | 245 CCGCtATGTAcGTGGGGATCTCTGCGGaTCTgTTtCTCgTcTCcCAGCTGTTCACctT |
| 1-8 | (I/1a) | 245 CGGCCCCTCTAcGTGGGGACTGTGCGGCTGTGCCGTCTCGTTcTGTGGtCAaCTGTTCACctT |
| 40 | (4a) | 245 CTGCCCTCTATGTTGGGAGACCCTCGGTGGtGcATTCTTGGTTGGcCAGATGTTCTCCTT |
| 42-43 | (4c) | 245 CtGCCCTCTACgTTGGaGAtCTGTGCGGTGGtGcAATCTTGGTTGGcCAGATGTTCTCCTT |
| 44 | (4d) | 245 CCGCCCTCTACATCGAGAGACGTGTGTGTGGGGGCGTCTTCTTGTTCTTGGcCAGATGTTCACCTT |
| 41 | (4b) | 245 CCGCCCTTCTACATTGGAGAGATCTGTGTGAGGCGTCTTCTTCCTAGTGGGCCAGCTGTTTGACTT |
| 45-50 | (5a) | 245 CCGCgCTATACGTCGGGACGCGTGGCCTGTGCCagTGTGTtGGTAGcCAaATGTTCAcCTA |
| 51 | (6a) | 245 CATCCCTGTACATCGGGGACCTGTGGCTCTCTCTCTTTTTGCGGGACAACTATTCACCTT |
| 1-51 | consensus | C        T  TA  T GG GA    TG GG        T  T    CA      T |

| SEQ ID NO: | Genotype | | |
|---|---|---|---|
| 30-33 | (IV/2b) | 306 ATCGCCaGAACgCCCACaACTTtACCCAagAGTGCAACTGTTCCATCTACCAAGGTCatATC |
| 34 | (2c) | 306 GTCGCCACAACCATACGTTTGTCCAGGAATGCAACTGTTCCATATACCGGGCCGCATT |
| 26-29 | (III/2a) | 306 CTTCGCCGCaaCaCCACTgGTTTGTTGTGCAaaTGCAATGCTCCATtGCTACCCTgGtACCATCC |
| 35-39 | (V/3a) | 306 CAGACCTCGTCGCCCATCAAACgGTTCCAGACACCTGTAACTGCTCGCTGTACCTATCCGGCCaTCTT |
| 9-25 | (II/1b) | 306 cTTCgCCTCGCcGgcATgaGACagtaCAgTaCCAaCTGCAaCTGCtCaaTCTATCCCgGcCacgTa |
| 1-8 | (I/1a) | 306 cTCtCCCAGgCgCCaCTGGACAACGACGCCaaGACTGCAATGTTCTaTCTATCCCgGCCATATa |
| 40 | (4a) | 306 TCGGCCGCGTCGCCACTGGACCACGCAGGAGTGCAATGTTCCATCTACTGGCCATATC |
| 42-43 | (4c) | 306 CCAGCCGCGACGCCACTAGCCACCACCCAAGACTGCAATTGTTCtATCTACgCAgGGCATaTc |
| 44 | (4d) | 306 CCAACCTCGCCGCCGCCACTGGACCAGACTGCAATTGTTCCATCTACACAGGACATATC |
| 41 | (4b) | 306 CCGACCGCGCCGCCGCCACTGGACCAGACTGGATTGCAACTGCTCCATCTACACAGGACATATC |
| 45-50 | (5a) | 306 TAGgCCTTCGCCAgCATactacgGTgCAgGACTGCAAcTGtTCCATTTACAGTgGCCATATC |
| 51 | (6a) | 306 TCAGCCCCGCCGTCATTGGACTGTCAAGACTGTCAACTGCAACTGCTCCATCTATACAGGCCACGTC |
| 1-51 | consensus | CC         C                    CA           TG AA TG TC   T TA       GG            T |

FIG. 1H-4

| SEQ ID NO: | Genotype | | |
|---|---|---|---|
| 30-33 | (IV/2b) | 367 | ACCGGCCACCGCATGGCACATGGACACATGATGCTaAACTGGTCACCAACTCTtACCATGATCC |
| 34 | (2c) | 367 | ACGGGACACCGCATGGCTTGGATATGGACACATGATGATGAACTGGTCGCCCATACCACCATGCTCC |
| 26-29 | (III/2a) | 367 | ACtGGaCACCGTATGCGaATGGCTTGGCATGGACACATGATGATGATGAACTGGTCGCCACGgCCACcaTGATCc |
| 35-39 | (V/3a) | 367 | TCAGGACATGCACCGCATGGCTTGGATATGGATATGGACACATGATGATGATGATGAACTGGTCCCCCGCtGTGGGTATGGTGG |
| 9-25 | (II/1b) | 367 | tCAGGTCAcCGCATGGCTTGGCATGGACATGGATATGATGGACACATGATGATGAACTGGTCaCCtACAgCaGCccTaGTgg |
| 1-8 | (I/1a) | 367 | ACGGGtCACCGCATGGCATGGCATGGACATGGCGTGGGACATGATGATGATGAACTGGTCCCCtACgaCgGCgCTGGTag |
| 40 | (4a) | 367 | ACCGGCCACAGGATGGCGTGGGACATGGATGATGATGAACTGGAGCCCTACCACCACCACTCTGCTCC |
| 42-43 | (4c) | 367 | ACgGGCCACAGcAGGATGGCATGGCATGGACATGGATGATGATGAACTGGAGTCCCACAACCACCCTGcTtC |
| 44 | (4d) | 367 | ACAGGACACAGAGAATGGCTTGGGACATGGACATGATGATGAATTGGAGCCCCACTGCGACGCTGGTCC |
| 41 | (4b) | 367 | TCGGGCCACAGACTGGCCTGGCATGGACATGGACATGATGATGATGAACTGGAGCCCCTACCAGCGCGCTGATTA |
| 45-50 | (5a) | 367 | ACcGGCCACCGCATGGCATGGACATGGCTTGGGACATGATGATGATGAACTGGTCACCtaCgACaCAGCcTTGgTGA |
| 51 | (6a) | 367 | ACCGGCCACAGAGATGGCTTGGGACATGGACATGATGATGATGAACTGGTCACCCACAACCACTCTGGTCC |
| 1-51 | consensus | | C GG CA G ATGGC TGGGA ATGATG T AA TGG CC C T T |

| SEQ ID NO: | Genotype | | |
|---|---|---|---|
| 30-33 | (IV/2b) | 428 | TcGCCCTAtGCgCGCtCGTGTtCCTGAgCTAGtCCTtgAaGTtGTCTTCGCgGCcCATTGGGG |
| 34 | (2c) | 428 | TGGCGTACTTGGTGCGCATCCCGGAAGTCATCTTGGATATTGTTACAGGAGGTCATTGGGG |
| 26-29 | (III/2a) | 428 | TGGCGTACGcGATGCGCGTTCCCGAGGTCATCaTAGACATCaTTaGCGCGGGCtCAcTGGGG |
| 35-39 | (V/3a) | 428 | TgGCGCACGTCCTGCGtcTGCGttTGCCCAGACCTtGTTCGACATAaTaGCcGGGGCCCATTGGGG |
| 9-25 | (II/1b) | 428 | TaTCGCAgtTaCTCCGgaTCCaCAAGCTgTgTGGAcaTGGTggCgGGGGCCCACTGGGG |
| 1-8 | (I/1a) | 428 | TaGCtCAGCTGCTCcGGaTCCgCAaGCCaTCTTGGACATGATCGCTGGtGCcCACTGGGG |
| 40 | (4a) | 428 | TCGCCCAGATCATGAGGGTCCCCACAGCCTTTCTCGGTaGAtCTACTCgCTGGAGGCACTGGGG |
| 42-43 | (4c) | 428 | TCGCCCAGTCATGAGGATCCTAGCACTCCTGGAGCCCATGGTTGCCGAGGCGCACTGGGG |
| 44 | (4d) | 428 | TCGCCCAACTTATGAGGATCCCAGGCCCATGGTCGACCTGTCGACCTGCTTGCTCACCGGCCACTGGGG |
| 41 | (4b) | 428 | TGGCTCAGATCTTACGGATCCGATCCTCTATCCTAGGTGACTTGCTCACCGGGGTCACTGGGG |
| 45-50 | (5a) | 428 | TGGCCCAGTcAgtTGCTACGGATTCCCAGtGTGTCATtGACATCATTGCCGGGGgCCACTGGGG |
| 51 | (6a) | 428 | TATCTAGCATCTTGAGGGTACCTGAGATTTGTGCGAGTGTGATATTGGTGCCATTGGGG |
| 1-51 | consensus | | T C G T CC T T GG G CA TGGGG |

FIG. 1H-5

| SEQ ID NO: | Genotype | | |
|---|---|---|---|
| 30-33 | (IV/2b) | 489 | cGTGGGTGTTTGGCTTGGCCTATTTCTCCATGCAgGGAGGCGTGGGCCAAaGTCATtGCCATC |
| 34 | (2c) | 489 | TGTAAtGTTTGGCCTCGCTTAGCCTACTTCTCCATGCAGGGATCGTGGGCGAAGGTCATCGTTATC |
| 26-29 | (III/2a) | 489 | CGTCatGTTcGGCTCtTaGCCTAGCTTCTCTATGCAGGAGCGTGGGCGAAaGTCgTTGTCATC |
| 35-39 | (V/3a) | 489 | CATCtTGGCgGGCCGGGCCTtGCCTACTATTACTCCATGCAgGGCAGGGAACTGGGCCAAGTCGCTAtCaTC |
| 9-25 | (II/1b) | 489 | agTCCTaGCGCGGGGCATAGCGTATTTCTCCATGtGgGGAACTGGGCTAAGGTCtTTgATTGTg |
| 1-8 | (I/1a) | 489 | AGTCCTaGCGGGGCATAGCGTATTTcTCCATGCAGCATGCAAGGCAATTGGGCGAAGGTCcTggTaGTg |
| 40 | (4a) | 489 | CGTCCTCGCGGGGCTTGGCGTGGCgTGGCgTACTTCAGtATGCAAGCTAAGCTAATTGGGCCAAAGTCATcCTGGTC |
| 42-43 | (4c) | 489 | cgTCCTTgTGGGtTGGCgTGGCATAGCGTACTTCAGCATGCAAGCTAAGCTAATTGGGCCAAAGTCATcCTGGTC |
| 44 | (4d) | 489 | CATTCTGGTTGGCATAGCGTACTTCAGCATGCAAGCTAAGCTAAGAGTAACTGGGCCAAGGTTATCCTGGTC |
| 41 | (4b) | 489 | AGTTCTCTGCTGTCTAGCTTTCTTCAGCATGCAAGCTAAGCTAACTGGGCTAACTGGGCGAAGGTCATCCTGGTC |
| 45-50 | (5a) | 489 | GGTCTTGTTcGCCGccGATACtTcGCGTCgCGCGTCTCgCCGTCCGGGCtaACTGGGCtAACTGGGCtAAGGTTgTCTGGTC |
| 51 | (6a) | 489 | GATACTACTAGCCGTTGCTACTTTGGCATGCCTACTGGCTGCAACTGGCTAAAAGTTCTGGCTGTT |

1-51 consensus    T    T    G    GC T  T                TGG      AA GT           T

| SEQ ID NO: | Genotype | | |
|---|---|---|---|
| 30-33 | (IV/2b) | 550 | CTCCCTcCTTGTcGCAGGAGTGGAtGCA |
| 34 | (2c) | 550 | CTCCTGCTGACTGCTGGGGTGGAGGCG |
| 26-29 | (III/2a) | 550 | CTTtTGCTgCTggCcGCTGGgGTGGACGCG |
| 35-39 | (V/3a) | 550 | AtGgTTAtGTTTTCAGGGTCGAtGCC |
| 9-25 | (II/1b) | 550 | aTGCTACTcTTTGCcGGcCGTtGAcGGg |
| 1-8 | (I/1a) | 550 | CGTtGCTGtTTtgCCGGCGCTcGAtGCG |
| 40 | (4a) | 550 | CTTTTCCTCTTTGCTCGCTGGGGTAGACGCC |
| 42-43 | (4c) | 550 | CTTTCCCTCtCGCTGGAGTTGATGCC |
| 44 | (4d) | 550 | CTGTTTCTCTTTGCCGGAGTCGACGCT |
| 41 | (4b) | 550 | CTATTCCTCTTTGCGGGGGTCGAGGGA |
| 45-50 | (5a) | 550 | tTGTTtCTGTTTGCGGGGGTCGATGcC |
| 51 | (6a) | 550 | CTGTTCCTATTTGCAGGGGTTGAAGCA |

1-51 consensus    T    T    T        C  GG GT GA  G

FIG. 2A-1

| SEQ ID NO: | Isolate | | |
|---|---|---|---|
| 56 | S14 | 1 | YQVRNStGLYHVTNDCPNSSIVYEtADAILHaPGCVPCVREGNtSRCWVAMTPTVATRDGK |
| 52 | DK7 | 1 | YQVRNSTGLYHVTNDCPNSSIVYEAADAILHTPGCVPCVREGNvSRCWVAMTPTVATRDGK |
| 59 | US11 | 1 | YQVRNSTGLYHVTNDCPNSSIVYEAADAILHTPGCVPCVREGNaSRCWVAMTPTVATRDGK |
| 55 | DR4 | 1 | YQVRNSTGLYHVTNDCPNSSIVYEAADAILHTPGCVPCVREGNtSRCWVAVTPTVATRDGK |
| 54 | DR1 | 1 | HQVRNSTGLYHVTNDCPNSSIVYEAADAILHaPGCVPCVREGNASRCWVAVTPTVATRDGK |
| 53 | DK9 | 1 | HQVRNSSGLYHVTNDCPNSSIVYEAADAILHSPGCVPCVREGNASKCWVAVAPTVATRDGK |
| 58 | SW1 | 1 | YQVRNSSGLYHVTNDCPNSSIVYETADAILHSPGCVPCVREdgApKCWVAVAPTVATRDGK |
| 57 | S18 | 1 | YQVRNStGLYHVTNDCPNSSIVYETADtILHSPGCVPCVREgnAsrCWVpVAPTVATRDGK |
| 52-59 | consensus | | yQVRNStGLYHVTNDCPNSSIVYEaAdAILH-PGCVPCVREgnasrCWVavtPTVATRDGK |

FIG. 2A-2

| SEQ ID NO: | Isolate | Sequence |
|---|---|---|
| 56 | S14 | LPatQLRRyIDLLVGSATLCSALYVGDLCGSVFLVGQLFTFSPRRlWTTQdCNCSIYPGHI 62 |
| 52 | DK7 | LPTaQLRRHIDLLVGSATLCSALYVGDLCGSVFLVGQLFTFSPRRHWTTQGCNCSIYPGHI 62 |
| 59 | US11 | LPTTQLRRHIDLLVGSATLCSALYVGDLCGSVFLVGQLFTFSPRRHWTTQGCNCSIYPGHI 62 |
| 55 | DR4 | LPTTQLRRHIDLLVGSATLCSALYVGDLCGSVFLVGQLFTFSPRRhWTTQGCNCSIYPGHI 62 |
| 54 | DR1 | LPTTQLRRHIDLLVGSATLCSALYVGDLCGSVFLVGQLFTFSPRRHWTTQDCNCSIYPGHI 62 |
| 53 | DK9 | LPTTQLRRHIDLLVGSATLCSALYVGDLCGSVFLVGQLFTFSPRRHWTTQDCNCSIYPGHI 62 |
| 58 | SW1 | LPATQLRRHIDLLVGSATLCSALYVGDLCGSVFLVSQLFTFSPRRHWTTQDCNCSIYPGHI 62 |
| 57 | S18 | LPATQLRRHIDLLVGSATLCSALYVGDLCGSVFLVSQLFTiSPRRHWTTQDCNCSIYPGHI 62 |
| 52-59 | consensus | LP-tQLRRhIDLLVGSATLCSALYVGDLCGSVFLVgQLFTfSPRrhWTTQdCNCSIYPGHI |

FIG. 2A-3

| SEQ ID NO: | Isolate | | |
|---|---|---|---|
| 56 | S14 | 123 | TGHRMAWDMMMNWSPTTALVVAQLLRIPQAILDMIAGAHWGVLAGIAYFSMVGNWAKVLVV |
| 52 | DK7 | 123 | TGHRMAWDMMMNWSPTTALVVAQLLRIPQAILDMIAGAHWGVLAGIAYFSMVGNWAKVLVV |
| 59 | US11 | 123 | TGHRMAWDMMMNWSPTaALVVAQLLRIPQAILDMIAGAHWGVLAGIAYFSMVGNWAKVLVV |
| 55 | DR4 | 123 | TGHRMAWDMMMNWSPTTALVVAQLLRIPQAILDMIAGAHWGVLAGIAYFSMVGNWAKVLVV |
| 54 | DR1 | 123 | TGHRMAWDMMMNWSPTTALVMAQLLRIPQAILDMIAGAHWGVLAGIAYFSMVGNWAKVLVV |
| 53 | DK9 | 123 | TGHRMAWDMMMNWSPTaALVMAQLLRIPQAILDMIAGAHWGVLAGIAYFSMVGNWAKVVVV |
| 58 | SW1 | 123 | TGHRMAWDMMMNWSPTTALVvAQLLRIPQAVLDMIAGAHWGVLAGIAYFSMVGNWAKVLiV |
| 57 | S18 | 123 | TGHRMAWDMMMNWSPTTALViAQLLRvPQAVLDMIAGAHWGVLAGIAYFSMaGNWAKVLiV |
| 52-59 | consensus | | TGHRMAWDMMMNWSPTtAlVvAQLLRiPQAiLDMIAGAHWGVLAGIAYFSMvGNWAKVlvV |

FIG. 2A-4

| SEQ ID NO: | Isolate | | |
|---|---|---|---|
| 56 | S14 | 184 | LLLFAGVDA |
| 52 | DK7 | 184 | LLLFAGVDA |
| 59 | US11 | 184 | LLLFAGVDA |
| 55 | DR4 | 184 | LLLFAGVDA |
| 54 | DR1 | 184 | LLLFAGVDA |
| 53 | DK9 | 184 | LLLFtGVDA |
| 58 | SW1 | 184 | LLLFsGVDA |
| 57 | S18 | 184 | LLLFaGVDA |
| 52-59 | consensus | | LLLFaGVDA |

FIG. 2B-1

| SEQ ID NO: | Isolate | | Sequence |
|---|---|---|---|
| 75 | T10 | 1 | YEVRNVSGmYHVTNDCSNSSIVfEAaDlIMHTPGCVPCVREgNsSRCWVALTPTLAARNtS |
| 62 | DK1 | 1 | YEVRNVSGvYHVTNDCSNSSIVYEAvDvIMHTPGCVPCVRENNhSRCWVALTPTLAARNAS |
| 64 | HK4 | 1 | hEVhNVSGiYHVTNDCSNSSIVYEAADMIMHTPGCVPCVRENNSSRCWVALTPTLAARNAS |
| 76 | US6 | 1 | YEVRNVSGmYHVTNDCSNSSIVYEAADMIMHTPGCVPCVRENNSSRCWVALTPTLAARNAS |
| 68 | IND8 | 1 | YEVRNVSGVYHVTNDCSNSSIVYEAADMIMHTPGCVPCVREGNfSsCWVALTPTLAARNAS |
| 67 | IND5 | 1 | YEVRNVSGVYHVTNDCSNSSIVYEAADMIMHTPGCVPCVREGNSSRCWVALTPTLAARNAS |
| 73 | SW2 | 1 | YEVRNVSGVYHVTNDCSNSSIVYEAADMIMHTPGCVPCVRBaNSSRCWVALTPTLAARNVS |
| 63 | HK3 | 1 | YEVRNVSGIYHVTNDCSNSSVVYETADMIMHTPGCVPCVRENNSSRCWVALTPTLAARNVS |
| 66 | HK8 | 1 | YEVRNVSGIYHVTNDCSNSSIVYETADMIMHTPGCmPCVRENNSSRCWVALTPTLAARNsS |
| 61 | D3 | 1 | YEVRNVSGVYqVTNDCSNSSIVYETADMIMHTPGCVPCVREdNSSRCWVALTPTLAARNAS |
| 74 | T3 | 1 | YEVRNVSGVYyVTNDCSNSSIVYETADMIMHTPGCVPCVREsNSSRCWVALTPTLAARNAS |
| 65 | HK5 | 1 | YEVRNVSGVYHVTNDCSNSSIVYETtDMIMHTPGCVPCVRENNSSRCWVALaPTLAARNAS |
| 71 | S45 | 1 | YEVRNVSGVYHVTNDCSNSSIVYETADMIMHTPGCVPCVRENNSSRCWVALTPTLAARNAS |
| 72 | SA10 | 1 | YEVRNVSGmYHVTNDCSNSSIVYEAADMIMHTPGCVPCVRENNSSRCWVALTPTLAARNSS |
| 69 | P10 | 1 | YEVRNVSGVYHVTNDCSNSSIVYEAADMIMHTPGCVPCVRENNSSRCWVALTPTLAARNSS |
| 60 | D1 | 1 | YEVRNVSGVYHVTNDCSNSSIVYEtADMIMHTPGCVPCVREdNSSRCWVALTPTLAARNgn |
| 70 | S9 | 1 | YEVRNVSGaYHVTNDCSNSSIVYEaADvIMHTPGCVPCVqEgNSSqCWVALTPTLAARNat |
| 60-76 | consensus | | yEVrNVSGvYhVTNDCSNsSivyEaaDmImHTPGCVPCVrEnNsSrCWVAltPTLAARNas |

FIG. 2B-2

| SEQ ID NO: | Isolate | | |
|---|---|---|---|
| 75 | T10 | 62 | vPTTTIRRHVDLLVGAAAFCSAMYVGDLCGSVFLVSQLFTFSPRRHETlQDCNCSIYPGH1 |
| 62 | DK1 | 62 | lPTTTIRRHVDLLVGAAAFCSAMYVGDLCGSVFLVSQLFTFSPRRHETaQDCNCSIYPGHV |
| 64 | HK4 | 62 | lPTTTIRRHVDLLVGAAAFCSAMYVGDLCGSVFLVSQLFTFSPRRHETVQDCNCSIYPGHV |
| 76 | US6 | 62 | VPTTTIRRHVDLLVGAAtFCSAMYVGDLCGSVFLVSQLFTFSPRRHETVQDCNCSIYPGHV |
| 68 | IND8 | 62 | VPTTTIRRHVDLLVGAAAFCSAMYVGDLCGSVFLiSQLFTFSPRqHETVQDCNCSIYPGHV |
| 67 | IND5 | 62 | VPTTTIRRHVDLLVGAAAFCSAMYVGDLCGSVFLVSQLFTFSPRRHETVQDCNCSIYPGHV |
| 73 | SW2 | 62 | VsTTTIRhHVDLLVGAAAFCSAMYVGDLCGSVFLVSQLFTFSPRRHETVQDCNCSIYPGHV |
| 63 | HK3 | 62 | VPTTTIRRHVDLLVGAAAFCSvMYVGDLCGSVFLVSQLFTFSPRRHETVQDCNCSlYPGHV |
| 66 | HK8 | 62 | VPTTTIRRHVDLLVGAAAFCSAMYVGDLCGSVFLVSQLFTFSPRRHETVQDCNCSIYPGHV |
| 61 | D3 | 62 | VPTTTIRRHVDLLVGAAAFCSAMYVGDLCGSVFLVSQLFTFSPRRHETVQeCNCSIYPGHV |
| 74 | T3 | 62 | VPTkTIRRHVDLLVGAAAFCSAMYVGDLCGSVFLVSQLFTFSPRRHETVQDCNCSIYPGHV |
| 65 | HK5 | 62 | VPTTaIRRHVDLLVGAAAFCSAMYVGDLCGSVFLVSQLFTFSPRRHETVQDCNCSIYPGHV |
| 71 | S45 | 62 | VPTTTIRRHVDLLVGAAAFCSAMYVGDLCGSVFLVSQLFTFSPRRHETVQDCNCSIYPGHV |
| 72 | SA10 | 62 | VPTTTIRRHVDLLVGAAAFCSAMYVGDLCGSVFLVSQLFTFSPRRyETVQDCNCSIYPGrV |
| 69 | P10 | 62 | VPTTAIRRHVDLLVGAAAFCSAMYVGDLCGSV1LvSQLFTFSPRRHwTVQDCNCSIYPGHV |
| 60 | D1 | 62 | VPTTAIRRHVDLLVGAAAFCSAMYVGDLCGSVFLlSQLFT1SPRRHETVQeCNCSIYPGHV |
| 70 | S9 | 62 | VPTTtIRRHVDLLVGAAvFCSAMYVGDLCGSVFLlSQLFTiSPRRHETVQnCNCSIYPGHV |

60-76 consensus vpTttiIRrHVDLLVGAAaFCSaMYVGDLCGSVFlvSQLFTfSPRrheTvQdCNCSiYPGhv

FIG. 2B-3

| SEQ ID NO: | Isolate | | |
|---|---|---|---|
| 75 | T10 | 123 | SGHRMAWDMMMNWSPTTALVvSQLLRIPQAVmDMVtGAHWGVLAGLAYYSMAGNWAKVLIV |
| 62 | DK1 | 123 | SGHRMAWDMMMNWSPTTALV1SQLLRIPQAVvDMVAGAHWGVLAGLAYYSMAGNWAKVLIV |
| 64 | HK4 | 123 | SGHRMAWDMMMNWSPTTAALVVSQLLRIPQAVMDMVAGAHWGVLAGLAYYSMVGNWAKVLIV |
| 76 | US6 | 123 | SGHRMAWDMMMNWSPTTAALVVSQLLRIPQAVMDMVAGAHWGVLAGLAYYSMVGNWAKVLIV |
| 68 | IND8 | 123 | SGHRMAWDMMMNWSPTTAALVVSQLLRIPQAVMDMVAGAHWGILAGLAYYSMVGNWAKVLIV |
| 66 | IND5 | 123 | SGHRMAWDMMMNWSPTTAALVVSQLLRIPQAVVDMVAGAHWGILAGLAYYSMVGNWAKVLIV |
| 67 | SW2 | 123 | SGHRMAWDMMMNWSPTTAALVVSQLLRIPQAVVDMVAGAHWGVLAGLAYYSMVGNWAKVLIV |
| 63 | HK3 | 123 | SGHRMAWDMMMNWSPTTAALVVSQLLRIPQAVVDMVAGAHWGVLAGLAYYSMVGNWAKVLIV |
| 66 | HK8 | 123 | SGHRMAWDMMMNWSPTtALVVSQLLRIPQAiVDMVAGAHWGVLAGLAYYSMVGNWAKVLIV |
| 61 | D3 | 123 | SGHRMAWDMMMNWSPTaALVVSQLLRIPQAVVDMVAGAHWGVLAGLAYYSMVGNWAKVLIV |
| 74 | T3 | 123 | TGHRMAWDMMMNWSPTTALVVSQLLRIPQAVVDMVAGAHWGVLAGLAYYSMVGNWAKVLIV |
| 65 | HK5 | 123 | TGHRMAWDMMMNWSPTTALVVSQLLRIPQAVVDMVAGAHWGVLAGLAYYSMVGNWAKVLIV |
| 71 | S45 | 123 | TGHRMAWDMMMNWSPTTALVVSQLLRIPQAI1DvVAGAHWGVLAGLAYYSMVGNWAKVLIV |
| 72 | SA10 | 123 | TGHRMAWDMMMNWSPTaALVVSQLLRIPQAVVDMVAGAHWGVLAGLAYYSMVGNWAKVLIV |
| 69 | P10 | 123 | sGHRMAWDMMMNWSPTtALVVSQLLRIPQAVVDMVAGAHWGVLAGLAYYSMVGNWAKVLIV |
| 60 | D1 | 123 | TGHRMAWDMMMNWSPTTALVVSQLLRIPQAVMDMVAGAHWGVLAGLAYYSMVGNWAKVLIV |
| 70 | S9 | 123 | TGHRMAWDMMMNWSPTTALVVSQLLRIPQAVMDMVAGAHWGVLAGLAYYSMVGNWAKVLIV |

| 60-76 | consensus | | sGHRMAWDMMMNWSPTaALVvSQLLRiPQAvvDmVaGAHWGvLAGLAYYSMvGNWAKVLIV |

FIG. 2B-4

| SEQ ID NO: | Isolate | | |
|---|---|---|---|
| 75 | T10 | 184 | mLLFAGVDG |
| 62 | DK1 | 184 | lLLFAGVDG |
| 64 | HK4 | 184 | mLLFAGVDG |
| 76 | US6 | 184 | lLLFAGVDG |
| 68 | IND8 | 184 | MLLFAGVDG |
| 67 | IND5 | 184 | MLLFAGVDG |
| 73 | SW2 | 184 | MLLFAGVDG |
| 63 | HK3 | 184 | MLLFAGVDG |
| 66 | HK8 | 184 | MLLFAGVDG |
| 61 | D3 | 184 | MLLFAGVDG |
| 74 | T3 | 184 | lLLFAGVDG |
| 65 | HK5 | 184 | MLLFAGVDG |
| 71 | S45 | 184 | MLLFAGVDG |
| 72 | SA10 | 184 | MLLFAGVDG |
| 69 | P10 | 184 | MLLFAGVDG |
| 60 | D1 | 184 | MLLFAGVDG |
| 70 | S9 | 184 | MLLFAGVDG |
| 60-76 | consensus | | mLLFAGVDG |

FIG. 2C-1

| SEQ ID NO: | Isolate | |
|---|---|---|
| 77 | T2 | 1 AQVrNTsrgYMVTNDCSNeSITWQLQAAVLHVPGCiPCErlGNTSRCWIPVtPNVAVRQPG |
| 78 | T4 | 1 AQVKNTtnSYMVTNDCSNDSITWQLQAAVLHVPGCVPCEktGNTSRCWIPVSPNVAVRQPG |
| 79 | T9 | 1 AeVKNTSTSYMVTNDCSNDSITWQLQAAVLHVPGCVPCErVGNaSRCWIPVSPNVAVQRPG |
| 80 | US10 | 1 vqVKNTSTSYMVTNDCSNDSITWQLeAAVLHVPGCVPCEkVGNtSRCWIPVSPNVAVQRPG |
| 77-80 | consensus | aqVkNTstsYMVTNDCSNdSITWQLqAAVLHVPGCvPCE-vGNtSRCWIPVsPNVAV--PG |

| SEQ ID NO: | Isolate | |
|---|---|---|
| 77 | T2 | 62 ALTQGLRTHIDMVVMSATLCSALYVGDLCGGVMLAAQMFIVSPrrHWFVQeCNCSIYPGTI |
| 78 | T4 | 62 ALTQGLRTHIDMVVMSATLCSALYVGDLCGGVMLAAQMFIVSPQHHWFVQdCNCSIYPGTI |
| 79 | T9 | 62 ALTQGLRTHIDMVVMSATLCSALYVGDLCGGVMLAAQMFIiSPQHHWFVQECNCSIYPGTI |
| 80 | US10 | 62 ALTQGLRTHIDMVVMSATLCSALYVGDfCGGmMLAAQMFIvSPrHHsFVQECNCSIYPGTI |
| 77-80 | consensus | ALTQGLRTHIDMVVMSATLCSALYVGDlCGGVMLAAQMFIvSP-hHwFVQeCNCSIYPGTI |

FIG. 2C-2

| SEQ ID NO: | Isolate | | |
|---|---|---|---|
| 77 | T2 | 123 | TGHRMAWDMMMNWSPTATMILAYAMRVPEVIiDIigGAHWGVMFGLAYFSMQGAWAKViVI |
| 78 | T4 | 123 | TGHRMAWDMMMNWSPTATMILAYAMRVPEVIlDIvSGAHWGVMFGLAYFSMQGAWAKVVVI |
| 79 | T9 | 123 | TGHRMAWDMMMNWSPTtTMILAYAMRVPEVIIDIISGAHWGVMFGLAYFSMQGAWAKVVVI |
| 80 | US10 | 123 | TGHRMAWDMMMNWSPTaTlILAYvMRVPEVIIDIISGAHWGV1FGLAYFSMQGAWAKVVVI |
| 77-80 | consensus | | TGHRMAWDMMMNWSPTaTmILAYaMRVPEVIiDIisGAHWGVmFGLAYFSMQGAWAKVvVI |

| SEQ ID NO: | Isolate | | |
|---|---|---|---|
| 77 | T2 | 184 | LLLAAGVDA |
| 78 | T4 | 184 | LLLAAGVDA |
| 79 | T9 | 184 | LLLtAGVDA |
| 80 | US10 | 184 | LLLaAGVDA |
| 77-80 | consensus | | LLlaAGVDA |

FIG. 2D-1

| SEQ ID NO: | Isolate | | |
|---|---|---|---|
| 82 | DK11 | 1 | VEVRNtSSSYYATNDCSNnSITWQLTNAVLHLPGCVPCENDNGTLHCWIQVTPNVAVKHRG |
| 83 | SW3 | 1 | VEVRNiSSSYYATNDCSNsSITWQLTNAVLHLPGCVPCENDNGTLHCWIQVTPNVAVKHRG |
| 84 | T8 | 1 | VEVRNtSfSYYATNDCSNNsITWQLTNAVLHLPGCVPCENDNGTLRCWIQVTPNVAVKHRG |
| 81 | DK8 | 1 | VEVRNiSsSYYATNDCSNNsITWQLTdAVLHLPGCVPCENDNGTLRCWIQVTPNVAVKHRG |
| 81-84 | consensus | | VEVRN-SsSYYATNDCSNnSITWQLTnAVLHLPGCVPCENDNGTL-CWIQVTPNVAVKHRG |

| SEQ ID NO: | Isolate | | |
|---|---|---|---|
| 82 | DK11 | 62 | ALTHNLRAHiDMIVMAATVCSALYVGDvCGAVMIVSQAFIvSPEhHhFTQECNCSIYQGhI |
| 83 | SW3 | 62 | ALTHNLRAHVDMIVMAATVCSALYVGDmCGAVMIVSQAFIISPERHNFTQECNCSIYQGrI |
| 84 | T8 | 62 | ALTHNLRTHVDVIVMAATVCSALYVGDVCGAVMIaSQAFIISPERHNFTQECNCSIYQGHI |
| 81 | DK8 | 62 | ALTHNLRTHVDVIVMAATVCSALYVGDVCGAVMIvSQAlIIISPERHNFTQECNCSIYQGHI |
| 81-84 | consensus | | ALTHNLR-HvD-IVMAATVCSALYVGDvCGAVMIvSQAFIiSPErHnFTQECNCSIYQGhI |

FIG. 2D-2

| SEQ ID NO: | Isolate | | |
|---|---|---|---|
| 82 | DK11 | 123 | TGHRMAWDMMLNWSPTLTMILAYAARVPELVLEVVFGGHWGVVFGLAYFSMQGAWAKVIAI |
| 83 | SW3 | 123 | TGHRMAWDMMLNWSPTLTMILAYAARVPELVLEVVFGGHWGVVFGLAYFSMQGAWAKVIAI |
| 84 | T8 | 123 | TGHRMAWDMMLNWSPTLTMILAYAARVPELVLEVVFGGHWGVVFGLAYFSMQGAWAKVIAI |
| 81 | DK8 | 123 | TGHRMAWDMMLNWSPTLTMILAYAARVPELaLqVVFGGHWGVVFGLAYFSMQGAWAKVIAI |
| 81-84 | consensus | | TGHRMAWDMMLNWSPTLTMILAYAARVPELvLeVVFGGHWGVVFGLAYFSMQGAWAKVIAI |

| SEQ ID NO: | Isolate | | |
|---|---|---|---|
| 82 | DK11 | 184 | LLLVAGVDA |
| 83 | SW3 | 184 | LLLVAGVDA |
| 84 | T8 | 184 | LLLVAGVDA |
| 81 | DK8 | 184 | LLLVAGVDA |
| 81-84 | consensus | | LLLVAGVDA |

FIG. 2E-1

| SEQ ID NO: | Isolate | |
|---|---|---|
| 86 | DK12 | 1 LEWRNVSGLYVLTNDCsNSSIVYEADDVILHTPGCVPCVQDGNTSTCWTSVTPTVAVRYVG |
| 87 | HK10 | 1 LEWRNVSGLYVLTNDCpNSSIVYEADDVILHTPGCVPCVQDGNTSTCWTSVTPTVAVRYVG |
| 88 | S2 | 1 LEWRNTSGLYVLTNDCSNSSIVYEADDVILHTPGCVPCVQDGNTSTCWTPVTPTVAVRYVG |
| 90 | S54 | 1 LEWRNTSGLYiLTNDCSNSSIVYEADDVILHTPGCVPCVQDGNTSTCWTPVTPTVAVRYVG |
| 89 | S52 | 1 LEWRNTSGLYvLTNDCSNSSIVYEADDVILHTPGCVPCVQDGNTSmCWTPVTPTVAVRYVG |
| 86-90 | consensus | LEWRNtSGLYvLTNDCsNSSIVYEADDVILHTPGCVPCVQDGNTStCWTpVTPTVAVRYVG |

| SEQ ID NO: | Isolate | |
|---|---|---|
| 86 | DK12 | 62 ATTASIRSHVDLLVGAATMCSALYVGDvCGAVFLVGQAFTFRPRRHQTVQTCNCSLYPGHL |
| 87 | HK10 | 62 ATTASIRSHVDLLVGAATMCSALYVGDMCGAVFLVGQAFTFRPRRHQTVQTCNCSLYPGHL |
| 88 | S2 | 62 ATTASIRSHVDLLVGAATMCSALYVGDMCGAVFLVGQAFTFRPRRHQTVQTCNCSLYPGHL |
| 90 | S54 | 62 ATTASIRSHVDLLVGAATLCSALYVGDMCGAVFLVGQAFTFRPRRHQTVQTCNCSLYPGHL |
| 89 | S52 | 62 ATTASIRSHVDLLVGAATLCSALYVGDMCGAVFLVGQAFTFRPRRHQTVQTCNCSLYPGHv |
| 86-90 | consensus | ATTASIRSHVDLLVGAATmCSALYVGDmCGAVFLVGQAFTFRPRRHQTVQTCNCSLYPGHl |

FIG. 2E-2

| SEQ ID NO: | Isolate | | |
|---|---|---|---|
| 86 | DK12 | 123 | SGHRMAWDMMMNWSPAVGMVVAHVLRLPQTLFDIIAGAHWGImAGLAYYSMQGNWAKVAII |
| 87 | HK10 | 123 | ------------------------------------------------------------ |
| 88 | S2 | 123 | ---------------------------------------------I-------------- |
| 90 | S54 | 123 | ------------------------v----------------------------------- |
| 89 | S52 | 123 | -----------------I----------I-------i----------------------v |
| 86-90 | consensus | | SGHRMAWDMMMNWSPAVGMVVAHvLRLPQTlFDIiAGAHWGIlAGLAYYSMQGNWAKVAIi |

| SEQ ID NO: | Isolate | | |
|---|---|---|---|
| 86 | DK12 | 184 | MVMFSGVDA |
| 87 | HK10 | 184 | --------- |
| 88 | S2 | 184 | MVMFSGVDA |
| 90 | S54 | 184 | MVMFSGVDA |
| 89 | S52 | 184 | MIMFSGVDA |
| 86-90 | consensus | | MvMFSGVDA |

FIG. 2F

| SEQ ID NO: | Isolate | | |
|---|---|---|---|
| 93 | Z7 | 1 | VNYhNASGVYHiTNDCPNSSImYEAEHHILHLPGCVPCVReGNQSRCWVALTPTVAAPYIG |
| 94 | Z6 | 1 | VNYrNASGVYHvTNDCPNSSIVYEAEHqILHLPGClPCVRvGNQSRCWVALTPTVAvsYIG |
| 93-94 consensus | (Z6) | | VNYrNASGVYHvTNDCPNSSIVYEAEHqILHLPGClPCVRvGNQSRCWVALTPTVAvsYIG |

| SEQ ID NO: | Isolate | | |
|---|---|---|---|
| 93 | Z7 | 62 | APLESiRRHVDlMVGAATVCSALYIGDLCGGVFLVGQMFSFQPRRHWTTQDCNCSIYAGHV |
| 94 | Z6 | 62 | APLdSLRRHVDlMVGAATVCSALYvGDLCGGaFLVGQMFSFQPRRHWTTQDCNCSIYAGHI |
| 93-94 consensus | (Z6) | | APLdSlRRHVDlMVGAATVCSALYvGDLCGGaFlVGQMFSFQPRRHWTTQDCNCSIYAGHi |

| SEQ ID NO: | Isolate | | |
|---|---|---|---|
| 93 | Z7 | 123 | TGHRMAWDMMMNWSPTTTLvLAQVMRIPSTLVDLLTGGHWGiLiGvAYFcMQANWAKVILV |
| 94 | Z6 | 123 | TGHRMAWDMMMNWSPTTTLlLAQVMRIPSTLVDLLAGGHWGvLVGlAYFSMQANWAKVILV |
| 93-94 consensus | (Z6) | | TGHRMAWDMMMNWSPTTTLlLAQVMRIPSTLVDLLaGGHWGvLvGlAYFsMQANWAKVILV |

| SEQ ID NO: | Isolate | | |
|---|---|---|---|
| 93 | Z7 | 184 | LFLyAGVDA |
| 94 | Z6 | 184 | LFLfAGVDA |
| 93-94 consensus | (Z6) | | LFLfAGVDA |

FIG. 2G-1

| SEQ ID NO: | Isolate | | |
|---|---|---|---|
| 98 | SA5 | 1 | VPYRNASGVYHVTNDCPNSSIVYEADNLILHAPGCVPCVKegNVSRCWVQITPTLSAPNLG |
| 100 | SA7 | 1 | VPYRNASGVYHVTNDCPNSSIVYEADNLILHAPGCVPCVRQnNVSRCWVQITPTLSAPNLG |
| 97 | SA4 | 1 | VPYRNASGVYHVTNDCPNSSIVYEADNLILHAPGCVPCVRQDNVSkCWVQITPTLSAPNLG |
| 96 | SA1 | 1 | VPYRNASGVYHVTNDCPNSSIVYEAdsLILHAPGCVPCVRQDNVSRCWVQITPTLSAPtfG |
| 99 | SA6 | 1 | VPYRNASGVYHVTNDCPNSSIVYEADDLILHAPGCVPCVRkDNVSRCWVhITPTLSAPSLG |
| 101 | SA13 | 1 | VPYRNASGVYHVTNDCPNSSIVYEADDLILHAPGCVPCVRggNVSRCWVqITPTLSAPSLG |
| 96-101 | consensus | | VPYRNASGVYHVTNDCPNSSIVYEAdNlILHAPGCVPCVrqdNVSrCWVqITPTLSAPnlG |

| SEQ ID NO: | Isolate | | |
|---|---|---|---|
| 98 | SA5 | 62 | AVTAPLRRvVDYLAGGAALCSALYVGDACGAVFLVGQMFtYRPRQHTTVQDCNCSIYSGHI |
| 100 | SA7 | 62 | AVTAPLRRAVDYLAGGAALCSALYVGDACGAVFLVGQMFsYRPRQHTTVQDCNCSIYSGHI |
| 97 | SA4 | 62 | AVTAPLRRAVDYLAGGAALCSALYVGDACGAVFLVGQMFTYRPRQHTTVQDCNCSIYSGHI |
| 96 | SA1 | 62 | AVTAPLRRAVDYLAGGAALCSALYVGDACGAVFLVGQMFTYRPRQHTTVQDCNCSIYSGHI |
| 99 | SA6 | 62 | AVTAPLRRAVDYLAGGAALCSALYVGDvCGA1FLVGQMFTYRPRQHaTVQDCNCSIYSGHI |
| 101 | SA13 | 62 | AVTAPLRRAVDYLAGGAALCSALYVGDaCGAVFLVGQMFTYsPRrHnvVQDCNCSIYSGHI |
| 96-101 | consensus | | AVTAPLRRaVDYLAGGAALCSALYVGDaCGAvFLVGQMFtYrPRqHttVQDCNCSIYSGHI |

FIG. 2G-2

| SEQ ID NO: | Isolate | | |
|---|---|---|---|
| 98 | SA5 | 123 | TGHRMAWDMMMNWSPTTALVMAQvLRIPQVVIDIIAGGHWGVLFAvAYFASAANWAKVVLV |
| 100 | SA7 | 123 | TGHRMAWDMMMNWSPTTALVMAQLLRIPQVVIDIIAGGHWGVLFAAAYFASAANWAKVVLV |
| 97 | SA4 | 123 | TGHRMAWDMMMNWSPTTALLMAQLLRIPQVVIDIIAGGHWGVLFAAAYFASAANWAKViLV |
| 96 | SA1 | 123 | TGHRMAWDMMMNWSPTTALLMAQLLRIPQVVIDIIAGGHWGVLFAAAYFASAANWAKVVLV |
| 99 | SA6 | 123 | TGHRMAWDMMMNWSPaTALVMAQMLRIPQVVIDIIAGGHWGVLFAAAYFASAANWAKVVLV |
| 101 | SA13 | 123 | TGHRMAWDMMMNWSPtTALVMAQllRIPQVVIDIIAGaHWGVLFAAAYaSAANWAKVVLV |
| 96-101 | consensus | | TGHRMAWDMMMNWSPtTALvMAQlLRIPQVVIDIIAGgHWGVLFAaAYfASAANWAKVvLV |

| SEQ ID NO: | Isolate | | |
|---|---|---|---|
| 98 | SA5 | 184 | LFLFAGVDg |
| 100 | SA7 | 184 | LFLFAGVDA |
| 97 | SA4 | 184 | LFLFAGVDA |
| 96 | SA1 | 184 | LFLFAGVDg |
| 99 | SA6 | 184 | LFLFAGVDA |
| 101 | SA13 | 184 | LFLFAGVDA |
| 96-101 | consensus | | LFLFAGVDa |

FIG. 2H-1

| SEQ ID NO: | Genotype | | |
|---|---|---|---|
| 81-84 | (IV/2b) | 1 | VEVRNiSsSYYATNDCSNnSITTWQLTnAVLHLPGCVPCENDNGTLrCWIQVTPNVAVKHRG |
| 85 | (2c) | 1 | VEVKDTGDSYMPTNDCSNSSIVWQLEGAVLHTPGCVPCERTANVSRCWVPVAPNLAISQPG |
| 77-80 | (III/2a) | 1 | aqVkNTstsYMVTNDCSNdSITWQLqAAVLHVPGCvPCEkvGNtSRCWIPVsPNVAVqqPG |
| 86-90 | (V/3a) | 1 | LEWRNtSGLYvLTNDCSNSSIVYEADDVILHTPGCVPCVQDGNTStCWTpVTPTVAVRYVG |
| 60-76 | (II/1b) | 1 | yEVrNVSGvYhVTNDCSNsSiVyEaaDmImHTPGCvPCVrEnNsSrCWVALtPTLAARNas |
| 52-59 | (I/1a) | 1 | yQVRNStGLYHVTNDCPNSSIVYEaADaILHsPGCVPCVREgnasrCWVavtPTVATRDGK |
| 91 | (4a) | 1 | EHYRNASGIYHITNDCPNSSIVYEADHHILHLPGCVPCVMIGNTSRCWTPVTPTVAVAHPG |
| 93-94 | (4c) | 1 | VNYrNASGVYHvTNDCPNSSIVYEAEHqILHLPGC1PCVRvGNQSRCWVALTPTVAvsYIG |
| 95 | (4d) | 1 | YNYRNSSGVYHVTNDCPNSSIVYETDYHILHLPGCVPCVREGNKSTCWVSLTPTVAAQHLN |
| 92 | (4b) | 1 | VHYRNASGVYHVTNDCPNTSIVYETEHHIMHLPGCVPCVRTENTSRCWVPLTPTVAAPYPN |
| 96-101 | (5a) | 1 | VPYRNASGVYHVTNDCPNSSIVYEADnLILHAPGCVPCVrqdNVSrCWVqITPTLSAPnlG |
| 102 | (6a) | 1 | LTYGNSSGLYHLTNDCPNSSIVLEADAMILHLPGCLPCVRVDDRSTCWHAVTPTLAIPNAS |

| 52-102 | consensus | Y TNDC N S H PGC PC CW P |

| SEQ ID NO: | Genotype | | |
|---|---|---|---|
| 81-84 | (IV/2b) | 62 | ALTHNLRtHvDmIVMAAATVCSALYVGDVCGAVMIvSQAfIiSPErHnFTQeCNCSIYQGhI |
| 85 | (2c) | 62 | ALTKGLRAHIDIIVMSATVCSALYVGDVCGALMLAAQVVVVSPQHHTFVQECNCSIYPGRI |
| 77-80 | (III/2a) | 62 | ALTQGLRTHIDMVVMSATLCSALYIGDVCGGvMLAAQMFIvSPqhHwFVQeCNCSIYPGTI |
| 86-90 | (V/3a) | 62 | ATTASIRSHVDLLVGAATmCSALYVGDmCGAVFLVGQAFTFRPRRHQTVQTCNCSLYPGH1 |
| 60-76 | (II/1b) | 62 | vpTttIRrHVDLLVGAAaFCSaMYVGDLCGSVFLvSQLFTfSPRrheTVQdCNCSiYPGhv |
| 52-59 | (I/1a) | 62 | LPatQLRRhIDLLVGSATLCSALYVGDLCGSVFLVgQLFTfSPRrhWTTQdCNCSIYPGHI |
| 91 | (4a) | 62 | APLESFRRHVDLMVGAATLCSALYVGDLCGGAFLMGQMITFRPRRHWTTQECNCSIYTGHI |
| 93-94 | (4c) | 62 | APLdSIRRHVDLMVGAATVCSALYvGDLCGGaFLVGQMFSFQPRRHWTTQDCNCSIYAGHi |
| 95 | (4d) | 62 | APLESLRRHVDLMVGGATLCSALYIGDVCGGVFLVGQLFTFQPRRHWTTQDCNCSIYTGHI |
| 92 | (4b) | 62 | APLESMRRHVDLMVGAATMCSAFYIGDLCGaCGAvFLVGQLFDFRPRRHWTTQDCNCSIYSGHI |
| 96-101 | (5a) | 62 | AVTAPLRRaVDYLAGGAALCSALYVGDaCGAvFLVGQMFYrPRqHttVQDCNCSIYSGHI |
| 102 | (6a) | 62 | TPATGFRRHVDLLAGAAVVCSSLYIGDLCGSLFLAGQLFTFQPRRHWTVQDCNCSIYTGHV |

| 52-102 | consensus | R D A CS Y GD CG Q P Q CNCS Y G |

FIG. 2H-2

| SEQ ID NO: | Genotype | | |
|---|---|---|---|
| 81-84 | (IV/2b) | 123 | TGHRMAWDMMILNWSPTLTMILAYAARVPELvLeVVFGGHWGVVFGLAYFSMQGAWAKVIAI |
| 85 | (2c) | 123 | TGHRMAWDMMMNWSPTTTMLLAYLVRIPEVILDIVTGGHWGVMFGLAYFSMQGSWAKVIVI |
| 77-80 | (III/2a) | 123 | TGHRMAWDMMMNWSPTaTmILAYaMRVPEVIiDIisGAHWGVmFGLAYFSMQGAWAKVvVI |
| 86-90 | (V/3a) | 123 | SGHRMAWDMMMNWSPAVGMVVAHvLRLPQT1FDIiAGAHWGIiAGLAYYSMQGNWAKVAIi |
| 60-76 | (II/1b) | 123 | sGHRMAWDMMMNWSPTaALVvSQLLRiPQAvvDmVaGAHWGvLAGLAYYSMvGNWAKVLIV |
| 52-59 | (I/1a) | 123 | TGHRMAWDMMMNWSPTtALvVAQLLRiPQAiLDMIAGAHWGVLAGIAYFSMvGNWAKV1vV |
| 91 | (4a) | 123 | TGHRMAWDMMMNWSPTTTLLLAQIMRVPTAFLDMVAGGHWGVLAGLAYFSMQGNWAKVVLV |
| 93-94 | (4c) | 123 | TGHRMAWDMMMNWSPTTTLLLAQVMRIPSTLvDLLaGGHWGVlvG1AYFSMQANWAKVILv |
| 95 | (4d) | 123 | TGHRMAWDMMMNWSPTATLVLAQILMRIPGAMVDLLAGGHWGILVGIAYFSMQANWAKVILv |
| 92 | (4b) | 123 | SGHRMAWDMMMNWSPTSALIMAQILRIPSILGDLLTGGHWGVLAGLAFFSMQSNWAKVILv |
| 96-101 | (5a) | 123 | TGHRMAWDMMMNWSPtTALvMAQlLRIPQVVIDIIAGgHWGVLFAaAYfASAANWAKVvLV |
| 102 | (6a) | 123 | TGHRMAWDMMMNWSPTTTLVLSSILRVPEICASVIFGGHWGILLAVAYFGMAGNWLKVLAV |

| 52-102 | consensus | GHRMAWDMM NWSP | R P | G HWG | A | W KV |

| SEQ ID NO: | Genotype | | |
|---|---|---|---|
| 81-84 | (IV/2b) | 184 | LLLVAGVDA |
| 85 | (2c) | 184 | LLLITAGVEA |
| 77-80 | (III/2a) | 184 | LlLaAGVDA |
| 86-90 | (V/3a) | 184 | MvMFSGVDA |
| 60-76 | (II/1b) | 184 | mLLFaGVDG |
| 52-59 | (I/1a) | 184 | LLLFaGVDA |
| 91 | (4a) | 184 | LFLFAGVDA |
| 93-94 | (4c) | 184 | LFlFAGVDA |
| 95 | (4d) | 184 | LFLFAGVDA |
| 92 | (4b) | 184 | LFLFAGVEG |
| 96-101 | (5a) | 184 | LFLFAGVDa |
| 102 | (6a) | 184 | LFLFAGVEA |

| 52-102 | consensus | GV |

NUCLEOTIDE AND DEDUCED AMINO ACID SEQUENCES OF THE ENVELOPE 1 GENE OF 51 ISOLATES OF HEPATITIS C VIRUS AND THE USE OF REAGENTS DERIVED FROM THESE SEQUENCES IN DIAGNOSTIC METHODS AND VACCINES

This is a divisional of co-pending application Ser. No. 08/086,428 filed Jun. 29, 1993.

FIELD OF INVENTION

The present invention is in the field of hepatitis virology. The invention relates to the complete nucleotide and deduced amino acid sequences of the envelope 1 (E1) gene of 51 hepatitis C virus (HCV) isolates from around the world and the grouping of these isolates into twelve distinct HCV genotypes. More specifically, this invention relates to oligonucleotides, peptides and recombinant proteins derived from the envelope 1 gene sequences of the 51 isolates of hepatitis C virus and to diagnostic methods and vaccines which employ these reagents.

BACKGROUND OF INVENTION

Hepatitis C, originally called non-A, non-B hepatitis, was first described in 1975 as a disease serologically distinct from hepatitis A and hepatitis B (Feinstone, S. M. et al. (1975) N. Engl. J. Med. 292:767–770). Although hepatitis C was (and is) the leading type of transfusion-associated hepatitis as well as an important part of community-acquired hepatitis, little progress was made in understanding the disease until the recent identification of hepatitis C virus (HCV) as the causative agent of hepatitis C via the cloning and sequencing of the HCV genome (Choo, A. L. et al. (1989) Science 288:359–362). The sequence information generated by this study resulted in the characterization of HCV as a small, enveloped, positive-stranded RNA virus and led to the demonstration that HCV is a major cause of both acute and chronic hepatitis worldwide (Weiner, A. J. et al. (1990) Lancet 335:1–3). These observations, combined with studies showing that over 50% of acute cases of hepatitis C progress to chronicity with 20% of these resulting in cirrhosis and an undetermined proportion progressing to liver cancer, have led to tremendous efforts by investigators within the hepatitis C field to develop diagnostic assays and vaccines which can detect and prevent hepatitis C infection.

The cloning and sequencing of the HCV genome by Choo et al. (1989) has permitted the development of serologic tests which can detect HCV or antibody to HCV (Kuo, G. et al. (1989) Science 244:362–364). In addition, the work of Choo et al. has also allowed the development of methods for detecting HCV infection via amplification of HCV RNA sequences by reverse transcription and cDNA polymerase chain reaction (RT-PCR) using primers derived from the HCV genomic sequence (Weiner, A. J. et al.). However, although the development of these diagnostic methods has resulted in improved diagnosis of HCV infection, only approximately 60% of cases of hepatitis C are associated with a factor identified as contributing to transmission of HCV (Alter, M. J. et al. (1989) JAMA 262:1201–1205). This observation suggests that effective control of hepatitis C transmission is likely to occur only via universal pediatric vaccination as has been initiated recently for hepatitis B virus. Unfortunately, attempts to date to protect chimpanzees from hepatitis C infection via administration of recombinant vaccines have had only limited success. Moreover, the apparent genetic heterogeneity of HCV, as indicated by the recent assignment of all available HCV isolates to one of four genotypes, I–IV (Okamoto, H. et al. (1992) J. Gen. Virol; 73:673–679), presents additional hurdles which must be overcome in order to develop accurate and effective diagnostic assays and vaccines.

For example, one possible obstacle to the development of effective hepatitis C vaccines would arise if the observed genetic heterogeneity of HCV reflects serologic heterogeneity. In such a case, the most genetically diverse strains of HCV may then represent different serotypes of HCV with the result being that infection with one strain may not protect against infection with another. Indeed, the inability of one strain to protect against infection with another strain was recently noted by both Farci et al. (Farci, P. et al. (1992) Science 258:135–140) and Prince et al. (Prince, A. M. et al. (1992) J. Infect. Dis. 165:438–443), each of whom presented evidence that while infection with one strain of HCV does modify the degree of the hepatitis C associated with the reinfection, it does not protect against reinfection with a closely related strain. The genetic heterogeneity among different HCV strains also increases the difficulty encountered in developing RT-PCR assays to detect HCV infection since such heterogeneity often results in false-negative results because of primer and template mismatch. In addition, currently used serologic tests for detection of HCV or for detection of antibody to HCV are not sufficiently well developed to detect all of the HCV genotypes which might exist in a given blood sample. Finally, in terms of choosing the proper treatment modality to combat hepatitis infection, the inability of presently available serologic assays to distinguish among the various genotypes of HCV represents a significant shortcoming in that recent reports suggest that an HCV-infected patient's response to therapy might be related to the genotype of the infectious virus (Yoshioka, K. et al. (1992) Hepatology 16:293–299; Kanai, K. et al. (1992) Lancet 339:1543; Lan, J. Y. N. et al. (1992) Hepatology 16:209A). Indeed, the data presented in the above studies suggest that the closely related genotypes I and II are less responsive to interferon therapy than are the closely related genotypes III and IV. Moreover, preliminary data by Pozzato et al. (Pozzato, G. et al. (1991) Lancet 338:509) suggests that different genotypes may be associated with different types or degrees of clinical disease. Taken together, these studies suggest that before effective vaccines against HCV infection can be developed, and indeed, before more accurate and effective methods for diagnosis and treatment of HCV infection can be produced, one must obtain a greater knowledge about the genetic and serologic diversity of HCV isolates.

In a recent attempt to gain an understanding of the extent of genetic heterogeneity among HCV strains, Bukh et al. carried out a detailed analysis of HCV isolates via the use of PCR technology to amplify different regions of the HCV genome (Bukh, J. et al. (1992a) Proc. Natl. Acad. Sci. 89:187–191). Following PCR amplification, the 5'-noncoding (5' NC) portion of the genomes of various HCV isolates were sequenced and it was found that primer pairs designed from conserved regions of the 5' NC region of the HCV genome were more sensitive for detecting the presence of HCV than were primer pairs representing other portions of the genome (Bukh, J. et al. (1992b) Proc. Natl. Acad. Sci. U.S.A. 89:4942–4946). In addition, the authors noted that although many of the HCV isolates examined could be classified into the four genotypes described by Okamoto et al. (1992), other previously undescribed genotypes emerged based on genetic heterogeneity observed in the 5' NC region of the various isolates. One of the most prominent of these newly noted genotypes comprised a group of related viruses that contained the most genetically divergent 5' NC regions of those studied. This group of viruses, tentatively classified as a fifth genotype, are very similar to strains recently described by others (Cha, T.-A et al. (1992) Proc. Natl. Acad. Sci. U.S.A. 89:7144–7148; Chan, S-W. et al. (1992) J. Gen. Virol., 73:1131–1141 and Lee, C-H et al. (1992) J. Clin. Microbio. 30:1602–1604). In addition, at least four more putative genotypes were identified thereby providing evidence that the genetic heterogeneity of HCV was more extensive than previously appreciated.

However, while the studies of Bukh et al. (1992a and b) provided new and useful information on the genetic heterogeneity of HCV, it is widely appreciated by those skilled in the art that the three structural genes of HCV, core (C), envelope (E1) and envelope 2/nonstructural 1 (E2/NS1) are the most important for the development of serologic diagnostics and vaccines since it is the product of these genes that constitutes the hepatitis C virion. Thus, a determination of the nucleotide sequence of one or all of the structural genes of a variety of HCV isolates would be useful in designing reagents for use in diagnostic assays and vaccines since a demonstration of genetic heterogeneity in a structural gene(s) of HCV isolates might suggest that some of the HCV genotypes represent distinct serotypes of HCV based upon the previously observed relationship between genetic heterogeneity and serologic heterogeneity among another group of single-stranded, positive-sense RNA viruses, the picornaviruses (Ruechert, R. R. "Picornaviridae and their replication", in Fields, B. N. et al., eds. Virology, New York: Raven Press, Ltd. (1990) 507–548).

SUMMARY OF INVENTION

The present invention relates to 51 cDNAs, each encoding the complete nucleotide sequence of the envelope 1 (E1) gene of an isolate of human hepatitis C virus (HCV).

The present invention also relates to the nucleic acid and deduced amino acid sequences of these E1 cDNAs.

It is an object of this invention to provide synthetic nucleic acid sequences capable of directing production of recombinant E1 proteins, as well as equivalent natural nucleic acid sequences. Such natural nucleic acid sequences may be isolated from a cDNA or genomic library from which the gene capable of directing synthesis of the E1 proteins may be identified and isolated. For purposes of this application, nucleic acid sequence refers to RNA, DNA, cDNA or any synthetic variant thereof which encodes for peptides.

The invention also relates to the method of preparing recombinant E1 proteins derived from the E1 cDNA sequences by cloning the nucleic acid and inserting the cDNA into an expression vector and expressing the recombinant protein in a host cell.

The invention also relates to isolated and substantially purified recombinant E1 proteins and analogs thereof encoded by the E1 cDNAs.

The invention further relates to the use of recombinant E1 proteins as diagnostic agents and as vaccines.

The invention also relates to the use of single-stranded antisense poly- or oligonucleotides derived from the E1 cDNAs to inhibit the expression of the hepatitis C E1 gene.

The invention further relates to multiple computer-generated alignments of the nucleotide and deduced amino acid sequences of the 51 E1 cDNAs. These multiple sequence alignments serve to highlight regions of homology and non-homology between different sequences and hence, can be used by one skilled in the art to design peptides and oligonucleotides useful as reagents in diagnostic assays and vaccines.

The invention therefore also relates to purified and isolated peptides and analogs thereof derived from E1 cDNA sequences.

The invention further relates to the use of these peptides as diagnostic agents and vaccines.

The present invention also encompasses methods of detecting antibodies specific for hepatitis C virus in biological samples. The methods of detecting HCV or antibodies to HCV disclosed in the present invention are useful for diagnosis of infection and disease caused by HCV and for monitoring the progression of such disease. Such methods are also useful for monitoring the efficacy of therapeutic agents during the course of treatment of HCV infection and disease in a mammal.

The invention also provides a kit for the detection of antibodies specific for HCV in a biological sample where said kit contains at least one purified and isolated peptide derived from the E1 cDNA sequences.

The invention further provides isolated and purified genotype-specific oligonucleotides and analogs thereof derived from E1 cDNA sequences.

The invention also relates to a method for detecting the presence of hepatitis C virus in a mammal, said method comprising analyzing the RNA of a mammal for the presence of hepatitis C virus. The invention further relates to a method for determining the genotype of hepatitis C virus present in a mammal. This method is useful in determining the proper course of treatment for an HCV-infected patient.

The invention also provides a diagnostic kit for the detection of hepatitis C virus in a biological sample. The kit comprises purified and isolated nucleic acid sequences useful as primers for reverse-transcription polymerase chain reaction (RT-PCR) analysis of RNA for the presence of hepatitis C virus.

The invention further provides a diagnostic kit for the determination of the genotype of a hepatitis C virus present in a mammal. The kit comprises purified and isolated nucleic acid sequences useful as primers for RT-PCR analysis of RNA for the presence of HCV in a biological sample and purified and isolated nucleic acid sequences useful as hybridization probes in determining the genotype of the HCV isolate detected in PCR.

This invention also relates to pharmaceutical compositions for use in prevention or treatment of hepatitis C in a mammal.

DESCRIPTION OF FIGURES

FIGS. 1A-1 through 1H-5 show computer generated sequence alignments of the nucleotide sequences of the 51 HCV E1 cDNAs. The single letter abbreviations used for the nucleotides shown in FIGS. 1A-1 through 1H-5 are those standardly used in the art. FIGS. 1A-1 through 1A-10 show the alignment of SEQ ID NOs:1–8 to produce a consensus sequence for genotype I/1a. FIGS. 1B-1 through 1B-10 show the alignment of SEQ ID NOs:9–25 to produce a consensus sequence for genotype II/1b. FIGS. 1C-1 through 1C-5 show the alignment of SEQ ID NOs:26–29 to produce a consensus sequence for genotype III/2a. FIGS. 1D-1 through 1D-5 show the alignment of SEQ ID NOs:30–33 to produce a consensus sequence for genotype IV/2b. FIGS. 1E-1 through 1E-5 show the alignment of SEQ ID NOs:35–39 to produce a consensus sequence for genotype V/3a. FIGS. 1F-1 through 1F-3 show the computer alignment of SEQ ID NOs:42–43 to produce a consensus sequence for genotype 4C. FIGS. 1G-1 through 1G-5 show the alignment of SEQ ID NOs:45–50 to produce a consensus sequence for genotype 5a. The nucleotides shown in capital letters in the consensus sequences of FIGS. 1A-1 through 1G-5 are those conserved within a genotype while nucleotides shown in lower case letters in the consensus sequences are those variable within a genotype. In addition, in FIGS. 1A-1 through 1E-5 and 1G-1 through 1G-5, when the lower case letter is shown in a consensus sequence, the lower case letter represents the nucleotide found most frequently in the sequences aligned to produce the consensus sequence. In FIGS. 1E-1 through 1E-5, the lower case letters shown in the consensus sequence are nucleotides in SEQ ID NO:42 which differ from nucleotides found in the same positions in SEQ ID NO:43. Finally, a hyphen at a nucleotide position in the consensus sequences in FIGS. 1A-1 through 1G-5 indicates that two nucleotides were found in equal numbers at that position in the aligned sequences. In the aligned sequences, nucleotides are shown in lower case letters if they differed from the nucleotides of both adjacent isolates. FIGS. 1H-1 through 1H-5 show the alignment of the consensus sequences of FIGS. 1A-1 through 1G-5 with SEQ ID NO:34 (genotype 2c), SEQ ID NO:40 (genotype 4a), SEQ ID NO:41 (genotype 4b), SEQ ID NO:44 (genotype 4d) and SEQ ID NO:51 (genotype 6a) to produce a consensus sequence for all twelve genotypes. This consensus sequence is shown as the bottom line of FIGS. 1H-1 through 1H-5 where the nucleotides shown in capital letters are conserved among all genotypes and a blank space indicates that the nucleotide at that position is not conserved among all genotypes.

FIGS. 2A-1 through 2H-2 show computer alignments of the deduced amino acid sequences of the 51 HCV E1 cDNAs. The single letter abbreviations used for the amino acids shown in FIGS. 2A-1 through 2H-2 follow the conventional amino acid shorthand for the twenty naturally occurring amino acids. FIGS. 2A-1 through 2A-4 show the alignment of SEQ ID NOs:52–59 to produce a consensus sequence for genotype I/1a. FIGS. 2B-1 through 2B-4 show the alignment of SEQ ID NOs:60–76 to produce a consensus sequence for genotype II/1b. FIGS. 2C-1 through 2C-2 show the alignment of SEQ ID NOs:77–80 to produce a consensus sequence for genotype III/2a. FIGS. 2D-1 and 2D-2 show the alignment of SEQ ID NOs:81–84 to produce a consensus sequence for genotype IV/2b. FIGS. 2E-1 and 2E-2 show the alignment of SEQ ID NOs:86–90 to produce a consensus sequence for genotype V/3a. FIG. 2F shows the computer alignment of SEQ ID NOs:93–94 to produce a consensus sequence for genotype 4c. FIGS. 2G-1 and 2G-2 show the alignment of SEQ ID NOs:96–101 to produce a consensus sequence for genotype 5a. The amino acids shown in capital letters in the consensus sequences of FIGS. 2A-1 through 2G-2 are those conserved within a genotype while amino acids shown in lower case letters in the consensus sequences are those variable within a genotype. In addition, in FIGS. 2A-1 through 2E-2 and 2G-1 through 2G-2 when the lower case letter is shown in a consensus sequence, the letter represents the amino acid found most frequently in the sequences aligned to produce the consensus sequence. In FIG. 2F, the lower case letters shown in the consensus sequence are amino acids in SEQ ID NO:93 which differ from amino acids found in the same positions in SEQ ID NO:94. Finally, a hyphen at an amino acid position in the consensus sequences of FIGS. 2A-1 through 2G-2 indicates that two amino acids were found in equal numbers at that position in the aligned sequences. In the aligned sequences, amino acids are shown in lower case letters if they differed from the amino acids of both adjacent isolates. FIGS. 2H-1 and 2H-2 show the alignment of the consensus sequences of FIGS. 1A–G with SEQ ID NO:85 (genotype 2c), SEQ ID NO:91 (genotype 4a), SEQ ID NO:92 (genotype 4b), SEQ ID NO:95 (genotype 4d) and SEQ ID NO:102 (genotype 6a) to produce a consensus sequence for all twelve genotypes. This consensus sequence is shown as the bottom line of FIGS. 2H-1 and 2H-2 where the amino acids shown in capital letters are conserved among all genotypes and a blank space indicates that the amino acid at that position is not conserved among all genotypes.

FIGS. 3A and 3B show multiple sequence alignment of the deduced amino acid sequence of the E1 gene of 51 HCV isolates collected worldwide. The consensus sequence of the E1 protein is shown in boldface (top). In the consensus sequence cysteine residues are highlighted with stars, potential N-linked glycosylation sites are underlined, and invariant amino acids are capitalized, whereas variable amino acids are shown in lower case letters. In the alignment, amino acids are shown in lower case letters if they differed from the amino acid of both adjacent isolates. Amino acid residues shown in bold print in the alignment represent residues which at that position in the amino acid sequence are genotype-specific. Amino acids that were invariant among all HCV isolates are shown as hyphens (-) in the alignment. Amino acid positions correspond to those of the HCV prototype sequence (HCV-1, Choo, L. et al. (1991) Proc. Natl. Acad. Sci. USA 88:2451–2455) with the first amino acid of the E1 protein at position 192. The grouping of isolates into 12 genotypes (I/1a, II/1b, III/2a, IV/2b, V/3a, 2c, 4a, 4b, 4c, 4d, 5a and 6a) is indicated.

FIG. 4 shows a dendrogram of the genetic relatedness of the twelve genotypes of HCV based on the percent amino acid identity of the E1 gene of the HCV genome. The twelve genotypes shown are designated as I/1a, II/1b, III/2a, IV/2b, V/3a, 2c, 4a, 4b, 4c, 4d, 5a and 6a. The shaded bars represent a range showing the maximum and minimum homology between the amino acid sequence of any one isolate of the genotype indicated and the amino acid sequence of any other isolate.

FIG. 5 shows the distribution of the complete E1 gene sequence of 74 HCV isolates into the twelve HCV genotypes in the 12 countries studied. For 51 of these HCV isolates, including 8 isolates of genotype I/1a, 17 isolates of genotype II/1b and 26 isolates comprising the additional 10 genotypes, the complete E1 gene sequence was determined. In the remaining 23 isolates, all of genotypes I/1a and II/1b, the genotype assignment was based on only a partial E1 gene sequence. The partially sequenced isolates did not represent additional genotypes in any of the 12 countries. The number of isolates of a particular genotype is given in each of the 12 countries studied. For ease of viewing, those genotypes designated by two terms (e.g., I/1a) are indicated by the latter term (e.g. 1a). The designations used for each country are: Denmark (DK); Dominican Republic (DR); Germany (D); Hong Kong (HK); India (IND); Sardinia, Italy (S); Peru (P); South Africa (SA); Sweden (SW); Taiwan (T); United States (US); and Zaire (Z). National borders depicted in this figure represent those existing at the time of sampling.

DETAILED DESCRIPTION OF INVENTION

Figure 4:
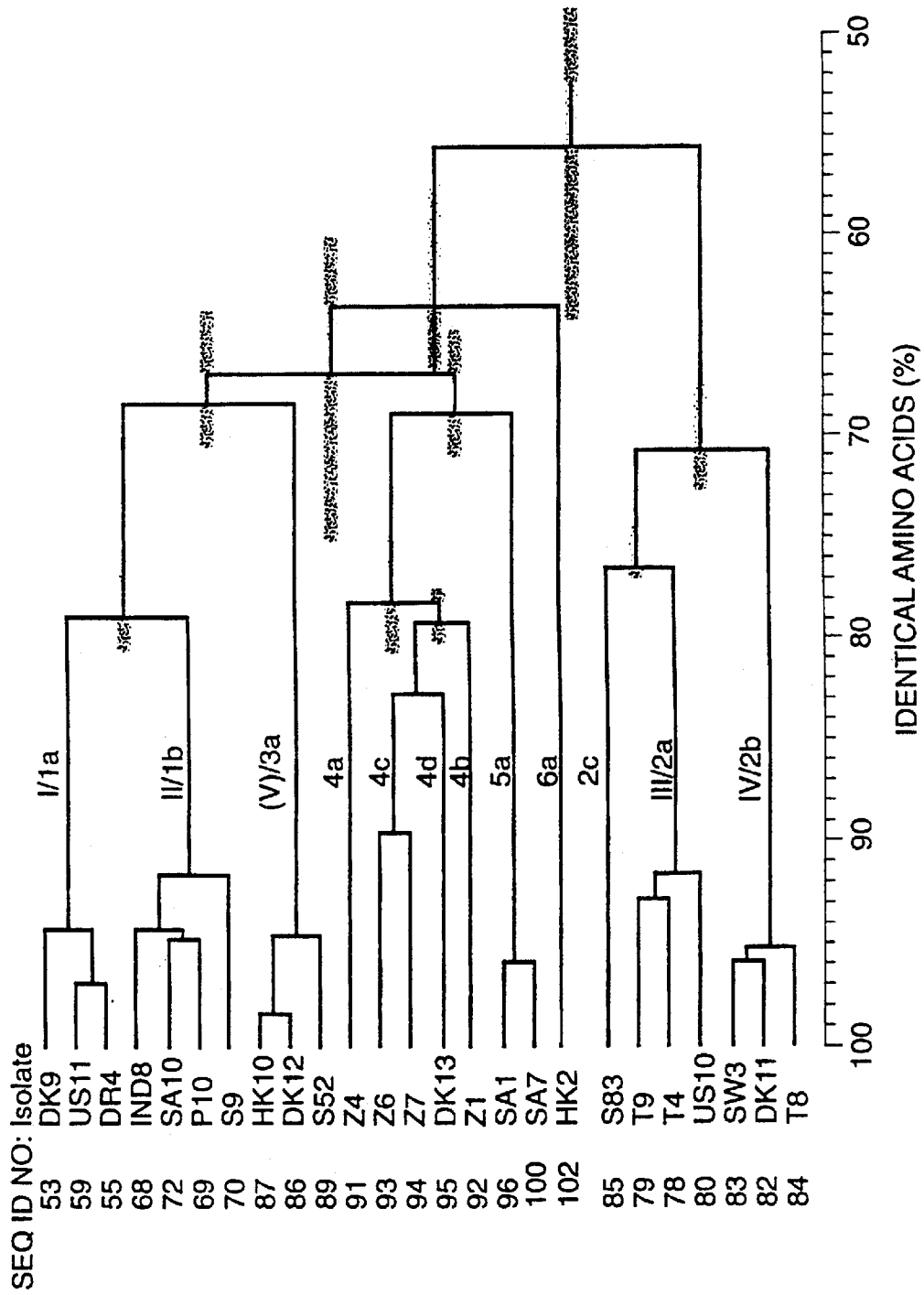

The present invention relates to 51 cDNAs, each encoding the complete nucleotide sequence of the envelope 1 (E1)

gene of an isolate of human hepatitis C virus (HCV). The cDNAs of the present invention were obtained as follows. Viral RNA was extracted from serum collected from humans infected with hepatitis C virus and the viral RNA was then reverse transcribed and amplified by polymerase chain reaction using primers deduced from the sequence of the HCV strain H-77 (Ogata, N. et al. (1991) Proc. Natl. Acad. Sci. U.S.A. 88:3392–3396). The amplified cDNA was then isolated by gel electrophoresis and sequenced.

The present invention further relates to the nucleotide sequences of the cDNAs encoding the E1 gene of the 51 HCV isolates. These nucleotide sequences are shown in the sequence listing as SEQ ID NO:1 through SEQ ID NO:51.

The abbreviations used for the nucleotides are those standardly used in the art.

The deduced amino acid sequence of each of SEQ ID NO:1 through SEQ ID NO:51 are presented in the sequence listing as SEQ ID NO:52 through SEQ ID NO:102 where the amino acid sequence in SEQ ID NO:52 is deduced from the nucleotide sequence shown in SEQ ID NO:1, the amino acid sequence shown in SEQ ID NO:53 is deduced from the nucleotide sequence shown in SEQ ID NO:2 and so on. The deduced amino acid sequence of each of SEQ ID Nos:52–102 starts at nucleotide 1 of the corresponding sequence shown in SEQ ID NOs:1–51 and extends 595 nucleotides.

The three letter abbreviations used in SEQ ID Nos:52–102 follow the conventional amino acid shorthand for the twenty naturally occurring amino acids.

Preferably, the E1 proteins or peptides of the present invention are substantially homologous to, and most preferably biologically equivalent to, the native HCV E1 proteins or peptides. By "biologically equivalent" as used throughout the specification and claims, it is meant that the compositions are immunogenicically equivalent to the native E1 proteins or peptides. The E1 proteins or peptides of the present invention may also stimulate the production of protective antibodies upon injection into a mammal that would serve to protect the mammal upon challenge with HCV. By "substantially homologous" as used throughout the ensuing specification and claims to describe E1 proteins and peptides, it is meant a degree of homology in the amino acid sequence to the native E1 proteins or peptides. Preferably the degree of homology is in excess of 90, preferably in excess of 95, with a particularly preferred group of proteins being in excess of 99 homologous with the native E1 proteins or peptides.

Variations are contemplated in the cDNA sequences shown in SEQ ID NO:1 through SEQ ID NO:51 which will result in a DNA sequence that is capable of directing production of analogs of the corresponding envelope 1 (E1) protein shown in SEQ ID NO:52 through SEQ ID NO:102. It should be noted that the DNA sequences set forth above represent a preferred embodiment of the present invention. Due to the degeneracy of the genetic code, it is to be understood that numerous choices of nucleotides may be made that will lead to a DNA sequence capable of directing production of the instant E1 protein or its analogs. As such, DNA sequences which are functionally equivalent to the sequence set forth above or which are functionally equivalent to sequences that would direct production of analogs of the E1 proteins produced pursuant to the amino acid sequences set forth above, are intended to be encompassed within the present invention.

The term analog as used throughout the specification or claims to describe the E1 proteins or peptides of the present invention, includes any protein or peptide having an amino acid residue sequence substantially identical to a sequence specifically shown herein in which one or more residues have been conservatively substituted with a biologically equivalent residue. Examples of conservative substitutions include the substitution of one-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or peptide is biologically equivalent to the native E1 protein or peptide.

"Chemical derivative" refers to an E1 protein or peptide having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The E1 protein or peptide of the present invention also includes any protein or peptide having one or more additions and/or deletions or residues relative to the sequence of a peptide whose sequence is shown herein, so long as the peptide is biologically equivalent to the native E1 protein or peptide.

The present invention also includes a recombinant DNA method for the manufacture of HCV E1 proteins. In this method, natural or synthetic nucleic acid sequences may be used to direct the production of E1 proteins.

In one embodiment of the invention, the method comprises:

(a) preparation of a nucleic acid sequence capable of directing a host organism to produce HCV E1 protein;

(b) cloning the nucleic acid sequence into a vector capable of being transferred into and replicated in a host organism, such vector containing operational elements for the nucleic acid sequence;

transferring the vector containing the nucleic acid and operational elements into a host organism capable of expressing the protein;

(d) culturing the host organism under conditions appropriate for amplification of the vector and expression of the protein; and (e) harvesting the protein.

In another embodiment of the invention, the method for the recombinant DNA synthesis of an HCV E1 protein encoded by any one of the nucleic acid sequences shown in SEQ ID NOs:1–51 comprises:

(a) culturing a transformed or transfected host organism containing a nucleic acid sequence capable of directing the host organism to produce a protein, under conditions such that the protein is produced, said protein exhibiting substantial homology to a native E1 protein isolated from HCV having the amino acid sequence according to any one of the amino acid sequences shown in SEQ ID NOs:52–102 or combinations thereof.

In one embodiment, the RNA sequence of an HCV isolate was isolated and cloned to cDNA as follows. Viral RNA is extracted from a biological sample collected from human subjects infected with hepatitis C and the viral RNA is then reverse transcribed and amplified by polymerase chain reaction using primers deduced from the sequence of HCV strain H-77 (Ogata et al. (1991)). Preferred primer sequences are shown as SEQ ID NOs:103–108 in the sequence listing. Once amplified, the PCR fragments are isolated by gel electrophoresis and sequenced.

The vectors contemplated for use in the present invention include any vectors into which a nucleic acid sequence as described above can be inserted, along with any preferred or required operational elements, and which vector can then be subsequently transferred into a host organism and replicated in such organisms. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable markers and at least one promoter sequence capable of initiating transcription of the nucleic acid sequence.

In construction of the recombinant for expression cloning vector of the present invention, it should additionally be noted that multiple copies of the nucleic acid sequence and its attendant operational elements may be inserted into each vector. In such an embodiment, the host organism would produce greater amounts per vector of the desired E1 protein. The number of multiple copies of the DNA sequence which may be inserted into the vector is limited only by the ability of the resultant vector due to its size, to be transferred into and replicated and transcribed in an appropriate host microorganism.

In another embodiment, restriction digest fragments containing a coding sequence for E1 proteins can be inserted into a suitable expression vector that functions in prokaryotic or eukaryotic cells. By suitable is meant that the vector is capable of carrying and expressing a complete nucleic acid sequence coding for E1 protein. Preferred expression vectors are those that function in a eukaryotic cell. Examples of such vectors include but are not limited to vaccinia virus vectors, adenovirus or herpes viruses. A preferred vector is the baculovirus transfer vector, pBlueBac.

In yet another embodiment, the selected recombinant expression vector may then be transfected into a suitable eukaryotic cell system for purposes of expressing the recombinant protein. Such eukaryotic cell systems include but are not limited to cell lines such as HeLa, MRC-5 or Cv-1. A preferred eukaryotic cell system is SF9 insect cells.

The expressed recombinant protein may be detected by methods known in the art including, but not limited to, Coomassie blue staining and Western blotting.

The present invention also relates to substantially purified and isolated recombinant E1 proteins. In one embodiment, the recombinant protein expressed by the SF9 cells can be obtained as a crude lysate or it can be purified by standard protein purification procedures known in the art which may include differential precipitation, molecular sieve chromatography, ion-exchange chromatography, isoelectric focusing, gel electrophoresis and affinity and immunoaffinity chromatography. The recombinant protein may be purified by passage through a column containing a resin which has bound thereto antibodies specific for the open reading frame (ORF) protein.

The present invention further relates to the use of recombinant E1 proteins as diagnostic agents and vaccines. In one embodiment, the expressed recombinant proteins of this invention can be used in immunoassays for diagnosing or prognosing hepatitis C in a mammal. For the purposes of the present invention, "mammal" as used throughout the specification and claims, includes, but is not limited to humans, chimpanzees, other primates and the like. In a preferred embodiment, the immunoassay is useful in diagnosing hepatitis C infection in humans.

Immunoassays of the present invention may be a radioimmunoassay, Western blot assay, immunofluorescent assay, enzyme immunoassay, chemiluminescent assay, immunohistochemical assay and the like. Standard techniques known in the art for ELISA are described in *Methods in Immunodiagnosis,* 2nd Edition, Rose and Bigazzi, eds., John Wiley and Sons, 1980 and Campbell et al., *Methods of Immunology,* W. A. Benjamin, Inc., 1964, both of which are incorporated herein by reference. Such assays may be a direct, indirect, competitive, or noncompetitive immunoassay as described in the art (Oellerich, M. 1984. *J. Clin. Chem. Clin.* BioChem 22:895–904) Biological samples appropriate for such detection assays include, but are not limited to serum, liver, saliva, lymphocytes or other mononuclear cells.

In a preferred embodiment, test serum is reacted with a solid phase reagent having surface-bound recombinant HCV E1 protein as an antigen. The solid surface reagent can be prepared by known techniques for attaching protein to solid support material. These attachment methods include non-specific adsorption of the protein to the support or covalent attachment of the protein to a reactive group on the support. After reaction of the antigen with anti-HCV antibody, unbound serum components are removed by washing and the antigen-antibody complex is reacted with a secondary antibody such as labelled anti-human antibody. The label may be an enzyme which is detected by incubating the solid support in the presence of a suitable fluorimetric or calorimetric reagent. Other detectable labels may also be used, such as radiolabels or colloidal gold, and the like.

The HCV E1 protein and analogs thereof may be prepared in the form of a kit, alone, or in combinations with other reagents such as secondary antibodies, for use in immunoassays.

In yet another embodiment the recombinant E1 proteins or analogs thereof can be used as a vaccine to protect mammals against challenge with Hepatitis C. The vaccine, which acts as an immunogen, may be a cell, cell lysate from cells transfected with a recombinant expression vector or a culture supernatant containing the expressed protein. Alternatively, the immunogen is a partially or substantially purified recombinant protein.

While it is possible for the immunogen to be administered in a pure or substantially pure form, it is preferable to present it as a pharmaceutical composition, formulation or preparation.

The formulations of the present invention, both. for veterinary and for human use, comprise an immunogen as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving the solid active ingredient in water containing physiologically compatible substances such as sodium chloride (e.g. 0.1–2.0 m), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are preferably incorporated in an amount of 0.11–10,000 parts by weight per part by weight of immunogens. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, anti-adsorption agent may be used.

Additional pharmaceutical methods may be employed to control the duration of action. Controlled release preparations may be achieved through the use of polymer to complex or adsorb the proteins or their derivatives. The controlled delivery may be exercised by selecting appropriate macromolecules (for example polyester, polyamino acids, polyvinyl pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the proteins, protein analogs or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc, magnesium stearate, crystalline cellulose, methyl cellulose, carboxymethyl cellulose, glycerin, sodium alginate or gum arabic among others.

The proteins of the present invention may be supplied in the form of a kit, alone, or in the form of a pharmaceutical composition as described above.

Vaccination can be conducted by conventional methods. For example, the immunogen or immunogens (i.e. the E1 protein may be administered alone or in combination with the E1 proteins derived from other isolates of HCV) can be used in a suitable diluent such as saline or water, or complete or incomplete adjuvants. Further, the immunogen(s) may or may not be bound to a carrier to make the protein(s) immunogenic. Examples of such carrier molecules include but are not limited to bovine serum albumin (BSA), keyhole limpet hemocyanin (KLH), tetanus toxoid, and the like. The immunogen(s) can be administered by any route appropriate for antibody production such as intravenous, intraperitoneal, intramuscular, subcutaneous, and the like. The immunogen (s) may be administered once or at periodic intervals until a significant titer of anti-HCV antibody is produced. The antibody may be detected in the serum using an immunoassay.

The administration of the immunogen(s) of the present invention may be for either a prophylactic or therapeutic purpose. When provided prophylactically, the immunogen (s) is provided in advance of any exposure to HCV or in advance of any symptom of any symptoms due to HCV infection. The prophylactic administration of the immunogen serves to prevent or attenuate any subsequent infection of HCV in a mammal. When provided therapeutically, the immunogen(s) is provided at (or shortly after) the onset of the infection or at the onset of any symptom of infection or disease caused by HCV. The therapeutic administration of the immunogen(s) serves to attenuate the infection or disease.

In addition to use as a vaccine, the compositions can be used to prepare antibodies to HCV E1 proteins. The antibodies can be used directly as antiviral agents. To prepare antibodies, a host animal is immunized using the E1 proteins native to the virus particle bound to a carrier as described above for vaccines. The host serum or plasma is collected following an appropriate time interval to provide a composition comprising antibodies reactive with the E1 protein of the virus particle. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-viral agents such as drugs.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, nonhuman mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985 Nature 314:446; Shaw et al., 1988 J. Natl. Cancer Inst. 80:15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Biedler al. 1988 J. Immunol. 141:4053, all incorporated herein by reference).

The antibodies or antigen binding fragments may also be produced by genetic engineering. The technology for expression of both heavy and light cain genes in *E. coli* is the subject of the PCT patent applications; publication number WO 901443, WO 901443, and WO 9014424 and in Huse et al., 1989 Science 246:1275–1281.

The antibodies can also be used as a means of enhancing the immune response. The antibodies can be administered in amount similar to those used for other therapeutic administrations of antibody. For example, normal immune globulin is administered at 0.02–0.1 ml/lb body weight during the early incubation period of other viral diseases such as rabies, measles, and hepatitis B to interfere with viral entry into cells. Thus, antibodies reactive with the HCV E1 protein can be passively administered alone or in conjunction with another anti-viral agent to a host infected with an HCV to enhance the immune response and/or the effectiveness of an antiviral drug.

Alternatively, anti-HCV E1 antibodies can be induced by administered anti-idiotype antibodies as immunogens. Conveniently, a purified anti-HCV E1 antibody preparation prepared as described above is used to induce anti-idiotype antibody in a host animal, the composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-HCV E1 antibodies, or by affinity chromatography using anti-HCV E1 antibodies bound to the affinity matrix. The anti-idiotype antibodies produced are similar in conformation to the authentic HCV E1 protein and may be used to prepare an HCV vaccine rather than using an HCV E1 protein.

When used as a means of inducing anti-HCV virus antibodies in an animal, the manner of injecting the antibody is the same as for vaccination purposes, namely intramuscularly, intraperitoneally, subcutaneously or the like in an effective concentration in a physiologically suitable diluent with or without adjuvant. One or more booster injections may be desirable.

The HCV E1 proteins of the invention are also intended for use in producing antiserum designed for pre- or post-exposure prophylaxis. Here an E1 protein, or mixture of E1 proteins is formulated with a suitable adjuvant and administered by injection to human volunteers, according to known methods for producing human antisera. Antibody response to the injected proteins is monitored, during a several-week period following immunization, by periodic serum sampling to detect the presence of anti-HCV E1 serum antibodies, using an immunoassay as described herein.

The antiserum from immunized individuals may be administered as a pre-exposure prophylactic measure for individuals who are at risk of contracting infection. The antiserum is also useful in treating an individual post-exposure, analogous to the use of high titer antiserum against hepatitis B virus for post-exposure prophylaxis.

For both in vivo use of antibodies to HCV virus-like particles and proteins and anti-idiotype antibodies and diagnostic use, it may be preferable to use monoclonal antibodies. Monoclonal anti-HCV E1 protein antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., N.Y., N.Y., pp. 56–97). To produce a human-human hybridoma, a human lymphocyte donor is selected. A donor known to be infected with HCV (where infection has been shown for example by the presence of anti-virus antibodies in the blood or by virus culture) may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies.

Antibodies secreted by the immortalized cells are screened to determine the clones that secrete antibodies of the desired specificity. For monoclonal anti-E1 antibodies, the antibodies must bind to HCV E1 protein. For monoclonal anti-idiotype antibodies, the antibodies must bind to anti-E1 protein antibodies. Cells producing antibodies of the desired specify are selected.

The present invention also relates to the use of single-stranded antisense poly- or oligonucleotides derived from nucleotide sequences substantially homologous to those shown in SEQ ID NOs:1–51 to inhibit the expression of hepatitis C E1 genes. By substantially homologous as used throughout the specification and claims to describe the nucleic acid sequences of the present invention, is meant a level of homology between the nucleic acid sequence and the SEQ ID NOs. referred to in that sentence. Preferably, the level of homology is in excess of 80%, more preferably in excess of 90%, with a preferred nucleic acid sequence being in excess of 95% homologous with the DNA sequence shown in the indicated SEQ ID NO. These anti-sense poly- or oligonucleotides can be either DNA or RNA. The targeted sequence is typically messenger RNA and more preferably, a single sequence required for processing or translation of the RNA. The anti-sense poly- or oligonucleotides can be conjugated to a polycation such as polylysine as disclosed in Lemaitre, M. et al. ((1989) Proc. Natl. Acad. Sci. USA 84:648–652) and this conjugate can be administrated to a mammal in an amount sufficient to hybridize to and inhibit the function of the messenger RNA.

The present invention further relates to multiple computer-generated alignments of the nucleotide and deduced amino acid sequences shown in SEQ ID NOs:1–102. Computer analysis of the nucleotide sequences shown in SEQ ID NOs.:1–51 and of the deduced amino acid sequences shown in SEQ ID NOs:52–102 can be carried out using commercially available computer programs known to one skilled in the art.

In one embodiment, computer analysis of SEQ ID NOs.:1–51 by the program GENALIGN (Intelligenetics, Inc. Mountainview, Calif.) results in distribution of the 51 sequences into twelve genotypes based upon the degree of variation of the sequences. For the purposes of the present invention, the nucleotide sequence identity of E1 cDNAs of HCV isolates of the same genotype is in the range of about 85% to about 100% whereas the identity of E1 cDNA sequences of different genotypes is in the range of about 50% to about 80%.

The grouping of SEQ ID NOs.:1–51 into twelve HCV genotypes is shown below.

| SEQ ID NOs: | Genotypes |
| --- | --- |
| 1–8 | I/1a |
| 9–25 | II/1b |
| 26–29 | III/2a |
| 30–33 | IV/2b |
| 34 | 2c |
| 35–39 | V/3a |
| 40 | 4a |
| 41 | 4b |
| 42–43 | 4c |
| 44 | 4d |
| 45–50 | 5a |
| 51 | 6a |

Figure 3A:
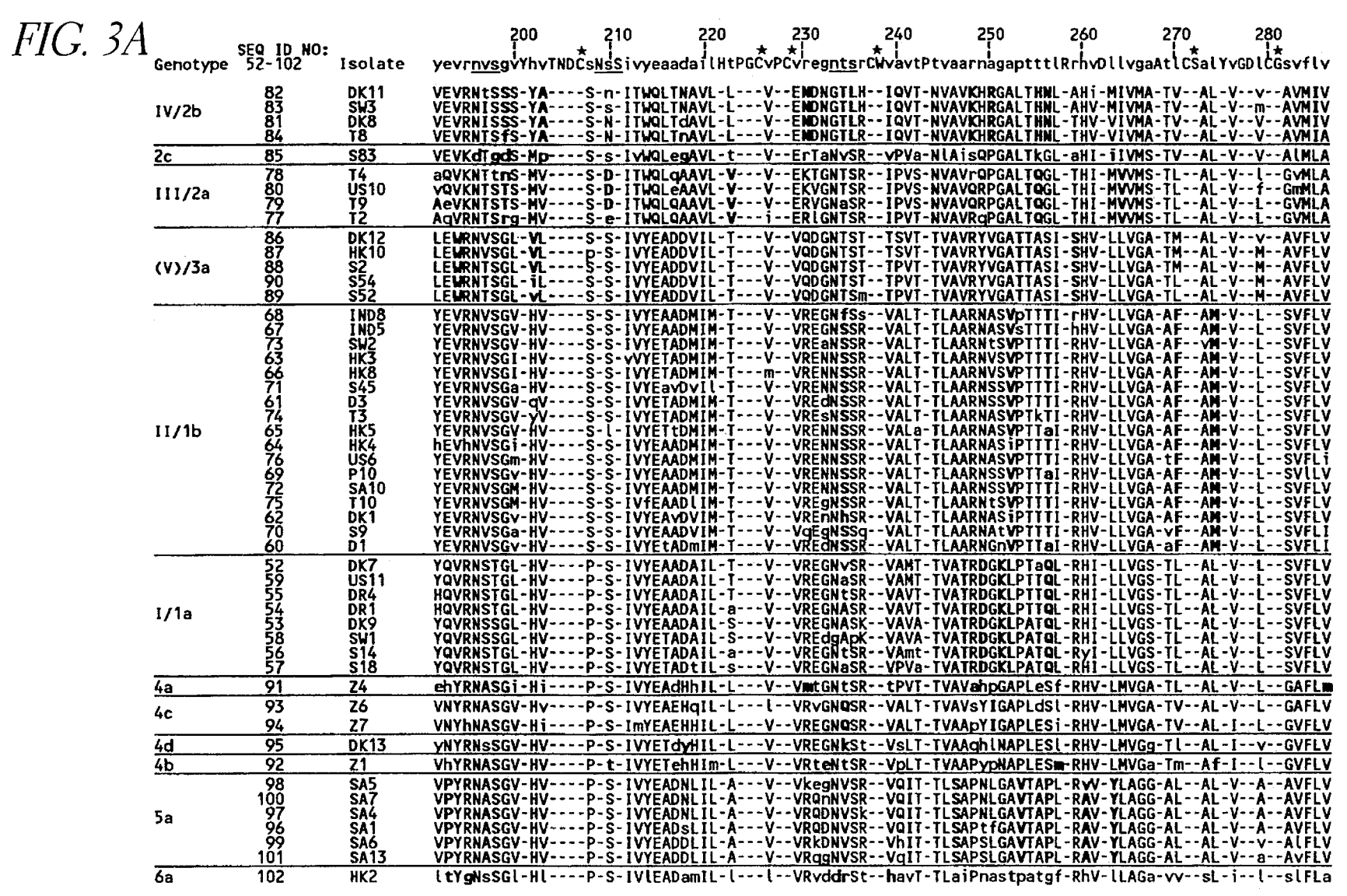

For those genotypes containing more than one E1 nucleotide sequence, computer alignment of the constituent nucleotide sequences of the genotype was conducted using GENALIGN in order to produce a consensus sequence for each genotype. These alignments and their resultant consensus sequences are shown in FIGS. 1A-1 through 1G-5 for the seven genotypes (I/1a, II/1b, III/2a, IV/2b, V/3a, 4c and 5a) which comprise more than one nucleotide sequence. Further alignment of the consensus sequences of FIGS. 1A-1 through 1G-5 with SEQ ID NO:34 (genotype 2c), SEQ ID NO:40 (genotype 4a), SEQ ID NO:41 (genotype 4b), SEQ ID NO:44 (genotype 4d) and SEQ ID NO:51 (genotype 6a) produces a consensus sequence for all twelve genotypes as shown in FIGS. 1H-1 through 1H-5. The multiple alignments of nucleotide sequences shown in FIGS. 1A-1 through 1H-5 serve to highlight regions of homology and non-homology between different sequences and hence, can be used by one skilled in the art to design oligonucleotides useful as reagents in diagnostic assays for HCV.

Examples of purified and isolated oligonucleotide sequences provided by the present invention are shown as SEQ ID NOs:109–135. The oligonucleotides shown in SEQ ID NOs:109–135 are useful as "genotype-specific" primers and probes since these oligonucleotides can hybridize specifically to the nucleotide sequence of the E1 gene of HCV isolates belonging to a single genotype. The genotype-specificity of the oligonucleotides shown in SEQ ID NOs:109–135 is as follows: SEQ ID NOs:109–110 are specific for genotype I/1a; SEQ ID NOs:111–112 are specific for genotype II/1b; SEQ ID NOs:113–114 are specific for genotype III/2a; SEQ ID NOs:115–116 are specific for genotype IV/2b; SEQ ID NOs:117–119 are specific for genotype 2c; SEQ ID NOs:120–122 are specific for genotype V/3a; SEQ ID NOs:123–124 are specific for genotype 4a; SEQ ID NOs:125–125 are specific for genotype 4b; SEQ ID NOs:127–128 are specific for genotype 4c; SEQ ID NOs:129–130 are specific for genotype 4d; SEQ ID NOs:131–132 are specific for genotype 5a and SEQ ID NOs:133–135 are specific for genotype 6a.

The oligonucleotides of this invention can be synthesized using any of the known methods of oligonucleotide synthesis (e.g., the phosphodiester method of Agarwal et al. 1972, Agnew. Chem. Int. Ed. Engl. 11:451, the phosphotriester method of Hsiung et al. 1979, Nucleic Acids Res 6:1371, or the automated diethylphosphoramidite method of Baeucage et al. 1981, Tetrahedron Letters 22:1859–1862), or they can be isolated fragments of naturally occurring or cloned DNA. In addition, those skilled in the art would be aware that oligonucleotides can be synthesized by automated instruments sold by a variety of manufacturers or can be commercially custom ordered and prepared. In a preferred embodiment, SEQ ID NO:103 through SEQ ID NO:135 are synthetic oligonucleotides.

The present invention also relates to a method for detecting the presence of HCV in a mammal, said method comprising analyzing the RNA of a mammal for the presence of hepatitis C virus.

The RNA to be analyzed can be isolated from serum, liver, saliva, lymphocytes or other mononuclear cells as viral RNA, whole cell RNA or as poly(A)$^+$ RNA. Whole cell RNA can be isolated by methods known to those skilled in the art. Such methods include extraction of RNA by differential precipitation (Birnbiom, H. C. (1988) Nucleic Acids Res., 16:1487–1497), extraction of RNA by organic solvents (Chomczynski, P. et al. (1987) Anal. Biochem., 162:156–159) and extraction of RNA with strong denaturants (Chirgwin, J.M. et al. (1979) Biochemistry, 18:5294–5299). Poly(A)$^+$ RNA can be selected from whole cell RNA by affinity chromatography on oligo-d(T) columns (Aviv, H. et al. (1972) Proc. Natl. Acad. Sci., 69:1408–1412). A preferred method of isolating RNA is extraction of viral RNA by the quanidium-phenol-chloroform method of Bukh et al. (1992a).

The methods for analyzing the RNA for the presence of HCV include Northern blotting (Alwine, J. C. et al. (1977) Proc. Natl. Acad. Sci., 74:5350–5354), dot and slot hybridization (Kafatos, F. C. et al. (1979) Nucleic Acids Res., 7:1541–1522), filter hybridization (Hollander, M. C. et al. (1990) Biotechniques; 9:174–179), RNase protection (Sambrook, J. et al. (1989) in "Molecular Cloning, A Laboratory Manual", Cold Spring Harbor Press, Plainview, N.Y.) and reverse-transcription polymerase chain reaction (RT-PCR) (Watson, J. D. et al. (1992) in "Recombinant DNA" Second Edition, W. H. Freeman and Company, New York). A preferred method is RT-PCR. In this method, the RNA can be reverse transcribed to first strand cDNA using a primer or primers derived from the nucleotide sequences shown in SEQ ID NOs:1–51. A preferred primer for reverse transcription is that shown in SEQ ID NO:104. Once the cDNAs are synthesized, PCR amplification is carried out using pairs of primers designed to hybridize with sequences in the HCV E1 cDNA which are an appropriate distance apart (at least about 50 nucleotides) to permit amplification of the cDNA and subsequent detection of the amplification product. Each primer of a pair is a single-stranded oligonucleotide of about 20 to about 60 bases in length where one primer (the "upstream" primer) is complementary to the original RNA and the second primer (the "downstream" primer) is complementary to the first strand of cDNA generated by reverse transcriptions of the RNA. The target sequence is generally about 100 to about 300 base pairs long but can be as large as 500–1500 base pairs. Optimization of the amplification reaction to obtain sufficiently specific hybridization to the E1 nucleotide sequence is well within the skill in the art and is preferably achieved by adjusting the annealing temperature.

In one embodiment, the primer pairs selected to amplify E1 cDNAs are universal primers. By "universal", as used to describe primers throughout the claims and specification, is meant those primer pairs which can amplify E1 gene fragments derived from an HCV isolate belonging to any one of the twelve genotypes of HCV described herein. Purified and isolated universal primers are used in Example 1 of the present invention and are shown as SEQ ID NOs:103–108 where SEQ ID NOs:103 and 104 represent one pair of primers, SEQ ID NOs:105 and 106 represent a second pair of primers and SEQ ID NOs:107–108 represent a third pair of primers.

In an alternative embodiment, primer pairs selected to amplify E1 cDNAs are genotype-specific primers. In the present invention, genotype-specific primer pairs can readily be derived from the following genotype-specific nucleotide domains: nucleotides 197–238 and 450–480 of the consensus sequence of genotype I/1a shown in FIGS. 1A-4 and 1A-8; nucleotides 197–238 and 450–480 of the consensus sequence of genotype II/1b shown in FIGS. 1B-4 and 1B-8; nucleotides 199–238 and 438–480 of the consensus sequence of genotype III/2a shown in FIGS. 1C-2 and 1C-4; nucleotides 124–177 and 450–480 of the consensus sequence of genotype IV/2b shown in FIGS. 1D-2 and 1D-4; nucleotides 124–177, 193–238 and 436–480 of SEQ ID NO:34 (genotype 2C); nucleotides 168–207, 294–339 and 406–480 of the consensus sequence of genotype V/3a shown in FIGS. 1E-2, 1E-3 and 1E-4; nucleotides 145–183 and 439–480 of SEQ ID NO:40 (genotype 4a); nucleotides 168–207 and 432–480 of SEQ ID NO:41 (genotype 4b); nucleotides 130–183 and 450–480 of the consensus sequence of genotype 4c shown in FIGS. 1F-1 and 1F-2; nucleotides 130–183 and 450–480 of SEQ ID NO:44 (genotype 4d); nucleotides 166–208 and 437–480 of the consensus sequence of genotype 5a shown in FIGS. 1G-2 and 1G-4 and nucleotides 168–207, 216–252 and 429–480 of SEQ ID NO:51 (genotype 6a). One skilled in the art would readily appreciate that in a pair of genotype-specific primers, each primer is derived from different genotype-specific nucleotide domains indicated above for a given genotype. Also, as described earlier, it is understood by one skilled in the art that each pair of primers comprises one primer which is complementary to the original viral RNA and the other which is complementary to the first strand of cDNA generated by reverse transcription of the viral RNA. For example, in a pair of genotype-specific primers for genotype 4b, one primer would have a nucleotide sequence derived from region 168–207 of SEQ ID NO:40 and the other primer would have a nucleotide sequence which is the complement of region 432–480 of SEQ ID NO:40. One skilled in the art would readily recognize that such genotype specific domains would also be useful in designing oligonucleotides for use as genotype-specific hybridization probes. Indeed, the sequences of such genotype-specific hybridization probes are disclosed later in the specification.

The amplification products of PCR can be detected either directly or indirectly. In one embodiment, direct detection of the amplification products is carried out via labelling of primer pairs. Labels suitable for labelling the primers of the present invention are known to one skilled in the art and include radioactive labels, biotin, avidin, enzymes and fluorescent molecules. The derived labels can be incorporated into the primers prior to performing the amplification reaction. A preferred labelling procedure utilizes radiolabeled ATP and T4 polynucleotide kinase (Sambrook, J. et al. (1989) in "Molecular Cloning, A Laboratory Manual", Cold Spring Harbor Press, Plainview, N.Y.). Alternatively, the desired label can be incorporated into the primer extension products during the amplification reaction in the form of one or more labelled dNTPs. In the present invention, the labelled amplified PCR products can be detected by agarose gel electrophoresis followed by ethidum bromide staining and visualization under ultraviolet light or via direct sequencing of the PCR-products.

In yet another embodiment, unlabelled amplification products can be detected via hybridization with labelled nucleic acid probes radioactively labelled or, labelled with biotin, in methods known to one skilled in the art such as dot and slot blot hybridization (Kafatos, F. C. et al. (1979) or filter hybridization (Hollander, M. C. et al. (1990)).

In one embodiment, the nucleic acid sequences used as probes are selected from, and substantially homologous to, SEQ ID NOs:1–51. Such probes are useful as universal probes in that they can detect in PCR-amplification products of E1 cDNAs of an HCV isolate belonging to any of the twelve HCV genotypes disclosed herein. The size of these probes can range from about 200 to about 500 nucleotides.

In an alternative embodiment, the present invention relates to a method for determining the genotype of a hepatitis C virus present in a mammal where said method comprises:

(a) amplifying RNA of a mammal via RT-PCR to produce amplification products;

(b) contacting said products with at least one genotype-specific oligonucleotide; and (c) detecting complexes of said products which bind to said oligonucleotide(s).

In this method, one embodiment of said amplification step is carried out using the universal primers (SEQ ID NO:103 through SEQ ID NO:108) as disclosed above. In step (b) of this method, the nucleic acid sequences used as probes are substantially homologous to the sequences shown in SEQ ID NOs:109–135. The probes disclosed in SEQ ID NOs.:109–135 are useful in specifically detecting PCR-amplification products of E1 cDNAs of HCV isolates belonging to one of the twelve HCV genotypes disclosed herein. In a preferred embodiment, probes having sequences substantially homologous to the sequences shown in SEQ ID NOs:109–135 are used alone or in combination with other probes specific to the same genotype.

For example, a probe having a sequence according to SEQ ID NO:109 can be used alone or in combination with a probe having a sequence according to SEQ ID NO:110. The probes derived from SEQ ID NOs:109–135 can range in size from about 30 to about 70 nucleotides and can be synthesized as described earlier.

The nucleic acid sequence used as a probe to detect PCR amplification products of the present invention can be labeled in single-stranded or double-stranded form. Labelling of the nucleic acid sequence can be carried out by techniques known to one skilled in the art. Such labelling techniques can include radiolabels and enzymes (Sambrook, J. et al. (1989) in "Molecular Cloning, A Laboratory Manual", Cold Spring Harbor Press, Plainview, N.Y.). In addition, there are known non-radioactive techniques for signal amplification including methods for attaching chemical moieties to pyrimidine and purine rings (Dale, R. N. K. et al. (1973) *Proc. Natl. Acad. Sci.,* 70:2238–2242; Heck, R. F. (1968) *S. Am. Chem. Soc.,* 90:5518–5523), methods which allow detection by chemiluminescence (Barton, S. K.

et al. (1992) *J. Am. Chem. Soc.,* 114:8736–8740) and methods utilizing biotinylated nucleic acid probes (Johnson, T. K. et al. (1983) *Anal. Biochem.,* 133:126–131; Erickson, P. F. et al. (1982) *J. of Immunology Methods,* 51:241–249; Matthaei, F. S. et al. (1986) *Anal. Biochem.,* 157:123–128) and methods which allow detection by fluorescence using commercially available products.

The present invention also relates to computer analysis of the amino acid sequences shown in SEQ ID NOs:52–102 by the program GENALIGN. This analysis groups the 51 amino acid sequences shown in SEQ ID NOs:52–102 into the twelve genotypes disclosed earlier in this application based upon the degree of variation of the amino acid sequences. For the purposes of the present invention, the amino acid sequence identity of E1 amino acid sequences of the same genotype ranges from about 85% to about 100% whereas the identity of E1 sequences of different genotypes ranges from about 45% to about 80%.

The grouping of SEQ ID NOs:52–102 into the twelve HCV genotypes is shown below:

| SEQ ID NOs: | Genotypes |
| --- | --- |
| 52–59 | I/1a |
| 60–76 | II/1b |
| 77–80 | III/2a |
| 81–84 | IV/2b |
| 85 | 2c |
| 86–90 | V/3a |
| 91 | 4a |
| 92 | 4b |
| 93–94 | 4c |
| 95 | 4d |
| 96–101 | 5a |
| 102 | 6a |

For those genotypes containing more than one E1 amino acid sequence, computer alignment of the constituent sequences of each genotype was conducted using the computer program GENALIGN in order to produce a consensus sequence for each genotype. These alignments and their resultant consensus sequences are shown in FIGS. 2A-1 through 2G-2 for the seven genotypes (I/1a, II/1b, III/2a, IV/2b, V/3a, 4c and 5a) which comprise more than one sequence. Further alignment of the consensus sequences shown in FIGS. 2A-1 through 2G-2 with the amino acid sequences of SEQ ID NO:85 (genotype 2c); SEQ ID NO:91 (genotype 4a); SEQ ID NO:92 (genotype 4b); SEQ ID NO:95 (genotype 4d) and SEQ ID NO:102 (genotype 6a) to produce a consensus amino acid sequence for all twelve genotypes is shown in FIGS. 2H-1 and 2H-2. The multiple alignment of E1 amino acid sequences shown in FIGS. 2A-1 through 2H-2 serves to highlight regions of homology and non-homology between amino acid sequences and hence, these alignments can readily be used by one skilled in the art to derive peptides useful in assays and vaccines for the diagnosis and prevention of HCV infection. Examples of purified and isolated peptides are provided by the present invention are shown as SEQ ID NOs:136–159. These peptides are derived from two regions of the amino acid sequences shown in FIGS. 2A-1 through 2H-2, amino acids 48–80 and amino acids 138–160. The peptides shown in SEQ ID NOs. 136–159 are useful as genotype-specific diagnostic reagents since they are capable of detecting an immune response specific to HCV isolates belonging to a single genotype. The genotype-specificity of the peptides shown in SEQ ID NOs:136–159 are as follows: SEQ ID NOs:136 and 148 are specific for genotype IV/2b; SEQ ID NOs:137 and 149 are specific for genotype 2c; SEQ ID NOs:138 and 150 are specific for genotype III/2a; SEQ ID NOs:139 and 151 are specific for genotype V/a; SEQ ID NOs:140 and 152 are specific for genotype II/1b; SEQ ID NOs:141 and 153 are specific for genotype I/1a; SEQ ID NOs:142 and 154 are specific for genotype 4a; SEQ ID NOs:143 and 155 are specific for genotype 4c; SEQ ID NOs:144 and 156 are specific for genotype 4d; SEQ ID NOs:145 and 157 are specific for genotype 4b; SEQ ID NOs:146 and 158 are specific for genotype 5a and SEQ ID NOs:147 and 159 are specific for genotype 6a. In SEQ ID NO:136, Xaa at position 22 is a residue of Ala or Thr, Xaa at position 24 is a residue of Val or Ile, Xaa at position 26 is a residue of Val or Met; in SEQ ID NO:138, Xaa at position 5 is a Ser or Thr residue, Xaa at position 11 is an Arg or Gln residue, Xaa at position 12 is an Arg or Gln residue; in SEQ ID NO:139, Xaa at position 3 is a Pro or Ser residue, Xaa at position 33 is a Leu or Met residue; in SEQ ID NO:140, Xaa at position 5 is a Thr or Ala residue, Xaa at position 13 is a Gly, Ala, Ser, Val or Thr residue, Xaa at position 14 is a Ser, Thr or Asn residue, Xaa at position 15 is a Val or Ile residue, Xaa at position 16 is a Pro or Ser residue, Xaa at position 18 is a Thr or Lys residue, Xaa at position 19 is a Thr or Ala residue, Xaa at position 22 is an Arg or His residue, Xaa at position 32 is an Ala, Val or Thr residue; in SEQ ID NO:141, Xaa at position 3 is an Ala or Pro residue, Xaa at position 4 is a Val or Met residue, Xaa at position 5 is a Thr or Ala residue, Xaa at position 17 is a Thr or Ala residue, Xaa at position 18 is a Thr or Ala residue, Xaa at position 23 is a His or Tyr residue; in SEQ ID NO:143, Xaa at position 10 is a Val or Ala residue, Xaa at position 11 is a Ser or Pro residue, Xaa at position 18 is an Asp or Glu residue Xaa at position 20 is a Leu or Ile residue; in SEQ ID NO:146, Xaa at position 3 is a Gln or His residue, Xaa at position 12 is an Asn, Ser or Thr residue, Xaa at position 13 is a Leu or Phe residue, Xaa at position 23 is an Ala or Val residue; in SEQ ID NO:148, Xaa at position 16 is a Val or Ala residue, Xaa at position 18 is a Glu or Gln residue; in SEQ ID NO:150, Xaa at position 2 is an Ala or Thr residue, Xaa at position 4 is a Met or Leu residue, Xaa at position 9 is an Ala or Val residue, Xaa at position 17 is an Ile or Leu residue, Xaa at position 20 is an Ile or Val residue, Xaa at position 21 is a Ser or Gly residue; in SEQ ID NO:151, Xaa at position 9 is a Val or Ile residue, Xaa at position 16 is a Leu or Val residue, Xaa at position 20 is an Ile or Leu residue; in SEQ ID NO:152, Xaa at position 2 is an Ala or Thr residue, Xaa at position 6 is a Val or Leu residue, Xaa at position 12 is an Ile or Leu residue, Xaa at position 16 is a Val or Ile residue, Xaa at position 17 is a Val, Leu or Met residue, Xaa at position 19 is a Met or Val residue, Xaa at position 21 is an Ala or Thr residue; in SEQ ID NO:153, Xaa at position 2 is a Thr or Ala residue, Xaa at position 6 is a Val, Ile or Met residue, Xaa at position 12 is an Ile or Val residue, Xaa at position 16 is a Ile or Val residue; in SEQ ID NO:155, Xaa at position 5 is a Leu or Val residue, Xaa at position 21 is a Thr or Ala residue; in SEQ ID NO:158, Xaa at position 1 is a Thr or Ala residue, Xaa at position 5 is a Val or Leu residue, Xaa at position 9 is a Leu, Met or Val residue, Xaa at position 23 is a Gly or Ala residue.

Those skilled in the art would be aware that the peptides of the present invention or analogs thereof can be synthesized by automated instruments sold by a variety of manufacturers or can be commercially custom-ordered and prepared. The term analog has been described earlier in the specification and for purposes of describing the peptides of the present invention, analogs can further include branched or non-linear arrangements of the peptide sequences shown in SEQ ID NOs:136–159.

Alternatively, peptides can be expressed from nucleic acid sequences where such sequences can be DNA, cDNA, RNA or any variant thereof which is capable of directing protein synthesis. In one embodiment, restriction digest fragments containing a coding sequence for a peptide can be inserted into a suitable expression vector that functions in prokaryotic or eukaryotic cells. Such restriction digest fragments may be obtained from clones isolated from prokaryotic or eukaryotic sources which encode the peptide sequence.

Suitable expression vectors and methods of isolating clones encoding the peptide sequences of the present invention have previously been described.

The preferred size of the peptides of the present invention is from about 8 to about 100 amino acids in length.

The present invention further relates to the use of the peptides shown in SEQ ID NOs:136–159 in methods of detecting antibodies specific for HCV in biological samples. In one embodiment, at least one peptide specific for a single genotype to be used in previously described immunoassays to detect antibodies specific for a single genotype of HCV. A preferred immunoassay is ELISA.

It is understood by one skilled in the art that the diagnostic assays described herein using genotype-specific oligonucleotides or genotype-specific peptides ca be useful in assisting one skilled in the art to choose a course of therapy for the HCV-infected individual.

In an alternative embodiment, a mixture of peptides can be used in an immunoassay to detect antibodies to any of the twelve genotypes of HCV. The mixture of peptides as disclosed herein, comprises at least one peptide selected from SEQ ID NOs:140–141 and 152–153; one peptide selected from SEQ ID NOs:136, 138, 148 and 150; one peptide selected from SEQ ID NOs:142–145 and 154–157; one peptide selected from SEQ ID NOs:146 and 158; one peptide selected from SEQ ID NOs:139 and 151; one peptide selected from SEQ ID NOs:138 and 150 and one peptide selected from SEQ ID NOs:140 and 159. In a preferred embodiment, the peptides of the present invention can be used in an ELISA assay as described previously for E1 proteins.

The peptides or analogs thereof may be prepared in the form of a kit, alone or in combinations with other reagents such as secondary antibodies, for use in immunoassay. In addition, since genotype-specific peptides shown in SEQ ID NOs:136–159 are derived from two variable regions in the E1 protein, amino acids 48–80 (SEQ ID NOs:136–147) and amino acids 138–160 (SEQ ID NOs:148–159), one skilled in the art would recognize that these peptides would be useful as vaccines against hepatitis C. In the present invention, a peptide from SEQ ID NOs:136–159 can be used alone or in combination with other peptides shown therein as immunogens in the vaccine. Formulations suitable for administering the peptide(s) of the present invention, routes of administration, pharmaceutical compositions comprising the peptides and so forth are the same as those previously described for recombinant E1 proteins. In addition, as described for E1 proteins, the peptide(s) can also be used to prepare antibodies to HCV-E1 protein.

The peptides of the present invention may also be supplied in the form of a kit, alone, or in the form of a pharmaceutical composition as described above for E1 proteins recombinant.

Any articles or patents referenced herein are incorporated by reference. The following examples illustrate various aspects of the invention but are in no way intended to limit the scope thereof.

MATERIALS

Serum used in these examples was obtained from 84 anti-HCV positive individuals that were previously found to be positive for HCV RNA in a cDNA PCR assay with primer set a from the 5' NC region of the HCV genome (Bukh, J. et al. (1992 (b)) Natl. Acad. Sci. USA 89:4942–4946). These samples were from 12 countries: Denmark (DK); Dominican Republic (DR); Germany (D); Hong Kong (HK); India (IND); Sardinia, Italy (S); Peru (P); South Africa (SA); Sweden (SW); Taiwan (T); United States (US); and Zaire (Z).

EXAMPLE 1

Identification of the DNA Sequence of the E1 Gene of 51 Isolates of HCV via RT-PCR Analysis of Viral RNA Using Universal Primers Viral RNA was extracted from 100 µl of serum by the guanidinium-phenol-chloroform method and the final RNA solution was divided into 10 equal aliquots and stored at −80° C. as described (Bukh, et al. (1992 (a)). The sequences of the synthetic oligonucleotides used in the RT-PCR assay, deduced from the sequence of HCV strain H-77 (Ogata, N. et al. (1991) Proc. Natl. Acad. Sci. USA 88:3392–3396), are shown as SEQ ID NOs:103–108. One aliquot of the final RNA solution, equivalent to 10 µl of serum, was used for cDNA synthesis that was performed in a 20 µl reaction mixture using avian myeloblastosis virus reverse transcriptase (Promega, Madison, Wis.) and SEQ ID NO:104 as a primer. The resulting cDNA was amplified in a "nested" PCR assay by Taq DNA polymerase (Amplitaq, Perkin-E1 mer/Cetus) as described previously (Bukh et al. (1992a)) with primer set e (SEQ ID NOs:103–106). Precautions were taken to avoid contamination with exogenous HCV nucleic acid (Bukh et al. 1992a)), and negative controls (normal, uninfected serum) were interspersed between every test sample in both the RNA extraction and cDNA PCR procedures. No false positive results were observed in the analysis. In most instances, amplified DNA (first or second PCR products) was reamplified with primers SEQ ID NO:107 and SEQ ID NO:108 prior to sequencing since these two primers contained EcoR1 sites which would facilitate future cloning of the E1 gene. Amplified DNA was purified by gel electrophoresis followed by glass-milk extraction (Geneclean, BIO 101, LaJolla, Calif.) and both strands were sequenced directly by the dideoxy-nucleotide chain termination method (Bachman, B. et al. (1990) Nucl. Acids Res. 18:1309)) with phage T7 DNA polymerase (Sequenase, United States Biochemicals, Cleveland, Ohio), [alpha $^{35}$S]dATP (Amersham, Arlington Heights, Ill.) or [alpha $^{33}$P] dATP (Amersham or DuPont, Wilmington, Del.) and sequencing primers. RNA extracted from serum containing HCV strain H-77, previously sequenced by Ogata, N. et al. (1991), was amplified with primer set e (SEQ ID NOs:103–106) and sequenced in parallel as a control. The nucleotide sequences of the envelope 1 (E1) gene of all 51 HCV isolates are shown as SEQ ID NOs:1–51. In all 51 HCV isolates, the E1 gene was exactly 576 nucleotides in length and did not have any in-frame stop codons.

EXAMPLE 2

Computer Analysis of the Nucleotide and Deduced Amino Acid Sequences of the E1 Gene of the 51 HCV Isolates Multiple computer-generated alignments of the nucleotide (SEQ ID NOs:1–51, FIGS. 1A-1 through 1H-5) and deduced amino acid sequences (SEQ ID NOs:52–102, FIGS. 2A-1 through 2H-2) of the cDNAs of the 51 HCV isolates constructed using the computer program GENALIGN (Miller, R. H. et al. (1990) Proc. Natl. Acad. Sci. USA 87:2057–2061) resulted in the 51 HCV isolates being divided into twelve genotypes based upon the degree of variation of the E1 gene sequence as shown in table 1.

HCV isolates. A site at position 196 was maintained in all isolates except the sole isolate of genotype 2c. Also, a site at position 234 was maintained in all isolates except one isolate of genotype I/1a, all four isolates of genotype Iv/2b and the sole isolate of genotype 6a. Conversely, only genotype IV/2b isolates had a potential glycosylation site at position 233. Further analysis revealed a highly conserved amino acid domain (aa 302–328) in the E1 protein with 20 (74.1%)

TABLE 1

Biochemistry: Bukh et al.
Percent nucleotide (nt) and amino acid (aa) sequence identify
of the E1 gene among the 12 HCV genotypes.

|         | I/1a | II/1b | III/2a | IV/2b | 2c | (V)/3a | 4a |
|---------|------|-------|--------|-------|-----|--------|-----|
|         | 89.9–97.6 | 72.0–76.2 | 59.2–63.7 | 56.1–58.3 | 60.8–62.8 | 63.0–66.3 | 63.9–67.2 |
| aa:     |      | 88.9–97.9 | 58.3–62.2 | 53.8–57.5 | 60.1–61.5 | 63.9–67.2 | 60.9–63.7 |
| I/1a    | 91.1–98.4 |      | 88.0–91.3 | 69.1–71.0 | 72.7–73.6 | 58.0–60.8 | 61.5–62.7 |
| II/1b   | 75.5–80.7 | 90.1–97.9 |     | 92.7–95.0 | 67.5–68.9 | 56.3–58.3 | 58.9–60.8 |
| III/2a  | 58.3–64.6 | 52.6–56.8 | 89.1–92.7 |     | —    | 57.5–58.2 | 59.2 |
| IV/2b   | 54.2–56.8 | 51.0–54.2 | 69.3–72.9 | 93.8–96.4 |    | 93.8–99.1 | 64.4–65.3 |
| 2c      | 56.3–60.4 | 52.6–55.7 | 74.5–77.1 | 67.7–69.8 | — |      | — |
| (V)/3a  | 64.1–68.8 | 66.7–70.8 | 54.7–58.9 | 54.2–56.8 | 52.1–53.6 | 94.3–98.4 |   |
| 4a      | 69.3–73.4 | 64.6–67.2 | 62.0–63.0 | 58.9–60.4 | 58.3 | 66.1–68.8 | — |
| 4b      | 66.7–69.3 | 66.1–70.3 | 53.6–56.3 | 52.1–53.1 | 53.6 | 62.0–64.6 | 76.0 |
| 4c      | 66.1–72.9 | 64.6–69.3 | 55.2–61.5 | 54.2–58.3 | 54.7–58.3 | 63.0–65.6 | 77.1–81.3 |
| 4d      | 73.4–75.5 | 66.7–70.3 | 56.3–58.9 | 55.2–55.7 | 54.2 | 63.5–64.6 | 78.1 |
| 5a      | 66.1–73.4 | 64.1–70.3 | 52.6–57.3 | 50.5–53.1 | 54.2–56.3 | 60.4–64.1 | 67.2–68.2 |
| 6a      | 64.6–65.6 | 62.5–65.6 | 49.0–51.0 | 49.0–50.5 | 50.5 | 57.8–58.9 | 66.1 |

|         | 4b | 4c | 4d | 5a | 6a | nt: |
|---------|-----|-----|-----|-----|-----|------|
|         | 64.9–66.8 | 62.7–64.4 | 67.7–69.4 | 62.3–67.2 | 62.2–63.9 | I/1a |
| aa:     | 63.4–65.8 | 61.6–65.1 | 63.0–65.5 | 62.2–66.5 | 61.6–63.0 | II/1b |
| I/1a    | 58.9–60.4 | 59.7–63.4 | 58.7–61.3 | 56.6–60.8 | 55.0–56.8 | III/2a |
| II/1b   | 56.4–57.6 | 57.1–59.9 | 57.5–59.0 | 53.5–56.6 | 53.6–55.2 | IV/2b |
| III/2a  | 58.5 | 58.0–58.3 | 58.9 | 56.9–57.1 | 57.6 | 2c |
| IV/2b   | 62.7–64.1 | 60.9–62.5 | 62.3–63.9 | 61.8–64.4 | 58.0–58.9 | (V)/3a |
| 2c      | 74.8 | 75.5–78.0 | 74.8 | 62.8–64.6 | 62.0 | 4a |
| (V)/3a  | —   | 74.0–74.8 | 72.0 | 63.9–64.6 | 62.7 | 4b |
| 4a      |     | 90.1 | 77.6–78.6 | 62.7–64.8 | 63.0–64.4 | 4c |
| 4b      | —   |     | —   | 64.4–66.1 | 64.1 | 4d |
| 4c      | 79.2–80.2 | 89.6 |   | 90.1–95.7 | 60.6–63.2 | 5a |
| 4d      | 77.6 | 82.8 | — |     | —   | 6a |
| 5a      | 65.1–67.2 | 67.7–71.4 | 69.3–71.4 | 92.7–97.4 |   |   |
| 6a      | 62.5 | 66.1–67.2 | 66.7 | 62.0–63.5 | — |   |

Nucleotide sequences analyzed in compiling the above table are shown in SEQ ID NOs: 1–51 while the amino acid sequences analyzed are shown in SEQ ID NOs: 52–102.
The grouping of SEQ ID NOs: into genotypes is previously described in the specification.

The nucleotide and amino acid sequence identity of HCV isolates of the same genotype was in the range of 88.0–99.1% and 89.1–98.4%, respectively, whereas that of HCV isolates of different genotypes was in the range of 53.5–78.6% and 49.0–82.8%, respectively. The latter differences are similar to those found when comparing the envelope gene sequences of the various serotypes of the related flaviviruses, as well as other RNA viruses. When microheterogenicity in a sequence was observed, defined as more than one prominent nucleotide at a specific position, the nucleotide that was identical to that of the HCV prototype (HCV1, Choo et al. (1989)) was reported if possible. Alternatively, the nucleotide that was identical to the most closely related isolate is shown.

Figure 3B:
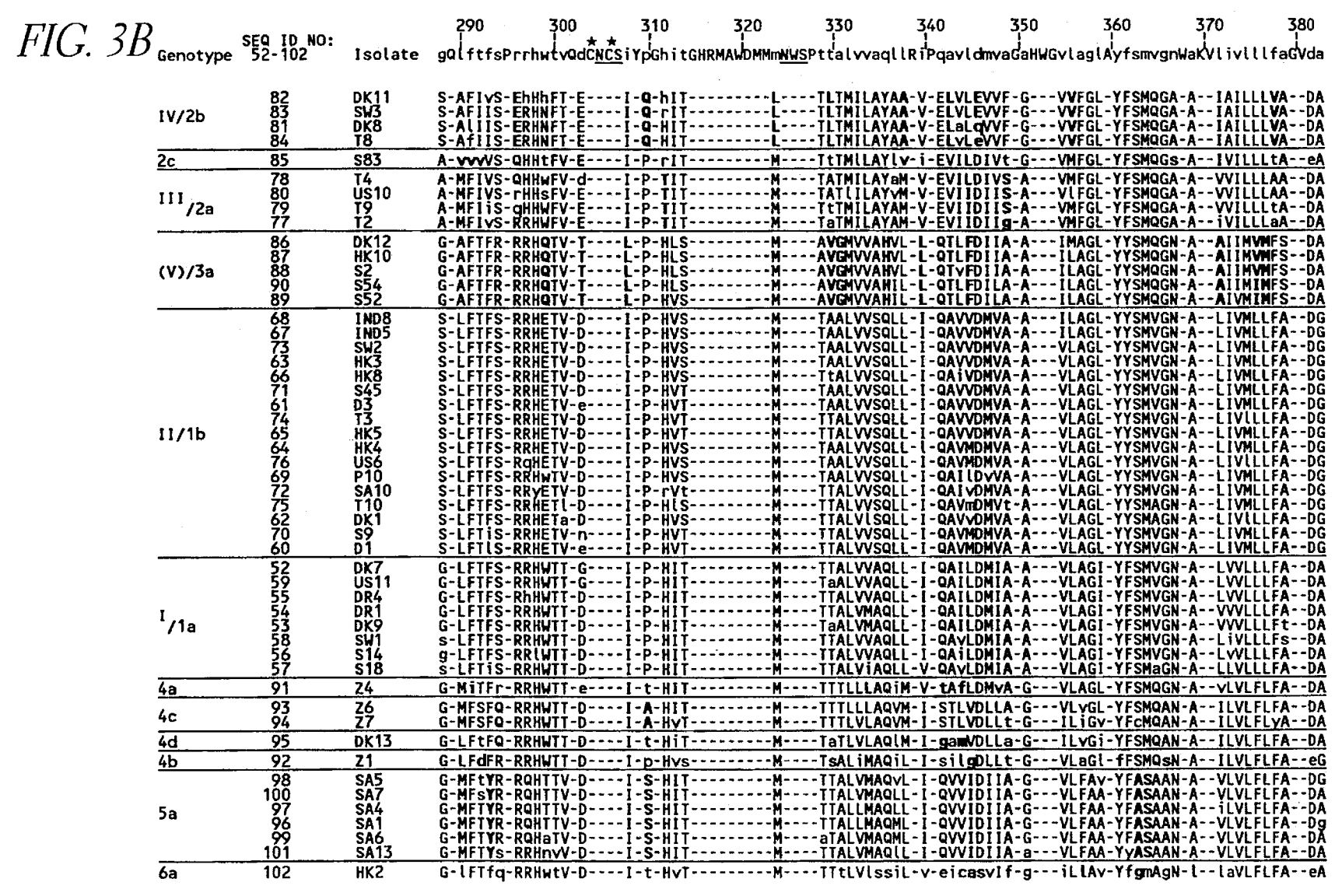

Analysis of the consensus sequence of the E1 protein of the 51 HCV isolates from this study demonstrated that a total of 60 (30.3%) of the 192 amino acids of the E1 protein were invariant among these isolates (FIGS. 3A and 3B). Most impressive, all 8 cysteine residues as well as 6 of 8 proline residues were invariant. The most abundant amino acids (e.g. alanine, valine and leucine) showed a very low degree of conservation. The consensus sequence of the E1 protein contained 5 potential N-linked glycosylation sites. Three sites at positions 209, 305 and 325 were maintained in all 51 of 27 amino acids invariant among all 51 HCV isolates. It is possible that the 5' and 3' ends of this domain are conserved due to important cysteine residues and N-linked glycosylation sites. The central sequence, 5'-GHRMAWDMM-3' (SEQ ID NO:160) (aa 315–323), may be conserved due to additional functional constraints on the protein structure. Finally, although the amino acid sequence surrounding the putative E1 protein cleavage site was variable, an amino acid doublet (GV) at position 380 was invariant among all HCV isolates.

A dendrogram of the genetic relatedness of the E1 protein of selected HCV isolates representing the 12 genotypes is shown in FIG. 4. This dendrogram was constructed using the program CLUSTAL (Weiner, A. J. et al. (1991) Virology 180:842–848) and had a limit of 25 sequences. The scale showing percent identity was added based upon manual calculation. From the 51 HCV isolates for which the complete sequence of the E1 gene region was obtained, 25 isolates representing the twelve genotypes were selected for analysis as follows. Among isolates with genotype I/1a (SEQ ID NOs:52–59), as well as among isolates with genotype II/1b (SEQ ID NOs:60–76) the two isolates with the lowest amino acid identity within each genotype were included. Among isolates of genotype IV/2b, isolate DK8

(SEQ ID NO:81) that has an amino acid identity of 96.4% to isolate T8 (SEQ ID NO:84) was excluded. Among isolates of genotype V/3a, isolates S2 (SEQ ID NO:88) and S54 (SEQ ID NO:90) that both shared 97.9% of the amino acids of isolates HK10 (SEQ ID NO:87) and S52 (SEQ ID NO:89) were excluded. Finally, among isolates of genotype VI, isolates SA4 (SEQ ID NO:97) and SA5 (SEQ ID NO:98) with an amino acid identity to isolate SA7 (SEQ ID NO:100) of 96.4% and 95.8%, respectively were excluded. This dendrogram in combination with the analysis of the E1 gene sequence of 51 HCV isolates in Table 1 demonstrates extensive heterogeneity of this important gene.

Figure 5:
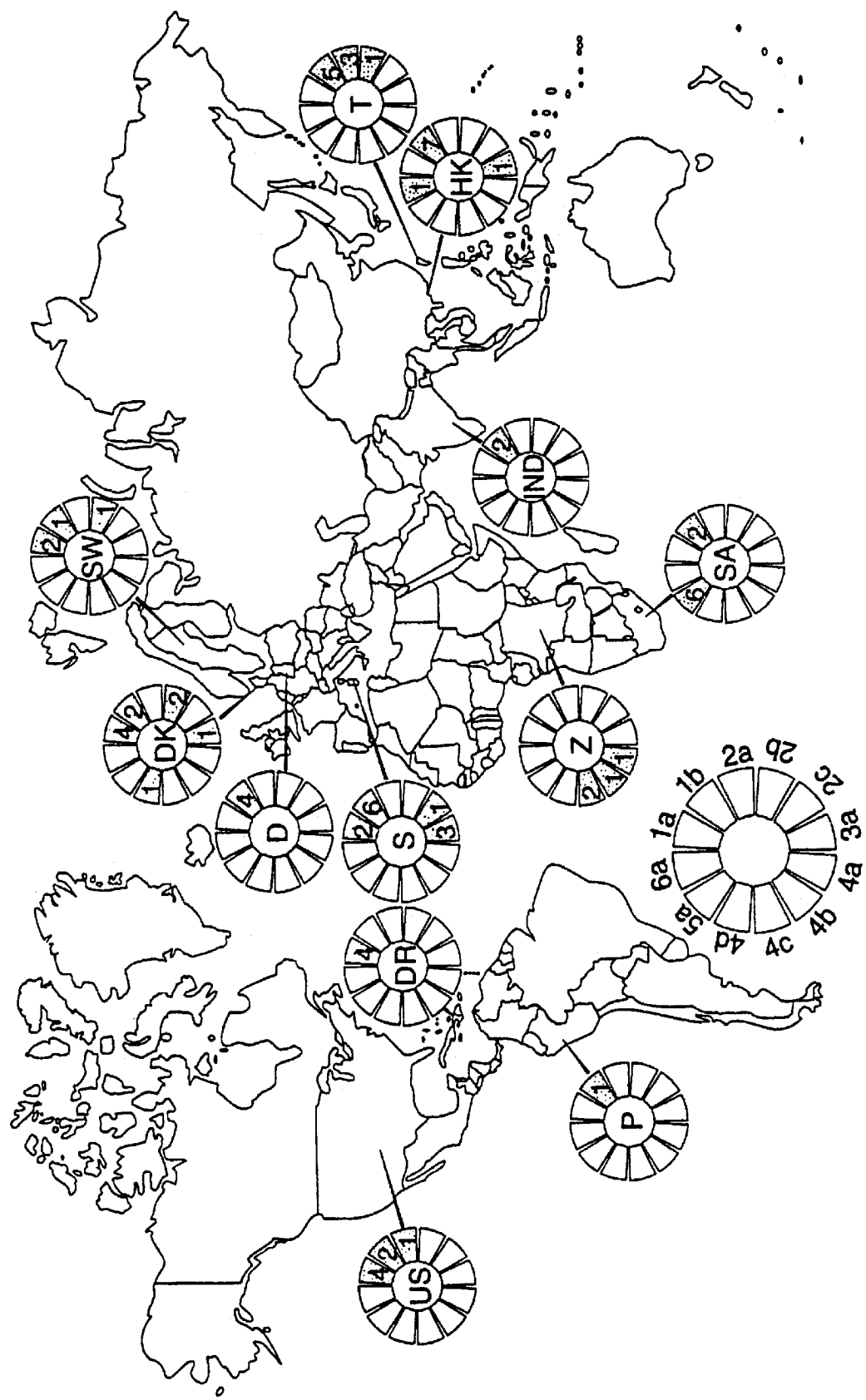

The worldwide distribution of the 12 genotypes among 74 HCV isolates is depicted in FIG. 5. The complete E1 gene sequence was determined in 51 of these HCV isolates (SEQ ID NOs:1–51), including 8 isolates of genotype I/1a, 17 isolates of genotype II/1b and 26 isolates comprising genotypes III/2a, IV/2b, 2c, 3a, 4a–4d, 5a and 6a. In the remaining 23 isolates, all of genotypes I/1a and II/1b, the genotype assignment was based on a partial E1 gene sequence since they did not represent additional genotypes in any of the 12 countries. The number of isolates of a particular genotype is given in each of the 12 countries studied. Of the twelve genotypes, genotypes I/1a and II/1b were the most common accounting for 48 (65%) of the 74 isolates. Analysis of the E1 gene sequences available in the GenBank data base at the time of this study revealed that all 44 such sequences were of genotypes I/1a, II/1b, III/2a and IV/2b. Thus, based upon E1 gene analysis, 8 new genotypes of HCV have been identified.

Also of interest, different HCV genotypes were frequently found in the same country, with the highest number of genotypes (five) being detected in Denmark. Of the twelve genotypes, genotypes I/1a, II/1b, III/2a, IV/2b and V/3a were widely distributed with genotype II/1b being identified in 11 of 12 countries studied (Zaire was the only exception). In addition, while genotypes I/1a and II/1b were predominant in the Americas, Europe and Asia, several new genotypes were predominant in Africa.

It was also found that genotypes I/1a, II/1b, III/2a, IV/2b and V/3a of HCV were widely distributed around the world, whereas genotypes 2c, 4a, 4b, 4d, 5a and 6a were identified only in discreet geographical regions. For example, the majority of isolates in South Africa comprised a new genotype (5a) and all isolates in Zaire comprised 3 new closely related genotypes (4a, 4b, 4c). These genotypes were not identified outside Africa.

EXAMPLE 3

Detection by ELISA Based on Antigen from Insect Cells Expressing Complete E1 Protein Expression of E1 protein in SF9 cells. A cDNA (SEQ ID NO:1) encoding the complete E1 protein of SEQ ID NO:52 is subcloned into pBlueBac—Transfer vector (Invitrogen) using standard subcloning procedures. The resultant recombinant expression vector is cotransfected into SF9 insect cells (Invitrogen) by the Ca precipitation method according to the Invitrogen protocol.

ELISA Based on Infected SF9 cells. $5 \times 10^6$ SF9 cells infected with the above-described recombinant expression vector are resuspended in 1 ml of 10 mM Tris-HCl, pH 7.5, 0.15M NaCl and are then frozen and thawed 3 times. 10 ul of this suspension is dissolved in 10 ml of carbonate buffer (pH 9.6) and used to cover one flexible microtiter assay plate (Falcon). Serum samples are diluted 1:20, 1:400 and 1:8000, or 1:100, 1:1000 and 1:10000. Blocking and washing solutions for use in the ELISA assay are PBS containing 10% fetal calf serum and 0.5% gelatin (blocking solution) and PBS with 0.05% Tween –20 (Sigma, St.Louis, Mo.) (washing solution). As a secondary antibody, peroxidase-conjugated goat IgG fraction to human IgG or horse radish peroxidase-labelled goat anti-Old or anti-New World monkey immunoglobulin is used. The results are determined by measuring the optical density (O.D.) at 405 nm.

To determine if insect cells-derived E1 protein representing genotype I/a of HCV could detect anti-HCV antibody in chimpanzees infected with genotype I/1a of HCV, three infected chimpanzees are examined. The serum of all 3 chimpanzees are found to seroconvert to anti-HCV.

EXAMPLE 4

Use of the Complete E1 Protein as a Vaccine

Mammals are immunized with purified or partially purified E1 protein in an amount sufficient to stimulate the production of protective antibodies. The immunized mammals challenged with various genotypes of HCV are protected.

It is understood by one skilled in the art that the recombinant E1 protein used in the above vaccine can also be used in combination with other recombinant E1 proteins having an amino acid sequence shown in SEQ ID NOs:52–102.

EXAMPLE 5

Determination of the Genotype of an HCV Isolate Via Hybridization of Genotype-Specific Oligonucleotides to RT-PCR Amplification Products.

Viral RNA is isolated from serum obtained from a mammal and is subjected to RT-PCR as in Example 1. Following amplification, the amplified DNA is purified as described in Example 1 and aliquots of 100 mg of amplification product are applied to twelve dots on a nitrocellulose filter set in a dot blot apparatus. The twelve dots are then cut into separate dots and each dot is hybridized to a $^{32}$p-labelled oligonucleotide specific for a single genotype of HCV. The oligonucleotides to be used as hybridization probes are selected from SEQ ID NOs:109–135.

EXAMPLE 6

ELISA Based on Synthetic Peptides Derived From E1 cDNA Sequences

Synthetic peptides specific for genotype I/1a and having amino acid sequences according to SEQ ID NOs:136–148 are placed in 0.1% PBS buffer and 50 ul of 1 mg/ml of peptide is used to cover each well of the microtiter assay plate. Serum samples from two mammals infected with genotype I/1a HCV and from one mammal infected with genotype 5a HCV are diluted as in Example 3 and the ELISA is carried out as in Example 3. Both mammals infected with genotype I HCV react positively with peptides while the mammal infected with genotype 5a HCV exhibit no reactivity.

EXAMPLE 7

Use of the E1 Peptides as a Vaccine

Since the E1 genotype-specific peptides of the present invention are derived from two variable regions in the complete E1 protein, there exists support for the use of these peptides as a vaccine to protect against a variety of HCV genotypes. Mammals are immunized with peptide(s) selected from SEQ ID NOs: 136–159 in an amount sufficient to stimulate production of protective antibodies. The immunized mammals challenged with various genotypes of HCV are protected.

What is claimed is:

1. A recombinant hepatitis C virus envelope 1 protein encoded by a gene whose nucleic acid sequence is selected from the group consisting of SEQ ID NO:1 through SEQ ID NO:51.

2. A recombinant hepatitis C virus envelope 1 protein whose amino acid sequence is selected from the group consisting of SEQ ID NO:52 through SEQ ID NO:102.

3. A kit for use in detecting the presence of antibodies to hepatitis C virus present in a biological sample, said kit comprising: at least one recombinant protein whose amino acid sequence is selected from the group consisting of SEQ ID NO: 52 through SEQ ID No: 102.

4. A purified and isolated peptide whose amino acid sequence is selected from the group consisting of SEQ ID NO: 136 through SEQ ID NO: 160.

5. A kit for use in detecting the presence of antibodies to hepatitis C virus in a biological sample said kit comprising: at least one peptide selected from the peptides of claim 4.

6. A purified and isolated peptide whose amino acid sequence is selected from the region shown in amino acid numbers 48–80, of any one of SEQ ID NOS: 52, 56 and 60–102, said sequence being at least 8 amino acids in length.

7. A kit for use in detecting the presence of antibodies to hepatitis C virus in a biological sample, said kit comprising: at least one peptide selected from the peptides of claim 6.

8. A purified and isolated peptide whose amino acid sequence is selected from the group consisting of SEQ ID NO: 141 where Xaa at position 3 is a proline residue, SEQ ID NO: 141 where the Xaa at position 4 is a valine, SEQ ID NO: 141 where the Xaa at position 5 is an alanine residue, SEQ ID NO: 141 where the Xaa at position 17 is a threonine residue, or SEQ ID NO: 141 where the Xaa at position 23 is a tyrosine residue.

9. A purified and isolated peptide whose amino acid sequence is selected from the region shown as amino acid numbers 110–136, in any one of SEQ ID NOS: 52–102, said sequence being at least eight amino acids in length.

10. A purified and isolated peptide whose amino acid sequence is selected from the region shown as amino acid numbers 138–160, in any one of SEQ ID NOS: 52–75 and 77–102, said sequence being at least 8 amino acids in length.

11. A purified and isolated peptide whose amino acid sequence is selected from the region shown as amino acid numbers 48–80, in any one of SEQ ID NOS: 52–102, said sequence being at least 23 amino acids in length.

* * * * *

SEQUENCE LISTING (1) GENERAL INFORMATION:

(iii) NUMBER OF SEQUENCES: 160

(2) INFORMATION FOR SEQ ID NO:1:

(i) SEQUENCE CHARACTERISTICS:
       (A) LENGTH: 576 base pairs
       (B) TYPE: nucleic acid
       (C) STRANDEDNESS: single
       (D) TOPOLOGY: linear (vi) ORIGINAL SOURCE:
       (A) ORGANISM: homosapiens
       (C) INDIVIDUAL ISOLATE: DK7

(xi) SEQUENCE DESCRIPTION: SEQ ID NO:1:

| | |
|---|---|
| TAC CAA GTG CGC AAC TCC ACG GGG CTT TAC CAT GTC ACC | 39 |
| AAT GAT TGC CCT AAC TCG AGT ATC GTG TAC GAG GCG GCC | 78 |
| GAT GCC ATC CTG CAC ACT CCG GGG TGT GTC CCT TGC GTT | 117 |
| CGC GAG GGT AAC GTC TCG AGG TGT TGG GTG GCG ATG ACC | 156 |
| CCC ACG GTG GCC ACC AGG GAT GGC AAA CTC CCC ACA GCG | 195 |
| CAG CTT CGA CGT CAC ATC GAT CTG CTC GTC GGG AGT GCC | 234 |
| ACC CTC TGT TCG GCC CTC TAC GTG GGG GAC CTG TGC GGG | 273 |
| TCT GTC TTT CTT GTC GGT CAA CTG TTT ACC TTC TCT CCC | 312 |
| AGG CGC CAC TGG ACG ACG CAA GGC TGC AAT TGT TCT ATC | 351 |
| TAT CCT GGC CAT ATA ACG GGT CAC CGC ATG GCG TGG GAT | 390 |
| ATG ATG ATG AAC TGG TCC CCT ACC ACG GCG TTG GTA GTA | 429 |
| GCT CAG CTG CTC CGG ATC CCG CAA GCC ATC TTG GAC ATG | 468 |
| ATC GCT GGT GCT CAC TGG GGA GTC CTG GCG GGC ATA GCG | 507 |
| TAT TTT TCC ATG GTG GGG AAC TGG GCG AAG GTC CTG GTA | 546 |
| GTG CTG CTG CTA TTT GCC GGC GTC GAC GCG | 576 |

(2) INFORMATION FOR SEQ ID NO:2:

(i) SEQUENCE CHARACTERISTICS:
       (A) LENGTH: 576 base pairs
       (B) TYPE: nucleic acid
       (C) STRANDEDNESS: single
       (D) TOPOLOGY: linear (vi) ORIGINAL SOURCE:
       (A) ORGANISM: homosapiens
       (C) INDIVIDUAL ISOLATE: DK9

(xi) SEQUENCE DESCRIPTION: SEQ ID NO:2:

| | |
|---|---|
| TAC CAA GTA CGC AAC TCC TCG GGC CTC TAC CAT GTC ACC | 39 |
| AAT GAT TGC CCT AAC TCG AGT ATT GTG TAC GAG GCG GCC | 78 |
| GAT GCC ATC CTG CAT TCT CCA GGG TGT GTC CCT TGC GTT | 117 |
| CGC GAG GGT AAC GCC TCG AAA TGT TGG GTG GCG GTG GCC | 156 |
| CCC ACG GTG GCC ACC AGG GAC GGC AAG CTC CCC GCA ACG | 195 |
| CAG CTT CGA CGT CAC ATC GAT CTG CTT GTC GGG AGC GCC | 234 |

```
ACC CTC TGC TCG GCC CTC TAT GTG GGG GAC TTG TGC GGG        273

TCT GTC TTC CTT GTC GGC CAA CTG TTC ACC TTC TCC CCC        312

AGA CGC CAC TGG ACA ACG CAA GAC TGC AAC TGT TCT ATC        351

TAC CCC GGC CAT ATT ACG GGT CAT CGC ATG GCG TGG GAT        390

ATG ATG ATG AAC TGG TCC CCT ACA GCA GCG CTG GTA ATG        429

GCG CAG CTG CTC AGG ATC CCG CAG GCC ATC TTG GAC ATG        468

ATC GCT GGT GCC CAC TGG GGA GTC CTA GCG GGC ATA GCG        507

TAT TTC TCC ATG GTG GGG AAC TGG GCG AAG GTC GTG GTG        546

GTA CTG TTG CTG TTT ACC GGC GTC GAT GCG                    576
```

(2) INFORMATION FOR SEQ ID NO:3:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DR1

(xi) SEQUENCE DESCRIPTION: SEQ ID NO:3:

```
CAC CAA GTG CGC AAC TCT ACA GGG CTT TAC CAT GTC ACC         39

AAT GAT TGC CCT AAT TCG AGT ATT GTG TAC GAG GCG GCC         78

GAT GCC ATC CTG CAC GCG CCG GGG TGT GTC CCT TGC GTT        117

CGC GAG GGT AAC GCC TCG AGG TGT TGG GTG GCG GTG ACC        156

CCC ACG GTG GCC ACC AGG GAC GGC AAA CTC CCC ACA ACG        195

CAG CTT CGA CGT CAC ATC GAC CTG CTT GTC GGG AGC GCC        234

ACC CTC TGC TCG GCC CTC TAC GTG GGG GAC CTG TGC GGG        273

TCT GTC TTC CTT GTC GGT CAA CTG TTC ACC TTT TCT CCC        312

AGG CGC CAC TGG ACA ACG CAA GAC TGC AAT TGT TCT ATC        351

TAT CCC GGC CAT ATA ACG GGA CAC CGT ATG GCA TGG GAT        390

ATG ATG ATG AAC TGG TCC CCT ACG ACA GCG CTG GTA ATG        429

GCT CAG CTG CTC CGG ATC CCA CAA GCC ATC TTG GAC ATG        468

ATC GCT GGA GCC CAC TGG GGA GTC CTA GCG GGC ATA GCG        507

TAT TTC TCC ATG GTG GGG AAC TGG GCG AAG GTC GTG GTA        546

GTG CTG TTG CTG TTT GCC GGC GTT GAT GCG                    576
```

(2) INFORMATION FOR SEQ ID NO:4:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DR4

(xi) SEQUENCE DESCRIPTION: SEQ ID NO:4:

```
CAC CAA GTG CGC AAC TCT ACA GGG CTT TAC CAT GTC ACC         39
```

-continued

| | |
|---|---|
| AAT GAT TGC CCT AAT TCG AGT ATT GTG TAC GAG GCG GCC | 78 |
| GAT GCC ATC CTG CAC ACG CCG GGG TGT GTC CCT TGC GTT | 117 |
| CGC GAG GGT AAC ACC TCG AGG TGT TGG GTG GCG GTG ACC | 156 |
| CCC ACG GTG GCC ACC AGG GAC GGC AAA CTC CCC ACA ACG | 195 |
| CAG CTC CGA CGT CAC ATC GAC CTG CTT GTC GGG AGC GCC | 234 |
| ACC CTC TGC TCG GCC CTC TAC GTG GGG GAC TTG TGC GGG | 273 |
| TCT GTC TTC CTT GTC GGT CAA CTG TTC ACC TTC TCT CCC | 312 |
| AGG CAC CAC TGG ACA ACG CAA GAC TGC AAT TGT TCC ATC | 351 |
| TAT CCC GGC CAT ATA ACG GGC CAC CGC ATG GCG TGG GAT | 390 |
| ATG ATG ATG AAC TGG TCC CCT ACG ACA GCG CTG GTA GTA | 429 |
| GCT CAG CTG CTC CGG ATC CCA CAA GCC ATC TTG GAC ATG | 468 |
| ATC GCT GGT GCC CAC TGG GGA GTC CTA GCG GGC ATA GCG | 507 |
| TAT TTC TCC ATG GTG GGG AAC TGG GCG AAG GTC CTG GTA | 546 |
| GTG CTG TTG CTG TTT GCC GGC GTT GAT GCG | 576 |

(2) INFORMATION FOR SEQ ID NO:5:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: S14

(xi) SEQUENCE DESCRIPTION: SEQ ID NO:5:

| | |
|---|---|
| TAC CAA GTG CGC AAC TCC ACG GGG CTT TAC CAT GTT ACC | 39 |
| AAT GAT TGC CCT AAC TCG AGT ATT GTG TAC GAG ACA GCT | 78 |
| GAT GCT ATC CTA CAC GCT CCG GGA TGT GTC CCT TGC GTT | 117 |
| CGT GAG GGT AAC ACC TCG AGG TGT TGG GTG GCG ATG ACC | 156 |
| CCC ACG GTG GCC ACC AGG GAC GGC AAA CTC CCC GCA ACG | 195 |
| CAG CTT CGA CGT TAC ATC GAT CTG CTT GTC GGG AGC GCC | 234 |
| ACC CTC TGT TCG GCC CTC TAC GTG GGG GAC TTG TGC GGG | 273 |
| TCT GTC TTT CTT GTC GGT CAG CTG TTT ACC TTC TCT CCC | 312 |
| AGG CGC CTC TGG ACG ACG CAA GAC TGC AAT TGT TCT ATC | 351 |
| TAT CCC GGC CAT ATA ACG GGT CAT CGC ATG GCA TGG GAT | 390 |
| ATG ATG ATG AAC TGG TCC CCT ACG ACG GCA CTG GTA GTA | 429 |
| GCT CAG CTG CTC CGG ATC CCA CAA GCC ATC TTG GAT ATG | 468 |
| ATC GCT GGT GCT CAC TGG GGA GTC CTA GCG GGC ATA GCG | 507 |
| TAT TTC TCC ATG GTG GGA AAC TGG GCG AAG GTC CTA GTG | 546 |
| GTG CTG CTG CTA TTC GCC GGC GTT GAC GCG | 576 |

(2) INFORMATION FOR SEQ ID NO:6:

(i) SEQUENCE CHARACTERISTICS:
        (A) LENGTH: 576 base pairs
        (B) TYPE: nucleic acid (C) STRANDEDNESS: single
        (D) TOPOLOGY: linear (vi) ORIGINAL SOURCE:
        (A) ORGANISM: homosapiens
        (C) INDIVIDUAL ISOLATE: S18

(xi) SEQUENCE DESCRIPTION: SEQ ID NO:6:

| | |
|---|---:|
| TAC CAA GTA CGC AAC TCC ACG GGC CTT TAC CAT GTC ACC | 39 |
| AAT GAC TGC CCT AAC TCG AGC ATT GTG TAC GAG ACG GCC | 78 |
| GAT ACC ATC CTA CAC TCT CCG GGG TGT GTC CCT TGC GTT | 117 |
| CGC GAG GGT AAC GCC TCG AGA TGT TGG GTG CCG GTG GCC | 156 |
| CCC ACA GTT GCC ACC AGG GAC GGC AAA CTC CCC GCA ACG | 195 |
| CAG CTT CGA CGT CAC ATC GAT CTG CTT GTT GGG AGC GCC | 234 |
| ACC CTC TGC TCG GCC CTC TAT GTG GGG GAC CTG TGC GGG | 273 |
| TCT GTC TTT CTT GTC AGC CAG CTG TTC ACT ATC TCC CCC | 312 |
| AGG CGC CAC TGG ACA ACG CAA GAC TGC AAC TGT TCT ATC | 351 |
| TAC CCC GGC CAT ATA ACG GGT CAC CGT ATG GCA TGG GAT | 390 |
| ATG ATG ATG AAC TGG TCC CCT ACA ACG GCG TTG GTA ATA | 429 |
| GCT CAG CTG CTC AGG GTC CCG CAA GCC GTC TTG GAC ATG | 468 |
| ATC GCT GGT GCC CAC TGG GGA GTC CTA GCG GGC ATA GCG | 507 |
| TAT TTC TCC ATG GCG GGG AAC TGG GCG AAG GTC CTG CTA | 546 |
| GTG CTG TTG CTG TTT GCC GGC GTC GAT GCG | 576 |

(2) INFORMATION FOR SEQ ID NO:7:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: SW1

(xi) SEQUENCE DESCRIPTION: SEQ ID NO:7:

| | |
|---|---:|
| TAC CAA GTA CGC AAC TCC TCG GGC CTT TAC CAT GTC ACC | 39 |
| AAT GAT TGC CCT AAC TCG AGT ATT GTG TAC GAG ACG GCC | 78 |
| GAT GCC ATT CTA CAC TCT CCA GGG TGT GTC CCT TGC GTT | 117 |
| CGC GAG GAT GGC GCC CCG AAG TGT TGG GTG GCG GTG GCC | 156 |
| CCC ACA GTC GCC ACT AGG GAC GGC AAA CTC CCT GCA ACG | 195 |
| CAG CTT CGA CGT CAC ATC GAT CTG CTT GTC GGA AGC GCC | 234 |
| ACC CTC TGC TCG GCC CTC TAC GTG GGG GAC TTG TGC GGG | 273 |
| TCT GTC TTT CTC GTC AGT CAA CTG TTC ACG TTC TCC CCC | 312 |
| AGG CGC CAC TGG ACA ACG CAA GAC TGT AAC TGT TCT ATC | 351 |
| TAT CCC GGC CAC ATA ACG GGT CAC CGC ATG GCA TGG GAT | 390 |
| ATG ATG ATG AAC TGG TCC CCC ACA ACA GCG CTG GTA GTA | 429 |
| GCT CAG CTG CTC AGG ATC CCG CAA GCC GTC TTG GAC ATG | 468 |
| ATC GCT GGT GCC CAC TGG GGA GTC CTA GCG GGC ATA GCG | 507 |

```
TAT TTC TCC ATG GTG GGG AAC TGG GCG AAG GTC CTG ATA           546
GTG CTG TTG CTG TTT TCC GGC GTC GAT GCG                       576

(2) INFORMATION FOR SEQ ID NO:8:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: US11

(xi) SEQUENCE DESCRIPTION: SEQ ID NO:8:

TAC CAA GTA CGC AAC TCC ACG GGG CTT TAC CAT GTC ACC            39
AAT GAT TGC CCT AAC TCG AGT ATT GTG TAC GAG GCG GCC            78
GAT GCC ATC CTG CAC ACT CCG GGG TGT GTT CCT TGC GTT           117
CGC GAG GGT AAC GCT TCG AGG TGT TGG GTG GCG ATG ACC           156
CCC ACG GTG GCC ACC AGG GAC GGC AAA CTC CCC ACA ACG           195
CAA CTT CGA CGT CAC ATC GAT CTG CTT GTC GGG AGC GCC           234
ACC CTC TGT TCG GCC CTC TAC GTG GGG GAC CTG TGC GGG           273
TCT GTC TTT CTT GTC GGT CAA CTG TTT ACC TTC TCT CCC           312
AGA CGC CAC TGG ACG ACG CAG GGC TGC AAT TGT TCT ATC           351
TAT CCC GGC CAT ATA ACG GGT CAC CGC ATG GCA TGG GAT           390
ATG ATG ATG AAC TGG TCC CCT ACG GCG GCG TTG GTG GTA           429
GCT CAG CTG CTC CGG ATC CCA CAA GCC ATC TTG GAC ATG           468
ATC GCT GGT GCT CAC TGG GGA GTC CTA GCG GGC ATA GCG           507
TAT TTC TCC ATG GTG GGG AAC TGG GCG AAG GTC CTG GTA           546
GTG CTG CTG CTA TTT GCC GGC GTC GAC GCG                       576

(2) INFORMATION FOR SEQ ID NO:9:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: D1

(xi) SEQUENCE DESCRIPTION: SEQ ID NO:9:

TAT GAA GTG CGC AAC GTG TCC GGG GTG TAC CAT GTC ACG            39
AAC GAC TGT TCC AAC TCG AGC ATT GTG TAT GAG ACA GCG            78
GAC ATG ATC ATG CAC ACC CCG GGT GCG TGT CCC TGC GTT           117
CGG GAG GAC AAC TCC TCT CGC TGC TGG GTA GCG CTC ACC           156
CCC ACG CTC GCG GCT AGG AAT GGC AAC GTC CCC ACT ACG           195
GCG ATA CGA CGC CAC GTC GAT TTG CTC GTT GGG GCG GCT           234
GCT TTC TGC TCC GCC ATG TAC GTG GGG GAT CTC TGC GGA           273
TCT GTT TTC CTC ATC TCC CAG CTG TTC ACC CTC TCG CCT           312
```

```
CGC CGG CAT GAG ACG GTA CAG GAG TGT AAT TGC TCA ATC           351

TAT CCC GGC CAC GTG ACA GGT CAC CGT ATG GCT TGG GAT           390

ATG ATG ATG AAC TGG TCA CCT ACA ACA GCC TTA GTG GTA           429

TCG CAG TTA CTC CGG ATC CCA CAA GCT GTC ATG GAC ATG           468

GTG GCG GGG GCC CAC TGG GGG GTC CTG GCG GGC CTC GCC           507

TAC TAT TCC ATG GTG GGG AAC TGG GCT AAG GTT TTG ATT           546

GTG ATG CTA CTC TTT GCT GGC GTT GAC GGC                       576
```

(2) INFORMATION FOR SEQ ID NO:10:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: D3

(xi) SEQUENCE DESCRIPTION: SEQ ID NO:10:

```
TAT GAA GTG CGC AAC GTG TCC GGG GTG TAC CAA GTC ACC            39

AAT GAC TGT TCC AAC TCG AGC ATC GTG TAT GAG ACA GCG            78

GAC ATG ATC ATG CAC ACC CCC GGG TGC GTG CCC TGC GTT           117

CGG GAG GAC AAC TCC TCT CGC TGC TGG GTA GCG CTC ACC           156

CCC ACG CTC GCG GCT AGG AAT AGC AGC GTC CCC ACT ACG           195

ACA ATA CGA CGC CAC GTC GAT TTG CTC GTT GGG GCG GCT           234

GCT TTC TGC TCC GCC ATG TAC GTG GGG GAT CTT TGC GGA           273

TCT GTT TTC CTC GTC TCC CAG CTG TTC ACC TTC TCG CCT           312

CGC CGG CAT GAG ACA GTA CAG GAA TGT AAC TGC TCA ATC           351

TAT CCC GGC CAC GTG ACA GGT CAC CGC ATG GCT TGG GAT           390

ATG ATG ATG AAC TGG TCG CCT ACA GCA GCC CTA GTG GTA           429

TCG CAG TTA CTC CGG ATC CCA CAA GCT GTC GTG GAC ATG           468

GTG GCG GGG GCC CAC TGG GGG GTC CTG GCG GGC CTC GCC           507

TAC TAT TCC ATG GTG GGG AAC TGG GCT AAG GTT TTG ATT           546

GTG ATG CTA CTC TTT GCT GGC GTC GAC GGC                       576
```

(2) INFORMATION FOR SEQ ID NO:11:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DK1

(xi) SEQUENCE DESCRIPTION: SEQ ID NO:11:

```
TAT GAA GTG CGC AAC GTG TCC GGG GTG TAC CAC GTC ACA            39

AAC GAC TGC TCC AAC TCA AGC ATC GTG TAT GAG GCA GTG            78

GAC GTG ATC ATG CAT ACC CCA GGG TGC GTG CCC TGC GTT           117
```

```
CGG GAG AAC AAC CAC TCC CGT TGC TGG GTA GCG CTC ACC            156

CCC ACG CTC GCG GCC AGG AAC GCC AGC ATC CCC ACT ACG            195

ACA ATA CGA CGC CAT GTC GAT TTG CTC GTT GGG GCG GCT            234

GCT TTC TGC TCC GCT ATG TAC GTG GGG GAC CTC TGC GGA            273

TCC GTT TTC CTC GTC TCT CAG CTG TTC ACC TTT TCA CCT            312

CGC CGG CAT GAG ACA GCA CAG GAC TGC AAC TGC TCA ATC            351

TAT CCC GGC CAC GTT TCA GGT CAC CGC ATG GCT TGG GAT            390

ATG ATG ATG AAC TGG TCA CCT ACA ACA GCC CTA GTG CTA            429

TCG CAG TTA CTC CGA ATC CCA CAA GCT GTC GTG GAC ATG            468

GTG GCG GGG GCC CAC TGG GGA GTC CTG GCG GGC CTC GCC            507

TAC TAC TCC ATG GCG GGG AAC TGG GCC AAG GTT TTA ATT            546

GTG TTG CTA CTC TTT GCC GGC GTT GAT GGG                        576

(2) INFORMATION FOR SEQ ID NO:12:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: HK3

(xi) SEQUENCE DESCRIPTION: SEQ ID NO:12:

TAT GAA GTG CGC AAC GTG TCC GGG ATA TAC CAT GTC ACG             39

AAC GAC TGC TCC AAC TCA AGC GTC GTG TAT GAG ACA GCA             78

GAC ATG ATC ATG CAT ACC CCT GGA TGC GTG CCC TGC GTA            117

CGG GAG AAC AAC TCC TCC CGC TGT TGG GTA GCG CTC ACT            156

CCC ACG CTC GCG GCC AGG AAC GTC AGC GTC CCC ACC ACG            195

ACA ATA CGA CGT CAC GTC GAC TTG CTC GTT GGG GCG GCT            234

GCC TTC TGC TCC GCT ATG TAC GTG GGG GAT CTC TGC GGA            273

TCT GTT TTC CTT GTC TCC CAG CTG TTC ACC TTC TCG CCT            312

CGC CGA CAC GAG ACA GTA CAG GAC TGC AAC TGC TCA CTC            351

TAT CCC GGC CAC GTA TCA GGT CAC CGC ATG GCT TGG GAT            390

ATG ATG ATG AAC TGG TCC CCT ACA GCA GCC CTA GTG GTG            429

TCG CAA TTA CTC CGG ATC CCG CAA GCT GTC GTG GAC ATG            468

GTG GCG GGG GCC CAC TGG GGA GTC CTA GCG GGC CTT GCC            507

TAC TAT TCC ATG GTG GGA AAC TGG GCT AAG GTT TTG ATT            546

GTG ATG CTA CTT TTT GCC GGC GTT GAT GGG                        576

(2) INFORMATION FOR SEQ ID NO:13:

(i) SEQUENCE CHARACTERISTICS:
        (A) LENGTH: 576 base pairs
        (B) TYPE: nucleic acid
        (C) STRANDEDNESS: single
        (D) TOPOLOGY: linear
```

(vi) ORIGINAL SOURCE:
        (A) ORGANISM: homosapiens
        (C) INDIVIDUAL ISOLATE: HK4

(xi) SEQUENCE DESCRIPTION: SEQ ID NO:13:

| | |
|---|---|
| CAT GAA GTG CAC AAC GTA TCC GGG ATC TAC CAT GTC ACG | 39 |
| AAC GAC TGC TCC AAC TCA AGT ATT GTG TAT GAG GCA GCG | 78 |
| GAC ATG ATC ATG CAT ACC CCC GGG TGC GTG CCC TGC GTC | 117 |
| CGG GAG AAC AAC TCC TCC CGT TGC TGG GTA GCG CTC ACT | 156 |
| CCC ACG CTC GCG GCC AGG AAC GCC AGC ATC CCC ACT ACG | 195 |
| ACA ATA CGA CGC CAT GTC GAC TTG CTC GTT GGG GCG GCT | 234 |
| GCT TTC TGC TCC GCC ATG TAC GTG GGA GAT CTC TGC GGA | 273 |
| TCT GTC TTC CTC GTC TCC CAG TTG TTC ACC TTC TCG CCT | 312 |
| CGC CGG CAT GAG ACG GTA CAG GAC TGC AAT TGC TCA ATC | 351 |
| TAT CCC GGC CAC GTA TCA GGT CAC CGC ATG GCT TGG GAT | 390 |
| ATG ATG ATG AAC TGG TCA CCT ACA GCA GCC CTA GTG GTA | 429 |
| TCG CAG TTA CTC CGA CTC CCA CAA GCT GTC ATG GAC ATG | 468 |
| GTG GCG GGA GCC CAC TGG GGA GTC CTA GCG GGC CTT GCT | 507 |
| TAC TAT TCC ATG GTG GGG AAC TGG GCC AAG GTT TTG ATT | 546 |
| GTG ATG CTA CTC TTT GCC GGC GTT GAC GGG | 576 |

(2) INFORMATION FOR SEQ ID NO:14:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: HK5

(xi) SEQUENCE DESCRIPTION: SEQ ID NO:14:

| | |
|---|---|
| TAT GAA GTG CGC AAC GTG TCC GGG GTA TAC CAT GTC ACG | 39 |
| AAC GAC TGC TCC AAC TTA AGC ATC GTG TAC GAG ACA ACG | 78 |
| GAC ATG ATC ATG CAC ACC CCT GGG TGC GTG CCC TGC GTT | 117 |
| CGG GAA AAC AAC TCC TCC CGT TGT TGG GTA GCG CTC GCC | 156 |
| CCC ACG CTC GCG GCC AGG AAC GCC AGC GTC CCC ACC ACG | 195 |
| GCA ATA CGA CGC CAC GTC GAC TTG CTC GTT GGG GCG GCT | 234 |
| GCT TTC TGC TCC GCT ATG TAC GTG GGG GAT CTT TGC GGA | 273 |
| TCT GTT TTC CTC GTC TCC CAG CTG TTC ACC TTC TCG CCT | 312 |
| CGC CGA CAC GAG ACG GTA CAG GAC TGC AAC TGC TCA ATC | 351 |
| TAT CCC GGC CAC GTA ACA GGT CAC CGC ATG GCT TGG GAT | 390 |
| ATG ATG ATG AAC TGG TCA CCT ACA ACA GCC CTA GTG GTG | 429 |
| TCG CAG TTA CTC CGG ATC CCG CAA GCT GTC GTG GAC ATG | 468 |
| GTA GCG GGG GCC CAC TGG GGG GTC CTG GCG GGC CTT GCC | 507 |
| TAC TAT TCC ATG GTG GGA AAC TGG GCT AAG GTT TTG ATT | 546 |

```
GTG ATG CTA CTT TTT GCC GGC GTT GAT GGG                              576
```

(2) INFORMATION FOR SEQ ID NO:15:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: HK8

(xi) SEQUENCE DESCRIPTION: SEQ ID NO:15:

```
TAT GAA GTG CGC AAC GTG TCC GGG ATA TAC CAT GTC ACG                  39
AAC GAC TGC TCC AAC TCA AGC ATC GTG TAT GAA ACA GCG                  78
GAC ATG ATT ATG CAT ACC CCT GGA TGC ATG CCC TGC GTT                  117
CGG GAG AAC AAC TCC TCC CGT TGC TGG GTG GCG CTC ACT                  156
CCC ACG CTC GCG GCT AGG AAT GTC AGC GTC CCC ACT ACG                  195
ACA ATA CGA CGC CAC GTC GAC TTG CTC GTT GGG GCG GCT                  234
GCT TTC TGC TCC GCT ATG TAC GTG GGG GAT CTC TGC GGA                  273
TCT GTT TTC CTC GTC TCC CAG CTG TTC ACC TTT TCG CCT                  312
CGC CGA CAC GAG ACG GTA CAG GAC TGC AAC TGC TCA ATC                  351
TAT CCC GGC CAC GTA TCA GGT CAC CGC ATG GCT TGG GAT                  390
ATG ATG ATG AAC TGG TCG CCC ACA ACA GCC CTA GTG GTG                  429
TCG CAG TTA CTC CGG ATC CCG CAA GCT ATC GTG GAC ATG                  468
GTG GCG GGG GCC CAC TGG GGA GTC CTA GCG GGC CTT GCC                  507
TAC TAT TCC ATG GTG GGC AAC TGG GCT AAG GTT TTG ATT                  546
GTG ATG CTA CTG TTT GCC GGC GTT GAT GGG                              576
```

(2) INFORMATION FOR SEQ ID NO:16:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: IND5

(xi) SEQUENCE DESCRIPTION: SEQ ID NO:16:

```
TAT GAA GTG CGC AAC GTG TCC GGG GTG TAC CAT GTC ACG                  39
AAC GAC TGC TCC AAC TCA AGT ATT GTG TAT GAG GCA GCG                  78
GAC ATG ATC ATG CAC ACT CCC GGG TGC GTG CCC TGC GTT                  117
CGG GAG GGC AAC TCC TCT CGC TGC TGG GTA GCG CTC ACT                  156
CCC ACT CTC GCG GCC AGG AAC GCC AGC GTC TCC ACC ACG                  195
ACA ATA CGA CAC CAC GTC GAT TTG CTC GTT GGG GCG GCT                  234
GCT TTC TGT TCC GCT ATG TAC GTG GGG GAT CTA TGC GGA                  273
TCT GTT TTC CTC GTC TCC CAG CTG TTC ACC TTC TCA CCG                  312
CGC CGG CAT GAG ACA GTA CAG GAC TGC AAT TGC TCC ATC                  351
```

```
TAT CCC GGC CAC GTA TCA GGT CAC CGC ATG GCC TGG GAT            390

ATG ATG ATG AAC TGG TCA CCT ACA GCA GCC CTA GTG GTA            429

TCG CAG TTG CTC CGG ATC CCA CAA GCT GTC GTG GAT ATG            468

GTG GCG GGG GCC CAC TGG GGA ATC CTG GCG GGC CTT GCC            507

TAC TAT TCC ATG GTA GGG AAC TGG GCT AAG GTT TTG ATT            546

GTG ATG CTA CTC TTT GCC GGC GTT GAC GGG                        576

(2) INFORMATION FOR SEQ ID NO:17:

(i) SEQUENCE CHARACTERISTICS:
        (A) LENGTH:  576 base pairs
        (B) TYPE:  nucleic acid
        (C) STRANDEDNESS:  single
        (D) TOPOLOGY:  linear (vi) ORIGINAL SOURCE:
        (A) ORGANISM:  homosapiens
        (C) INDIVIDUAL ISOLATE:  IND8

(xi) SEQUENCE DESCRIPTION: SEQ ID NO:17:

TAT GAG GTG CGC AAC GTG TCC GGG GTG TAC CAT GTC ACG             39

AAC GAC TGC TCC AAC TCA AGT ATT GTG TAT GAG GCA GCG             78

GAC ATG ATC ATG CAC ACC CCC GGG TGC GTG CCC TGC GTT            117

CGG GAG GGC AAC TTC TCT AGT TGC TGG GTA GCG CTC ACT            156

CCC ACT CTC GCG GCT AGG AAC GCC AGC GTC CCC ACC ACG            195

ACA ATA CGA CGC CAC GTC GAT TTG CTC GTT GGG GCG GCT            234

GCT TTC TGT TCC GCT ATG TAC GTG GGG GAT CTC TGC GGA            273

TCT GTT TTC CTT GTC TCC CAG CTG TTC ACC TTC TCA CCG            312

CGC CGG CAT GAG ACA GTA CAG GAC TGC AAT TGC TCC ATC            351

TAT CCC GGC CAC GTA TCA GGT CAC CGC ATG GCT TGG GAT            390

ATG ATG ATG AAC TGG TCA CCT ACA GCG GCC CTA GTG GTA            429

TCG CAG TTG CTC CGG ATC CCA CAA GCT GTC GTG GAT ATG            468

GTG GCG GGG GCC CAC TGG GGA ATC CTG GCG GGC CTT GCC            507

TAC TAT TCC ATG GTA GGG AAC TGG GCT AAG GTT TTG ATT            546

GTG ATG CTA CTC TTT GCC GGC GTT GAC GGG                        576

(2) INFORMATION FOR SEQ ID NO:18:

(i) SEQUENCE CHARACTERISTICS:
        (A) LENGTH:  576 base pairs
        (B) TYPE:  nucleic acid
        (C) STRANDEDNESS:  single
        (D) TOPOLOGY:  linear (vi) ORIGINAL SOURCE:
        (A) ORGANISM:  homosapiens
        (C) INDIVIDUAL ISOLATE:  P10

(xi) SEQUENCE DESCRIPTION: SEQ ID NO:18:

TAT GAA GTG CGC AAC GTG TCC GGG GTG TAC CAT GTC ACG             39

AAC GAC TGC TCC AAC TCA AGT ATT GTG TAT GAG GCA GCG             78

GAC ATG ATA ATG CAC ACC CCC GGG TGC GTG CCC TGT GTT            117

CGG GAG AAC AAC TCC TCC CGC TGC TGG GTA GCG CTC ACT            156
```

```
CCC ACA CTC GCG GCT AGG AAT TCC AGC GTC CCA ACT ACG        195

GCA ATA CGA CGC CAT GTC GAT TTG CTC GTT GGG GCG GCT        234

GCT TTC TGC TCC GCT ATG TAC GTG GGG GAT CTC TGC GGA        273

TCT GTT CTC CTC GTC TCC CAG CTG TTC ACC TTC TCA CCT        312

CGC CGG CAT TGG ACA GTA CAG GAC TGC AAT TGT TCA ATC        351

TAT CCT GGC CAC GTA TCA GGT CAC CGC ATG GCT TGG GAT        390

ATG ATG ATG AAC TGG TCG CCC ACA GCA GCC CTA GTG GTG        429

TCG CAG CTA CTC CGG ATC CCA CAA GCT ATC TTG GAT GTG        468

GTG GCG GGG GCC CAC TGG GGA GTC CTG GCG GGC CTT GCC        507

TAC TAT TCC ATG GTG GGG AAC TGG GCT AAG GTC TTG ATT        546

GTG ATG CTA CTC TTT GCC GGC GTT GAC GGA                    576

(2) INFORMATION FOR SEQ ID NO:19:

(i) SEQUENCE CHARACTERISTICS:
        (A) LENGTH:  576 base pairs
        (B) TYPE:  nucleic acid
        (C) STRANDEDNESS:  single
        (D) TOPOLOGY:  linear (vi) ORIGINAL SOURCE:
        (A) ORGANISM:  homosapiens
        (C) INDIVIDUAL ISOLATE:  S9

(xi) SEQUENCE DESCRIPTION: SEQ ID NO:19:

TAT GAA GTG CGC AAC GTA TCC GGG GCG TAC CAT GTC ACG         39

AAC GAC TGC TCC AAC TCA AGT ATT GTG TAC GAG GCA GCG         78

GAC GTG ATC ATG CAT ACC CCC GGG TGT GTA CCC TGC GTT        117

CAG GAG GGT AAC TCC TCC CAA TGC TGG GTG GCG CTC ACC        156

CCC ACG CTC GCG GCC AGG AAC GCT ACC GTC CCC ACC ACG        195

ACA ATA CGA CGT CAT GTC GAT TTG CTC GTT GGG GCG GCT        234

GTT TTC TGC TCC GCT ATG TAC GTG GGG GAC CTG TGC GGA        273

TCT GTT TTC CTC ATC TCC CAG CTG TTC ACC ATC TCG CCC        312

CGT CGG CAT GAG ACA GTA CAG AAC TGC AAT TGC TCA ATC        351

TAT CCC GGA CAC GTG ACA GGT CAT CGC ATG GCC TGG GAT        390

ATG ATG ATG AAC TGG TCG CCT ACA ACA GCC CTA GTG GTA        429

TCG CAG CTA CTC CGG ATC CCA CAA GCT GTC ATG GAT ATG        468

GTG GCG GGG GCC CAC TGG GGA GTC CTG GCG GGC CTC GCC        507

TAC TAT TCC ATG GTG GGG AAC TGG GCT AAG GTT TTG ATT        546

GTG ATG CTA CTT TTT GCT GGT GTT GAC GGG                    576

(2) INFORMATION FOR SEQ ID NO:20:

(i) SEQUENCE CHARACTERISTICS:
        (A) LENGTH:  576 base pairs
        (B) TYPE:  nucleic acid
        (C) STRANDEDNESS:  single
        (D) TOPOLOGY:  linear (vi) ORIGINAL SOURCE:
        (A) ORGANISM:  homosapiens
        (C) INDIVIDUAL ISOLATE:  S45
```

(xi) SEQUENCE DESCRIPTION: SEQ ID NO:20:

| | |
|---|---|
| TAT GAA GTG CGC AAC GTG TCC GGG GCG TAC CAT GTC ACG | 39 |
| AAC GAC TGC TCC AAC TCA AGC ATT GTG TAT GAG GCA GTG | 78 |
| GAC GTG ATC CTG CAC ACC CCT GGG TGC GTG CCC TGC GTT | 117 |
| CGG GAG AAC AAC TCC TCC CGT TGC TGG GTG GCG CTC ACT | 156 |
| CCC ACG CTC GCG GCC AGG AAC TCC AGC GTC CCC ACT ACG | 195 |
| ACA ATA CGA CGT CAC GTC GAT TTG CTC GTT GGG GCG GCT | 234 |
| GCT TTC TGC TCC GCT ATG TAC GTG GGG GAT CTC TGC GGA | 273 |
| TCT GTT TTC CTT GTT TCC CAG CTG TTC ACC TTC TCG CCT | 312 |
| CGT CGG CAT GAG ACA GTA CAG GAC TGC AAC TGT TCA ATC | 351 |
| TAT CCC GGC CAC GTA ACA GGT CAC CGC ATG GCT TGG GAT | 390 |
| ATG ATG ATG AAC TGG TCG CCT ACA GCA GCC TTA GTG GTA | 429 |
| TCG CAG TTA CTC CGG ATC CCA CAA GCT GTC GTG GAC ATG | 468 |
| GTG GCG GGG GCC CAC TGG GGA GTC CTG GCG GGC CTT GCC | 507 |
| TAC TAT TCC ATG GTG GGG AAC TGG GCT AAG GTT CTG ATT | 546 |
| GTG ATG CTA CTC TTT GCC GGC GTT GAC GGG | 576 |

(2) INFORMATION FOR SEQ ID NO:21:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: SA10

(xi) SEQUENCE DESCRIPTION: SEQ ID NO:21:

| | |
|---|---|
| TAT GAA GTG CGC AAC GTG TCC GGG ATG TAC CAT GTC ACG | 39 |
| AAC GAC TGC TCC AAC TCA AGC ATT GTG TAT GAG GCA GCG | 78 |
| GAC ATG ATC ATG CAC ACC CCC GGG TGC GTG CCC TGC GTT | 117 |
| CGG GAG AAC AAC TCC TCC CGC TGC TGG GTA GCG CTC ACT | 156 |
| CCC ACG CTC GCG GCC AGG AAC TCC AGC GTC CCC ACT ACG | 195 |
| ACA ATA CGA CGC CAC GTC GAT TTG CTC GTT GGG GCG GCT | 234 |
| GCT TTC TGC TCC GCC ATG TAC GTG GGG GAC CTC TGC GGA | 273 |
| TCT GTT TTC CTT GTC TCC CAG CTG TTC ACC TTC TCG CCT | 312 |
| CGC CGG TAT GAG ACA GTA CAG GAC TGC AAT TGC TCA ATC | 351 |
| TAT CCC GGC CGC GTA ACA GGT CAC CGC ATG GCT TGG GAT | 390 |
| ATG ATG ATG AAC TGG TCA CCT ACA ACA GCT CTA GTA GTA | 429 |
| TCG CAG TTA CTC CGG ATC CCA CAA GCT ATC GTG GAC ATG | 468 |
| GTG GCG GGG GCC CAC TGG GGA GTC CTA GCG GGC CTT GCC | 507 |
| TAC TAT TCC ATG GTG GGG AAC TGG GCT AAG GTT TTG ATT | 546 |
| GTT ATG CTA CTC TTT GCC GGC GTT GAC GGG | 576 |

(2) INFORMATION FOR SEQ ID NO:22:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: SW2

(xi) SEQUENCE DESCRIPTION: SEQ ID NO:22:

```
TAT GAA GTG CGC AAC GTG TCC GGG GTG TAT CAT GTC ACG        39
AAC GAC TGT TCC AAC TCA AGC ATT GTG TAT GAG ACA GCG        78
GAC ATG ATC ATG CAT ACC CCC GGG TGC GTG CCC TGC GTT       117
CGG GAG GCC AAC TCC TCC CGC TGC TGG GTA GCG CTC ACT       156
CCC ACG CTA GCA GCC AGG AAC ACC AGC GTC CCC ACT ACG       195
ACA ATA CGA CGC CAC GTC GAT TTG CTC GTT GGG GCG GCT       234
GCT TTC TGC TCC GTT ATG TAC GTG GGG GAT CTC TGC GGA       273
TCT GTT TTC CTC GTC TCC CAG CTG TTC ACT TTT TCA CCT       312
CGC CGG CAC GAG ACA GTA CAG GAC TGC AAC TGT TCC ATC       351
TAT CCC GGC CAC GTA TCA GGT CAC CGC ATG GCT TGG GAC       390
ATG ATG ATG AAC TGG TCA CCT ACA GCA GCC CTG GTG GTA       429
TCG CAG TTA CTC CGG ATC CCA CAA GCT GTC GTG GAC ATG       468
GTA GCG GGG GCC CAC TGG GGA GTC CTG GCG GGC CTT GCA       507
TAC TAT TCC ATG GTG GGG AAC TGG GCT AAG GTT TTG ATT       546
GTG ATG CTA CTC TTT GCT GGC GTT GAC GGG                    576
```

(2) INFORMATION FOR SEQ ID NO:23:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T3

(xi) SEQUENCE DESCRIPTION: SEQ ID NO:23:

```
TAC GAA GTG CGC AAC GTG TCC GGG GTG TAC TAT GTC ACG        39
AAC GAC TGT TCC AAC TCA AGC ATT GTG TAT GAG ACA GCG        78
GAC ATG ATC ATG CAC ACC CCT GGG TGC GTG CCC TGC GTT       117
CGG GAG AGC AAT TCC TCC CGC TGC TGG GTA GCG CTT ACT       156
CCC ACG CTC GCG GCC AGG AAC GCC AGC GTC CCC ACT AAG       195
ACA ATA CGA CGT CAC GTC GAC TTG CTC GTT GGG GCG GCT       234
GCT TTC TGT TCC GCT ATG TAC GTG GGG GAT CTC TGC GGA       273
TCT GTT TTC CTC GTC TCC CAG CTG TTC ACT TTC TCG CCT       312
CGC CGG CAT GAG ACA GTA CAG GAC TGC AAC TGC TCA ATC       351
TAT CCC GGC CAC GTA ACA GGT CAC CGT ATG GCT TGG GAT       390
```

```
ATG ATG ATG AAC TGG TCG CCC ACA ACG GCA CTA GTG GTG            429

TCG CAG TTG CTC CGG ATC CCA CAA GCT GTC GTG GAC ATG            468

GTG GCG GGG GCC CAC TGG GGA GTC CTG GCG GGC CTT GCC            507

TAC TAT TCC ATG GTG GGG AAC TGG GCT AAG GTT TTG ATT            546

GTG CTG CTA CTC TTT GCC GGC GTT GAT GGG                        576
```

(2) INFORMATION FOR SEQ ID NO:24:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T10

(xi) SEQUENCE DESCRIPTION: SEQ ID NO:24:

```
TAT GAA GTG CGC AAC GTG TCC GGG ATG TAC CAT GTC ACG            39

AAC GAC TGC TCC AAC TCA AGC ATT GTG TTT GAG GCA GCG            78

GAC TTG ATC ATG CAC ACC CCC GGG TGC GTG CCC TGC GTT            117

CGG GAG GGC AAC TCC TCC CGC TGC TGG GTA GCG CTC ACT            156

CCC ACG CTC GCG GCC AGG AAC ACC AGC GTC CCC ACT ACG            195

ACG ATA CGA CGC CAT GTC GAT TTG CTC GTT GGG GCG GCT            234

GCT TTC TGC TCC GCT ATG TAT GTG GGA GAC CTC TGC GGA            273

TCT GTT TTC CTC GTC TCT CAG CTG TTC ACC TTC TCG CCT            312

CGC CGG CAT GAG ACT TTG CAG GAC TGC AAC TGC TCA ATC            351

TAT CCC GGC CAT CTG TCA GGT CAC CGC ATG GCT TGG GAC            390

ATG ATG ATG AAC TGG TCG CCT ACA ACA GCT CTA GTG GTG            429

TCG CAG TTA CTC CGG ATC CCA CAA GCT GTC ATG GAC ATG            468

GTG ACA GGG GCC CAC TGG GGA GTC CTG GCG GGC CTT GCC            507

TAC TAT TCC ATG GCG GGG AAC TGG GCT AAG GTT TTA ATT            546

GTG ATG CTA CTC TTT GCC GGC GTT GAT GGG                        576
```

(2) INFORMATION FOR SEQ ID NO:25:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: US6

(xi) SEQUENCE DESCRIPTION: SEQ ID NO:25:

```
TAT GAA GTG CGC AAC GTG TCC GGG ATG TAC CAT GTC ACG            39

AAC GAC TGC TCC AAC TCA AGC ATT GTG TAT GAG GCA GCG            78

GAC ATG ATC ATG CAC ACT CCC GGG TGC GTG CCC TGT GTT            117

CGG GAG AAC AAT TCC TCC CGC TGC TGG GTA GCG CTC ACT            156

CCC ACG CTC GCG GCC AGG AAC GCT AGC GTC CCC ACT ACG            195
```

```
ACA ATA CGA CGC CAC GTC GAT TTG CTC GTT GGG GCG GCT          234

ACT TTC TGC TCC GCT ATG TAC GTG GGG GAC CTC TGC GGG          273

TCC GTT TTC CTC ATC TCC CAG CTG TTC ACC TTC TCG CCT          312

CGT CAG CAT GAG ACA GTA CAG GAC TGC AAT TGT TCA ATC          351

TAT CCC GGC CAC GTA TCA GGT CAC CGC ATG GCT TGG GAT          390

ATG ATG ATG AAT TGG TCA CCT ACA GCA GCC CTA GTG GTA          429

TCG CAG TTA CTC CGG ATC CCA CAA GCT GTC ATG GAC ATG          468

GTG GCG GGG GCC CAC TGG GGA GTC CTG GCG GGC CTT GCC          507

TAC TAT TCC ATG GTG GGG AAC TGG GCT AAG GTT CTG ATT          546

GTG TTG CTA CTC TTT GCC GGC GTT GAC GGG                      576

(2) INFORMATION FOR SEQ ID NO:26:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T2

(xi) SEQUENCE DESCRIPTION: SEQ ID NO:26:

GCC CAA GTG AGG AAC ACC AGC CGC GGT TAC ATG GTG ACT           39

AAC GAC TGT TCC AAT GAG AGC ATC ACC TGG CAG CTC CAA           78

GCC GCG GTT CTC CAC GTC CCC GGG TGT ATC CCG TGT GAG          117

AGG CTG GGA AAT ACA TCC CGA TGC TGG ATA CCG TCA ACA          156

CCA AAC GTG GCC GTG CGG CAG CCC GGC GCT CTT ACG CAG          195

GGC TTG CGG ACG CAC ATC GAC ATG GTT GTG ATG TCC GCC          234

ACG CTC TGC TCT GCC CTC TAC GTG GGG GAC CTC TGC GGC          273

GGG GTG ATG CTC GCA GCC CAG ATG TTC ATT GTC TCG CCG          312

CGA CGC CAC TGG TTT GTG CAA GAA TGC AAT TGC TCC ATC          351

TAC CCC GGT ACC ATC ACT GGA CAC CGT ATG GCA TGG GAC          390

ATG ATG ATG AAC TGG TCG CCC ACA GCC ACC ATG ATC CTG          429

GCG TAC GCG ATG CGC GTT CCC GAG GTC ATC ATA GAC ATC          468

ATC GGC GGG GCT CAC TGG GGC GTC ATG TTT GGC TTG GCC          507

TAC TTC TCT ATG CAG GGA GCG TGG GCG AAG GTC ATT GTC          546

ATC CTC TTG CTG GCT GCT GGG GTG GAC GCG                      576

(2) INFORMATION FOR SEQ ID NO:27:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T4
```

(xi) SEQUENCE DESCRIPTION: SEQ ID NO:27:

| | |
|---|---|
| GCA CAA GTG AAG AAC ACC ACT AAC AGC TAC ATG GTG ACC | 39 |
| AAC GAC TGT TCT AAT GAC AGC ATC ACT TGG CAG CTC CAG | 78 |
| GCC GCG GTC CTC CAC GTC CCC GGG TGT GTC CCG TGC GAG | 117 |
| AAA ACG GGA AAT ACA TCT CGG TGC TGG ATA CCG GTT TCA | 156 |
| CCA AAC GTG GCC GTG CGG CAG CCC GGC GCC CTC ACG CAG | 195 |
| GGC TTG CGG ACG CAC ATT GAC ATG GTT GTG ATG TCC GCC | 234 |
| ACG CTC TGC TCT GCT CTT TAC GTG GGG GAC CTC TGC GGC | 273 |
| GGG GTG ATG CTC GCA GCC CAG ATG TTC ATC GTC TCG CCG | 312 |
| CAA CAT CAC TGG TTT GTG CAA GAC TGC AAT TGC TCT ATC | 351 |
| TAC CCT GGC ACC ATC ACT GGA CAC CGT ATG GCA TGG GAT | 390 |
| ATG ATG ATG AAC TGG TCG CCC ACG GCC ACC ATG ATC CTG | 429 |
| GCG TAC GCG ATG CGC GTT CCC GAG GTC ATC TTA GAC ATC | 468 |
| GTT AGC GGG GCA CAC TGG GGC GTC ATG TTC GGC TTG GCC | 507 |
| TAC TTC TCT ATG CAG GGA GCG TGG GCG AAA GTC GTT GTC | 546 |
| ATC CTT CTG CTG GCC GCT GGG GTG GAC GCG | 576 |

(2) INFORMATION FOR SEQ ID NO:28:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T9

(xi) SEQUENCE DESCRIPTION: SEQ ID NO:28:

| | |
|---|---|
| GCC GAA GTG AAG AAC ACC AGT ACC AGC TAC ATG GTG ACA | 39 |
| AAT GAC TGT TCC AAC GAC AGC ATC ACC TGG CAA CTC CAG | 78 |
| GCC GCG GTC CTC CAC GTC CCC GGG TGC GTC CCG TGC GAG | 117 |
| AGA GTT GGA AAC GCG TCG CGG TGC TGG ATA CCG GTC TCG | 156 |
| CCA AAC GTA GCT GTG CAG CGG CCT GGC GCC CTC ACG CAG | 195 |
| GGC TTG CGG ACG CAC ATC GAC ATG GTT GTG ATG TCC GCC | 234 |
| ACG CTC TGC TCC GCT CTC TAC GTG GGG GAT CTC TGC GGC | 273 |
| GGG GTA ATG CTC GCC GCT CAG ATG TTC ATT ATC TCG CCG | 312 |
| CAG CAC CAC TGG TTT GTG CAG GAA TGC AAC TGC TCC ATT | 351 |
| TAC CCT GGT ACC ATC ACT GGA CAC CGT ATG GCA TGG GAC | 390 |
| ATG ATG ATG AAC TGG TCG CCC ACA ACC ACC ATG ATC TTG | 429 |
| GCG TAC GCG ATG CGC GTT CCC GAG GTC ATC ATA GAC ATC | 468 |
| ATC AGC GGA GCT CAC TGG GGC GTC ATG TTC GGC CTA GCC | 507 |
| TAC TTC TCT ATG CAG GGA GCG TGG GCG AAG GTC GTT GTC | 546 |
| ATC CTG TTG CTC ACC GCT GGC GTG GAC GCG | 576 |

(2) INFORMATION FOR SEQ ID NO:29:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: 10

(xi) SEQUENCE DESCRIPTION: SEQ ID NO:29:

```
GTC CAA GTG AAA AAC ACC AGT ACC AGC TAT ATG GTG ACC          39
AAT GAC TGC TCC AAC GAC AGC ATC ACT TGG CAA CTT GAG          78
GCT GCG GTC CTC CAC GTT CCC GGG TGT GTC CCG TGC GAG         117
AAA GTG GGA AAT ACA TCT CGG TGC TGG ATA CCG GTC TCA         156
CCA AAT GTG GCC GTG CAG CGG CCT GGC GCC CTC ACG CAG         195
GGC TTG CGG ACT CAC ATC GAC ATG GTC GTG ATG TCC GCC         234
ACG CTC TGC TCC GCT CTT TAC GTG GGG GAC TTC TGC GGT         273
GGG ATG ATG CTC GCA GCC CAA ATG TTC ATT GTC TCG CCG         312
CGC CAC CAC TCG TTT GTG CAG GAA TGC AAC TGC TCC ATC         351
TAC CCC GGT ACC ATC ACC GGG CAC CGT ATG GCA TGG GAC         390
ATG ATG ATG AAC TGG TCG CCC ACG GCC ACT TTG ATC CTG         429
GCG TAC GTG ATG CGC GTT CCC GAG GTC ATC ATA GAC ATC         468
ATT AGC GGG GCG CAT TGG GGC GTC TTG TTC GGC TTA GCC         507
TAC TTC TCT ATG CAG GGA GCG TGG GCG AAA GTC GTT GTC         546
ATC CTT CTG CTA GCC GCT GGG GTG GAC GCG                     576
```

(2) INFORMATION FOR SEQ ID NO:30:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DK8

(xi) SEQUENCE DESCRIPTION: SEQ ID NO:30:

```
GTG GAA GTC AGG AAC ATC AGT TCC AGC TAC TAC GCC ACC          39
AAT GAT TGC TCA AAC AAC AGC ATC ACC TGG CAA CTC ACC          78
GAC GCA GTT CTC CAC CTT CCC GGA TGC GTC CCA TGT GAG         117
AAT GAC AAT GGC ACC CTG CGC TGC TGG ATA CAA GTG ACA         156
CCT AAT GTG GCT GTG AAA CAC CGC GGC GCA CTT ACT CAT         195
AAC CTG CGA ACA CAC GTC GAC GTG ATC GTA ATG GCA GCT         234
ACG GTC TGC TCG GCC TTG TAT GTG GGA GAC GTA TGC GGG         273
GCC GTG ATG ATC GTG TCG CAG GCT CTC ATA ATA TCG CCT         312
GAA CGC CAC AAC TTT ACC CAG GAG TGC AAC TGT TCC ATC         351
TAC CAA GGT CAT ATC ACC GGC CAC CGC ATG GCA TGG GAC         390
```

```
ATG ATG CTA AAC TGG TCA CCA ACT CTT ACC ATG ATC CTC           429

GCC TAT GCC GCT CGT GTT CCT GAG CTA GCC CTC CAG GTT           468

GTC TTC GGC GGC CAT TGG GGC GTG GTG TTT GGC TTG GCC           507

TAT TTC TCC ATG CAG GGA GCG TGG GCC AAA GTC ATT GCC           546

ATC CTC CTT CTT GTC GCA GGA GTG GAT GCA                        576

(2) INFORMATION FOR SEQ ID NO:31:

(i) SEQUENCE CHARACTERISTICS:
        (A) LENGTH:  576 base pairs
        (B) TYPE:  nucleic acid
        (C) STRANDEDNESS:  single
        (D) TOPOLOGY:  linear (vi) ORIGINAL SOURCE:
        (A) ORGANISM:  homosapiens
        (C) INDIVIDUAL ISOLATE:  DK11

(xi) SEQUENCE DESCRIPTION: SEQ ID NO:31:

GTG GAA GTC AGG AAC ACC AGT TCT AGT TAC TAC GCC ACC            39

AAT GAT TGC TCA AAC AAC AGC ATC ACC TGG CAA CTC ACC            78

AAC GCA GTT CTC CAC CTT CCC GGA TGC GTC CCA TGT GAG           117

AAT GAC AAT GGC ACC CTG CAC TGC TGG ATA CAA GTG ACA           156

CCT AAT GTG GCT GTG AAA CAC CGC GGC GCA CTC ACT CAC           195

AAC CTG CGA GCA CAT ATA GAT ATG ATT GTA ATG GCA GCT           234

ACG GTC TGC TCG GCC TTG TAT GTG GGA GAC GTG TGC GGG           273

GCC GTG ATG ATC GTG TCG CAG GCT TTC ATA GTA TCG CCA           312

GAA CAC CAC CAC TTT ACC CAA GAG TGC AAC TGT TCC ATC           351

TAC CAA GGT CAC ATC ACC GGC CAC CGC ATG GCA TGG GAC           390

ATG ATG CTT AAC TGG TCA CCA ACT CTC ACC ATG ATC CTC           429

GCC TAT GCC GCC CGT GTT CCT GAG CTA GTC CTT GAA GTC           468

GTC TTC GGT GGT CAT TGG GGT GTG GTG TTT GGC TTG GCC           507

TAT TTC TCC ATG CAG GGA GCG TGG GCC AAG GTC ATT GCC           546

ATC CTC CTT CTT GTA GCA GGA GTG GAT GCA                        576

(2) INFORMATION FOR SEQ ID NO:32:

(i) SEQUENCE CHARACTERISTICS:
        (A) LENGTH:  576 base pairs
        (B) TYPE:  nucleic acid
        (C) STRANDEDNESS:  single
        (D) TOPOLOGY:  linear (vi) ORIGINAL SOURCE:
        (A) ORGANISM:  homosapiens
        (C) INDIVIDUAL ISOLATE:  SW3

(xi) SEQUENCE DESCRIPTION: SEQ ID NO:32:

GTG GAA GTC AGG AAC ATC AGT TCT AGC TAC TAT GCC ACC            39

AAT GAT TGC TCA AAC AGC AGC ATC ACC TGG CAA CTC ACC            78

AAC GCA GTC CTC CAC CTT CCC GGA TGC GTC CCG TGT GAG           117

AAT GAT AAT GGC ACC CTG CAC TGC TGG ATA CAA GTG ACA           156

CCT AAT GTG GCT GTG AAA CAC CGC GGC GCG CTC ACT CAC           195
```

| | |
|---|---|
| AAC CTG CGA GCA CAC GTC GAT ATG ATC GTA ATG GCA GCT | 234 |
| ACG GTC TGC TCG GCC TTG TAT GTG GGA GAC ATG TGC GGG | 273 |
| GCC GTG ATG ATC GTG TCG CAG GCT TTC ATA ATA TCG CCA | 312 |
| GAA CGC CAC AAC TTT ACC CAA GAG TGC AAC TGT TCC ATC | 351 |
| TAC CAA GGT CGT ATC ACC GGC CAC CGC ATG GCG TGG GAC | 390 |
| ATG ATG CTA AAC TGG TCA CCA ACT CTT ACC ATG ATC CTT | 429 |
| GCC TAT GCC GCT CGT GTT CCT GAG CTA GTC CTT GAA GTT | 468 |
| GTC TTC GGC GGC CAT TGG GGC GTG GTG TTT GGC TTG GCC | 507 |
| TAT TTC TCC ATG CAA GGA GCG TGG GCC AAG GTC ATT GCC | 546 |
| ATC CTC CTG CTT GTC GCA GGA GTG GAT GCA | 576 |

(2) INFORMATION FOR SEQ ID NO:33:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: T8

(xi) SEQUENCE DESCRIPTION: SEQ ID NO:33:

| | |
|---|---|
| GTG GAA GTT AGA AAC ACC AGT TTT AGC TAC TAC GCC ACC | 39 |
| AAT GAT TGC TCG AAC AAC AGC ATC ACC TGG CAG CTC ACC | 78 |
| AAC GCA GTT CTC CAC CTT CCC GGA TGC GTC CCA TGT GAG | 117 |
| AAT GAC AAT GGC ACC TTG CGC TGC TGG ATA CAA GTA ACA | 156 |
| CCT AAT GTG GCT GTG AAA CAC CGT GGC GCA CTC ACT CAC | 195 |
| AAC CTG CGA ACG CAT GTC GAC GTG ATC GTA ATG GCA GCT | 234 |
| ACG GTC TGC TCG GCC TTG TAT GTG GGG GAC GTG TGC GGG | 273 |
| GCC GTG ATG ATA GCG TCG CAG GCT TTC ATA ATA TCG CCA | 312 |
| GAA CGC CAC AAC TTC ACC CAG GAG TGC AAC TGT TCC ATC | 351 |
| TAC CAA GGT CAT ATC ACC GGC CAC CGC ATG GCA TGG GAC | 390 |
| ATG ATG CTG AAC TGG TCA CCA ACT CTC ACC ATG ATC CTC | 429 |
| GCC TAC GCT GCT CGT GTG CCT GAA CTA GTC CTT GAA GTT | 468 |
| GTC TTC GGC GGC CAT TGG GGC GTG GTG TTT GGC TTG GCC | 507 |
| TAT TTC TCC ATG CAA GGA GCG TGG GCC AAA GTC ATC GCC | 546 |
| ATC CTC CTC CTT GTC GCA GGA GTG GAC GCA | 576 |

(2) INFORMATION FOR SEQ ID NO:34:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: S83

(xi) SEQUENCE DESCRIPTION: SEQ ID NO:34:

| | |
|---|---|
| GTG GAG GTC AAG GAC ACC GGC GAC TCC TAC ATG CCG ACC | 39 |
| AAC GAT TGC TCC AAC TCT AGT ATC GTT TGG CAG CTT GAA | 78 |
| GGA GCA GTG CTT CAT ACT CCT GGA TGC GTC CCT TGT GAG | 117 |
| CGT ACC GCC AAC GTC TCT CGA TGT TGG GTG CCG GTT GCC | 156 |
| CCC AAT CTC GCC ATA AGT CAA CCT GGC GCT CTC ACT AAG | 195 |
| GGC CTG CGA GCA CAC ATC GAT ATC ATC GTG ATG TCT GCT | 234 |
| ACG GTC TGT TCT GCC CTT TAT GTG GGG GAC GTG TGT GGC | 273 |
| GCG CTG ATG CTG GCC GCT CAG GTC GTC GTC GTG TCG CCA | 312 |
| CAA CAC CAT ACG TTT GTC CAG GAA TGC AAC TGT TCC ATA | 351 |
| TAC CCG GGC CGC ATT ACG GGA CAC CGC ATG GCT TGG GAT | 390 |
| ATG ATG ATG AAC TGG TCG CCC ACT ACC ACC ATG CTC CTG | 429 |
| GCG TAC TTG GTG CGC ATC CCG GAA GTC ATC TTG GAT ATT | 468 |
| GTT ACA GGA GGT CAT TGG GGT GTA ATG TTT GGC CTC GCT | 507 |
| TAC TTC TCC ATG CAG GGA TCG TGG GCG AAG GTC ATC GTT | 546 |
| ATC CTC CTG CTG ACT GCT GGG GTG GAG GCG | 576 |

(2) INFORMATION FOR SEQ ID NO:35:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DK12

(xi) SEQUENCE DESCRIPTION: SEQ ID NO:35:

| | |
|---|---|
| TTA GAG TGG CGG AAT GTG TCC GGC CTC TAC GTC CTT ACC | 39 |
| AAC GAC TGT TCC AAT AGC AGT ATC GTG TAT GAG GCC GAT | 78 |
| GAC GTC ATT CTG CAC ACA CCT GGC TGT GTA CCT TGT GTT | 117 |
| CAG GAC GGC AAT ACA TCT ACG TGC TGG ACC TCA GTG ACG | 156 |
| CCT ACA GTG GCA GTC AGG TAC GTC GGA GCA ACC ACC GCT | 195 |
| TCG ATA CGC AGT CAT GTG GAC CTG CTA GTG GGC GCG GCC | 234 |
| ACG ATG TGC TCT GCG CTC TAC GTG GGT GAT GTG TGT GGG | 273 |
| GCC GTC TTC CTT GTG GGA CAA GCC TTC ACG TTC AGA CCT | 312 |
| CGT CGC CAT CAA ACA GTC CAG ACC TGT AAC TGC TCG CTG | 351 |
| TAC CCA GGC CAT CTT TCA GGA CAT CGA ATG GCT TGG GAT | 390 |
| ATG ATG ATG AAT TGG TCC CCC GCT GTG GGT ATG GTG GTA | 429 |
| GCG CAC GTC CTG CGT CTG CCC CAG ACC TTG TTC GAC ATA | 468 |
| ATA GCT GGG GCC CAT TGG GGC ATC ATG GCG GGC CTA GCC | 507 |
| TAT TAC TCC ATG CAG GGC AAC TGG GCC AAG GTC GCT ATC | 546 |
| ATC ATG GTT ATG TTT TCA GGA GTC GAT GCC | 576 |

(2) INFORMATION FOR SEQ ID NO:36:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: HK10

(xi) SEQUENCE DESCRIPTION: SEQ ID NO:36:

```
CTA GAG TGG CGG AAT GTG TCT GGC CTC TAT GTC CTT ACC              39
AAC GAC TGT CCC AAT AGC AGT ATT GTG TAT GAG GCC GAT              78
GAC GTC ATT CTG CAC ACA CCT GGC TGT GTA CCT TGT GTT             117
CAG GAC GGC AAT ACA TCC ACG TGC TGG ACC TCG GTG ACA             156
CCT ACA GTG GCA GTC AGG TAC GTC GGA GCA ACC ACC GCC             195
TCG ATA CGC AGT CAT GTG GAC CTG TTA GTG GGC GCG GCC             234
ACG ATG TGC TCT GCG CTC TAC GTG GGC GAT ATG TGT GGG             273
GCC GTC TTC CTC GTG GGA CAA GCC TTC ACG TTC AGA CCG             312
CGT CGC CAT CAA ACG GTC CAG ACC TGT AAC TGC TCG CTG             351
TAC CCA GGC CAC CTT TCA GGA CAT CGA ATG GCT TGG GAT             390
ATG ATG ATG AAT TGG TCC CCC GCC GTG GGT ATG GTG GTG             429
GCG CAC GTC CTG CGG TTG CCC CAG ACC TTG TTC GAC ATA             468
ATA GCC GGG GCC CAT TGG GGC ATC TTG GCA GGC CTA GCC             507
TAT TAC TCC ATG CAG GGC AAC TGG GCC AAG GTC GCT ATC             546
ATC ATG GTT ATG TTT TCA GGG GTC GAT GCC                         576
```

(2) INFORMATION FOR SEQ ID NO:37:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: S2

(xi) SEQUENCE DESCRIPTION: SEQ ID NO:37:

```
CTA GAG TGG CGG AAT ACG TCT GGC CTC TAT GTC CTC ACC              39
AAC GAC TGT TCC AAT AGC AGT ATT GTG TAT GAG GCC GAT              78
GAC GTT ATT CTG CAC ACA CCT GGC TGT GTA CCT TGT GTT             117
CAG GAC GGT AAT ACA TCC ACG TGC TGG ACC CCA GTG ACA             156
CCT ACA GTG GCA GTC AGG TAT GTC GGA GCA ACC ACC GCT             195
TCG ATA CGC AGT CAT GTG GAC CTA TTG GTG GGC GCG GCC             234
ACT ATG TGC TCT GCG CTC TAC GTG GGT GAT ATG TGT GGG             273
GCC GTC TTT CTC GTG GGA CAA GCC TTC ACG TTC AGA CCT             312
CGT CGC CAT CAA ACG GTC CAG ACC TGT AAC TGC TCG CTG             351
TAC CCA GGC CAT CTT TCA GGA CAT CGC ATG GCT TGG GAT             390
```

-continued

| | |
|---|---|
| ATG ATG ATG AAT TGG TCC CCC GCT GTG GGT ATG GTG GTG | 429 |
| GCG CAC GTT CTG CGT TTG CCC CAG ACC GTG TTC GAC ATA | 468 |
| ATA GCC GGG GCC CAT TGG GGC ATC TTG GCG GGC CTA GCC | 507 |
| TAT TAC TCC ATG CAA GGC AAC TGG GCC AAG GTC GCT ATC | 546 |
| ATC ATG GTT ATG TTT TCA GGG GTC GAC GCC | 576 |

(2) INFORMATION FOR SEQ ID NO:38:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: S52

(xi) SEQUENCE DESCRIPTION: SEQ ID NO:38:

| | |
|---|---|
| CTA GAG TGG CGG AAT ACG TCT GGC CTC TAT GTC CTT ACC | 39 |
| AAC GAC TGT TCC AAT AGC AGT ATT GTG TAT GAG GCC GAT | 78 |
| GAC GTC ATT CTG CAC ACA CCC GGC TGT GTA CCT TGT GTT | 117 |
| CAG GAC GGC AAT ACA TCC ATG TGC TGG ACC CCA GTG ACA | 156 |
| CCT ACG GTG GCA GTC AGG TAC GTC GGA GCA ACC ACC GCT | 195 |
| TCG ATA CGC AGT CAT GTG GAC CTA TTA GTG GGC GCG GCC | 234 |
| ACG CTG TGC TCT GCG CTC TAT GTG GGT GAT ATG TGT GGG | 273 |
| GCC GTC TTT CTC GTG GGA CAA GCC TTC ACG TTC AGA CCT | 312 |
| CGT CGC CAT CAA ACG GTC CAG ACC TGT AAC TGC TCG CTG | 351 |
| TAC CCA GGC CAT GTT TCA GGA CAT CGA ATG GCT TGG GAT | 390 |
| ATG ATG ATG AAT TGG TCC CCC GCT GTG GGT ATG GTG GTG | 429 |
| GCG CAC ATC CTG CGA TTG CCC CAG ACC TTG TTT GAC ATA | 468 |
| CTG GCC GGG GCC CAT TGG GGC ATC TTG GCG GGC CTA GCC | 507 |
| TAT TAT TCT ATG CAG GGC AAC TGG GCC AAG GTC GCT ATT | 546 |
| GTC ATG ATT ATG TTT TCA GGG GTC GAT GCC | 576 |

(2) INFORMATION FOR SEQ ID NO:39:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: S54

(xi) SEQUENCE DESCRIPTION: SEQ ID NO:39:

| | |
|---|---|
| CTA GAG TGG CGG AAT ACG TCT GGC CTC TAT ATC CTT ACC | 39 |
| AAC GAC TGT TCC AAT AGC AGT ATT GTG TAT GAG GCC GAT | 78 |
| GAC GTC ATT CTG CAC ACA CCC GGC TGT GTA CCT TGT GTT | 117 |
| CAG GAC GGC AAT ACA TCC ACG TGC TGG ACC CCA GTG ACA | 156 |
| CCT ACG GTG GCA GTC AGG TAC GTC GGA GCA ACC ACC GCT | 195 |

-continued

```
TCG ATA CGC AGT CAT GTG GAC CTA TTA GTG GGC GCG GCC            234

ACG CTG TGC TCT GCG CTC TAT GTG GGT GAT ATG TGT GGG            273

GCC GTC TTT CTC GTG GGA CAA GCC TTC ACG TTC AGA CCT            312

CGT CGC CAT CAA ACG GTC CAG ACC TGT AAC TGC TCG CTG            351

TAC CCA GGC CAT CTT TCA GGA CAT CGA ATG GCT TGG GAT            390

ATG ATG ATG AAT TGG TCC CCC GCT GTG GGT ATG GTG GTG            429

GCG CAC ATC CTG CGA TTG CCC CAG ACC TTG TTT GAC ATA            468

CTG GCC GGG GCC CAT TGG GGC ATC TTG GCG GGC CTA GCC            507

TAT TAT TCT ATG CAG GGC AAC TGG GCC AAG GTC GCT ATC            546

ATC ATG ATT ATG TTT TCA GGG GTC GAT GCC                        576
```

(2) INFORMATION FOR SEQ ID NO:40:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: Z4

(xi) SEQUENCE DESCRIPTION: SEQ ID NO:40:

```
GAG CAC TAC CGG AAT GCT TCG GGC ATC TAT CAC ATC ACC             39

AAT GAT TGT CCG AAT TCC AGT ATA GTC TAT GAA GCT GAC             78

CAT CAC ATC CTA CAC TTG CCG GGG TGC GTA CCC TGT GTG            117

ATG ACT GGG AAC ACA TCG CGT TGC TGG ACG CCG GTG ACG            156

CCT ACA GTG GCT GTC GCA CAC CCG GGC GCT CCG CTT GAG            195

TCG TTC CGG CGA CAT GTG GAC TTA ATG GTA GGC GCG GCC            234

ACT TTG TGT TCT GCC CTC TAT GTT GGG GAC CTC TGC GGA            273

GGT GCC TTC CTG ATG GGG CAG ATG ATC ACT TTT CGG CCG            312

CGT CGC CAC TGG ACC ACG CAG GAG TGC AAT TGT TCC ATC            351

TAC ACT GGC CAT ATC ACC GGC CAC AGG ATG GCG TGG GAC            390

ATG ATG ATG AAC TGG AGC CCT ACC ACC ACT CTG CTC CTC            429

GCC CAG ATC ATG AGG GTC CCC ACA GCC TTT CTC GAC ATG            468

GTT GCC GGA GGC CAC TGG GGC GTC CTC GCG GGC TTG GCG            507

TAC TTC AGC ATG CAA GGC AAT TGG GCC AAG GTA GTC CTG            546

GTC CTT TTC CTC TTT GCT GGG GTA GAC GCC                        576
```

(2) INFORMATION FOR SEQ ID NO:41:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: Z1

-continued (xi) SEQUENCE DESCRIPTION: SEQ ID NO:41:

| | |
|---|---|
| GTG CAC TAC CGG AAT GCT TCG GGC GTC TAT CAT GTC ACC | 39 |
| AAT GAT TGC CCT AAC ACC AGC ATA GTG TAC GAG ACG GAG | 78 |
| CAC CAC ATC ATG CAC TTG CCA GGG TGT GTC CCC TGT GTG | 117 |
| CGG ACG GAG AAT ACT TCT CGC TGC TGG GTG CCC TTG ACC | 156 |
| CCC ACT GTG GCC GCG CCC TAT CCC AAC GCA CCG TTA GAG | 195 |
| TCC ATG CGC AGG CAT GTA GAC CTG ATG GTG GGT GCG GCT | 234 |
| ACT ATG TGT TCC GCC TTC TAC ATT GGA GAT CTG TGT GGA | 273 |
| GGC GTC TTC CTA GTG GGC CAG CTG TTC GAC TTC CGA CCG | 312 |
| CGC CGG CAC TGG ACC ACC CAG GAT TGC AAC TGC TCC ATC | 351 |
| TAT CCT GGT CAC GTC TCG GGC CAC AGG ATG GCC TGG GAC | 390 |
| ATG ATG ATG AAC TGG AGC CCT ACC AGC GCG CTG ATT ATG | 429 |
| GCT CAG ATC TTA CGG ATC CCC TCT ATC CTA GGT GAC TTG | 468 |
| CTC ACC GGG GGT CAC TGG GGA GTT CTT GCT GGT CTA GCT | 507 |
| TTC TTC AGC ATG CAG AGT AAC TGG GCG AAG GTC ATC CTG | 546 |
| GTC CTA TTC CTC TTT GCC GGG GTC GAG GGA | 576 |

(2) INFORMATION FOR SEQ ID NO:42:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: Z6

(xi) SEQUENCE DESCRIPTION: SEQ ID NO:42:

| | |
|---|---|
| GTT AAC TAT CGC AAT GCC TCG GGC GTC TAT CAC GTC ACC | 39 |
| AAC GAC TGC CCG AAC TCG AGC ATA GTG TAT GAG GCC GAA | 78 |
| CAC CAG ATC TTA CAC CTC CCA GGG TGC TTG CCC TGT GTG | 117 |
| AGG GTT GGG AAT CAG TCA CGC TGC TGG GTG GCC CTT ACT | 156 |
| CCC ACC GTG GCG GTG TCT TAT ATC GGT GCT CCG CTT GAC | 195 |
| TCC CTC CGG AGA CAT GTG GAC CTG ATG GTG GGC GCC GCT | 234 |
| ACT GTA TGC TCT GCC CTC TAC GTT GGA GAT CTG TGC GGT | 273 |
| GGT GCA TTC TTG GTT GGC CAG ATG TTC TCC TTC CAG CCG | 312 |
| CGA CGC CAC TGG ACT ACG CAG GAC TGC AAT TGT TCT ATC | 351 |
| TAC GCA GGG CAT ATC ACG GGC CAC AGG ATG GCA TGG GAC | 390 |
| ATG ATG ATG AAC TGG AGT CCC ACA ACC ACC CTG CTT CTC | 429 |
| GCC CAG GTC ATG AGG ATC CCT AGC ACT CTG GTA GAT CTA | 468 |
| CTC GCT GGA GGG CAC TGG GGC GTC CTT GTT GGG TTG GCG | 507 |
| TAC TTC AGT ATG CAA GCT AAT TGG GCC AAA GTC ATC CTG | 546 |
| GTC CTT TTC CTC TTC GCT GGA GTT GAT GCC | 576 |

(2) INFORMATION FOR SEQ ID NO:43:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: Z7

(xi) SEQUENCE DESCRIPTION: SEQ ID NO:43:

| | |
|---|---|
| GTC AAC TAT CAC AAT GCC TCG GGC GTC TAT CAC ATC ACC | 39 |
| AAC GAC TGC CCG AAC TCG AGC ATA ATG TAT GAG GCC GAA | 78 |
| CAC CAC ATC CTA CAC CTC CCA GGG TGC GTA CCC TGT GTG | 117 |
| AGG GAG GGG AAC CAG TCA CGC TGC TGG GTG GCC CTT ACT | 156 |
| CCC ACC GTG GCG GCG CCT TAT ATC GGT GCA CCG CTT GAA | 195 |
| TCC ATC CGG AGA CAT GTG GAC CTG ATG GTA GGC GCT GCT | 234 |
| ACA GTG TGC TCC GCT CTC TAC ATT GGG GAC CTG TGC GGT | 273 |
| GGC GTA TTT TTG GTT GGT CAG ATG TTT TCT TTC CAG CCG | 312 |
| CGA CGC CAC TGG ACT ACG CAG GAC TGC AAT TGT TCC ATC | 351 |
| TAT GCG GGG CAC GTT ACA GGC CAC AGA ATG GCA TGG GAC | 390 |
| ATG ATG ATG AAC TGG AGT CCC ACA ACC ACC TTG GTC CTC | 429 |
| GCC CAG GTT ATG AGG ATC CCT AGC ACT CTG GTG GAC CTA | 468 |
| CTC ACT GGA GGG CAC TGG GGT ATC CTT ATC GGG GTG GCA | 507 |
| TAC TTC TGC ATG CAA GCT AAT TGG GCC AAG GTC ATT CTG | 546 |
| GTC CTT TTC CTC TAC GCT GGA GTT GAT GCC | 576 |

(2) INFORMATION FOR SEQ ID NO:44:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: DK13

(xi) SEQUENCE DESCRIPTION: SEQ ID NO:44:

| | |
|---|---|
| TAC AAC TAT CGC AAC AGC TCG GGT GTC TAC CAT GTC ACC | 39 |
| AAC GAT TGC CCG AAC TCG AGC ATA GTC TAT GAA ACC GAT | 78 |
| TAC CAC ATC TTA CAC CTC CCG GGA TGC GTT CCT TGC GTG | 117 |
| AGG GAA GGG AAC AAG TCT ACA TGC TGG GTG TCT CTC ACC | 156 |
| CCC ACC GTG GCT GCG CAA CAT CTG AAT GCT CCG CTT GAG | 195 |
| TCT TTG AGA CGT CAC GTG GAT CTG ATG GTG GGC GGC GCC | 234 |
| ACT CTC TGC TCC GCC CTC TAC ATC GGA GAC GTG TGT GGG | 273 |
| GGT GTG TTC TTG GTC GGT CAA CTG TTC ACC TTC CAA CCT | 312 |
| CGC CGC CAC TGG ACC ACC CAA GAC TGC AAT TGT TCC ATC | 351 |
| TAC ACA GGA CAT ATC ACA GGA CAC AGA ATG GCT TGG GAC | 390 |

```
ATG ATG ATG AAT TGG AGC CCC ACT GCG ACG CTG GTC CTC                429

GCC CAA CTT ATG AGG ATC CCA GGC GCC ATG GTC GAC CTG                468

CTT GCA GGC GGC CAC TGG GGC ATT CTG GTT GGC ATA GCG                507

TAC TTC AGC ATG CAA GCT AAT TGG GCC AAG GTT ATC CTG                546

GTC CTG TTT CTC TTT GCT GGA GTC GAC GCT                            576

(2) INFORMATION FOR SEQ ID NO:45:

(i) SEQUENCE CHARACTERISTICS:
        (A) LENGTH:  576 base pairs
        (B) TYPE:  nucleic acid
        (C) STRANDEDNESS:  single
        (D) TOPOLOGY:  linear (vi) ORIGINAL SOURCE:
        (A) ORGANISM:  homosapiens
        (C) INDIVIDUAL ISOLATE:  SA1

(xi) SEQUENCE DESCRIPTION: SEQ ID NO:45:

GTT CCC TAC CGG AAT GCC TCT GGG GTT TAC CAT GTC ACC                 39

AAT GAC TGC CCA AAC TCC TCC ATA GTC TAC GAG GCT GAT                 78

AGC CTG ATC TTG CAC GCA CCT GGC TGC GTG CCC TGT GTC                117

AGG CAA GAT AAT GTC AGT AGG TGC TGG GTC CAA ATC ACC                156

CCC ACA CTG TCA GCC CCG ACC TTC GGA GCG GTC ACG GCT                195

CCT CTT CGG AGG GCC GTT GAC TAC TTA GCG GGA GGA GCT                234

GCT CTC TGC TCC GCA CTA TAC GTC GGC GAC GCG TGC GGG                273

GCA GTG TTT CTG GTA GGC CAA ATG TTC ACC TAT AGG CCT                312

CGC CAG CAT ACC ACA GTG CAG GAC TGC AAC TGT TCC ATT                351

TAC AGT GGC CAT ATC ACC GGC CAC CGG ATG GCT TGG GAC                390

ATG ATG ATG AAT TGG TCA CCT ACG ACA GCC TTG CTG ATG                429

GCC CAG ATG CTA CGG ATC CCC CAG GTG GTC ATA GAC ATC                468

ATA GCC GGG GGC CAC TGG GGG GTC TTG TTT GCC GCC GCA                507

TAC TTT GCG TCG GCC GCC AAC TGG GCT AAG GTA GTG CTG                546

GTT CTG TTC CTG TTT GCG GGG GTC GAT GGC                            576

(2) INFORMATION FOR SEQ ID NO:46:

(i) SEQUENCE CHARACTERISTICS:
        (A) LENGTH:  576 base pairs
        (B) TYPE:  nucleic acid
        (C) STRANDEDNESS:  single
        (D) TOPOLOGY:  linear (vi) ORIGINAL SOURCE:
        (A) ORGANISM:  homosapiens
        (C) INDIVIDUAL ISOLATE:  SA4

(xi) SEQUENCE DESCRIPTION: SEQ ID NO:46:

GTT CCC TAC CGA AAC GCC TCT GGG GTT TAT CAT GTC ACC                 39

AAT GAT TGC CCA AAC TCT TCC ATA GTT TAC GAG GCT GAT                 78

AAC CTG ATC TTG CAT GCA CCT GGT TGC GTG CCT TGT GTC                117

AGG CAA GAT AAT GTC AGT AAG TGC TGG GTC CAA ATC ACC                156

CCC ACG TTG TCA GCC CCG AAT CTC GGA GCG GTC ACG GCT                195
```

```
CCT CTT CGG AGG GCC GTT GAC TAC TTA GCG GGA GGG GCT        234

GCC CTC TGC TCC GCA CTA TAC GTC GGG GAC GCG TGC GGG        273

GCA GTG TTT TTG GTA GGC CAA ATG TTC ACC TAT AGG CCT        312

CGC CAG CAC ACT ACG GTG CAA GAC TGC AAT GCT CTT ATT        351

TAC AGT GGC CAT ATC ACC GGC CAC CGG ATG GCA TGG GAC        390

ATG ATG ATG AAT TGG TCA CCT ACG ACG GCC TTG CTG ATG        429

GCC CAG TTG CTA CGG ATT CCC CAG GTG GTC ATC GAC ATC        468

ATT GCC GGG GGC CAC TGG GGG GTC TTG TTT GCC GCC GCA        507

TAT TTC GCG TCA GCG GCT AAC TGG GCT AAG GTT ATA CTG        546

GTC TTG TTT CTG TTT GCG GGG GTC GAT GCC                    576
```

(2) INFORMATION FOR SEQ ID NO:47:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: SA5

(xi) SEQUENCE DESCRIPTION: SEQ ID NO:47:

```
GTC CCC TAC CGA AAT GCC TCT GGG GTT TAT CAT GTC ACC         39

AAT GAT TGC CCA AAC TCT TCC ATA GTC TAC GAG GCT GAT         78

AAC CTG ATT CTG CAC GCA CCT GGT TGC GTG CCC TGT GTC        117

AAG GAA GGT AAT GTC AGT AGG TGC TGG GTC CAA ATC ACC        156

CCC ACA TTG TCA GCC CCG AAC CTC GGA GCG GTC ACG GCT        195

CCT CTT CGG AGG GTC GTT GAC TAC TTA GCG GGA GGG GCT        234

GCC CTC TGC TCC GCA CTA TAC GTC GGG GAC GCG TGC GGG        273

GCA GTG TTC TTG GTA GGC CAA ATG TTC ACC TAT AGG CCT        312

CGC CAG CAT ACT ACG GTG CAG GAC TGC AAC TGT TCC ATT        351

TAC AGC GGC CAT ATC ACC GGC CAC CGA ATG GCA TGG GAC        390

ATG ATG ATG AAT TGG TCA CCT ACG ACA GCC TTG GTG ATG        429

GCC CAG GTG CTA CGG ATT CCC CAA GTG GTC ATT GAC ATC        468

ATT GCC GGG GGC CAC TGG GGG GTC TTG TTC GCC GTC GCA        507

TAC TTC GCG TCA GCG GCT AAC TGG GCT AAG GTT GTG CTG        546

GTC CTG TTT CTG TTT GCG GGG GTC GAT GGC                    576
```

(2) INFORMATION FOR SEQ ID NO:48:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: SA6

(xi) SEQUENCE DESCRIPTION: SEQ ID NO:48:

| | |
|---|---|
| GTT CCT TAC CGG AAT GCC TCT GGG GTG TAT CAT GTT ACC | 39 |
| AAT GAT TGC CCA AAC TCT TCC ATA GTC TAT GAG GCT GAT | 78 |
| GAC CTG ATC CTA CAC GCA CCT GGC TGC GTG CCC TGT GTC | 117 |
| CGG AAG GAT AAT GTC AGT AGA TGC TGG GTT CAT ATC ACC | 156 |
| CCC ACA CTA TCA GCC CCG AGC CTC GGA GCG GTC ACG GCT | 195 |
| CCT CTT CGG AGG GCC GTT GAT TAC TTG GCG GGA GGG GCC | 234 |
| GCC CTG TGC TCC GCG TTA TAC GTC GGA GAC GTG TGC GGG | 273 |
| GCA TTG TTT TTG GTA GGC CAA ATG TTC ACC TAT AGG CCT | 312 |
| CGC CAG CAT GCT ACG GTA CAG GAC TGC AAC TGC TCC ATT | 351 |
| TAC AGT GGC CAT ATC ACT GGC CAC CGG ATG GCA TGG GAC | 390 |
| ATG ATG ATG AAT TGG TCA CCC GCG ACA GCC TTG GTG ATG | 429 |
| GCC CAA ATG CTA CGG ATT CCC CAG GTG GTC ATT GAC ATC | 468 |
| ATT GCC GGG GGC CAC TGG GGG GTC TTG TTC GCC GCT GCA | 507 |
| TAC TTC GCG TCG GCG GCT AAC TGG GCT AAG GTT GTG CTG | 546 |
| GTC TTG TTT CTG TTT GCG GGG GTT GAT GCC | 576 |

(2) INFORMATION FOR SEQ ID NO:49:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: SA7

(xi) SEQUENCE DESCRIPTION: SEQ ID NO:49:

| | |
|---|---|
| GTC CCC TAC CGA AAT GCC TCC GGG GTT TAT CAT GTC ACC | 39 |
| AAT GAT TGC CCG AAC TCT TCC ATA GTC TAT GAG GCT GAC | 78 |
| AAC CTG ATC CTG CAC GCA CCT GGT TGC GTG CCC TGT GTC | 117 |
| AGA CAA AAT AAT GTC AGT AGG TGC TGG GTC CAA ATC ACC | 156 |
| CCC ACA TTG TCA GCC CCG AAC CTC GGA GCG GTC ACG GCT | 195 |
| CCT CTT CGG AGG GCC GTT GAC TAC CTA GCG GGA GGG GCT | 234 |
| GCC CTC TGC TCC GCG CTA TAC GTC GGG GAC GCG TGC GGG | 273 |
| GCA GTG TTT TTG GTA GGC CAG ATG TTC AGC TAT AGG CCT | 312 |
| CGC CAG CAC ACT ACG GTG CAG GAC TGC AAC TGT TCC ATT | 351 |
| TAC AGT GGC CAT ATC ACC GGC CAC CGA ATG GCA TGG GAC | 390 |
| ATG ATG ATG AAT TGG TCA CCT ACG ACA GCC TTG GTG ATG | 429 |
| GCC CAG TTG CTA CGG ATT CCC CAG GTG GTC ATC GAC ATC | 468 |
| ATT GCC GGG GGC CAC TGG GGG GTC TTG TTC GCC GCC GCA | 507 |
| TAT TTC GCG TCA GCG GCT AAC TGG GCT AAG GTT GTG CTG | 546 |
| GTC TTG TTT CTG TTT GCG GGG GTC GAT GCC | 576 |

(2) INFORMATION FOR SEQ ID NO:50:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: SA13

(xi) SEQUENCE DESCRIPTION: SEQ ID NO:50:

```
GTT CCC TAC CGA AAT GCC TCT GGG GTT TAT CAT GTC ACC        39
AAT GAT TGC CCA AAC TCT TCC ATC GTC TAC GAG GCT GAT        78
GAC CTG ATC TTA CAC GCA CCT GGT TGC GTG CCC TGT GTT       117
AGG CAG GGT AAT GTC AGT AGG TGC TGG GTC CAG ATC ACC       156
CCC ACA CTG TCA GCC CCG AGC CTC GGA GCG GTC ACG GCT       195
CCT CTT CGG AGG GCC GTT GAC TAC TTA GCG GGG GGG GCT       234
GCC CTT TGC TCC GCG TTA TAC GTC GGA GAC GCG TGC GGG       273
GCA GTG TTT TTG GTA GGT CAA ATG TTC ACC TAT AGC CCT       312
CGC CGG CAT AAT GTT GTG CAG GAC TGC AAC TGT TCC ATT       351
TAC AGT GGC CAC ATC ACC GGC CAC CGG ATG GCA TGG GAC       390
ATG ATG ATG AAT TGG TCA CCT ACA ACA GCT TTG GTG ATG       429
GCC CAG TTG TTA CGG ATT CCC CAG GTG GTC ATT GAC ATC       468
ATT GCC GGG GCC CAC TGG GGG GTC TTG TTC GCC GCC GCA       507
TAC TAC GCG TCG GCG GCT AAC TGG GCC AAG GTT GTG CTG       546
GTC CTG TTT CTG TTT GCG GGG GTC GAT GCC               576
```

(2) INFORMATION FOR SEQ ID NO:51:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (vi) ORIGINAL SOURCE:
        (A) ORGANISM: homosapiens
        (C) INDIVIDUAL ISOLATE: HK2

(xi) SEQUENCE DESCRIPTION: SEQ ID NO:51:

```
CTT ACC TAC GGC AAC TCC AGT GGG CTA TAC CAT CTC ACA        39
AAT GAT TGC CCC AAC TCC AGC ATC GTG CTG GAG GCG GAT        78
GCT ATG ATC TTG CAT TTG CCT GGA TGC TTG CCT TGT GTG       117
AGG GTC GAT GAT CGG TCC ACC TGT TGG CAT GCT GTG ACC       156
CCC ACC CTG GCC ATA CCA AAT GCT TCC ACG CCC GCA ACG       195
GGA TTC CGC AGG CAT GTG GAT CTT CTT GCG GGC GCC GCA       234
GTG GTT TGC TCA TCC CTG TAC ATC GGG GAC CTG TGT GGC       273
TCT CTC TTT TTG GCG GGA CAA CTA TTC ACC TTT CAG CCC       312
CGC CGT CAT TGG ACT GTG CAA GAC TGC AAC TGC TCC ATC       351
TAT ACA GGC CAC GTC ACC GGC CAC AGG ATG GCT TGG GAC       390
```

```
ATG ATG ATG AAC TGG TCA CCC ACA ACC ACT CTG GTC CTA                          429

TCT AGC ATC TTG AGG GTA CCT GAG ATT TGT GCG AGT GTG                          468

ATA TTT GGT GGC CAT TGG GGG ATA CTA CTA GCC GTT GCC                          507

TAC TTT GGC ATG GCT GGC AAC TGG CTA AAA GTT CTG GCT                          546

GTT CTG TTC CTA TTT GCA GGG GTT GAA GCA                                      576
```

(2) INFORMATION FOR SEQ ID NO:52:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DK7

(xi) SEQUENCE DESCRIPTION: SEQ ID NO:52:

```
Tyr Gln Val Arg Asn Ser Thr Gly Leu Tyr His Val Thr Asn Asp
                 5                  10                  15

Cys Pro Asn Ser Ser Ile Val Tyr Glu Ala Ala Asp Ala Ile Leu
                20                  25                  30

His Thr Pro Gly Cys Val Pro Cys Val Arg Glu Gly Asn Val Ser
                35                  40                  45

Arg Cys Trp Val Ala Met Thr Pro Thr Val Ala Thr Arg Asp Gly
                50                  55                  60

Lys Leu Pro Thr Ala Gln Leu Arg Arg His Ile Asp Leu Leu Val
                65                  70                  75

Gly Ser Ala Thr Leu Cys Ser Ala Leu Tyr Val Gly Asp Leu Cys
                80                  85                  90

Gly Ser Val Phe Leu Val Gly Gln Leu Phe Thr Phe Ser Pro Arg
                95                 100                 105

Arg His Trp Thr Thr Gln Gly Cys Asn Cys Ser Ile Tyr Pro Gly
               110                 115                 120

His Ile Thr Gly His Arg Met Ala Trp Asp Met Met Met Asn Trp
               125                 130                 135

Ser Pro Thr Thr Ala Leu Val Val Ala Gln Leu Leu Arg Ile Pro
               140                 145                 150

Gln Ala Ile Leu Asp Met Ile Ala Gly Ala His Trp Gly Val Leu
               155                 160                 165

Ala Gly Ile Ala Tyr Phe Ser Met Val Gly Asn Trp Ala Lys Val
               170                 175                 180

Leu Val Val Leu Leu Leu Phe Ala Gly Val Asp Ala
               185                 190
```

(2) INFORMATION FOR SEQ ID NO:53:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DK9

(xi) SEQUENCE DESCRIPTION: SEQ ID NO:53:

```
Tyr Gln Val Arg Asn Ser Ser Gly Leu Tyr His Val Thr Asn Asp
                 5                  10                  15

Cys Pro Asn Ser Ser Ile Val Tyr Glu Ala Ala Asp Ala Ile Leu
                20                  25                  30

His Ser Pro Gly Cys Val Pro Cys Val Arg Glu Gly Asn Ala Ser
                35                  40                  45

Lys Cys Trp Val Ala Val Ala Pro Thr Val Ala Thr Arg Asp Gly
                50                  55                  60

Lys Leu Pro Ala Thr Gln Leu Arg Arg His Ile Asp Leu Leu Val
                65                  70                  75

Gly Ser Ala Thr Leu Cys Ser Ala Leu Tyr Val Gly Asp Leu Cys
                80                  85                  90

Gly Ser Val Phe Leu Val Gly Gln Leu Phe Thr Phe Ser Pro Arg
                95                 100                 105

Arg His Trp Thr Thr Gln Asp Cys Asn Cys Ser Ile Tyr Pro Gly
               110                 115                 120

His Ile Thr Gly His Arg Met Ala Trp Asp Met Met Met Asn Trp
               125                 130                 135

Ser Pro Thr Ala Ala Leu Val Met Ala Gln Leu Leu Arg Ile Pro
               140                 145                 150

Gln Ala Ile Leu Asp Met Ile Ala Gly Ala His Trp Gly Val Leu
               155                 160                 165

Ala Gly Ile Ala Tyr Phe Ser Met Val Gly Asn Trp Ala Lys Val
               170                 175                 180

Val Val Val Leu Leu Leu Phe Thr Gly Val Asp Ala
               185                 190
```

(2) INFORMATION FOR SEQ ID NO:54:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DR1

(xi) SEQUENCE DESCRIPTION: SEQ ID NO:54:

```
His Gln Val Arg Asn Ser Thr Gly Leu Tyr His Val Thr Asn Asp
                 5                  10                  15

Cys Pro Asn Ser Ser Ile Val Tyr Glu Ala Ala Asp Ala Ile Leu
                20                  25                  30

His Ala Pro Gly Cys Val Pro Cys Val Arg Glu Gly Asn Ala Ser
                35                  40                  45

Arg Cys Trp Val Ala Val Thr Pro Thr Val Ala Thr Arg Asp Gly
                50                  55                  60

Lys Leu Pro Thr Thr Gln Leu Arg Arg His Ile Asp Leu Leu Val
                65                  70                  75

Gly Ser Ala Thr Leu Cys Ser Ala Leu Tyr Val Gly Asp Leu Cys
                80                  85                  90

Gly Ser Val Phe Leu Val Gly Gln Leu Phe Thr Phe Ser Pro Arg
                95                 100                 105

Arg His Trp Thr Thr Gln Asp Cys Asn Cys Ser Ile Tyr Pro Gly
               110                 115                 120
```

```
His Ile Thr Gly His Arg Met Ala Trp Asp Met Met Met Asn Trp
                125                 130                 135

Ser Pro Thr Thr Ala Leu Val Met Ala Gln Leu Leu Arg Ile Pro
                140                 145                 150

Gln Ala Ile Leu Asp Met Ile Ala Gly Ala His Trp Gly Val Leu
                155                 160                 165

Ala Gly Ile Ala Tyr Phe Ser Met Val Gly Asn Trp Ala Lys Val
                170                 175                 180

Val Val Val Leu Leu Leu Phe Ala Gly Val Asp Ala
                185                 190

(2) INFORMATION FOR SEQ ID NO:55:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DR4

(xi) SEQUENCE DESCRIPTION: SEQ ID NO:55:

His Gln Val Arg Asn Ser Thr Gly Leu Tyr His Val Thr Asn Asp
                  5                  10                  15

Cys Pro Asn Ser Ser Ile Val Tyr Glu Ala Ala Asp Ala Ile Leu
                 20                  25                  30

His Thr Pro Gly Cys Val Pro Cys Val Arg Glu Gly Asn Thr Ser
                 35                  40                  45

Arg Cys Trp Val Ala Val Thr Pro Thr Val Ala Thr Arg Asp Gly
                 50                  55                  60

Lys Leu Pro Thr Thr Gln Leu Arg Arg His Ile Asp Leu Leu Val
                 65                  70                  75

Gly Ser Ala Thr Leu Cys Ser Ala Leu Tyr Val Gly Asp Leu Cys
                 80                  85                  90

Gly Ser Val Phe Leu Val Gly Gln Leu Phe Thr Phe Ser Pro Arg
                 95                 100                 105

His His Trp Thr Thr Gln Asp Cys Asn Cys Ser Ile Tyr Pro Gly
                110                 115                 120

His Ile Thr Gly His Arg Met Ala Trp Asp Met Met Met Asn Trp
                125                 130                 135

Ser Pro Thr Thr Ala Leu Val Val Ala Gln Leu Leu Arg Ile Pro
                140                 145                 150

Gln Ala Ile Leu Asp Met Ile Ala Gly Ala His Trp Gly Val Leu
                155                 160                 165

Ala Gly Ile Ala Tyr Phe Ser Met Val Gly Asn Trp Ala Lys Val
                170                 175                 180

Leu Val Val Leu Leu Leu Phe Ala Gly Val Asp Ala
                185                 190

(2) INFORMATION FOR SEQ ID NO:56:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown
```

-continued

```
    (vi) ORIGINAL SOURCE:
         (A) ORGANISM: homosapiens
         (C) INDIVIDUAL ISOLATE: S14

(xi) SEQUENCE DESCRIPTION: SEQ ID NO:56:

Tyr Gln Val Arg Asn Ser Thr Gly Leu Tyr His Val Thr Asn Asp
                 5                  10                  15

Cys Pro Asn Ser Ser Ile Val Tyr Glu Thr Ala Asp Ala Ile Leu
                20                  25                  30

His Ala Pro Gly Cys Val Pro Cys Val Arg Glu Gly Asn Thr Ser
                35                  40                  45

Arg Cys Trp Val Ala Met Thr Pro Thr Val Ala Thr Arg Asp Gly
                50                  55                  60

Lys Leu Pro Ala Thr Gln Leu Arg Arg Tyr Ile Asp Leu Leu Val
                65                  70                  75

Gly Ser Ala Thr Leu Cys Ser Ala Leu Tyr Val Gly Asp Leu Cys
                80                  85                  90

Gly Ser Val Phe Leu Val Gly Gln Leu Phe Thr Phe Ser Pro Arg
                95                 100                 105

Arg Leu Trp Thr Thr Gln Asp Cys Asn Cys Ser Ile Tyr Pro Gly
               110                 115                 120

His Ile Thr Gly His Arg Met Ala Trp Asp Met Met Met Asn Trp
               125                 130                 135

Ser Pro Thr Thr Ala Leu Val Val Ala Gln Leu Leu Arg Ile Pro
               140                 145                 150

Gln Ala Ile Leu Asp Met Ile Ala Gly Ala His Trp Gly Val Leu
               155                 160                 165

Ala Gly Ile Ala Tyr Phe Ser Met Val Gly Asn Trp Ala Lys Val
               170                 175                 180

Leu Val Val Leu Leu Leu Phe Ala Gly Val Asp Ala
               185                 190

(2) INFORMATION FOR SEQ ID NO:57:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
         (A) ORGANISM: homosapiens
         (C) INDIVIDUAL ISOLATE: S18

(xi) SEQUENCE DESCRIPTION: SEQ ID NO:57:

Tyr Gln Val Arg Asn Ser Thr Gly Leu Tyr His Val Thr Asn Asp
                 5                  10                  15

Cys Pro Asn Ser Ser Ile Val Tyr Glu Thr Ala Asp Thr Ile Leu
                20                  25                  30

His Ser Pro Gly Cys Val Pro Cys Val Arg Glu Gly Asn Ala Ser
                35                  40                  45

Arg Cys Trp Val Pro Val Ala Pro Thr Val Ala Thr Arg Asp Gly
                50                  55                  60

Lys Leu Pro Ala Thr Gln Leu Arg Arg His Ile Asp Leu Leu Val
                65                  70                  75

Gly Ser Ala Thr Leu Cys Ser Ala Leu Tyr Val Gly Asp Leu Cys
                80                  85                  90
```

```
Gly Ser Val Phe Leu Val Ser Gln Leu Phe Thr Ile Ser Pro Arg
                95                  100                 105

Arg His Trp Thr Thr Gln Asp Cys Asn Cys Ser Ile Tyr Pro Gly
                110                 115                 120

His Ile Thr Gly His Arg Met Ala Trp Asp Met Met Met Asn Trp
                125                 130                 135

Ser Pro Thr Thr Ala Leu Val Ile Ala Gln Leu Leu Arg Val Pro
                140                 145                 150

Gln Ala Val Leu Asp Met Ile Ala Gly Ala His Trp Gly Val Leu
                155                 160                 165

Ala Gly Ile Ala Tyr Phe Ser Met Ala Gly Asn Trp Ala Lys Val
                170                 175                 180

Leu Leu Val Leu Leu Leu Phe Ala Gly Val Asp Ala
                185                 190
```

(2) INFORMATION FOR SEQ ID NO:58:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SW1

(xi) SEQUENCE DESCRIPTION: SEQ ID NO:58:

```
Tyr Gln Val Arg Asn Ser Ser Gly Leu Tyr His Val Thr Asn Asp
                5                   10                  15

Cys Pro Asn Ser Ser Ile Val Tyr Glu Thr Ala Asp Ala Ile Leu
                20                  25                  30

His Ser Pro Gly Cys Val Pro Cys Val Arg Glu Asp Gly Ala Pro
                35                  40                  45

Lys Cys Trp Val Ala Val Ala Pro Thr Val Ala Thr Arg Asp Gly
                50                  55                  60

Lys Leu Pro Ala Thr Gln Leu Arg Arg His Ile Asp Leu Leu Val
                65                  70                  75

Gly Ser Ala Thr Leu Cys Ser Ala Leu Tyr Val Gly Asp Leu Cys
                80                  85                  90

Gly Ser Val Phe Leu Val Ser Gln Leu Phe Thr Phe Ser Pro Arg
                95                  100                 105

Arg His Trp Thr Thr Gln Asp Cys Asn Cys Ser Ile Tyr Pro Gly
                110                 115                 120

His Ile Thr Gly His Arg Met Ala Trp Asp Met Met Met Asn Trp
                125                 130                 135

Ser Pro Thr Thr Ala Leu Val Val Ala Gln Leu Leu Arg Ile Pro
                140                 145                 150

Gln Ala Val Leu Asp Met Ile Ala Gly Ala His Trp Gly Val Leu
                155                 160                 165

Ala Gly Ile Ala Tyr Phe Ser Met Val Gly Asn Trp Ala Lys Val
                170                 175                 180

Leu Ile Val Leu Leu Leu Phe Ser Gly Val Asp Ala
                185                 190
```

(2) INFORMATION FOR SEQ ID NO:59:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: US11

(xi) SEQUENCE DESCRIPTION: SEQ ID NO:59:

Tyr Gln Val Arg Asn Ser Thr Gly Leu Tyr His Val Thr Asn Asp
                 5                  10                  15

Cys Pro Asn Ser Ser Ile Val Tyr Glu Ala Ala Asp Ala Ile Leu
                20                  25                  30

His Thr Pro Gly Cys Val Pro Cys Val Arg Glu Gly Asn Ala Ser
                35                  40                  45

Arg Cys Trp Val Ala Met Thr Pro Thr Val Ala Thr Arg Asp Gly
                50                  55                  60

Lys Leu Pro Thr Thr Gln Leu Arg Arg His Ile Asp Leu Leu Val
                65                  70                  75

Gly Ser Ala Thr Leu Cys Ser Ala Leu Tyr Val Gly Asp Leu Cys
                80                  85                  90

Gly Ser Val Phe Leu Val Gly Gln Leu Phe Thr Phe Ser Pro Arg
                95                 100                 105

Arg His Trp Thr Thr Gln Gly Cys Asn Cys Ser Ile Tyr Pro Gly
               110                 115                 120

His Ile Thr Gly His Arg Met Ala Trp Asp Met Met Met Asn Trp
               125                 130                 135

Ser Pro Thr Ala Ala Leu Val Val Ala Gln Leu Leu Arg Ile Pro
               140                 145                 150

Gln Ala Ile Leu Asp Met Ile Ala Gly Ala His Trp Gly Val Leu
               155                 160                 165

Ala Gly Ile Ala Tyr Phe Ser Met Val Gly Asn Trp Ala Lys Val
               170                 175                 180

Leu Val Val Leu Leu Leu Phe Ala Gly Val Asp Ala
               185                 190

(2) INFORMATION FOR SEQ ID NO:60:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: D1

(xi) SEQUENCE DESCRIPTION: SEQ ID NO:60:

Tyr Glu Val Arg Asn Val Ser Gly Val Tyr His Val Thr Asn Asp
                 5                  10                  15

Cys Ser Asn Ser Ser Ile Val Tyr Glu Thr Ala Asp Met Ile Met
                20                  25                  30

His Thr Pro Gly Cys Val Pro Cys Val Arg Glu Asp Asn Ser Ser
                35                  40                  45

Arg Cys Trp Val Ala Leu Thr Pro Thr Leu Ala Ala Arg Asn Gly
                50                  55                  60

```
Asn Val Pro Thr Thr Ala Ile Arg Arg His Val Asp Leu Leu Val
                65                  70                  75

Gly Ala Ala Ala Phe Cys Ser Ala Met Tyr Val Gly Asp Leu Cys
                80                  85                  90

Gly Ser Val Phe Leu Ile Ser Gln Leu Phe Thr Leu Ser Pro Arg
                95                 100                 105

Arg His Glu Thr Val Gln Glu Cys Asn Cys Ser Ile Tyr Pro Gly
               110                 115                 120

His Val Thr Gly His Arg Met Ala Trp Asp Met Met Met Asn Trp
               125                 130                 135

Ser Pro Thr Thr Ala Leu Val Val Ser Gln Leu Leu Arg Ile Pro
               140                 145                 150

Gln Ala Val Met Asp Met Val Ala Gly Ala His Trp Gly Val Leu
               155                 160                 165

Ala Gly Leu Ala Tyr Tyr Ser Met Val Gly Asn Trp Ala Lys Val
               170                 175                 180

Leu Ile Val Met Leu Leu Phe Ala Gly Val Asp Gly
               185                 190
```

(2) INFORMATION FOR SEQ ID NO:61:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: D3

(xi) SEQUENCE DESCRIPTION: SEQ ID NO:61:

```
Tyr Glu Val Arg Asn Val Ser Gly Val Tyr Gln Val Thr Asn Asp
                 5                  10                  15

Cys Ser Asn Ser Ser Ile Val Tyr Glu Thr Ala Asp Met Ile Met
                20                  25                  30

His Thr Pro Gly Cys Val Pro Cys Val Arg Glu Asp Asn Ser Ser
                35                  40                  45

Arg Cys Trp Val Ala Leu Thr Pro Thr Leu Ala Ala Arg Asn Ser
                50                  55                  60

Ser Val Pro Thr Thr Thr Ile Arg Arg His Val Asp Leu Leu Val
                65                  70                  75

Gly Ala Ala Ala Phe Cys Ser Ala Met Tyr Val Gly Asp Leu Cys
                80                  85                  90

Gly Ser Val Phe Leu Val Ser Gln Leu Phe Thr Phe Ser Pro Arg
                95                 100                 105

Arg His Glu Thr Val Gln Glu Cys Asn Cys Ser Ile Tyr Pro Gly
               110                 115                 120

His Val Thr Gly His Arg Met Ala Trp Asp Met Met Met Asn Trp
               125                 130                 135

Ser Pro Thr Ala Ala Leu Val Val Ser Gln Leu Leu Arg Ile Pro
               140                 145                 150

Gln Ala Val Val Asp Met Val Ala Gly Ala His Trp Gly Val Leu
               155                 160                 165

Ala Gly Leu Ala Tyr Tyr Ser Met Val Gly Asn Trp Ala Lys Val
               170                 175                 180
```

```
Leu Ile Val Met Leu Leu Phe Ala Gly Val Asp Gly
            185                 190
```

(2) INFORMATION FOR SEQ ID NO:62:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: DK1

(xi) SEQUENCE DESCRIPTION: SEQ ID NO:62:

```
Tyr Glu Val Arg Asn Val Ser Gly Val Tyr His Val Thr Asn Asp
              5                   10                  15

Cys Ser Asn Ser Ser Ile Val Tyr Glu Ala Val Asp Val Ile Met
             20                   25                  30

His Thr Pro Gly Cys Val Pro Cys Val Arg Glu Asn Asn His Ser
             35                   40                  45

Arg Cys Trp Val Ala Leu Thr Pro Thr Leu Ala Ala Arg Asn Ala
             50                   55                  60

Ser Ile Pro Thr Thr Thr Ile Arg Arg His Val Asp Leu Leu Val
             65                   70                  75

Gly Ala Ala Ala Phe Cys Ser Ala Met Tyr Val Gly Asp Leu Cys
             80                   85                  90

Gly Ser Val Phe Leu Val Ser Gln Leu Phe Thr Phe Ser Pro Arg
             95                  100                 105

Arg His Glu Thr Ala Gln Asp Cys Asn Cys Ser Ile Tyr Pro Gly
            110                  115                 120

His Val Ser Gly His Arg Met Ala Trp Asp Met Met Met Asn Trp
            125                  130                 135

Ser Pro Thr Thr Ala Leu Val Leu Ser Gln Leu Leu Arg Ile Pro
            140                  145                 150

Gln Ala Val Val Asp Met Val Ala Gly Ala His Trp Gly Val Leu
            155                  160                 165

Ala Gly Leu Ala Tyr Tyr Ser Met Ala Gly Asn Trp Ala Lys Val
            170                  175                 180

Leu Ile Val Leu Leu Leu Phe Ala Gly Val Asp Gly
            185                  190
```

(2) INFORMATION FOR SEQ ID NO:63:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK3

(xi) SEQUENCE DESCRIPTION: SEQ ID NO:63:

```
Tyr Glu Val Arg Asn Val Ser Gly Ile Tyr His Val Thr Asn Asp
              5                   10                  15

Cys Ser Asn Ser Ser Val Val Tyr Glu Thr Ala Asp Met Ile Met
             20                   25                  30
```

-continued

```
His Thr Pro Gly Cys Val Pro Cys Val Arg Glu Asn Asn Ser Ser
                 35                  40                  45

Arg Cys Trp Val Ala Leu Thr Pro Thr Leu Ala Ala Arg Asn Val
                 50                  55                  60

Ser Val Pro Thr Thr Thr Ile Arg Arg His Val Asp Leu Leu Val
                 65                  70                  75

Gly Ala Ala Ala Phe Cys Ser Ala Met Tyr Val Gly Asp Leu Cys
                 80                  85                  90

Gly Ser Val Phe Leu Val Ser Gln Leu Phe Thr Phe Ser Pro Arg
                 95                 100                 105

Arg His Glu Thr Val Gln Asp Cys Asn Cys Ser Leu Tyr Pro Gly
                110                 115                 120

His Val Ser Gly His Arg Met Ala Trp Asp Met Met Met Asn Trp
                125                 130                 135

Ser Pro Thr Ala Ala Leu Val Val Ser Gln Leu Leu Arg Ile Pro
                140                 145                 150

Gln Ala Val Val Asp Met Val Ala Gly Ala His Trp Gly Val Leu
                155                 160                 165

Ala Gly Leu Ala Tyr Tyr Ser Met Val Gly Asn Trp Ala Lys Val
                170                 175                 180

Leu Ile Val Met Leu Leu Phe Ala Gly Val Asp Gly
                185                 190
```

(2) INFORMATION FOR SEQ ID NO:64:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK4

(xi) SEQUENCE DESCRIPTION: SEQ ID NO:64:

```
His Glu Val His Asn Val Ser Gly Ile Tyr His Val Thr Asn Asp
                  5                  10                  15

Cys Ser Asn Ser Ile Val Tyr Glu Ala Ala Asp Met Ile Met
                 20                  25                  30

His Thr Pro Gly Cys Val Pro Cys Val Arg Glu Asn Asn Ser Ser
                 35                  40                  45

Arg Cys Trp Val Ala Leu Thr Pro Thr Leu Ala Ala Arg Asn Ala
                 50                  55                  60

Ser Ile Pro Thr Thr Thr Ile Arg Arg His Val Asp Leu Leu Val
                 65                  70                  75

Gly Ala Ala Ala Phe Cys Ser Ala Met Tyr Val Gly Asp Leu Cys
                 80                  85                  90

Gly Ser Val Phe Leu Val Ser Gln Leu Phe Thr Phe Ser Pro Arg
                 95                 100                 105

Arg His Glu Thr Val Gln Asp Cys Asn Cys Ser Ile Tyr Pro Gly
                110                 115                 120

His Val Ser Gly His Arg Met Ala Trp Asp Met Met Met Asn Trp
                125                 130                 135

Ser Pro Thr Ala Ala Leu Val Val Ser Gln Leu Leu Arg Leu Pro
                140                 145                 150
```

```
Gln Ala Val Met Asp Met Val Ala Gly Ala His Trp Gly Val Leu
                155                 160                 165

Ala Gly Leu Ala Tyr Tyr Ser Met Val Gly Asn Trp Ala Lys Val
                170                 175                 180

Leu Ile Val Met Leu Leu Phe Ala Gly Val Asp Gly
                185                 190
```

(2) INFORMATION FOR SEQ ID NO:65:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK5

(xi) SEQUENCE DESCRIPTION: SEQ ID NO:65:

```
Tyr Glu Val Arg Asn Val Ser Gly Val Tyr His Val Thr Asn Asp
                  5                  10                  15

Cys Ser Asn Leu Ser Ile Val Tyr Glu Thr Thr Asp Met Ile Met
                 20                  25                  30

His Thr Pro Gly Cys Val Pro Cys Val Arg Glu Asn Asn Ser Ser
                 35                  40                  45

Arg Cys Trp Val Ala Leu Ala Pro Thr Leu Ala Ala Arg Asn Ala
                 50                  55                  60

Ser Val Pro Thr Thr Ala Ile Arg Arg His Val Asp Leu Leu Val
                 65                  70                  75

Gly Ala Ala Ala Phe Cys Ser Ala Met Tyr Val Gly Asp Leu Cys
                 80                  85                  90

Gly Ser Val Phe Leu Val Ser Gln Leu Phe Thr Phe Ser Pro Arg
                 95                 100                 105

Arg His Glu Thr Val Gln Asp Cys Asn Cys Ser Ile Tyr Pro Gly
                110                 115                 120

His Val Thr Gly His Arg Met Ala Trp Asp Met Met Met Asn Trp
                125                 130                 135

Ser Pro Thr Thr Ala Leu Val Val Ser Gln Leu Leu Arg Ile Pro
                140                 145                 150

Gln Ala Val Val Asp Met Val Ala Gly Ala His Trp Gly Val Leu
                155                 160                 165

Ala Gly Leu Ala Tyr Tyr Ser Met Val Gly Asn Trp Ala Lys Val
                170                 175                 180

Leu Ile Val Met Leu Leu Phe Ala Gly Val Asp Gly
                185                 190
```

(2) INFORMATION FOR SEQ ID NO:66:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK8

(xi) SEQUENCE DESCRIPTION: SEQ ID NO:66:

```
Tyr Glu Val Arg Asn Val Ser Gly Ile Tyr His Val Thr Asn Asp
                  5                  10                  15

Cys Ser Asn Ser Ser Ile Val Tyr Glu Thr Ala Asp Met Ile Met
                 20                  25                  30

His Thr Pro Gly Cys Met Pro Cys Val Arg Glu Asn Asn Ser Ser
                 35                  40                  45

Arg Cys Trp Val Ala Leu Thr Pro Thr Leu Ala Ala Arg Asn Val
                 50                  55                  60

Ser Val Pro Thr Thr Thr Ile Arg Arg His Val Asp Leu Leu Val
                 65                  70                  75

Gly Ala Ala Ala Phe Cys Ser Ala Met Tyr Val Gly Asp Leu Cys
                 80                  85                  90

Gly Ser Val Phe Leu Val Ser Gln Leu Phe Thr Phe Ser Pro Arg
                 95                 100                 105

Arg His Glu Thr Val Gln Asp Cys Asn Cys Ser Ile Tyr Pro Gly
                110                 115                 120

His Val Ser Gly His Arg Met Ala Trp Asp Met Met Met Asn Trp
                125                 130                 135

Ser Pro Thr Thr Ala Leu Val Val Ser Gln Leu Leu Arg Ile Pro
                140                 145                 150

Gln Ala Ile Val Asp Met Val Ala Gly Ala His Trp Gly Val Leu
                155                 160                 165

Ala Gly Leu Ala Tyr Tyr Ser Met Val Gly Asn Trp Ala Lys Val
                170                 175                 180

Leu Ile Val Met Leu Leu Phe Ala Gly Val Asp Gly
                185                 190
```

(2) INFORMATION FOR SEQ ID NO:67:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: IND5

(xi) SEQUENCE DESCRIPTION: SEQ ID NO:67:

```
Tyr Glu Val Arg Asn Val Ser Gly Val Tyr His Val Thr Asn Asp
                  5                  10                  15

Cys Ser Asn Ser Ser Ile Val Tyr Glu Ala Ala Asp Met Ile Met
                 20                  25                  30

His Thr Pro Gly Cys Val Pro Cys Val Arg Glu Gly Asn Ser Ser
                 35                  40                  45

Arg Cys Trp Val Ala Leu Thr Pro Thr Leu Ala Ala Arg Asn Ala
                 50                  55                  60

Ser Val Ser Thr Thr Thr Ile Arg His His Val Asp Leu Leu Val
                 65                  70                  75

Gly Ala Ala Ala Phe Cys Ser Ala Met Tyr Val Gly Asp Leu Cys
                 80                  85                  90

Gly Ser Val Phe Leu Val Ser Gln Leu Phe Thr Phe Ser Pro Arg
                 95                 100                 105

Arg His Glu Thr Val Gln Asp Cys Asn Cys Ser Ile Tyr Pro Gly
                110                 115                 120
```

```
His Val Ser Gly His Arg Met Ala Trp Asp Met Met Met Asn Trp
                125                 130                 135

Ser Pro Thr Ala Ala Leu Val Val Ser Gln Leu Leu Arg Ile Pro
                140                 145                 150

Gln Ala Val Val Asp Met Val Ala Gly Ala His Trp Gly Ile Leu
                155                 160                 165

Ala Gly Leu Ala Tyr Tyr Ser Met Val Gly Asn Trp Ala Lys Val
                170                 175                 180

Leu Ile Val Met Leu Leu Phe Ala Gly Val Asp Gly
                185                 190
```

(2) INFORMATION FOR SEQ ID NO:68:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: IND8

(xi) SEQUENCE DESCRIPTION: SEQ ID NO:68:

```
Tyr Glu Val Arg Asn Val Ser Gly Val Tyr His Val Thr Asn Asp
                 5                  10                  15

Cys Ser Asn Ser Ile Val Tyr Glu Ala Ala Asp Met Ile Met
                20                  25                  30

His Thr Pro Gly Cys Val Pro Cys Val Arg Glu Gly Asn Phe Ser
                35                  40                  45

Ser Cys Trp Val Ala Leu Thr Pro Thr Leu Ala Ala Arg Asn Ala
                50                  55                  60

Ser Val Pro Thr Thr Thr Ile Arg Arg His Val Asp Leu Leu Val
                65                  70                  75

Gly Ala Ala Ala Phe Cys Ser Ala Met Tyr Val Gly Asp Leu Cys
                80                  85                  90

Gly Ser Val Phe Leu Val Ser Gln Leu Phe Thr Phe Ser Pro Arg
                95                  100                 105

Arg His Glu Thr Val Gln Asp Cys Asn Cys Ser Ile Tyr Pro Gly
                110                 115                 120

His Val Ser Gly His Arg Met Ala Trp Asp Met Met Met Asn Trp
                125                 130                 135

Ser Pro Thr Ala Ala Leu Val Val Ser Gln Leu Leu Arg Ile Pro
                140                 145                 150

Gln Ala Val Val Asp Met Val Ala Gly Ala His Trp Gly Ile Leu
                155                 160                 165

Ala Gly Leu Ala Tyr Tyr Ser Met Val Gly Asn Trp Ala Lys Val
                170                 175                 180

Leu Ile Val Met Leu Leu Phe Ala Gly Val Asp Gly
                185                 190
```

(2) INFORMATION FOR SEQ ID NO:69:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
    (A) ORGANISM: homosapiens
    (C) INDIVIDUAL ISOLATE: P10

(xi) SEQUENCE DESCRIPTION: SEQ ID NO:69:

```
Tyr Glu Val Arg Asn Val Ser Gly Val Tyr His Val Thr Asn Asp
                 5                  10                  15
Cys Ser Asn Ser Ser Ile Val Tyr Glu Ala Ala Asp Met Ile Met
                20                  25                  30
His Thr Pro Gly Cys Val Pro Cys Val Arg Glu Asn Asn Ser Ser
                35                  40                  45
Arg Cys Trp Val Ala Leu Thr Pro Thr Leu Ala Ala Arg Asn Ser
                50                  55                  60
Ser Val Pro Thr Thr Ala Ile Arg Arg His Val Asp Leu Leu Val
                65                  70                  75
Gly Ala Ala Ala Phe Cys Ser Ala Met Tyr Val Gly Asp Leu Cys
                80                  85                  90
Gly Ser Val Leu Leu Val Ser Gln Leu Phe Thr Phe Ser Pro Arg
                95                 100                 105
Arg His Trp Thr Val Gln Asp Cys Asn Cys Ser Ile Tyr Pro Gly
               110                 115                 120
His Val Ser Gly His Arg Met Ala Trp Asp Met Met Met Asn Trp
               125                 130                 135
Ser Pro Thr Ala Ala Leu Val Val Ser Gln Leu Leu Arg Ile Pro
               140                 145                 150
Gln Ala Ile Leu Asp Val Val Ala Gly Ala His Trp Gly Val Leu
               155                 160                 165
Ala Gly Leu Ala Tyr Tyr Ser Met Val Gly Asn Trp Ala Lys Val
               170                 175                 180
Leu Ile Val Met Leu Leu Phe Ala Gly Val Asp Gly
               185                 190
```

(2) INFORMATION FOR SEQ ID NO:70:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: S9

(xi) SEQUENCE DESCRIPTION: SEQ ID NO:70:

```
Tyr Glu Val Arg Asn Val Ser Gly Ala Tyr His Val Thr Asn Asp
                 5                  10                  15
Cys Ser Asn Ser Ser Ile Val Tyr Glu Ala Ala Asp Val Ile Met
                20                  25                  30
His Thr Pro Gly Cys Val Pro Cys Val Gln Glu Gly Asn Ser Ser
                35                  40                  45
Gln Cys Trp Val Ala Leu Thr Pro Thr Leu Ala Ala Arg Asn Ala
                50                  55                  60
Thr Val Pro Thr Thr Thr Ile Arg Arg His Val Asp Leu Leu Val
                65                  70                  75
Gly Ala Ala Val Phe Cys Ser Ala Met Tyr Val Gly Asp Leu Cys
                80                  85                  90
```

Gly Ser Val Phe Leu Ile Ser Gln Leu Phe Thr Ile Ser Pro Arg
            95                 100                105

Arg His Glu Thr Val Gln Asn Cys Asn Cys Ser Ile Tyr Pro Gly
            110                115                120

His Val Thr Gly His Arg Met Ala Trp Asp Met Met Met Asn Trp
            125                130                135

Ser Pro Thr Thr Ala Leu Val Val Ser Gln Leu Leu Arg Ile Pro
            140                145                150

Gln Ala Val Met Asp Met Val Ala Gly Ala His Trp Gly Val Leu
            155                160                165

Ala Gly Leu Ala Tyr Tyr Ser Met Val Gly Asn Trp Ala Lys Val
            170                175                180

Leu Ile Val Met Leu Leu Phe Ala Gly Val Asp Gly
            185                190

(2) INFORMATION FOR SEQ ID NO:71:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: S45

(xi) SEQUENCE DESCRIPTION: SEQ ID NO:71:

Tyr Glu Val Arg Asn Val Ser Gly Ala Tyr His Val Thr Asn Asp
             5                 10                 15

Cys Ser Asn Ser Ser Ile Val Tyr Glu Ala Val Asp Val Ile Leu
            20                 25                 30

His Thr Pro Gly Cys Val Pro Cys Val Arg Glu Asn Asn Ser Ser
            35                 40                 45

Arg Cys Trp Val Ala Leu Thr Pro Thr Leu Ala Ala Arg Asn Ser
            50                 55                 60

Ser Val Pro Thr Thr Thr Ile Arg Arg His Val Asp Leu Leu Val
            65                 70                 75

Gly Ala Ala Ala Phe Cys Ser Ala Met Tyr Val Gly Asp Leu Cys
            80                 85                 90

Gly Ser Val Phe Leu Val Ser Gln Leu Phe Thr Phe Ser Pro Arg
            95                 100                105

Arg His Glu Thr Val Gln Asp Cys Asn Cys Ser Ile Tyr Pro Gly
            110                115                120

His Val Thr Gly His Arg Met Ala Trp Asp Met Met Met Asn Trp
            125                130                135

Ser Pro Thr Ala Ala Leu Val Val Ser Gln Leu Leu Arg Ile Pro
            140                145                150

Gln Ala Val Val Asp Met Val Ala Gly Ala His Trp Gly Val Leu
            155                160                165

Ala Gly Leu Ala Tyr Tyr Ser Met Val Gly Asn Trp Ala Lys Val
            170                175                180

Leu Ile Val Met Leu Leu Phe Ala Gly Val Asp Gly
            185                190

(2) INFORMATION FOR SEQ ID NO:72:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA10

(xi) SEQUENCE DESCRIPTION: SEQ ID NO:72:

```
Tyr Glu Val Arg Asn Val Ser Gly Met Tyr His Val Thr Asn Asp
              5                  10                  15
Cys Ser Asn Ser Ser Ile Val Tyr Glu Ala Ala Asp Met Ile Met
             20                  25                  30
His Thr Pro Gly Cys Val Pro Cys Val Arg Glu Asn Asn Ser Ser
             35                  40                  45
Arg Cys Trp Val Ala Leu Thr Pro Thr Leu Ala Ala Arg Asn Ser
             50                  55                  60
Ser Val Pro Thr Thr Thr Ile Arg Arg His Val Asp Leu Leu Val
             65                  70                  75
Gly Ala Ala Ala Phe Cys Ser Ala Met Tyr Val Gly Asp Leu Cys
             80                  85                  90
Gly Ser Val Phe Leu Val Ser Gln Leu Phe Thr Phe Ser Pro Arg
             95                 100                 105
Arg Tyr Glu Thr Val Gln Asp Cys Asn Cys Ser Ile Tyr Pro Gly
            110                 115                 120
Arg Val Thr Gly His Arg Met Ala Trp Asp Met Met Met Asn Trp
            125                 130                 135
Ser Pro Thr Thr Ala Leu Val Val Ser Gln Leu Leu Arg Ile Pro
            140                 145                 150
Gln Ala Ile Val Asp Met Val Ala Gly Ala His Trp Gly Val Leu
            155                 160                 165
Ala Gly Leu Ala Tyr Tyr Ser Met Val Gly Asn Trp Ala Lys Val
            170                 175                 180
Leu Ile Val Met Leu Leu Phe Ala Gly Val Asp Gly
            185                 190
```

(2) INFORMATION FOR SEQ ID NO:73:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SW2

(xi) SEQUENCE DESCRIPTION: SEQ ID NO:73:

```
Tyr Glu Val Arg Asn Val Ser Gly Val Tyr His Val Thr Asn Asp
              5                  10                  15
Cys Ser Asn Ser Ser Ile Val Tyr Glu Thr Ala Asp Met Ile Met
             20                  25                  30
His Thr Pro Gly Cys Val Pro Cys Val Arg Glu Ala Asn Ser Ser
             35                  40                  45
Arg Cys Trp Val Ala Leu Thr Pro Thr Leu Ala Ala Arg Asn Thr
             50                  55                  60
```

```
Ser Val Pro Thr Thr Thr Ile Arg Arg His Val Asp Leu Leu Val
                65                  70                  75

Gly Ala Ala Ala Phe Cys Ser Val Met Tyr Val Gly Asp Leu Cys
                80                  85                  90

Gly Ser Val Phe Leu Val Ser Gln Leu Phe Thr Phe Ser Pro Arg
                95                 100                 105

Arg His Glu Thr Val Gln Asp Cys Asn Cys Ser Ile Tyr Pro Gly
               110                 115                 120

His Val Ser Gly His Arg Met Ala Trp Asp Met Met Met Asn Trp
               125                 130                 135

Ser Pro Thr Ala Ala Leu Val Val Ser Gln Leu Leu Arg Ile Pro
               140                 145                 150

Gln Ala Val Val Asp Met Val Ala Gly Ala His Trp Gly Val Leu
               155                 160                 165

Ala Gly Leu Ala Tyr Tyr Ser Met Val Gly Asn Trp Ala Lys Val
               170                 175                 180

Leu Ile Val Met Leu Leu Phe Ala Gly Val Asp Gly
               185                 190
```

(2) INFORMATION FOR SEQ ID NO:74:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T3

(xi) SEQUENCE DESCRIPTION: SEQ ID NO:74:

```
Tyr Glu Val Arg Asn Val Ser Gly Val Tyr Tyr Val Thr Asn Asp
                 5                  10                  15

Cys Ser Asn Ser Ser Ile Val Tyr Glu Thr Ala Asp Met Ile Met
                20                  25                  30

His Thr Pro Gly Cys Val Pro Cys Val Arg Glu Ser Asn Ser Ser
                35                  40                  45

Arg Cys Trp Val Ala Leu Thr Pro Thr Leu Ala Ala Arg Asn Ala
                50                  55                  60

Ser Val Pro Thr Lys Thr Ile Arg Arg His Val Asp Leu Leu Val
                65                  70                  75

Gly Ala Ala Ala Phe Cys Ser Ala Met Tyr Val Gly Asp Leu Cys
                80                  85                  90

Gly Ser Val Phe Leu Val Ser Gln Leu Phe Thr Phe Ser Pro Arg
                95                 100                 105

Arg His Glu Thr Val Gln Asp Cys Asn Cys Ser Ile Tyr Pro Gly
               110                 115                 120

His Val Thr Gly His Arg Met Ala Trp Asp Met Met Met Asn Trp
               125                 130                 135

Ser Pro Thr Thr Ala Leu Val Val Ser Gln Leu Leu Arg Ile Pro
               140                 145                 150

Gln Ala Val Val Asp Met Val Ala Gly Ala His Trp Gly Val Leu
               155                 160                 165

Ala Gly Leu Ala Tyr Tyr Ser Met Val Gly Asn Trp Ala Lys Val
               170                 175                 180
```

```
Leu Ile Val Leu Leu Leu Phe Ala Gly Val Asp Gly
            185                 190

(2) INFORMATION FOR SEQ ID NO:75:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T10

(xi) SEQUENCE DESCRIPTION: SEQ ID NO:75:

Tyr Glu Val Arg Asn Val Ser Gly Met Tyr His Val Thr Asn Asp
              5                  10                  15

Cys Ser Asn Ser Ser Ile Val Phe Glu Ala Ala Asp Leu Ile Met
             20                  25                  30

His Thr Pro Gly Cys Val Pro Cys Val Arg Glu Gly Asn Ser Ser
             35                  40                  45

Arg Cys Trp Val Ala Leu Thr Pro Thr Leu Ala Ala Arg Asn Thr
             50                  55                  60

Ser Val Pro Thr Thr Thr Ile Arg Arg His Val Asp Leu Leu Val
             65                  70                  75

Gly Ala Ala Ala Phe Cys Ser Ala Met Tyr Val Gly Asp Leu Cys
             80                  85                  90

Gly Ser Val Phe Leu Val Ser Gln Leu Phe Thr Phe Ser Pro Arg
             95                 100                 105

Arg His Glu Thr Leu Gln Asp Cys Asn Cys Ser Ile Tyr Pro Gly
            110                 115                 120

His Leu Ser Gly His Arg Met Ala Trp Asp Met Met Met Asn Trp
            125                 130                 135

Ser Pro Thr Thr Ala Leu Val Val Ser Gln Leu Leu Arg Ile Pro
            140                 145                 150

Gln Ala Val Met Asp Met Val Thr Gly Ala His Trp Gly Val Leu
            155                 160                 165

Ala Gly Leu Ala Tyr Tyr Ser Met Ala Gly Asn Trp Ala Lys Val
            170                 175                 180

Leu Ile Val Met Leu Leu Phe Ala Gly Val Asp Gly
            185                 190

(2) INFORMATION FOR SEQ ID NO:76:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: US6

(xi) SEQUENCE DESCRIPTION: SEQ ID NO:76:

Tyr Glu Val Arg Asn Val Ser Gly Met Tyr His Val Thr Asn Asp
              5                  10                  15

Cys Ser Asn Ser Ser Ile Val Tyr Glu Ala Ala Asp Met Ile Met
             20                  25                  30
```

```
His Thr Pro Gly Cys Val Pro Cys Val Arg Glu Asn Asn Ser Ser
                35                  40                  45

Arg Cys Trp Val Ala Leu Thr Pro Thr Leu Ala Ala Arg Asn Ala
                50                  55                  60

Ser Val Pro Thr Thr Thr Ile Arg Arg His Val Asp Leu Leu Val
                65                  70                  75

Gly Ala Ala Thr Phe Cys Ser Ala Met Tyr Val Gly Asp Leu Cys
                80                  85                  90

Gly Ser Val Phe Leu Ile Ser Gln Leu Phe Thr Phe Ser Pro Arg
                95                 100                 105

Gln His Glu Thr Val Gln Asp Cys Asn Cys Ser Ile Tyr Pro Gly
               110                 115                 120

His Val Ser Gly His Arg Met Ala Trp Asp Met Met Met Asn Trp
               125                 130                 135

Ser Pro Thr Ala Ala Leu Val Val Ser Gln Leu Leu Arg Ile Pro
               140                 145                 150

Gln Ala Val Met Asp Met Val Ala Gly Ala His Trp Gly Val Leu
               155                 160                 165

Ala Gly Leu Ala Tyr Tyr Ser Met Val Gly Asn Trp Ala Lys Val
               170                 175                 180

Leu Ile Val Leu Leu Leu Phe Ala Gly Val Asp Gly
               185                 190
```

(2) INFORMATION FOR SEQ ID NO:77:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T2

(xi) SEQUENCE DESCRIPTION: SEQ ID NO:77:

```
Ala Gln Val Arg Asn Thr Ser Arg Gly Tyr Met Val Thr Asn Asp
                 5                  10                  15

Cys Ser Asn Glu Ser Ile Thr Trp Gln Leu Gln Ala Ala Val Leu
                20                  25                  30

His Val Pro Gly Cys Ile Pro Cys Glu Arg Leu Gly Asn Thr Ser
                35                  40                  45

Arg Cys Trp Ile Pro Val Thr Pro Asn Val Ala Val Arg Gln Pro
                50                  55                  60

Gly Ala Leu Thr Gln Gly Leu Arg Thr His Ile Asp Met Val Val
                65                  70                  75

Met Ser Ala Thr Leu Cys Ser Ala Leu Tyr Val Gly Asp Leu Cys
                80                  85                  90

Gly Gly Val Met Leu Ala Ala Gln Met Phe Ile Val Ser Pro Arg
                95                 100                 105

Arg His Trp Phe Val Gln Glu Cys Asn Cys Ser Ile Tyr Pro Gly
               110                 115                 120

Thr Ile Thr Gly His Arg Met Ala Trp Asp Met Met Met Asn Trp
               125                 130                 135

Ser Pro Thr Ala Thr Met Ile Leu Ala Tyr Ala Met Arg Val Pro
               140                 145                 150
```

```
Glu Val Ile Ile Asp Ile Ile Gly Gly Ala His Trp Gly Val Met
            155                 160                 165

Phe Gly Leu Ala Tyr Phe Ser Met Gln Gly Ala Trp Ala Lys Val
            170                 175                 180

Ile Val Ile Leu Leu Leu Ala Ala Gly Val Asp Ala
            185                 190
```

(2) INFORMATION FOR SEQ ID NO:78:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T4

(xi) SEQUENCE DESCRIPTION: SEQ ID NO:78:

```
Ala Gln Val Lys Asn Thr Thr Asn Ser Tyr Met Val Thr Asn Asp
             5                  10                  15

Cys Ser Asn Asp Ser Ile Thr Trp Gln Leu Gln Ala Ala Val Leu
            20                  25                  30

His Val Pro Gly Cys Val Pro Cys Glu Lys Thr Gly Asn Thr Ser
            35                  40                  45

Arg Cys Trp Ile Pro Val Ser Pro Asn Val Ala Val Arg Gln Pro
            50                  55                  60

Gly Ala Leu Thr Gln Gly Leu Arg Thr His Ile Asp Met Val Val
            65                  70                  75

Met Ser Ala Thr Leu Cys Ser Ala Leu Tyr Val Gly Asp Leu Cys
            80                  85                  90

Gly Gly Val Met Leu Ala Ala Gln Met Phe Ile Val Ser Pro Gln
            95                  100                 105

His His Trp Phe Val Gln Asp Cys Asn Cys Ser Ile Tyr Pro Gly
            110                 115                 120

Thr Ile Thr Gly His Arg Met Ala Trp Asp Met Met Met Asn Trp
            125                 130                 135

Ser Pro Thr Ala Thr Met Ile Leu Ala Tyr Ala Met Arg Val Pro
            140                 145                 150

Glu Val Ile Leu Asp Ile Val Ser Gly Ala His Trp Gly Val Met
            155                 160                 165

Phe Gly Leu Ala Tyr Phe Ser Met Gln Gly Ala Trp Ala Lys Val
            170                 175                 180

Val Val Ile Leu Leu Leu Ala Ala Gly Val Asp Ala
            185                 190
```

(2) INFORMATION FOR SEQ ID NO:79:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T9

(xi) SEQUENCE DESCRIPTION: SEQ ID NO:79:

Ala Glu Val Lys Asn Thr Ser Thr Ser Tyr Met Val Thr Asn Asp
                 5                  10                  15

Cys Ser Asn Asp Ser Ile Thr Trp Gln Leu Gln Ala Ala Val Leu
                20                  25                  30

His Val Pro Gly Cys Val Pro Cys Glu Arg Val Gly Asn Ala Ser
                35                  40                  45

Arg Cys Trp Ile Pro Val Ser Pro Asn Val Ala Val Gln Arg Pro
                50                  55                  60

Gly Ala Leu Thr Gln Gly Leu Arg Thr His Ile Asp Met Val Val
                65                  70                  75

Met Ser Ala Thr Leu Cys Ser Ala Leu Tyr Val Gly Asp Leu Cys
                80                  85                  90

Gly Gly Val Met Leu Ala Ala Gln Met Phe Ile Ile Ser Pro Gln
                95                 100                 105

His His Trp Phe Val Gln Glu Cys Asn Cys Ser Ile Tyr Pro Gly
               110                 115                 120

Thr Ile Thr Gly His Arg Met Ala Trp Asp Met Met Met Asn Trp
               125                 130                 135

Ser Pro Thr Thr Thr Met Ile Leu Ala Tyr Ala Met Arg Val Pro
               140                 145                 150

Glu Val Ile Ile Asp Ile Ile Ser Gly Ala His Trp Gly Val Met
               155                 160                 165

Phe Gly Leu Ala Tyr Phe Ser Met Gln Gly Ala Trp Ala Lys Val
               170                 175                 180

Val Val Ile Leu Leu Leu Thr Ala Gly Val Asp Ala
               185                 190

(2) INFORMATION FOR SEQ ID NO:80:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: US10

(xi) SEQUENCE DESCRIPTION: SEQ ID NO:80:

Val Gln Val Lys Asn Thr Ser Thr Ser Tyr Met Val Thr Asn Asp
                 5                  10                  15

Cys Ser Asn Asp Ser Ile Thr Trp Gln Leu Glu Ala Ala Val Leu
                20                  25                  30

His Val Pro Gly Cys Val Pro Cys Glu Lys Val Gly Asn Thr Ser
                35                  40                  45

Arg Cys Trp Ile Pro Val Ser Pro Asn Val Ala Val Gln Arg Pro
                50                  55                  60

Gly Ala Leu Thr Gln Gly Leu Arg Thr His Ile Asp Met Val Val
                65                  70                  75

Met Ser Ala Thr Leu Cys Ser Ala Leu Tyr Val Gly Asp Phe Cys
                80                  85                  90

Gly Gly Met Met Leu Ala Ala Gln Met Phe Ile Val Ser Pro Arg
                95                 100                 105

His His Ser Phe Val Gln Glu Cys Asn Cys Ser Ile Tyr Pro Gly
               110                 115                 120

```
Thr Ile Thr Gly His Arg Met Ala Trp Asp Met Met Asn Trp
            125                 130                 135

Ser Pro Thr Ala Thr Leu Ile Leu Ala Tyr Val Met Arg Val Pro
            140                 145                 150

Glu Val Ile Ile Asp Ile Ile Ser Gly Ala His Trp Gly Val Leu
            155                 160                 165

Phe Gly Leu Ala Tyr Phe Ser Met Gln Gly Ala Trp Ala Lys Val
            170                 175                 180

Val Val Ile Leu Leu Leu Ala Ala Gly Val Asp Ala
            185                 190
```

(2) INFORMATION FOR SEQ ID NO:81:

(i) SEQUENCE CHARACTERISTICS:
        (A) LENGTH:  192 amino acids
        (B) TYPE:  amino acid
        (C) STRANDEDNESS:  unknown
        (D) TOPOLOGY:  unknown (vi) ORIGINAL SOURCE:
        (A) ORGANISM:  homosapiens
        (C) INDIVIDUAL ISOLATE:  DK8

(xi) SEQUENCE DESCRIPTION: SEQ ID NO:81:

```
Val Glu Val Arg Asn Ile Ser Ser Tyr Tyr Ala Thr Asn Asp
             5                  10                  15

Cys Ser Asn Asn Ser Ile Thr Trp Gln Leu Thr Asp Ala Val Leu
            20                  25                  30

His Leu Pro Gly Cys Val Pro Cys Glu Asn Asp Asn Gly Thr Leu
            35                  40                  45

Arg Cys Trp Ile Gln Val Thr Pro Asn Val Ala Val Lys His Arg
            50                  55                  60

Gly Ala Leu Thr His Asn Leu Arg Thr His Val Asp Val Ile Val
            65                  70                  75

Met Ala Ala Thr Val Cys Ser Ala Leu Tyr Val Gly Asp Val Cys
            80                  85                  90

Gly Ala Val Met Ile Val Ser Gln Ala Leu Ile Ile Ser Pro Glu
            95                  100                 105

Arg His Asn Phe Thr Gln Glu Cys Asn Cys Ser Ile Tyr Gln Gly
            110                 115                 120

His Ile Thr Gly His Arg Met Ala Trp Asp Met Met Leu Asn Trp
            125                 130                 135

Ser Pro Thr Leu Thr Met Ile Leu Ala Tyr Ala Ala Arg Val Pro
            140                 145                 150

Glu Leu Ala Leu Gln Val Val Phe Gly Gly His Trp Gly Val Val
            155                 160                 165

Phe Gly Leu Ala Tyr Phe Ser Met Gln Gly Ala Trp Ala Lys Val
            170                 175                 180

Ile Ala Ile Leu Leu Leu Val Ala Gly Val Asp Ala
            185                 190
```

(2) INFORMATION FOR SEQ ID NO:82:

(i) SEQUENCE CHARACTERISTICS:
        (A) LENGTH:  192 amino acids
        (B) TYPE:  amino acid
        (C) STRANDEDNESS:  unknown
        (D) TOPOLOGY:  unknown (vi) ORIGINAL SOURCE:
    (A) ORGANISM: homosapiens
    (C) INDIVIDUAL ISOLATE: DK11

(xi) SEQUENCE DESCRIPTION: SEQ ID NO:82:

```
Val Glu Val Arg Asn Thr Ser Ser Ser Tyr Tyr Ala Thr Asn Asp
                 5                  10                  15

Cys Ser Asn Asn Ser Ile Thr Trp Gln Leu Thr Asn Ala Val Leu
                20                  25                  30

His Leu Pro Gly Cys Val Pro Cys Glu Asn Asp Asn Gly Thr Leu
                35                  40                  45

His Cys Trp Ile Gln Val Thr Pro Asn Val Ala Val Lys His Arg
                50                  55                  60

Gly Ala Leu Thr His Asn Leu Arg Ala His Ile Asp Met Ile Val
                65                  70                  75

Met Ala Ala Thr Val Cys Ser Ala Leu Tyr Val Gly Asp Val Cys
                80                  85                  90

Gly Ala Val Met Ile Val Ser Gln Ala Phe Ile Val Ser Pro Glu
                95                  100                 105

His His His Phe Thr Gln Glu Cys Asn Cys Ser Ile Tyr Gln Gly
                110                 115                 120

His Ile Thr Gly His Arg Met Ala Trp Asp Met Met Leu Asn Trp
                125                 130                 135

Ser Pro Thr Leu Thr Met Ile Leu Ala Tyr Ala Ala Arg Val Pro
                140                 145                 150

Glu Leu Val Leu Glu Val Val Phe Gly Gly His Trp Gly Val Val
                155                 160                 165

Phe Gly Leu Ala Tyr Phe Ser Met Gln Gly Ala Trp Ala Lys Val
                170                 175                 180

Ile Ala Ile Leu Leu Leu Val Ala Gly Val Asp Ala
                185                 190
```

(2) INFORMATION FOR SEQ ID NO:83:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SW3

(xi) SEQUENCE DESCRIPTION: SEQ ID NO:83:

```
Val Glu Val Arg Asn Ile Ser Ser Ser Tyr Tyr Ala Thr Asn Asp
                 5                  10                  15

Cys Ser Asn Ser Ser Ile Thr Trp Gln Leu Thr Asn Ala Val Leu
                20                  25                  30

His Leu Pro Gly Cys Val Pro Cys Glu Asn Asp Asn Gly Thr Leu
                35                  40                  45

His Cys Trp Ile Gln Val Thr Pro Asn Val Ala Val Lys His Arg
                50                  55                  60

Gly Ala Leu Thr His Asn Leu Arg Ala His Val Asp Met Ile Val
                65                  70                  75

Met Ala Ala Thr Val Cys Ser Ala Leu Tyr Val Gly Asp Met Cys
                80                  85                  90
```

```
Gly Ala Val Met Ile Val Ser Gln Ala Phe Ile Ile Ser Pro Glu
                95                 100                 105

Arg His Asn Phe Thr Gln Glu Cys Asn Cys Ser Ile Tyr Gln Gly
                110                 115                 120

Arg Ile Thr Gly His Arg Met Ala Trp Asp Met Met Leu Asn Trp
                125                 130                 135

Ser Pro Thr Leu Thr Met Ile Leu Ala Tyr Ala Ala Arg Val Pro
                140                 145                 150

Glu Leu Val Leu Glu Val Val Phe Gly Gly His Trp Gly Val Val
                155                 160                 165

Phe Gly Leu Ala Tyr Phe Ser Met Gln Gly Ala Trp Ala Lys Val
                170                 175                 180

Ile Ala Ile Leu Leu Leu Val Ala Gly Val Asp Ala
                185                 190
```

(2) INFORMATION FOR SEQ ID NO:84:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: T8

(xi) SEQUENCE DESCRIPTION: SEQ ID NO:84:

```
Val Glu Val Arg Asn Thr Ser Phe Ser Tyr Tyr Ala Thr Asn Asp
                5                   10                  15

Cys Ser Asn Asn Ser Ile Thr Trp Gln Leu Thr Asn Ala Val Leu
                20                  25                  30

His Leu Pro Gly Cys Val Pro Cys Glu Asn Asp Asn Gly Thr Leu
                35                  40                  45

Arg Cys Trp Ile Gln Val Thr Pro Asn Val Ala Val Lys His Arg
                50                  55                  60

Gly Ala Leu Thr His Asn Leu Arg Thr His Val Asp Val Ile Val
                65                  70                  75

Met Ala Ala Thr Val Cys Ser Ala Leu Tyr Val Gly Asp Val Cys
                80                  85                  90

Gly Ala Val Met Ile Ala Ser Gln Ala Phe Ile Ile Ser Pro Glu
                95                  100                 105

Arg His Asn Phe Thr Gln Glu Cys Asn Cys Ser Ile Tyr Gln Gly
                110                 115                 120

His Ile Thr Gly His Arg Met Ala Trp Asp Met Met Leu Asn Trp
                125                 130                 135

Ser Pro Thr Leu Thr Met Ile Leu Ala Tyr Ala Ala Arg Val Pro
                140                 145                 150

Glu Leu Val Leu Glu Val Val Phe Gly Gly His Trp Gly Val Val
                155                 160                 165

Phe Gly Leu Ala Tyr Phe Ser Met Gln Gly Ala Trp Ala Lys Val
                170                 175                 180

Ile Ala Ile Leu Leu Leu Val Ala Gly Val Asp Ala
                185                 190
```

(2) INFORMATION FOR SEQ ID NO:85:

(i) SEQUENCE CHARACTERISTICS:
      (A) LENGTH: 192 amino acids
      (B) TYPE: amino acid
      (C) STRANDEDNESS: unknown
      (D) TOPOLOGY: unknown (vi) ORIGINAL SOURCE:
      (A) ORGANISM: homosapiens
      (C) INDIVIDUAL ISOLATE: S83

(xi) SEQUENCE DESCRIPTION: SEQ ID NO:85:

```
Val Glu Val Lys Asp Thr Gly Asp Ser Tyr Met Pro Thr Asn Asp
             5                  10                  15

Cys Ser Asn Ser Ser Ile Val Trp Gln Leu Glu Gly Ala Val Leu
            20                  25                  30

His Thr Pro Gly Cys Val Pro Cys Glu Arg Thr Ala Asn Val Ser
            35                  40                  45

Arg Cys Trp Val Pro Val Ala Pro Asn Leu Ala Ile Ser Gln Pro
            50                  55                  60

Gly Ala Leu Thr Lys Gly Leu Arg Ala His Ile Asp Ile Ile Val
            65                  70                  75

Met Ser Ala Thr Val Cys Ser Ala Leu Tyr Val Gly Asp Val Cys
            80                  85                  90

Gly Ala Leu Met Leu Ala Ala Gln Val Val Val Ser Pro Gln
            95                 100                 105

His His Thr Phe Val Gln Glu Cys Asn Cys Ser Ile Tyr Pro Gly
           110                 115                 120

Arg Ile Thr Gly His Arg Met Ala Trp Asp Met Met Met Asn Trp
           125                 130                 135

Ser Pro Thr Thr Thr Met Leu Leu Ala Tyr Leu Val Arg Ile Pro
           140                 145                 150

Glu Val Ile Leu Asp Ile Val Thr Gly Gly His Trp Gly Val Met
           155                 160                 165

Phe Gly Leu Ala Tyr Phe Ser Met Gln Gly Ser Trp Ala Lys Val
           170                 175                 180

Ile Val Ile Leu Leu Leu Thr Ala Gly Val Glu Ala
           185                 190
```

(2) INFORMATION FOR SEQ ID NO:86:

(i) SEQUENCE CHARACTERISTICS:
      (A) LENGTH: 192 amino acids
      (B) TYPE: amino acid
      (C) STRANDEDNESS: unknown
      (D) TOPOLOGY: unknown (vi) ORIGINAL SOURCE:
      (A) ORGANISM: homosapiens
      (C) INDIVIDUAL ISOLATE: DK12

(xi) SEQUENCE DESCRIPTION: SEQ ID NO:86:

```
Leu Glu Trp Arg Asn Val Ser Gly Leu Tyr Val Leu Thr Asn Asp
             5                  10                  15

Cys Ser Asn Ser Ser Ile Val Tyr Glu Ala Asp Asp Val Ile Leu
            20                  25                  30

His Thr Pro Gly Cys Val Pro Cys Val Gln Asp Gly Asn Thr Ser
            35                  40                  45

Thr Cys Trp Thr Ser Val Thr Pro Thr Val Ala Val Arg Tyr Val
            50                  55                  60
```

```
Gly Ala Thr Thr Ala Ser Ile Arg Ser His Val Asp Leu Leu Val
                65                  70                  75

Gly Ala Ala Thr Met Cys Ser Ala Leu Tyr Val Gly Asp Val Cys
                80                  85                  90

Gly Ala Val Phe Leu Val Gly Gln Ala Phe Thr Phe Arg Pro Arg
                95                 100                 105

Arg His Gln Thr Val Gln Thr Cys Asn Cys Ser Leu Tyr Pro Gly
               110                 115                 120

His Leu Ser Gly His Arg Met Ala Trp Asp Met Met Met Asn Trp
               125                 130                 135

Ser Pro Ala Val Gly Met Val Val Ala His Val Leu Arg Leu Pro
               140                 145                 150

Gln Thr Leu Phe Asp Ile Ile Ala Gly Ala His Trp Gly Ile Met
               155                 160                 165

Ala Gly Leu Ala Tyr Tyr Ser Met Gln Gly Asn Trp Ala Lys Val
               170                 175                 180

Ala Ile Ile Met Val Met Phe Ser Gly Val Asp Ala
               185                 190
```

(2) INFORMATION FOR SEQ ID NO:87:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK10

(xi) SEQUENCE DESCRIPTION: SEQ ID NO:87:

```
Leu Glu Trp Arg Asn Val Ser Gly Leu Tyr Val Leu Thr Asn Asp
                 5                  10                  15

Cys Pro Asn Ser Ser Ile Val Tyr Glu Ala Asp Asp Val Ile Leu
                20                  25                  30

His Thr Pro Gly Cys Val Pro Cys Val Gln Asp Gly Asn Thr Ser
                35                  40                  45

Thr Cys Trp Thr Ser Val Thr Pro Thr Val Ala Val Arg Tyr Val
                50                  55                  60

Gly Ala Thr Thr Ala Ser Ile Arg Ser His Val Asp Leu Leu Val
                65                  70                  75

Gly Ala Ala Thr Met Cys Ser Ala Leu Tyr Val Gly Asp Met Cys
                80                  85                  90

Gly Ala Val Phe Leu Val Gly Gln Ala Phe Thr Phe Arg Pro Arg
                95                 100                 105

Arg His Gln Thr Val Gln Thr Cys Asn Cys Ser Leu Tyr Pro Gly
               110                 115                 120

His Leu Ser Gly His Arg Met Ala Trp Asp Met Met Met Asn Trp
               125                 130                 135

Ser Pro Ala Val Gly Met Val Val Ala His Val Leu Arg Leu Pro
               140                 145                 150

Gln Thr Leu Phe Asp Ile Ile Ala Gly Ala His Trp Gly Ile Leu
               155                 160                 165

Ala Gly Leu Ala Tyr Tyr Ser Met Gln Gly Asn Trp Ala Lys Val
               170                 175                 180
```

Ala Ile Ile Met Val Met Phe Ser Gly Val Asp Ala
            185                 190

(2) INFORMATION FOR SEQ ID NO:88:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: S2

(xi) SEQUENCE DESCRIPTION: SEQ ID NO:88:

Leu Glu Trp Arg Asn Thr Ser Gly Leu Tyr Val Leu Thr Asn Asp
             5                  10                  15

Cys Ser Asn Ser Ser Ile Val Tyr Glu Ala Asp Asp Val Ile Leu
            20                  25                  30

His Thr Pro Gly Cys Val Pro Cys Val Gln Asp Gly Asn Thr Ser
            35                  40                  45

Thr Cys Trp Thr Pro Val Thr Pro Thr Val Ala Val Arg Tyr Val
            50                  55                  60

Gly Ala Thr Thr Ala Ser Ile Arg Ser His Val Asp Leu Leu Val
            65                  70                  75

Gly Ala Ala Thr Met Cys Ser Ala Leu Tyr Val Gly Asp Met Cys
            80                  85                  90

Gly Ala Val Phe Leu Val Gly Gln Ala Phe Thr Phe Arg Pro Arg
            95                 100                 105

Arg His Gln Thr Val Gln Thr Cys Asn Cys Ser Leu Tyr Pro Gly
           110                 115                 120

His Leu Ser Gly His Arg Met Ala Trp Asp Met Met Met Asn Trp
           125                 130                 135

Ser Pro Ala Val Gly Met Val Val Ala His Val Leu Arg Leu Pro
           140                 145                 150

Gln Thr Val Phe Asp Ile Ile Ala Gly Ala His Trp Gly Ile Leu
           155                 160                 165

Ala Gly Leu Ala Tyr Tyr Ser Met Gln Gly Asn Trp Ala Lys Val
           170                 175                 180

Ala Ile Ile Met Val Met Phe Ser Gly Val Asp Ala
           185                 190

(2) INFORMATION FOR SEQ ID NO:89:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: S52

(xi) SEQUENCE DESCRIPTION: SEQ ID NO:89:

Leu Glu Trp Arg Asn Thr Ser Gly Leu Tyr Val Leu Thr Asn Asp
             5                  10                  15

Cys Ser Asn Ser Ser Ile Val Tyr Glu Ala Asp Asp Val Ile Leu
            20                  25                  30

-continued

```
His Thr Pro Gly Cys Val Pro Cys Val Gln Asp Gly Asn Thr Ser
                35                  40                  45

Met Cys Trp Thr Pro Val Thr Pro Thr Val Ala Val Arg Tyr Val
                50                  55                  60

Gly Ala Thr Thr Ala Ser Ile Arg Ser His Val Asp Leu Leu Val
                65                  70                  75

Gly Ala Ala Thr Leu Cys Ser Ala Leu Tyr Val Gly Asp Met Cys
                80                  85                  90

Gly Ala Val Phe Leu Val Gly Gln Ala Phe Thr Phe Arg Pro Arg
                95                 100                 105

Arg His Gln Thr Val Gln Thr Cys Asn Cys Ser Leu Tyr Pro Gly
               110                 115                 120

His Val Ser Gly His Arg Met Ala Trp Asp Met Met Met Asn Trp
               125                 130                 135

Ser Pro Ala Val Gly Met Val Val Ala His Ile Leu Arg Leu Pro
               140                 145                 150

Gln Thr Leu Phe Asp Ile Leu Ala Gly Ala His Trp Gly Ile Leu
               155                 160                 165

Ala Gly Leu Ala Tyr Tyr Ser Met Gln Gly Asn Trp Ala Lys Val
               170                 175                 180

Ala Ile Val Met Ile Met Phe Ser Gly Val Asp Ala
               185                 190
```

(2) INFORMATION FOR SEQ ID NO:90:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: S54

(xi) SEQUENCE DESCRIPTION: SEQ ID NO:90:

```
Leu Glu Trp Arg Asn Thr Ser Gly Leu Tyr Ile Leu Thr Asn Asp
                 5                  10                  15

Cys Ser Asn Ser Ser Ile Val Tyr Glu Ala Asp Asp Val Ile Leu
                20                  25                  30

His Thr Pro Gly Cys Val Pro Cys Val Gln Asp Gly Asn Thr Ser
                35                  40                  45

Thr Cys Trp Thr Pro Val Thr Pro Thr Val Ala Val Arg Tyr Val
                50                  55                  60

Gly Ala Thr Thr Ala Ser Ile Arg Ser His Val Asp Leu Leu Val
                65                  70                  75

Gly Ala Ala Thr Leu Cys Ser Ala Leu Tyr Val Gly Asp Met Cys
                80                  85                  90

Gly Ala Val Phe Leu Val Gly Gln Ala Phe Thr Phe Arg Pro Arg
                95                 100                 105

Arg His Gln Thr Val Gln Thr Cys Asn Cys Ser Leu Tyr Pro Gly
               110                 115                 120

His Leu Ser Gly His Arg Met Ala Trp Asp Met Met Met Asn Trp
               125                 130                 135

Ser Pro Ala Val Gly Met Val Val Ala His Ile Leu Arg Leu Pro
               140                 145                 150
```

```
Gln Thr Leu Phe Asp Ile Leu Ala Gly Ala His Trp Gly Ile Leu
                155                 160                 165

Ala Gly Leu Ala Tyr Tyr Ser Met Gln Gly Asn Trp Ala Lys Val
                170                 175                 180

Ala Ile Ile Met Ile Met Phe Ser Gly Val Asp Ala
                185                 190
```

(2) INFORMATION FOR SEQ ID NO:91:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: Z4

(xi) SEQUENCE DESCRIPTION: SEQ ID NO:91:

```
Glu His Tyr Arg Asn Ala Ser Gly Ile Tyr His Ile Thr Asn Asp
                  5                  10                  15

Cys Pro Asn Ser Ser Ile Val Tyr Glu Ala Asp His His Ile Leu
                 20                  25                  30

His Leu Pro Gly Cys Val Pro Cys Val Met Thr Gly Asn Thr Ser
                 35                  40                  45

Arg Cys Trp Thr Pro Val Thr Pro Thr Val Ala Val Ala His Pro
                 50                  55                  60

Gly Ala Pro Leu Glu Ser Phe Arg Arg His Val Asp Leu Met Val
                 65                  70                  75

Gly Ala Ala Thr Leu Cys Ser Ala Leu Tyr Val Gly Asp Leu Cys
                 80                  85                  90

Gly Gly Ala Phe Leu Met Gly Gln Met Ile Thr Phe Arg Pro Arg
                 95                 100                 105

Arg His Trp Thr Thr Gln Glu Cys Asn Cys Ser Ile Tyr Thr Gly
                110                 115                 120

His Ile Thr Gly His Arg Met Ala Trp Asp Met Met Met Asn Trp
                125                 130                 135

Ser Pro Thr Thr Thr Leu Leu Leu Ala Gln Ile Met Arg Val Pro
                140                 145                 150

Thr Ala Phe Leu Asp Met Val Ala Gly Gly His Trp Gly Val Leu
                155                 160                 165

Ala Gly Leu Ala Tyr Phe Ser Met Gln Gly Asn Trp Ala Lys Val
                170                 175                 180

Val Leu Val Leu Phe Leu Phe Ala Gly Val Asp Ala
                185                 190
```

(2) INFORMATION FOR SEQ ID NO:92:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: Z1

(xi) SEQUENCE DESCRIPTION: SEQ ID NO:92:

Val His Tyr Arg Asn Ala Ser Gly Val Tyr His Val Thr Asn Asp
                5                  10                 15

Cys Pro Asn Thr Ser Ile Val Tyr Glu Thr Glu His His Ile Met
               20                  25                 30

His Leu Pro Gly Cys Val Pro Cys Val Arg Thr Glu Asn Thr Ser
               35                  40                 45

Arg Cys Trp Val Pro Leu Thr Pro Thr Val Ala Ala Pro Tyr Pro
               50                  55                 60

Asn Ala Pro Leu Glu Ser Met Arg Arg His Val Asp Leu Met Val
               65                  70                 75

Gly Ala Ala Thr Met Cys Ser Ala Phe Tyr Ile Gly Asp Leu Cys
               80                  85                 90

Gly Gly Val Phe Leu Val Gly Gln Leu Phe Asp Phe Arg Pro Arg
               95                 100                105

Arg His Trp Thr Thr Gln Asp Cys Asn Cys Ser Ile Tyr Pro Gly
              110                 115                120

His Val Ser Gly His Arg Met Ala Trp Asp Met Met Met Asn Trp
              125                 130                135

Ser Pro Thr Ser Ala Leu Ile Met Ala Gln Ile Leu Arg Ile Pro
              140                 145                150

Ser Ile Leu Gly Asp Leu Leu Thr Gly His Trp Gly Val Leu
              155                 160                165

Ala Gly Leu Ala Phe Phe Ser Met Gln Ser Asn Trp Ala Lys Val
              170                 175                180

Ile Leu Val Leu Phe Leu Phe Ala Gly Val Glu Gly
              185                 190

(2) INFORMATION FOR SEQ ID NO:93:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: Z6

(xi) SEQUENCE DESCRIPTION: SEQ ID NO:93:

Val Asn Tyr Arg Asn Ala Ser Gly Val Tyr His Val Thr Asn Asp
                5                  10                 15

Cys Pro Asn Ser Ser Ile Val Tyr Glu Ala Glu His Gln Ile Leu
               20                  25                 30

His Leu Pro Gly Cys Leu Pro Cys Val Arg Val Gly Asn Gln Ser
               35                  40                 45

Arg Cys Trp Val Ala Leu Thr Pro Thr Val Ala Val Ser Tyr Ile
               50                  55                 60

Gly Ala Pro Leu Asp Ser Leu Arg Arg His Val Asp Leu Met Val
               65                  70                 75

Gly Ala Ala Thr Val Cys Ser Ala Leu Tyr Val Gly Asp Leu Cys
               80                  85                 90

Gly Gly Ala Phe Leu Val Gly Gln Met Phe Ser Phe Gln Pro Arg
               95                 100                105

Arg His Trp Thr Thr Gln Asp Cys Asn Cys Ser Ile Tyr Ala Gly
              110                 115                120

```
His Ile Thr Gly His Arg Met Ala Trp Asp Met Met Met Asn Trp
                125                 130                 135

Ser Pro Thr Thr Thr Leu Leu Leu Ala Gln Val Met Arg Ile Pro
                140                 145                 150

Ser Thr Leu Val Asp Leu Leu Ala Gly Gly His Trp Gly Val Leu
                155                 160                 165

Val Gly Leu Ala Tyr Phe Ser Met Gln Ala Asn Trp Ala Lys Val
                170                 175                 180

Ile Leu Val Leu Phe Leu Phe Ala Gly Val Asp Ala
                185                 190
```

(2) INFORMATION FOR SEQ ID NO:94:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: Z7

(xi) SEQUENCE DESCRIPTION: SEQ ID NO:94:

```
Val Asn Tyr His Asn Ala Ser Gly Val Tyr His Ile Thr Asn Asp
                5                   10                  15

Cys Pro Asn Ser Ser Ile Met Tyr Glu Ala Glu His His Ile Leu
                20                  25                  30

His Leu Pro Gly Cys Val Pro Cys Val Arg Glu Gly Asn Gln Ser
                35                  40                  45

Arg Cys Trp Val Ala Leu Thr Pro Thr Val Ala Ala Pro Tyr Ile
                50                  55                  60

Gly Ala Pro Leu Glu Ser Ile Arg Arg His Val Asp Leu Met Val
                65                  70                  75

Gly Ala Ala Thr Val Cys Ser Ala Leu Tyr Ile Gly Asp Leu Cys
                80                  85                  90

Gly Gly Val Phe Leu Val Gly Gln Met Phe Ser Phe Gln Pro Arg
                95                  100                 105

Arg His Trp Thr Thr Gln Asp Cys Asn Cys Ser Ile Tyr Ala Gly
                110                 115                 120

His Val Thr Gly His Arg Met Ala Trp Asp Met Met Met Asn Trp
                125                 130                 135

Ser Pro Thr Thr Thr Leu Val Leu Ala Gln Val Met Arg Ile Pro
                140                 145                 150

Ser Thr Leu Val Asp Leu Leu Thr Gly Gly His Trp Gly Ile Leu
                155                 160                 165

Ile Gly Val Ala Tyr Phe Cys Met Gln Ala Asn Trp Ala Lys Val
                170                 175                 180

Ile Leu Val Leu Phe Leu Tyr Ala Gly Val Asp Ala
                185                 190
```

(2) INFORMATION FOR SEQ ID NO:95:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown

```
        (vi) ORIGINAL SOURCE:
              (A) ORGANISM:  homosapiens
              (C) INDIVIDUAL ISOLATE:  DK13

(xi) SEQUENCE DESCRIPTION: SEQ ID NO:95:

Tyr Asn Tyr Arg Asn Ser Ser Gly Val Tyr His Val Thr Asn Asp
                  5                  10                  15

Cys Pro Asn Ser Ser Ile Val Tyr Glu Thr Asp Tyr His Ile Leu
                 20                  25                  30

His Leu Pro Gly Cys Val Pro Cys Val Arg Glu Gly Asn Lys Ser
                 35                  40                  45

Thr Cys Trp Val Ser Leu Thr Pro Thr Val Ala Ala Gln His Leu
                 50                  55                  60

Asn Ala Pro Leu Glu Ser Leu Arg Arg His Val Asp Leu Met Val
                 65                  70                  75

Gly Gly Ala Thr Leu Cys Ser Ala Leu Tyr Ile Gly Asp Val Cys
                 80                  85                  90

Gly Gly Val Phe Leu Val Gly Gln Leu Phe Thr Phe Gln Pro Arg
                 95                 100                 105

Arg His Trp Thr Thr Gln Asp Cys Asn Cys Ser Ile Tyr Thr Gly
                110                 115                 120

His Ile Thr Gly His Arg Met Ala Trp Asp Met Met Met Asn Trp
                125                 130                 135

Ser Pro Thr Ala Thr Leu Val Leu Ala Gln Leu Met Arg Ile Pro
                140                 145                 150

Gly Ala Met Val Asp Leu Leu Ala Gly Gly His Trp Gly Ile Leu
                155                 160                 165

Val Gly Ile Ala Tyr Phe Ser Met Gln Ala Asn Trp Ala Lys Val
                170                 175                 180

Ile Leu Val Leu Phe Leu Phe Ala Gly Val Asp Ala
                185                 190

(2) INFORMATION FOR SEQ ID NO:96:

(i) SEQUENCE CHARACTERISTICS:
              (A) LENGTH:  192 amino acids
              (B) TYPE:  amino acid
              (C) STRANDEDNESS:  unknown
              (D) TOPOLOGY:  unknown (vi) ORIGINAL SOURCE:
              (A) ORGANISM:  homosapiens
              (C) INDIVIDUAL ISOLATE:  SA1

(xi) SEQUENCE DESCRIPTION: SEQ ID NO:96:

Val Pro Tyr Arg Asn Ala Ser Gly Val Tyr His Val Thr Asn Asp
                  5                  10                  15

Cys Pro Asn Ser Ser Ile Val Tyr Glu Ala Asp Ser Leu Ile Leu
                 20                  25                  30

His Ala Pro Gly Cys Val Pro Cys Val Arg Gln Asp Asn Val Ser
                 35                  40                  45

Arg Cys Trp Val Gln Ile Thr Pro Thr Leu Ser Ala Pro Thr Phe
                 50                  55                  60

Gly Ala Val Thr Ala Pro Leu Arg Arg Ala Val Asp Tyr Leu Ala
                 65                  70                  75

Gly Gly Ala Ala Leu Cys Ser Ala Leu Tyr Val Gly Asp Ala Cys
                 80                  85                  90
```

```
Gly Ala Val Phe Leu Val Gly Gln Met Phe Thr Tyr Arg Pro Arg
             95                 100                 105

Gln His Thr Thr Val Gln Asp Cys Asn Cys Ser Ile Tyr Ser Gly
            110                 115                 120

His Ile Thr Gly His Arg Met Ala Trp Asp Met Met Met Asn Trp
            125                 130                 135

Ser Pro Thr Thr Ala Leu Leu Met Ala Gln Met Leu Arg Ile Pro
            140                 145                 150

Gln Val Val Ile Asp Ile Ile Ala Gly Gly His Trp Gly Val Leu
            155                 160                 165

Phe Ala Ala Ala Tyr Phe Ala Ser Ala Ala Asn Trp Ala Lys Val
            170                 175                 180

Val Leu Val Leu Phe Leu Phe Ala Gly Val Asp Gly
            185                 190
```

(2) INFORMATION FOR SEQ ID NO:97:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA4

(xi) SEQUENCE DESCRIPTION: SEQ ID NO:97:

```
Val Pro Tyr Arg Asn Ala Ser Gly Val Tyr His Val Thr Asn Asp
              5                  10                  15

Cys Pro Asn Ser Ser Ile Val Tyr Glu Ala Asp Asn Leu Ile Leu
             20                  25                  30

His Ala Pro Gly Cys Val Pro Cys Val Arg Gln Asp Asn Val Ser
             35                  40                  45

Lys Cys Trp Val Gln Ile Thr Pro Thr Leu Ser Ala Pro Asn Leu
             50                  55                  60

Gly Ala Val Thr Ala Pro Leu Arg Arg Ala Val Asp Tyr Leu Ala
             65                  70                  75

Gly Gly Ala Ala Leu Cys Ser Ala Leu Tyr Val Gly Asp Ala Cys
             80                  85                  90

Gly Ala Val Phe Leu Val Gly Gln Met Phe Thr Tyr Arg Pro Arg
             95                 100                 105

Gln His Thr Thr Val Gln Asp Cys Asn Cys Ser Ile Tyr Ser Gly
            110                 115                 120

His Ile Thr Gly His Arg Met Ala Trp Asp Met Met Met Asn Trp
            125                 130                 135

Ser Pro Thr Thr Ala Leu Leu Met Ala Gln Leu Leu Arg Ile Pro
            140                 145                 150

Gln Val Val Ile Asp Ile Ile Ala Gly Gly His Trp Gly Val Leu
            155                 160                 165

Phe Ala Ala Ala Tyr Phe Ala Ser Ala Ala Asn Trp Ala Lys Val
            170                 175                 180

Ile Leu Val Leu Phe Leu Phe Ala Gly Val Asp Ala
            185                 190
```

```
(2) INFORMATION FOR SEQ ID NO:98:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA5

(xi) SEQUENCE DESCRIPTION: SEQ ID NO:98:

Val Pro Tyr Arg Asn Ala Ser Gly Val Tyr His Val Thr Asn Asp
                 5                  10                  15

Cys Pro Asn Ser Ser Ile Val Tyr Glu Ala Asp Asn Leu Ile Leu
                20                  25                  30

His Ala Pro Gly Cys Val Pro Cys Val Lys Glu Gly Asn Val Ser
                35                  40                  45

Arg Cys Trp Val Gln Ile Thr Pro Thr Leu Ser Ala Pro Asn Leu
                50                  55                  60

Gly Ala Val Thr Ala Pro Leu Arg Arg Val Val Asp Tyr Leu Ala
                65                  70                  75

Gly Gly Ala Ala Leu Cys Ser Ala Leu Tyr Val Gly Asp Ala Cys
                80                  85                  90

Gly Ala Val Phe Leu Val Gly Gln Met Phe Thr Tyr Arg Pro Arg
                95                 100                 105

Gln His Thr Thr Val Gln Asp Cys Asn Cys Ser Ile Tyr Ser Gly
               110                 115                 120

His Ile Thr Gly His Arg Met Ala Trp Asp Met Met Met Asn Trp
               125                 130                 135

Ser Pro Thr Thr Ala Leu Val Met Ala Gln Val Leu Arg Ile Pro
               140                 145                 150

Gln Val Val Ile Asp Ile Ile Ala Gly Gly His Trp Gly Val Leu
               155                 160                 165

Phe Ala Val Ala Tyr Phe Ala Ser Ala Ala Asn Trp Ala Lys Val
               170                 175                 180

Val Leu Val Leu Phe Leu Phe Ala Gly Val Asp Gly
               185                 190

(2) INFORMATION FOR SEQ ID NO:99:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA6

(xi) SEQUENCE DESCRIPTION: SEQ ID NO:99:

Val Pro Tyr Arg Asn Ala Ser Gly Val Tyr His Val Thr Asn Asp
                 5                  10                  15

Cys Pro Asn Ser Ser Ile Val Tyr Glu Ala Asp Asp Leu Ile Leu
                20                  25                  30

His Ala Pro Gly Cys Val Pro Cys Val Arg Lys Asp Asn Val Ser
                35                  40                  45

Arg Cys Trp Val His Ile Thr Pro Thr Leu Ser Ala Pro Ser Leu
                50                  55                  60
```

```
Gly Ala Val Thr Ala Pro Leu Arg Arg Ala Val Asp Tyr Leu Ala
                65                  70                  75

Gly Gly Ala Ala Leu Cys Ser Ala Leu Tyr Val Gly Asp Val Cys
                80                  85                  90

Gly Ala Leu Phe Leu Val Gly Gln Met Phe Thr Tyr Arg Pro Arg
                95                 100                 105

Gln His Ala Thr Val Gln Asp Cys Asn Cys Ser Ile Tyr Ser Gly
               110                 115                 120

His Ile Thr Gly His Arg Met Ala Trp Asp Met Met Met Asn Trp
               125                 130                 135

Ser Pro Ala Thr Ala Leu Val Met Ala Gln Met Leu Arg Ile Pro
               140                 145                 150

Gln Val Val Ile Asp Ile Ile Ala Gly Gly His Trp Gly Val Leu
               155                 160                 165

Phe Ala Ala Ala Tyr Phe Ala Ser Ala Ala Asn Trp Ala Lys Val
               170                 175                 180

Val Leu Val Leu Phe Leu Phe Ala Gly Val Asp Ala
               185                 190
```

(2) INFORMATION FOR SEQ ID NO:100:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA7

(xi) SEQUENCE DESCRIPTION: SEQ ID NO:100:

```
Val Pro Tyr Arg Asn Ala Ser Gly Val Tyr His Val Thr Asn Asp
                 5                  10                  15

Cys Pro Asn Ser Ser Ile Val Tyr Glu Ala Asp Asn Leu Ile Leu
                20                  25                  30

His Ala Pro Gly Cys Val Pro Cys Val Arg Gln Asn Asn Val Ser
                35                  40                  45

Arg Cys Trp Val Gln Ile Thr Pro Thr Leu Ser Ala Pro Asn Leu
                50                  55                  60

Gly Ala Val Thr Ala Pro Leu Arg Arg Ala Val Asp Tyr Leu Ala
                65                  70                  75

Gly Gly Ala Ala Leu Cys Ser Ala Leu Tyr Val Gly Asp Ala Cys
                80                  85                  90

Gly Ala Val Phe Leu Val Gly Gln Met Phe Ser Tyr Arg Pro Arg
                95                 100                 105

Gln His Thr Thr Val Gln Asp Cys Asn Cys Ser Ile Tyr Ser Gly
               110                 115                 120

His Ile Thr Gly His Arg Met Ala Trp Asp Met Met Met Asn Trp
               125                 130                 135

Ser Pro Thr Thr Ala Leu Val Met Ala Gln Leu Leu Arg Ile Pro
               140                 145                 150

Gln Val Val Ile Asp Ile Ile Ala Gly Gly His Trp Gly Val Leu
               155                 160                 165

Phe Ala Ala Ala Tyr Phe Ala Ser Ala Ala Asn Trp Ala Lys Val
               170                 175                 180
```

-continued

```
Val Leu Val Leu Phe Leu Phe Ala Gly Val Asp Ala
            185                 190
```

(2) INFORMATION FOR SEQ ID NO:101:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: SA13

(xi) SEQUENCE DESCRIPTION: SEQ ID NO:101:

```
Val Pro Tyr Arg Asn Ala Ser Gly Val Tyr His Val Thr Asn Asp
                  5                  10                  15

Cys Pro Asn Ser Ser Ile Val Tyr Glu Ala Asp Asp Leu Ile Leu
                 20                  25                  30

His Ala Pro Gly Cys Val Pro Cys Val Arg Gln Gly Asn Val Ser
                 35                  40                  45

Arg Cys Trp Val Gln Ile Thr Pro Thr Leu Ser Ala Pro Ser Leu
                 50                  55                  60

Gly Ala Val Thr Ala Pro Leu Arg Arg Ala Val Asp Tyr Leu Ala
                 65                  70                  75

Gly Gly Ala Ala Leu Cys Ser Ala Leu Tyr Val Gly Asp Ala Cys
                 80                  85                  90

Gly Ala Val Phe Leu Val Gly Gln Met Phe Thr Tyr Ser Pro Arg
                 95                 100                 105

Arg His Asn Val Val Gln Asp Cys Asn Cys Ser Ile Tyr Ser Gly
                110                 115                 120

His Ile Thr Gly His Arg Met Ala Trp Asp Met Met Met Asn Trp
                125                 130                 135

Ser Pro Thr Thr Ala Leu Val Met Ala Gln Leu Leu Arg Ile Pro
                140                 145                 150

Gln Val Val Ile Asp Ile Ile Ala Gly Ala His Trp Gly Val Leu
                155                 160                 165

Phe Ala Ala Ala Tyr Tyr Ala Ser Ala Ala Asn Trp Ala Lys Val
                170                 175                 180

Val Leu Val Leu Phe Leu Phe Ala Gly Val Asp Ala
                185                 190
```

(2) INFORMATION FOR SEQ ID NO:102:

(i) SEQUENCE CHARACTERISTICS:
        (A) LENGTH: 192 amino acids
        (B) TYPE: amino acid
        (C) STRANDEDNESS: unknown
        (D) TOPOLOGY: unknown (vi) ORIGINAL SOURCE:
        (A) ORGANISM: homosapiens
        (C) INDIVIDUAL ISOLATE: HK2

(xi) SEQUENCE DESCRIPTION: SEQ ID NO:102:

```
Leu Thr Tyr Gln Asn Ser Ser Gln Leu Tyr His Leu Thr Asn Asp
                 1                  10                  15

Cys Pro Asn Ser Ser Ile Val Leu Glu Ala Asp Ala Met Ile Leu
                20                  25                  30
```

```
His Leu Pro Gln Cys Leu Pro Cys Val Arg Val Asp Asp Arg Ser
                35                  40                  45

Thr Cys Trp His Ala Val Thr Pro Thr Leu Ala Ile Pro Asn Ala
                50                  55                  60

Ser Thr Pro Ala Thr Gln Phe Arg Arg His Val Asp Leu Leu Ala
                65                  70                  75

Gln Ala Ala Val Val Cys Ser Ser Leu Tyr Ile Gln Asp Leu Cys
                80                  85                  90

Gln Ser Leu Phe Leu Ala Gln Gln Leu Phe Thr Phe Gln Pro Arg
                95                 100                 105

Arg His Trp Thr Val Gln Asp Cys Asn Cys Ser Ile Tyr Thr Gln
               110                 115                 120

His Val Thr Gln His Arg Met Ala Trp Asp Met Met Met Asn Trp
               125                 130                 135

Ser Pro Thr Thr Thr Leu Val Leu Ser Ser Ile Leu Arg Val Pro
               140                 145                 150

Glu Ile Cys Ala Ser Val Ile Phe Gln Gln His Trp Gln Ile Leu
               155                 160                 165

Leu Ala Val Ala Tyr Phe Gln Met Ala Gln Asn Trp Leu Lys Val
               170                 175                 180

Leu Ala Val Leu Phe Leu Phe Ala Gln Val Glu Ala
               185                 190
```

(2) INFORMATION FOR SEQ ID NO:103:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:103:

GCGTCCGGGT TCTGGAAGAC GGCGTGAACT ATGCAACAGG                40

(2) INFORMATION FOR SEQ ID NO:104:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:104:

AGGCTTTCAT TGCAGTTCAA GGCCGTGCTA TTGATGTGCC                40

(2) INFORMATION FOR SEQ ID NO:105:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:105:

AAGACGGCGT GAACTATGCA ACAGGGAACC TTCCTGGTTG                40

(2) INFORMATION FOR SEQ ID NO:106:

(i) SEQUENCE CHARACTERISTICS:
        (A) LENGTH: 40 base pairs
        (B) TYPE: nucleic acid (C) STRANDEDNESS: single
            (D) TOPOLOGY: linear (xi) SEQUENCE DESCRIPTION: SEQ ID NO:106:

AGTTCAAGGC CGTGCTATTG ATGTGCCAAC TGCCGTTGGT                              40

(2) INFORMATION FOR SEQ ID NO:107:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:107:

AAGACGGCGT GAATTCTGCA ACAGGGAACC TTCCTGGTTG                              40

(2) INFORMATION FOR SEQ ID NO:108:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO:108:

AGTTCAAGGC CGTGGAATTC ATGTGCCAAC TGCCGTTGGT                              40

(2) INFORMATION FOR SEQ ID NO:109:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:109:

ARCTYCGACG TYACATCGAY CTGCTYGTYG GRAGYGCCAC CC                           42

(2) INFORMATION FOR SEQ ID NO:110:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:110:

RCARGCCRTC TTGGAYATGA TCGCTGGWGC Y                                       31

(2) INFORMATION FOR SEQ ID NO:111:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:111:

CRATACGACR YCAYGTCGAY TTGCTCGTTG GGGCGGCTRY YT                           42

(2) INFORMATION FOR SEQ ID NO:112:

(i) SEQUENCE CHARACTERISTICS:
            (A) LENGTH: 31 base pairs
            (B) TYPE: nucleic acid (C) STRANDEDNESS: single
        (D) TOPOLOGY: linear (xi) SEQUENCE DESCRIPTION: SEQ ID NO:112:

RCAAGCTRTC RTGGAYRTGG TRRCRGGRGC C                                31

(2) INFORMATION FOR SEQ ID NO:113:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:113:

TTGCGGACKC ACATYGACAT GGTYGTGATG TCCGCCACGC                       40

(2) INFORMATION FOR SEQ ID NO:114:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:114:

GATGCGCGTT CCCGAGGTCA TCWTAGACAT CRTYRGCGGR GCD                   43

(2) INFORMATION FOR SEQ ID NO:115:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:115:

AATGGCACCY TGCRCTGCTG GATACAAGTR ACACCTAATG TGGCTGTGAA            50

ACAC                                                              54

(2) INFORMATION FOR SEQ ID NO:116:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:116:

TGARCTAGYC CTYSARGTYG TCTTCGGYGG Y                                31

(2) INFORMATION FOR SEQ ID NO:117:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:117:

GCCAACGTCT CTCGATGTTG GGTGCCGGTT GCCCCCAATC TCGCCATAAG            50

TCAA                                                              54

(2) INFORMATION FOR SEQ ID NO:118:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:118:

AAGGGCCTGC GAGCACACAT CGATATCATC GTGATGTCTG CTACGG          46

(2) INFORMATION FOR SEQ ID NO:119:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:119:

TTGGTGCGCA TCCCGGAAGT CATCTTGGAT ATTGTTACAG GAGGT           45

(2) INFORMATION FOR SEQ ID NO:120:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:120:

AGTCAGGTAY GTCGGAGCAA CCACCGCYTC GATACGCAGT               40

(2) INFORMATION FOR SEQ ID NO:121:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:121:

AGCCTTCACG TTCAGACCKC GTCGCCATCA AACRGTCCAG ACCTGT          46

(2) INFORMATION FOR SEQ ID NO:122:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (xi) SEQUENCE DESCRIPTION: SEQ ID NO:122:

TCCCCCGCYG TGGGTATGGT GGTRGCGCAC RTYCTGCGDY TGCCCCAGAC       50

CKTGTTYGAC ATAMTRGCYG GGGCC                             75

(2) INFORMATION FOR SEQ ID NO:123:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:123:

ACGCCGGTGA CGCCTACAGT GGCTGTCGCA CACCCGGGC                39

(2) INFORMATION FOR SEQ ID NO:124:

(i) SEQUENCE CHARACTERISTICS:
            (A) LENGTH: 42 base pairs
            (B) TYPE:   nucleic acid
            (C) STRANDEDNESS: single
            (D) TOPOLOGY:  linear (xi) SEQUENCE DESCRIPTION: SEQ ID NO:124:

ATGAGGGTCC CCACAGCCTT TCTCGACATG GTTGCCGGAG GC                          42

(2) INFORMATION FOR SEQ ID NO:125:

(i) SEQUENCE CHARACTERISTICS:
            (A) LENGTH: 40 base pairs
            (B) TYPE:   nucleic acid
            (C) STRANDEDNESS: single
            (D) TOPOLOGY:  linear (xi) SEQUENCE DESCRIPTION: SEQ ID NO:125:

CGCGCCCTAT CCCAACGCAC CGTTAGAGTC CATGCGCAGG                             40

(2) INFORMATION FOR SEQ ID NO:126:

(i) SEQUENCE CHARACTERISTICS:
            (A) LENGTH: 49 base pairs
            (B) TYPE:   nucleic acid
            (C) STRANDEDNESS: single
            (D) TOPOLOGY:  linear (xi) SEQUENCE DESCRIPTION: SEQ ID NO:126:

TCAGATCTTA CGGATCCCCT CTATCCTAGG TGACTTGCTC ACCGGGGGT                   49

(2) INFORMATION FOR SEQ ID NO:127:

(i) SEQUENCE CHARACTERISTICS:
            (A) LENGTH: 54 base pairs
            (B) TYPE:   nucleic acid
            (C) STRANDEDNESS: single
            (D) TOPOLOGY:  linear (xi) SEQUENCE DESCRIPTION: SEQ ID NO:127:

CAGTCACGCT GCTGGGTGGC CCTTACTCCC ACCGTGGCGG YGYCTTATAT                  50

CGGT                                                                    54

(2) INFORMATION FOR SEQ ID NO:128:

(i) SEQUENCE CHARACTERISTICS:
            (A) LENGTH: 31 base pairs
            (B) TYPE:   nucleic acid
            (C) STRANDEDNESS: single
            (D) TOPOLOGY:  linear (xi) SEQUENCE DESCRIPTION: SEQ ID NO:128:

TAGCACTCTG GTRGAYCTAC TCRCTGGAGG G                                      31

(2) INFORMATION FOR SEQ ID NO:129:

(i) SEQUENCE CHARACTERISTICS:
            (A) LENGTH: 54 base pairs
            (B) TYPE:   nucleic acid
            (C) STRANDEDNESS: single
            (D) TOPOLOGY:  linear (xi) SEQUENCE DESCRIPTION: SEQ ID NO:129:

AAGTCTACAT GCTGGGTGTC TCTCACCCCC ACCGTGGCTG CGCAACATCT            50

GAAT            54

(2) INFORMATION FOR SEQ ID NO:130:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:130:

AGGCGCCATG GTCGACCTGC TTGCAGGCGG C            31

(2) INFORMATION FOR SEQ ID NO:131:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:131:

TCAGCCCCGA VYYTCGGAGC GGTCACGGCT CCTCTTCGGA GGG            43

(2) INFORMATION FOR SEQ ID NO:132:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:132:

TGYTACGGAT YCCCCARGTG GTCATHGACA TCATWGCCGG GGSC            44

(2) INFORMATION FOR SEQ ID NO:133:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:133:

CATACCAAAT GCTTCCACGC CCGCAACGGG ATTCCGCAGG            40

(2) INFORMATION FOR SEQ ID NO:134:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:134:

TCTTCTTGCG GGCGCCGCAG TGGTTTGCTC ATCCCTG            37

(2) INFORMATION FOR SEQ ID NO:135:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:135:

ATCTAGCATC TTGAGGGTAC CTGAGATTTG TGCGAGTGTG ATATTTGGTG        50

GC        52

(2) INFORMATION FOR SEQ ID NO:136:

(i) SEQUENCE CHARACTERISTICS:
        (A) LENGTH: 33 amino acids
        (B) TYPE: amino acid
        (C) STRANDEDNESS: unknown
        (D) TOPOLOGY: unknown (xi) SEQUENCE DESCRIPTION: SEQ ID NO:136:

Trp Ile Gln Val Thr Pro Asn Val Ala Val Lys His Arg Gly Ala
            5                  10               15

Leu Thr His Asn Leu Arg Xaa His Xaa Asp Xaa Ile Val Met Ala
          20                25              30

Ala Thr Val (2) INFORMATION FOR SEQ ID NO:137:

(i) SEQUENCE CHARACTERISTICS:
        (A) LENGTH: 33 amino acids
        (B) TYPE: amino acid
        (C) STRANDEDNESS: unknown
        (D) TOPOLOGY: unknown (xi) SEQUENCE DESCRIPTION: SEQ ID NO:137:

Trp Val Pro Val Ala Pro Asn Leu Ala Ile Ser Gln Pro Gly Ala
            5                  10               15

Leu Thr Lys Gly Leu Arg Ala His Ile Asp Ile Ile Val Met Ser
          20                25              30

Ala Thr Val (2) INFORMATION FOR SEQ ID NO:138:

(i) SEQUENCE CHARACTERISTICS:
        (A) LENGTH: 33 amino acids
        (B) TYPE: amino acid
        (C) STRANDEDNESS: unknown
        (D) TOPOLOGY: unknown (xi) SEQUENCE DESCRIPTION: SEQ ID NO:138:

Trp Ile Pro Val Xaa Pro Asn Val Ala Val Xaa Xaa Pro Gly Ala
            5                  10               15

Leu Thr Gln Gly Leu Arg Thr His Ile Asp Met Val Val Met Ser
          20                25              30

Ala Thr Leu (2) INFORMATION FOR SEQ ID NO:139:

(i) SEQUENCE CHARACTERISTICS:
        (A) LENGTH: 33 amino acids
        (B) TYPE: amino acid
        (C) STRANDEDNESS: unknown
        (D) TOPOLOGY: unknown (xi) SEQUENCE DESCRIPTION: SEQ ID NO:139:

Trp Thr Xaa Val Thr Pro Thr Val Ala Val Arg Tyr Val Gly Ala
            5                  10               15

Thr Thr Ala Ser Ile Arg Ser His Val Asp Leu Leu Val Gly Ala
            20                  25                  30

Ala Thr Xaa (2) INFORMATION FOR SEQ ID NO:140:

(i) SEQUENCE CHARACTERISTICS:
        (A) LENGTH: 33 amino acids
        (B) TYPE:  amino acid
        (C) STRANDEDNESS:  unknown
        (D) TOPOLOGY:  unknown (xi) SEQUENCE DESCRIPTION: SEQ ID NO:140:

Trp Val Ala Leu Xaa Pro Thr Leu Ala Ala Arg Asn Xaa Xaa Xaa
                5                  10                  15

Xaa Thr Xaa Xaa Ile Arg Xaa His Val Asp Leu Leu Val Gly Ala
            20                  25                  30

Ala Xaa Phe (2) INFORMATION FOR SEQ ID NO:141:

(i) SEQUENCE CHARACTERISTICS:
        (A) LENGTH: 33 amino acids
        (B) TYPE:  amino acid
        (C) STRANDEDNESS:  unknown
        (D) TOPOLOGY:  unknown (xi) SEQUENCE DESCRIPTION: SEQ ID NO:141:

Trp Val Xaa Xaa Xaa Pro Thr Val Ala Thr Arg Asp Gly Lys Leu
                5                  10                  15

Pro Xaa Xaa Gln Leu Arg Arg Xaa Ile Asp Leu Leu Val Gly Ser
            20                  25                  30

Ala Thr Leu (2) INFORMATION FOR SEQ ID NO:142:

(i) SEQUENCE CHARACTERISTICS:
        (A) LENGTH: 33 amino acids
        (B) TYPE:  amino acid
        (C) STRANDEDNESS:  unknown
        (D) TOPOLOGY:  unknown (xi) SEQUENCE DESCRIPTION: SEQ ID NO:142:

Trp Thr Pro Val Thr Pro Thr Val Ala Val Ala His Pro Gly Ala
                5                  10                  15

Pro Leu Glu Ser Phe Arg Arg His Val Asp Leu Met Val Gly Ala
            20                  25                  30

Ala Thr Leu (2) INFORMATION FOR SEQ ID NO:143:

(i) SEQUENCE CHARACTERISTICS:
        (A) LENGTH: 33 amino acids
        (B) TYPE:  amino acid
        (C) STRANDEDNESS:  unknown
        (D) TOPOLOGY:  unknown (xi) SEQUENCE DESCRIPTION: SEQ ID NO:143:

Trp Val Ala Leu Thr Pro Thr Val Ala Xaa Xaa Tyr Ile Gly Ala
                5                  10                  15

```
Pro Leu Xaa Ser Xaa Arg Arg His Val Asp Leu Met Val Gly Ala
            20                  25                  30

Ala Thr Val
```

(2) INFORMATION FOR SEQ ID NO:144:

(i) SEQUENCE CHARACTERISTICS:
        (A) LENGTH: 33 amino acids
        (B) TYPE: amino acid
        (C) STRANDEDNESS: unknown
        (D) TOPOLOGY: unknown (xi) SEQUENCE DESCRIPTION: SEQ ID NO:144:

```
Trp Val Ser Leu Thr Pro Thr Val Ala Ala Gln His Leu Asn Ala
            5                   10                  15

Pro Leu Glu Ser Leu Arg Arg His Val Asp Leu Met Val Gly Gly
            20                  25                  30

Ala Thr Leu
```

(2) INFORMATION FOR SEQ ID NO:145:

(i) SEQUENCE CHARACTERISTICS:
        (A) LENGTH: 33 amino acids
        (B) TYPE: amino acid
        (C) STRANDEDNESS: unknown
        (D) TOPOLOGY: unknown (xi) SEQUENCE DESCRIPTION: SEQ ID NO:145:

```
Trp Val Pro Leu Thr Pro Thr Val Ala Ala Pro Tyr Pro Asn Ala
            5                   10                  15

Pro Leu Glu Ser Met Arg Arg His Val Asp Leu Met Val Gly Ala
            20                  25                  30

Ala Thr Met
```

(2) INFORMATION FOR SEQ ID NO:146:

(i) SEQUENCE CHARACTERISTICS:
        (A) LENGTH: 33 amino acids
        (B) TYPE: amino acid
        (C) STRANDEDNESS: unknown
        (D) TOPOLOGY: unknown (xi) SEQUENCE DESCRIPTION: SEQ ID NO:146:

```
Trp Val Xaa Ile Thr Pro Thr Leu Ser Ala Pro Xaa Xaa Gly Ala
            5                   10                  15

Val Thr Ala Pro Leu Arg Arg Xaa Val Asp Tyr Leu Ala Gly Gly
            20                  25                  30

Ala Ala Leu
```

(2) INFORMATION FOR SEQ ID NO:147:

(i) SEQUENCE CHARACTERISTICS:
        (A) LENGTH: 33 amino acids
        (B) TYPE: amino acid
        (C) STRANDEDNESS: unknown
        (D) TOPOLOGY: unknown (xi) SEQUENCE DESCRIPTION: SEQ ID NO:147:

```
Trp His Ala Val Thr Pro Thr Leu Ala Ile Pro Asn Ala Ser Thr
            5                   10                  15
```

-continued

Pro Ala Thr Gly Phe Arg Arg His Val Asp Leu Leu Ala Gly Ala
                20                  25                  30

Ala Val Val (2) INFORMATION FOR SEQ ID NO:148:

(i) SEQUENCE CHARACTERISTICS:
        (A) LENGTH: 23 amino acids
        (B) TYPE:   amino acid
        (C) STRANDEDNESS:  unknown
        (D) TOPOLOGY:  unknown (xi) SEQUENCE DESCRIPTION: SEQ ID NO:148:

Thr Leu Thr Met Ile Leu Ala Tyr Ala Ala Arg Val Pro Glu Leu
                 5                  10                  15

Xaa Leu Xaa Val Val Phe Gly Gly
                20

(2) INFORMATION FOR SEQ ID NO:149:

(i) SEQUENCE CHARACTERISTICS:
        (A) LENGTH: 23 amino acids
        (B) TYPE:   amino acid
        (C) STRANDEDNESS:  unknown
        (D) TOPOLOGY:  unknown (xi) SEQUENCE DESCRIPTION: SEQ ID NO:149:

Thr Thr Thr Met Leu Leu Ala Tyr Leu Val Arg Ile Pro Glu Val
                 5                  10                  15

Ile Leu Asp Ile Val Thr Gly Gly
                20

(2) INFORMATION FOR SEQ ID NO:150:

(i) SEQUENCE CHARACTERISTICS:
        (A) LENGTH: 23 amino acids
        (B) TYPE:   amino acid
        (C) STRANDEDNESS:  unknown
        (D) TOPOLOGY:  unknown (xi) SEQUENCE DESCRIPTION: SEQ ID NO:150:

Thr Xaa Thr Xaa Ile Leu Ala Tyr Xaa Met Arg Val Pro Glu Val
                 5                  10                  15

Ile Xaa Asp Ile Xaa Xaa Gly Ala
                20

(2) INFORMATION FOR SEQ ID NO:151:

(i) SEQUENCE CHARACTERISTICS:
        (A) LENGTH: 23 amino acids
        (B) TYPE:   amino acid
        (C) STRANDEDNESS:  unknown
        (D) TOPOLOGY:  unknown (xi) SEQUENCE DESCRIPTION: SEQ ID NO:151:

Ala Val Gly Met Val Val Ala His Xaa Leu Arg Leu Pro Gln Thr
                 5                  10                  15

Xaa Phe Asp Ile Xaa Ala Gly Ala
                20

(2) INFORMATION FOR SEQ ID NO:152:

(i) SEQUENCE CHARACTERISTICS:
        (A) LENGTH: 23 amino acids
        (B) TYPE:   amino acid

```
        (C) STRANDEDNESS: unknown
        (D) TOPOLOGY: unknown (xi) SEQUENCE DESCRIPTION: SEQ ID NO:152:

Thr Xaa Ala Leu Val Xaa Ser Gln Leu Leu Arg Xaa Pro Gln Ala
                5                   10                  15

Xaa Xaa Asp Xaa Val Xaa Gly Ala
            20

(2) INFORMATION FOR SEQ ID NO:153:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (xi) SEQUENCE DESCRIPTION: SEQ ID NO:153:

Thr Xaa Ala Leu Val Xaa Ala Gln Leu Leu Arg Xaa Pro Gln Ala
                5                   10                  15

Xaa Leu Asp Met Ile Ala Gly Ala
            20

(2) INFORMATION FOR SEQ ID NO:154:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (xi) SEQUENCE DESCRIPTION: SEQ ID NO:154:

Thr Thr Thr Leu Leu Leu Ala Gln Ile Met Arg Val Pro Thr Ala
                5                   10                  15

Phe Leu Asp Met Val Ala Gly Gly
            20

(2) INFORMATION FOR SEQ ID NO:155:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (xi) SEQUENCE DESCRIPTION: SEQ ID NO:155:

Thr Thr Thr Leu Xaa Leu Ala Gln Val Met Arg Ile Pro Ser Thr
                5                   10                  15

Leu Val Asp Leu Leu Xaa Gly Gly
            20

(2) INFORMATION FOR SEQ ID NO:156:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (xi) SEQUENCE DESCRIPTION: SEQ ID NO:156:

Thr Ala Thr Leu Val Leu Ala Gln Leu Met Arg Ile Pro Gly Ala
                5                   10                  15

Met Val Asp Leu Leu Ala Gly Gly
            20
```

(2) INFORMATION FOR SEQ ID NO:157:

(i) SEQUENCE CHARACTERISTICS:
        (A) LENGTH: 23 amino acids
        (B) TYPE:  amino acid
        (C) STRANDEDNESS:  unknown
        (D) TOPOLOGY:  unknown (xi) SEQUENCE DESCRIPTION: SEQ ID NO:157:

Thr Ser Ala Leu Ile Met Ala Gln Ile Leu Arg Ile Pro Ser Ile
            5                   10               15

Leu Gly Asp Leu Leu Thr Gly Gly
            20

(2) INFORMATION FOR SEQ ID NO:158:

(i) SEQUENCE CHARACTERISTICS:
        (A) LENGTH: 23 amino acids
        (B) TYPE:  amino acid
        (C) STRANDEDNESS:  unknown
        (D) TOPOLOGY:  unknown (xi) SEQUENCE DESCRIPTION: SEQ ID NO:158:

Xaa Thr Ala Leu Xaa Met Ala Gln Xaa Leu Arg Ile Pro Gln Val
            5                   10               15

Val Ile Asp Ile Ile Ala Gly Xaa
            20

(2) INFORMATION FOR SEQ ID NO:159:

(i) SEQUENCE CHARACTERISTICS:
        (A) LENGTH: 23 amino acids
        (B) TYPE:  amino acid
        (C) STRANDEDNESS:  unknown
        (D) TOPOLOGY:  unknown (xi) SEQUENCE DESCRIPTION: SEQ ID NO:159:

Thr Thr Thr Leu Val Leu Ser Ser Ile Leu Arg Val Pro Glu Ile
            5                   10               15

Cys Ala Ser Val Ile Phe Gly Gly
            20

(2) INFORMATION FOR SEQ ID NO:160:

(i) SEQUENCE CHARACTERISTICS:
        (A) LENGTH: 9 amino acids
        (B) TYPE:  amino acid
        (C) STRANDEDNESS:  unknown
        (D) TOPOLOGY:  unknown (xi) SEQUENCE DESCRIPTION: SEQ ID NO:160:

Gly His Arg Met Ala Trp Asp Met Met
1            5